US010767193B2

(12) United States Patent
Seebeck et al.

(10) Patent No.: US 10,767,193 B2
(45) Date of Patent: Sep. 8, 2020

(54) ENGINEERED CAS9 SYSTEMS FOR EUKARYOTIC GENOME MODIFICATION

(71) Applicant: Sigma-Aldrich Co., LLC, St. Louis, MO (US)

(72) Inventors: Timothy Seebeck, St. Louis, MO (US); Fuqiang Chen, St. Louis, MO (US); Gregory D. Davis, St. Louis, MO (US)

(73) Assignee: Sigma-Aldrich Co. LLC, St. Louis, MO (US)

(*) Notice: Subject to any disclaimer, the term of this patent is extended or adjusted under 35 U.S.C. 154(b) by 0 days.

(21) Appl. No.: 16/277,823

(22) Filed: Feb. 15, 2019

(65) Prior Publication Data

US 2019/0249200 A1 Aug. 15, 2019

Related U.S. Application Data

(60) Provisional application No. 62/720,525, filed on Aug. 21, 2018, provisional application No. 62/631,304, filed on Feb. 15, 2018.

(51) Int. Cl.
   C12N 15/113 (2010.01)
   C12N 9/22 (2006.01)
   C12N 15/85 (2006.01)
   C12N 15/90 (2006.01)
   C12N 15/10 (2006.01)

(52) U.S. Cl.
   CPC ............. *C12N 15/907* (2013.01); *C12N 9/22* (2013.01); *C12N 15/102* (2013.01); *C12N 15/113* (2013.01); *C12N 15/85* (2013.01); *C07K 2319/00* (2013.01); *C12N 2310/20* (2017.05); *C12Y 301/21001* (2013.01)

(58) Field of Classification Search
   CPC .................................................. C12N 2310/20
   See application file for complete search history.

(56) References Cited

U.S. PATENT DOCUMENTS

| 2014/0068797 A1 | 3/2014 | Doudna et al. |
| 2017/0314015 A1 | 11/2017 | Friedland et al. |

FOREIGN PATENT DOCUMENTS

| WO | WO-2013176772 A1 * | 11/2013 | ........... C12N 15/102 |
| WO | 2014/089290 A1 | 6/2014 | |
| WO | 2016/054326 A1 | 4/2016 | |
| WO | WO-2018108339 A9 * | 9/2018 | ............... C12N 9/22 |
| WO | 2019/025984 A1 | 2/2019 | |

OTHER PUBLICATIONS

Type II CRISPR RNA-guided endonuclease Cas9 from Bacillus smithii. GenBank Accession No. WP_003354196.1, Oct. 2015, printed as p. 1/1. (Year: 2015).*

Mougiakos et al. Characterizing a thermostable Cas9 for bacterial genome editing and silencing. Nature Communications, vol. 8, 1647, Nov. 21, 2017, printed as pp. 1/11-11/11, including pp. 1/26-26/26 of Supplementary Information. (Year: 2017).*

Karvelis et al. Methods for decoding Cas9 protospacer adjacent motif (PAM) sequences: A brief overview. Methods, vol. 121-122, pp. 3-8, Mar. 24, 2017. (Year: 2017).*

Liu et al. Efficient gene targeting in zebrafish mediated by a zebrafish-codon-optimized Cas9 and evaluation of off-target effect. Journal of Genetics and Genomics, vol. 41, pp. 43-46, 2014, including pp. 1/4-4/4 of Supplementary Data, and Supplementary Figures 1-2, printed as pp. 1-4-4/4. (Year: 2014).*

Palermo et al. Protospacer adjacent motif-induced allostery activates CRISPR-Cas9. Journal of the American Chemical Society, vol. 139, pp. 16028-16031, Aug. 2, 2017, including pp. 1/39-39/39. (Year: 2017).*

Anders et al. Structural basis of Pam-dependent target DNA recognition by the Cas9 endonuclease. Nature, vol. 569, pp. 569-573, Sep. 2014, including 1/2-2/2 of Methods, and pp. 1/9-9/9 of Extended Data. (Year: 2014).*

Brouns, Stan J., "A Swiss Army Knife of Immunity", Science, vol. 337, No. 6096, Aug. 2012, pp. 808-809.

Darroll, Dana, "A CRISPR Approach to Gene Targeting", Molecular Therapy, vol. 20, No. 9, Sep. 2012, pp. 1658-1660.

Cong, et al. "Multiplex Genome Engineering Using CRISPR/Cas Systems" Science, 2013, vol. 339. pp. 819-823.

Deltcheva, et al., "CRISPR RNA Maturation by Trans-Encoded Small RNA and Host Factor RNase III", Nature, vol. 471, Mar. 2011, pp. 602-607.

Edraki, et al., "A Compact, High-Accuracy Cas9 with a Dinucleotide PAM for in Vivo Genome Editing", Molecular Cell, vol. 73, No. 4, Dec. 20, 2018, 14 pages, Supplemental Information Only.

Jinek, et al., "A Programmable Dual-RNA-Guided DNA Endonuclease in Adaptive Bacterial Immunity", Science, vol. 337, Aug. 2012, 45 pages.

Jinek, et al., "RNA-programmed genome editing in human cells", eLIFE, vol. 2, 2013, pp. 1-9.

Jinek, et al., "Supplementary Materials for—a Programmable Dual-RNA-Guided DNA Endonuclease in Adaptive Bacterial Immunity", Science, 2012, 37 pages.

Kleinstiver, et al., "Engineered CRISPR-Cas9 Nucleases with Altered PAM Specificities", Nature, vol. 523, No. 7561, Jul. 23, 2015, 17 pages.

Mali, et al., "Cas9 as a Versatile Tool for Engineering Biology", Nature Methods, vol. 10, No. 10, Oct. 1, 2013, pp. 957-963.

Ran, et al., "Double Nicking by RNA-Guided CRISPR Cas9 for Enhanced Genome Editing Specificity", Cell, vol. 154, Sep. 2013, pp. 1380-1389.

Ran, et al., "Genome Engineering using the CRISPR-Cas9 System", Nature Protocols, vol. 8, No. 11, 2013, pp. 2281-2308.

(Continued)

*Primary Examiner* — Jennifer Dunston
(74) *Attorney, Agent, or Firm* — Benjamin S. Sodey; Sigma-Aldrich Co. LLC

(57) ABSTRACT

Engineered Cas9 systems that utilize alternate protospacer adjacent motifs for target DNA binding, nucleic acids encoding the engineered Cas9 systems, and methods of using the engineered Cas9 systems for modifying target chromosomal sequences in eukaryotic cells.

26 Claims, 4 Drawing Sheets

Specification includes a Sequence Listing.

(56) References Cited

OTHER PUBLICATIONS

Ran, et al., "In Vivo Genome Editing using *Staphylococcus aureus* Cas9", Along with supplemental material, Nature, vol. 520, Apr. 2015, pp. 186-191.
International Search Report and Written Opinion received for PCT Application No. PCT/US2019/018335, dated Jul. 8, 2019, 22 pages.

* cited by examiner

ENGINEERED CAS9 SYSTEMS FOR EUKARYOTIC GENOME MODIFICATION

CROSS-REFERENCE TO RELATED APPLICATIONS

This application claims the benefit of U.S. Provisional Application Ser. No. 62/631,304, filed Feb. 15, 2018, and U.S. Provisional Application Ser. No. 62/720,525, filed Aug. 21, 2018, the disclosure of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 12, 2019, is named P18_023US_SL.txt and is 367,427 bytes in size.

FIELD

The present disclosure relates to engineered Cas9 systems, nucleic acids encoding said systems, and methods of using said systems for genome modification.

BACKGROUND

The recent development of the bacterial class 2 Clustered Regularly Interspaced Short Palindromic Repeats (CRISPR) and CRISPR-associated (Cas) CRISPR/Cas systems as genome editing tools has provided unprecedented ease and simplicity to engineer site-specific endonucleases for eukaryotic genome modification. However, because each CRISPR/Cas system requires a specific protospacer adjacent motif (PAM) for target DNA binding, each system is limited to certain genomic sites. Although the currently most widespread adopted *Streptococcus pyogenes* Cas9 (SpyCas9) uses a frequently occurring PAM (5'-NGG-3') for targeting, it is still excluded from many genomic sites lacking such a motif, since eukaryotic genomes, especially those of mammals and plants, are highly complex and heterogeneous in DNA sequence. Moreover, precision gene editing using homology-directed repair (HDR) or base editors such as dCas9/cytidine deaminase and dCas9/adenosine deaminase often requires a precise DNA binding position, even at the single base pair resolution, to achieve an optimal editing outcome. Therefore, there is a need to develop new CRISPR/Cas systems that use novel PAMs for targeting to increase genome coverage density.

SUMMARY

Among the various aspects of the present disclosure include engineered Cas9 systems comprising engineered Cas9 proteins and engineered guide RNAs, wherein each engineered guide RNA is designed to complex with an engineered Cas9 protein and the engineered guide RNA comprises a 5' guide sequence designed to hybridize with a target sequence in a double-stranded sequence, wherein the target sequence is 5' to a protospacer adjacent motif (PAM) and the PAM has a sequence as listed in Table A.

Another aspect of the present disclosure encompasses a plurality of nucleic acids encoding said engineered Cas9 systems and at least one vector comprising the plurality of said nucleic acids.

A further aspect includes eukaryotic cells comprising at least one engineered Cas9 system and/or at least one nucleic acid encoding said engineered Cas9 system.

Still another aspect of the present disclosure encompasses methods for modifying chromosomal sequences in eukaryotic cells. The methods comprise introducing into the eukaryotic cell at least one engineered Cas9 system comprising an engineered Cas9 protein and an engineered guide RNA and/or at least one nucleic acid encoding said engineered Cas9 system and, optionally, at least one donor polynucleotide, wherein the at least one engineered guide RNA guides the at least one engineered Cas9 protein to the target site in the chromosomal sequence such that modification of the chromosomal sequence occurs.

Other aspects and features of the disclosure are detailed bellow.

DETAILED DESCRIPTION

Figure 1:
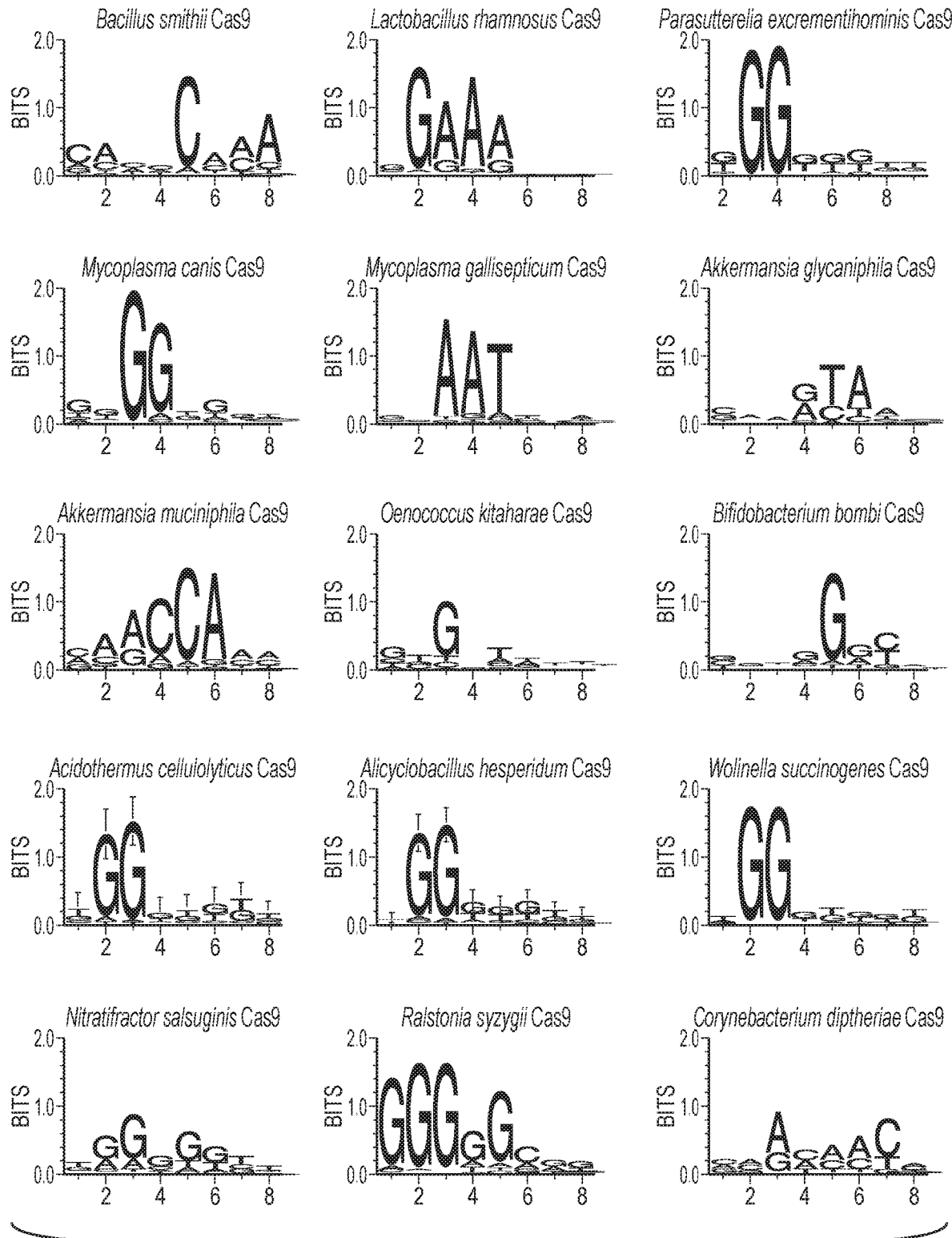
FIG. 1 shows the WebLogo analysis of protospacer adjacent motifs (PAM) required for in vitro target DNA cleavage by Cas9 orthologs. Numbers on the horizontal axis indicate the position of the nucleotide in the PAM sequence.

The present disclosure provides orthologous Cas9 systems that use alternate PAMs for target DNA binding, thereby increasing genome coverage density. For example, some of these alternate PAMs comprise A and/or T residues, and other alternate PAMS are GC-rich. As such, the engineered Cas9 systems that utilize these alternate PAMs enable targeted genome editing or genome modification of previously inaccessible genomic loci.

(I) Engineered Cas9 Systems

One aspect of the present disclosure provides engineered Cas9 systems comprising engineered Cas9 proteins and engineered guide RNAs, wherein each engineered guide RNA is designed to complex with a specific engineered Cas9 protein. Each engineered guide RNA comprises a 5' guide sequence designed to hybridize with a target sequence in a double-stranded sequence, wherein the target sequence is 5' to a protospacer adjacent motif (PAM) and the PAM has a sequence as listed in Table A. These engineered Cas9 systems do not occur naturally.

(a) Engineered Cas9 Proteins

The engineered Cas9 protein comprises at least one amino acid substitution, insertion, or deletion relative to its wild-type counterpart. Cas9 protein is the single effector protein in type II CRISPR systems, which are present in various bacteria. The engineered Cas9 protein disclosed herein can be from *Acaryochloris* sp., *Acetohalobium* sp., *Acidaminococcus* sp., *Acidithiobacillus* sp., *Acidothermus* sp., *Akkermansia* sp., *Alicyclobacillus* sp., *Allochromatium* sp., *Ammonifex* sp., *Anabaena* sp., *Arthrospira* sp., *Bacillus* sp., *Bifidobacterium* sp., *Burkholderiales* sp., *Caldicelulosiruptor* sp., *Campylobacter* sp., *Candidatus* sp., *Clostridium* sp., *Corynebacterium* sp., *Crocosphaera* sp., *Cyanothece* sp., *Exiguobacterium* sp., *Finegoldia* sp., *Francisella* sp., *Ktedonobacter* sp., *Lachnospiraceae* sp., *Lactobacillus* sp., *Lyngbya* sp., *Marinobacter* sp., *Methanohalobium* sp., *Microscilla* sp., *Microcoleus* sp., *Microcystis* sp., *Mycoplasma* sp., *Natranaerobius* sp., *Neisseria* sp., *Nitratifractor* sp., *Nitrosococcus* sp., *Nocardiopsis* sp., *Nodularia* sp., *Nostoc* sp., *Oenococcus* sp., *Oscillatoria* sp., *Parasutterella* sp., *Pelotomaculum* sp., *Petrotoga* sp., *Polaromonas* sp., *Prevotella* sp., *Pseudoalteromonas* sp., *Ralstonia* sp., *Staphylococcus* sp., *Streptococcus* sp., *Streptomyces* sp., *Streptosporangium* sp., *Synechococcus* sp., *Thermosipho* sp., *Verrucomicrobia* sp., and *Wolinella* sp.

In certain embodiments, the engineered Cas9 protein disclosed herein is from *Acidothermus* sp., *Akkermansia* sp., *Alicyclobacillus* sp., *Bacillus* sp., *Bifidobacterium* sp., *Burkholderiales* sp., *Corynebacterium* sp., *Lactobacillus* sp., *Mycoplasma* sp., *Nitratifractor* sp., *Oenococcus* sp., *Parasutterella* sp., *Ralstonia* sp., or *Wolinella* sp.

In specific embodiments, the engineered Cas9 protein disclosed herein is from *Acidothermus cellulolyticus* (Ace), *Akkermansia glycaniphila* (Agl), *Akkermansia muciniphila* (Amu), *Alicyclobacillus hesperidum* (Ahe), *Bacillus smithii* (Bsm), *Bifidobacterium bombi* (Bbo), *Corynebacterium diphtheria* (Cdi), *Lactobacillus rhamnosus* (Lrh), *Mycoplasma canis* (Mca), *Mycoplasma gallisepticum* (Mga), *Nitratifractor salsuginis* (Nsa), *Oenococcus kitaharae* (Oki), *Parasutterella excrementihominis* (Pex), *Ralstonia syzygii* (Rsy), or *Wolinella succinogenes* (Wsu).

Wild-type Cas9 proteins comprise two nuclease domains, i.e., RuvC and HNH domains, each of which cleaves one strand of a double-stranded sequence. Cas9 proteins also comprise REC domains that interact with the guide RNA (e.g., REC1, REC2) or the RNA/DNA heteroduplex (e.g., REC3), and a domain that interacts with the protospacer-adjacent motif (PAM) (i.e., PAM-interacting domain).

The Cas9 protein can be engineered to comprise one or more modifications (i.e., a substitution of at least one amino acid, a deletion of at least one amino acid, an insertion of at least one amino acid) such that the Cas9 protein has altered activity, specificity, and/or stability.

For example, Cas9 protein can be engineered by one or more mutations and/or deletions to inactivate one or both of the nuclease domains. Inactivation of one nuclease domain generates a Cas9 protein that cleaves one strand of a double-stranded sequence (i.e., a Cas9 nickase). The RuvC domain can be inactivated by mutations such as D10A, D8A, E762A, and/or D986A, and the HNH domain can be inactivated by mutations such as H840A, H559A, N854A, N856A, and/or N863A (with reference to the numbering system of *Streptococcus pyogenes* Cas9, SpyCas9). Inactivation of both nuclease domains generates a Cas9 protein having no cleavage activity (i.e., a catalytically inactive or dead Cas9).

The Cas9 protein can also be engineered by one or more amino acid substitutions, deletions, and/or insertions to have improved targeting specificity, improved fidelity, altered PAM specificity, decreased off-target effects, and/or increased stability. Non-limiting examples of one or more mutations that improve targeting specificity, improve fidelity, and/or decrease off-target effects include N497A, R661A, Q695A, K810A, K848A, K855A, Q926A, K1003A, R1060A, and/or D1135E (with reference to the numbering system of SpyCas9).

(i) Heterologous Domains

The Cas9 protein can be engineered to comprise at least one heterologous domain, i.e., Cas9 is fused to one or more heterologous domains. In situations in which two or more heterologous domains are fused with Cas9, the two or more heterologous domains can be the same or they can be different. The one or more heterologous domains can be fused to the N terminal end, the C terminal end, an internal location, or combination thereof. The fusion can be direct via a chemical bond, or the linkage can be indirect via one or more linkers. In various embodiments, the heterologous domain can be a nuclear localization signal, a cell-penetrating domain, a marker domain, a chromatin disrupting domain, an epigenetic modification domain (e.g., a cytidine deaminase domain, a histone acetyltransferase domain, and the like), a transcriptional regulation domain, an RNA aptamer binding domain, or a non-Cas9 nuclease domain.

In some embodiments the one or more heterologous domains can be a nuclear localization signal (NLS). Non-limiting examples of nuclear localization signals include PKKKRKV (SEQ ID NO:78), PKKKRRV (SEQ ID NO:79), KRPAATKKAGQAKKKK (SEQ ID NO:80), YGRKKRRQRRR (SEQ ID NO:81), RKKRRQRRR (SEQ ID NO:82), PAAKRVKLD (SEQ ID NO:83), RQRRNELKRSP (SEQ ID NO:84), VSRKRPRP (SEQ ID NO:85), PPKKARED (SEQ ID NO:86), PQPKKKPL (SEQ ID NO:87), SALIKKKKKMAP (SEQ ID NO:88), PKQKKRK (SEQ ID NO:89), RKLKKKIKKL (SEQ ID NO:90), REKKKFLKRR (SEQ ID NO:91), KRKGDEVDGVDEVAKKKSKK (SEQ ID NO:92), RKCLQAGMNLEARKTKK (SEQ ID NO:93), NQSSNFGPMKGGNFGGRSSGPYGGGGQYFAKPRNQGGY (SEQ ID NO:94), and RMRIZFKNKGKDTAELRRRRVEVSVELRKAKKDEQILKRRNV (SEQ ID NO:95).

In other embodiments, the one or more heterologous domains can be a cell-penetrating domain. Examples of suitable cell-penetrating domains include, without limit, GRKKRRQRRRPPQPKKKRKV (SEQ ID NO:96), PLSSIFSRIGDPPKKKRKV (SEQ ID NO:97), GALFLGWLGAAGSTMGAPKKKRKV (SEQ ID NO:98), GALFLGFLGAAGSTMGAWSQPKKKRKV (SEQ ID NO:99), KETWWETWWVTEWSQPKKKRKV (SEQ ID NO:100), YARAAARQARA (SEQ ID NO:101), THRLPRRRRRR (SEQ ID NO:102), GGRRARRRRRR (SEQ ID NO:103), RRQRRTSKLMKR (SEQ ID NO:104), GWTLNSAGYL-LGKINLKALAALAKKIL (SEQ ID NO:105), KALAWEAKLAKALAKALAKHLAKALAKALKCEA (SEQ ID NO:106), and RQIKIWFQNRRMKWKK (SEQ ID NO:107).

In alternate embodiments, the one or more heterologous domains can be a marker domain. Marker domains include fluorescent proteins and purification or epitope tags. Suitable fluorescent proteins include, without limit, green fluorescent proteins (e.g., GFP, eGFP, GFP-2, tagGFP, turboGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., BFP, EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), orange fluorescent proteins (e.g., mOrange, mKO, Kusabira-Orange, Monomeric Kusabira-Orange, mTangerine, tdTomato), or combinations thereof. The marker domain can comprise tandem repeats of one or more fluorescent proteins (e.g., Suntag). Non-limiting examples of suitable purification or epitope tags include 6×His (SEQ ID NO: 134), FLAG®, HA, GST, Myc, SAM, and the like. Non-limiting examples of heterologous fusions which facilitate detection or enrichment of CRISPR complexes include streptavidin (Kipriyanov et al., Human Antibodies, 1995, 6(3):93-101), avidin (Airenne et al., Biomolecular Engineering, 1999, 16(1-4):87-92), monomeric forms of avidin (Laitinen et al., Journal of Biological Chemistry, 2003, 278(6):4010-4014), peptide tags which facilitate biotinylation during recombinant production (Cull et al., Methods in Enzymology, 2000, 326:430-440).

In still other embodiments, the one or more heterologous domain can be a chromatin modulating motif (CMM). Non-limiting examples of CMMs include nucleosome interacting peptides derived from high mobility group (HMG) proteins (e.g., HMGB1, HMGB2, HMGB3, HMGN1, HMGN2, HMGN3a, HMGN3b, HMGN4, and HMGN5 proteins), the central globular domain of histone H1 variants (e.g., histone H1.0, H1.1, H1.2, H1.3, H1.4, H1.5, H1.6, H1.7, H1.8, H1.9, and H.1.10), or DNA binding domains of chromatin remodeling complexes (e.g., SWI/SNF (SWItch/Sucrose Non-Fermentable), ISWI (Imitation SWItch), CHD (Chromodomain-Helicase-DNA binding), Mi-2/NuRD (Nucleosome Remodeling and Deacetylase), INO80, SWR1, and RSC complexes. In other embodiments, CMMs also can be derived from topoisomerases, helicases, or viral proteins. The source of the CMM can and will vary. CMMs can be from humans, animals (i.e., vertebrates and invertebrates), plants, algae, or yeast. Non-limiting examples of specific CMMs are listed in the table below. Persons of skill in the art can readily identify homologs in other species and/or the relevant fusion motif therein.

| Protein | Accession No. | Fusion Motif |
| --- | --- | --- |
| Human HMGN1 | P05114 | Full length |
| Human HMGN2 | P05204 | Full length |
| Human HMGN3a | Q15651 | Full length |
| Human HMGN3b | Q15651-2 | Full length |
| Human HMGN4 | O00479 | Full length |
| Human HMGN5 | P82970 | Nucleosome binding motif |

-continued

| Protein | Accession No. | Fusion Motif |
| --- | --- | --- |
| Human HMGB1 | P09429 | Box A |
| Human histone H1.0 | P07305 | Globular motif |
| Human histone H1.2 | P16403 | Globular motif |
| Human CHD1 | O14646 | DNA binding motif |
| Yeast CHD1 | P32657 | DNA binding motif |
| Yeast ISWI | P38144 | DNA binding motif |
| Human TOP1 | P11387 | DNA binding motif |
| Human herpesvirus 8 LANA | J9QSF0 | Nucleosome binding motif |
| Human CMV IE1 | P13202 | Chromatin tethering motif |
| *M. leprae* DNA helicase | P40832 | HhH binding motif |

In yet other embodiments, the one or more heterologous domains can be an epigenetic modification domain. Non-limiting examples of suitable epigenetic modification domains include those with DNA deamination (e.g., cytidine deaminase, adenosine deaminase, guanine deaminase), DNA methyltransferase activity (e.g., cytosine methyltransferase), DNA demethylase activity, DNA amination, DNA oxidation activity, DNA helicase activity, histone acetyltransferase (HAT) activity (e.g., HAT domain derived from E1A binding protein p300), histone deacetylase activity, histone methyltransferase activity, histone demethylase activity, histone kinase activity, histone phosphatase activity, histone ubiquitin ligase activity, histone deubiquitinating activity, histone adenylation activity, histone deadenylation activity, histone SUMOylating activity, histone deSUMOylating activity, histone ribosylation activity, histone deribosylation activity, histone myristoylation activity, histone demyristoylation activity, histone citrullination activity, histone alkylation activity, histone dealkylation activity, or histone oxidation activity. In specific embodiments, the epigenetic modification domain can comprise cytidine deaminase activity, adenosine deaminase activity, histone acetyltransferase activity, or DNA methyltransferase activity.

In other embodiments, the one or more heterologous domains can be a transcriptional regulation domain (i.e., a transcriptional activation domain or transcriptional repressor domain). Suitable transcriptional activation domains include, without limit, herpes simplex virus VP16 domain, VP64 (i.e., four tandem copies of VP16), VP160 (i.e., ten tandem copies of VP16), NFκB p65 activation domain (p65), Epstein-Barr virus R transactivator (Rta) domain, VPR (i.e., VP64+p65+Rta), p300-dependent transcriptional activation domains, p53 activation domains 1 and 2, heat-shock factor 1 (HSF1) activation domains, Smad4 activation domains (SAD), cAMP response element binding protein (CREB) activation domains, E2A activation domains, nuclear factor of activated T-cells (NFAT) activation domains, or combinations thereof. Non-limiting examples of suitable transcriptional repressor domains include Kruppel-associated box (KRAB) repressor domains, Mxi repressor domains, inducible cAMP early repressor (ICER) domains, YY1 glycine rich repressor domains, Sp1-like repressors, E(spl) repressors, IκB repressors, Sin3 repressors, methyl-CpG binding protein 2 (MeCP2) repressors, or combinations thereof. Transcriptional activation or transcriptional repressor domains can be genetically fused to the Cas9 protein or bound via noncovalent protein-protein, protein-RNA, or protein-DNA interactions.

In further embodiments, the one or more heterologous domains can be an RNA aptamer binding domain (Konermann et al., Nature, 2015, 517(7536):583-588; Zalatan et al., Cell, 2015, 160(1-2):339-50). Examples of suitable RNA aptamer protein domains include MS2 coat protein (MCP), PP7 bacteriophage coat protein (PCP), Mu bacteriophage Com protein, lambda bacteriophage N22 protein, stem-loop binding protein (SLBP), Fragile X mental retardation syndrome-related protein 1 (FXR1), proteins derived from bacteriophage such as AP205, BZ13, f1, f2, fd, fr, ID2, JP34/GA, JP501, JP34, JP500, KU1, M11, M12, MX1, NL95, PP7, φCb5, φCb8r, φCb12r, φCb23r, Qβ, R17, SP-β, TW18, TW19, and VK, fragments thereof, or derivatives thereof.

In yet other embodiments, the one or more heterologous domains can be a non-Cas9 nuclease domain. Suitable nuclease domains can be obtained from any endonuclease or exonuclease. Non-limiting examples of endonucleases from which a nuclease domain can be derived include, but are not limited to, restriction endonucleases and homing endonucleases. In some embodiments, the nuclease domain can be derived from a type II-S restriction endonuclease. Type II-S endonucleases cleave DNA at sites that are typically several base pairs away from the recognition/binding site and, as such, have separable binding and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In some embodiments, the nuclease domain can be a FokI nuclease domain or a derivative thereof. The type II-S nuclease domain can be modified to facilitate dimerization of two different nuclease domains. For example, the cleavage domain of FokI can be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI nuclease domains are targets for modification. In specific embodiments, the FokI nuclease domain can comprise a first FokI half-domain comprising Q486E, I499L, and/or N496D mutations, and a second FokI half-domain comprising E490K, I538K, and/or H537R mutations.

The one or more heterologous domains can be linked directly to the Cas9 protein via one or more chemical bonds (e.g., covalent bonds), or the one or more heterologous domains can be linked indirectly to the Cas9 protein via one or more linkers.

A linker is a chemical group that connects one or more other chemical groups via at least one covalent bond. Suitable linkers include amino acids, peptides, nucleotides, nucleic acids, organic linker molecules (e.g., maleimide derivatives, N-ethoxybenzylimidazole, biphenyl-3,4',5-tricarboxylic acid, p-aminobenzyloxycarbonyl, and the like), disulfide linkers, and polymer linkers (e.g., PEG). The linker can include one or more spacing groups including, but not limited to alkylene, alkenylene, alkynylene, alkyl, alkenyl, alkynyl, alkoxy, aryl, heteroaryl, aralkyl, aralkenyl, aralkynyl and the like. The linker can be neutral, or carry a positive or negative charge. Additionally, the linker can be cleavable such that the linker's covalent bond that connects the linker to another chemical group can be broken or cleaved under certain conditions, including pH, temperature, salt concentration, light, a catalyst, or an enzyme. In some embodiments, the linker can be a peptide linker. The peptide linker can be a flexible amino acid linker (e.g., comprising small, non-polar or polar amino acids). Non-limiting examples of flexible linkers include LEGGGS (SEQ ID NO:108), TGSG (SEQ ID NO:109), GGSGGGSG (SEQ ID NO:110), (GGGGS)$_{1-4}$ (SEQ ID NO:111), and (Gly)$_{6-8}$ (SEQ ID NO:112). Alternatively, the peptide linker can be a rigid amino acid linker. Such linkers include (EAAAK)$_{1-4}$ (SEQ ID NO:113), A(EAAAK)$_{2-5}$A (SEQ ID NO:114), PAPAP (SEQ ID NO:115), and (AP)$_{6-8}$ (SEQ ID NO:116). Additional examples of suitable linkers are well known in the art and programs to design linkers are readily available (Crasto et al., Protein Eng., 2000, 13(5):309-312).

In some embodiments, the engineered Cas9 proteins can be produced recombinantly in cell-free systems, bacterial cells, or eukaryotic cells and purified using standard purification means. In other embodiments, the engineered Cas9 proteins are produced in vivo in eukaryotic cells of interest from nucleic acids encoding the engineered Cas9 proteins (see section (II) below).

In embodiments in which the engineered Cas9 protein comprises nuclease or nickase activity, the engineered Cas9 protein can further comprise at least one nuclear localization signal, cell-penetrating domain, and/or marker domain, as well as at least one chromatin disrupting domain. In embodiments in which the engineered Cas9 protein is linked to an epigenetic modification domain, the engineered Cas9 protein can further comprise at least one nuclear localization signal, cell-penetrating domain, and/or marker domain, as well as at least one chromatin disrupting domain. Furthermore, in embodiments in which the engineered Cas9 protein is linked to a transcriptional regulation domain, the engineered Cas9 protein can further comprise at least one nuclear localization signal, cell-penetrating domain, and/or marker domain, as well as at least one chromatin disrupting domain and/or at least one RNA aptamer binding domain.

(ii) Specific Engineered Cas9 Proteins

In specific embodiments, the engineered Cas9 protein is from *Bacillus smithii*, *Lactobacillus rhamnosus*, *Parasutterella excrementihominis*, *Mycoplasma canis*, *Mycoplasma gallisepticum*, *Akkermansia glycaniphila*, *Akkermansia muciniphila*, *Oenococcus kitaharae*, *Bifidobacterium bombi*, *Acidothermus cellulolyticus*, *Alicyclobacillus hesperidum*, *Wolinella succinogenes*, *Nitratifractor salsuginis*, *Ralstonia syzygii*, or *Corynebacterium diphtheria* and is linked to at least one NLS. In some iterations, the engineered Cas9 protein can have at least about 75%, at least about 80%, at least about 85%, at least about 90%, at least about 95%, or at least about 99% sequence identity to SEQ ID NO:2, 4, 6, 8, 10, 12, 14, 16, 18, 20, 22, 24, 26, 28, or 30. In certain embodiments, the engineered Cas9 protein can have at least about 95% sequence identity to SEQ ID NO:2, 4, 6, 8, 10, 12, 14, 16, 18, 20, 22, 24, 26, 28, or 30. In other iterations, the engineered Cas9 protein has the amino acid sequence of SEQ ID NO:2, 4, 6, 8, 10, 12, 14, 16, 18, 20, 22, 24, 26, 28, or 30.

In other embodiments, the engineered Cas9 protein can be a *Bacillus smithii*, *Lactobacillus rhamnosus*, *Parasutterella excrementihominis*, *Mycoplasma canis*, *Mycoplasma gallisepticum*, *Akkermansia glycaniphila*, *Akkermansia muciniphila*, *Oenococcus kitaharae*, *Bifidobacterium bombi*, *Acidothermus cellulolyticus*, *Alicyclobacillus hesperidum*, *Wolinella succinogenes*, *Nitratifractor salsuginis*, *Ralstonia syzygii*, or *Corynebacterium diphtheria* Cas9 protein linked to at least one chromatin modulating motif (CMM). The linkage between the Cas9 protein and the CMM can be direct or via a linker. The Cas9-CMM fusion protein can further comprise at least one NLS. In particular embodiments, the Cas9-CMM fusion protein can have at least about 75%, at least about 80%, at least about 85%, at least about 90%, at least about 95%, or at least about 99% sequence identity to SEQ ID NO:117, 118, 119, 120, 121, 122, 123, or 124. In certain embodiments, the Cas9-CMM fusion protein can have at least about 95% sequence identity to SEQ ID NO:117, 118, 119, 120, 121, 122, 123, or 124. In specific iterations, the Cas9-CMM fusion protein has the amino acid sequence of SEQ ID NO:117, 118, 119, 120, 121, 122, 123, or 124.

(b) Engineered Guide RNAs

The engineered guide RNA is designed to complex with a specific engineered Cas9 protein. A guide RNA comprises (i) a CRISPR RNA (crRNA) that contains a guide sequence at the 5' end that hybridizes with a target sequence and (ii) a transacting crRNA (tracrRNA) sequence that recruits the Cas9 protein. The crRNA guide sequence of each guide RNA is different (i.e., is sequence specific). The tracrRNA sequence is generally the same in guide RNAs designed to complex with a Cas9 protein from a particular bacterial species.

The crRNA guide sequence is designed to hybridize with a target sequence (i.e., protospacer) in a double-stranded sequence. In general, the complementarity between the crRNA and the target sequence is at least 80%, at least 85%, at least 90%, at least 95%, or at least 99%. In specific embodiments, the complementarity is complete (i.e., 100%). In various embodiments, the length of the crRNA guide sequence can range from about 15 nucleotides to about 25 nucleotides. For example, the crRNA guide sequence can be about 15, 16, 17, 18, 19, 20, 21, 22, 23, 24, or 25 nucleotides in length. In specific embodiments, the crRNA is about 19, 20, or 21 nucleotides in length. In one embodiment, the crRNA guide sequence has a length of 20 nucleotides.

The guide RNA comprises repeat sequence that forms at least one stem loop structure, which interacts with the Cas9 protein, and 3' sequence that remains single-stranded. The length of each loop and stem can vary. For example, the loop can range from about 3 to about 10 nucleotides in length, and the stem can range from about 6 to about 20 base pairs in length. The stem can comprise one or more bulges of 1 to about 10 nucleotides. The length of the single-stranded 3' region can vary. The tracrRNA sequence in the engineered guide RNA generally is based upon the coding sequence of wild type tracrRNA in the bacterial species of interest. The wild-type sequence can be modified to facilitate secondary structure formation, increased secondary structure stability, facilitate expression in eukaryotic cells, and so forth. For example, one or more nucleotide changes can be introduced into the guide RNA coding sequence (see Example 3, below). The tracrRNA sequence can range in length from about 50 nucleotides to about 300 nucleotides. In various embodiments, the tracrRNA can range in length from about 50 to about 90 nucleotides, from about 90 to about 110 nucleotides, from about 110 to about 130 nucleotides, from about 130 to about 150 nucleotides, from about 150 to about 170 nucleotides, from about 170 to about 200 nucleotides, from about 200 to about 250 nucleotides, or from about 250 to about 300 nucleotides.

In general, the engineered guide RNA is a single molecule (i.e., a single guide RNA or sgRNA), wherein the crRNA sequence is linked to the tracrRNA sequence. In some embodiments, however, the engineered guide RNA can be two separate molecules. A first molecule comprising the crRNA that contains 3' sequence (comprising from about 6 to about 20 nucleotides) that is capable of base pairing with the 5' end of a second molecule, wherein the second molecule comprises the tracrRNA that contains 5' sequence (comprising from about 6 to about 20 nucleotides) that is capable of base pairing with the 3' end of the first molecule.

In some embodiments, the tracrRNA sequence of the engineered guide RNA can be modified to comprise one or more aptamer sequences (Konermann et al., Nature, 2015, 517(7536):583-588; Zalatan et al., Cell, 2015, 160(1-2):339-50). Suitable aptamer sequences include those that bind adaptor proteins chosen from MCP, PCP, Com, SLBP, FXR1, AP205, BZ13, f1, f2, fd, fr, ID2, JP34/GA, JP501, JP34, JP500, KU1, M11, M12, MX1, NL95, PP7, φCb5, φCb8r, φCb12r, φCb23r, Qβ, R17, SP-β, TW18, TW19, VK, fragments thereof, or derivatives thereof. Those of skill in the art appreciate that the length of the aptamer sequence can vary.

In other embodiments, the guide RNA can further comprise at least one detectable label. The detectable label can be a fluorophore (e.g., FAM, TMR, Cy3, Cy5, Texas Red, Oregon Green, Alexa Fluors, Halo tags, or suitable fluorescent dye), a detection tag (e.g., biotin, digoxigenin, and the like), quantum dots, or gold particles.

The guide RNA can comprise standard ribonucleotides and/or modified ribonucleotides. In some embodiment, the guide RNA can comprise standard or modified deoxyribonucleotides. In embodiments in which the guide RNA is enzymatically synthesized (i.e., in vivo or in vitro), the guide RNA generally comprises standard ribonucleotides. In embodiments in which the guide RNA is chemically synthesized, the guide RNA can comprise standard or modified ribonucleotides and/or deoxyribonucleotides. Modified ribonucleotides and/or deoxyribonucleotides include base modifications (e.g., pseudouridine, 2-thiouridine, N6-methyladenosine, and the like) and/or sugar modifications (e.g., 2'-O-methy, 2'-fluoro, 2'-amino, locked nucleic acid (LNA), and so forth). The backbone of the guide RNA can also be modified to comprise phosphorothioate linkages, boranophosphate linkages, or peptide nucleic acids.

In specific embodiments, the engineered guide RNA has at least about 75%, at least about 80%, at least about 85%, at least about 90%, at least about 95%, or at least about 99% sequence identity to SEQ ID NO:31, 32, 33, 34, 35, 36, 37, 38, 39, 40, 41, 42, 43, 44, or 45. In some embodiments, the engineered Cas9 guide RNA has the sequence of SEQ ID NO:31, 32, 33, 34, 35, 36, 37, 38, 39, 40, 41, 42, 43, 44, or 45.

(c) PAM Sequence

The engineered Cas9 systems detailed above target specific sequences in double-stranded DNA that are located upstream of novel PAM sequences. The PAM sequences preferred by the engineered Cas9 systems were identified in vitro using a library of degenerate PAMS (see Example 1 and FIG. 1), and confirmed by sequencing after genome editing experiments (see Example 2). The PAM for each of the engineered Cas9 system disclosed herein is presented in Table A, below.

TABLE A

PAM Sequences

| Engineered Cas9 system | PAM (5'-3')* |
|---|---|
| *Bacillus smithii* Cas9 (BsmCas9) | NNNNCAAA |
| *Lactobacillus rhamnosus* Cas9 (LrhCas9) | NGAAA |
| *Parasutterella excrementihominis* Cas9 (PexCas9) | NGG |
| *Mycoplasma canis* Cas9 (McaCas9) | NNGG |
| *Mycoplasma gaffisepticum* Cas9 (MgaCas9) | NNAAT |
| *Akkermansia glycaniphila* Cas9 (AgICas9) | NNNRTA |

TABLE A-continued

PAM Sequences

| Engineered Cas9system | PAM (5'-3')* |
|---|---|
| *Akkermansia muciniphila* Cas9 (AmuCas9) | MMACCA |
| *Oenococcus kitaharae* Cas9 (OkiCas9) | NNG |
| *Bifidobacterium bombi* Cas9 (BboCas9) | NNNNGRY |
| *Acidothermus cellulolyticus* Cas9 (AceCas9) | NGG |
| *Alicyclobacillus hesperidum* Cas9 (AheCas9) | NGG |
| *Wolinella succinogenes* Cas9 (WsuCas9) | NGG |
| *Nitratifractor salsuginis* Cas9 (NsaCas9) | NRGNK |
| *Ralstonia syzygfi* Cas9 (RsyCas9) | GGGRG |
| *Corynebacterium diphtheria* Cas9 (CdiCas9) | NNAMMMC |

*K is G or T; M is A or C; R is A or G; Y is C or T; and N is A, C, G, or T.

(II) Nucleic Acids

A further aspect of the present disclosure provides nucleic acids encoding the engineered Cas9 systems described above in section (I). The systems can be encoded by single nucleic acids or multiple nucleic acids. The nucleic acids can be DNA or RNA, linear or circular, single-stranded or double-stranded. The RNA or DNA can be codon optimized for efficient translation into protein in the eukaryotic cell of interest. Codon optimization programs are available as freeware or from commercial sources.

In some embodiments, nucleic acid encodes a protein having at least about 75%, at least about 80%, at least about 85%, at least about 90%, at least about 95%, or at least about 99% sequence identity to the amino acid sequence of SEQ ID NO:2, 4, 6, 8, 10, 12, 14, 16, 18, 20, 22, 24, 26, 28, or 30. In certain embodiments, the nucleic acid encoding the engineered Cas9 protein can have at least about 75%, at least about 80%, at least about 85%, at least about 90%, at least about 95%, or at least about 99% sequence identity to the DNA sequence of SEQ ID NO:1, 3, 5, 7, 9, 11, 13, 15, 17, 19, 21, 23, 25, 27, or 29. In certain embodiments, the DNA encoding the engineered Cas9 protein has the DNA sequence of SEQ ID NO:1, 3, 5, 7, 9, 11, 13, 15, 17, 19, 21, 23, 25, 27, or 29. In additional embodiments, the nucleic acid encodes a protein having at least about 75%, at least about 80%, at least about 85%, at least about 90%, at least about 95%, or at least about 99% sequence identity to the amino acid sequence of SEQ ID NO:117, 118, 119, 120, 121, 122, 123, or 124.

In some embodiments, the nucleic acid encoding the engineered Cas9 protein can be RNA. The RNA can be enzymatically synthesized in vitro. For this, DNA encoding the engineered Cas9 protein can be operably linked to a promoter sequence that is recognized by a phage RNA polymerase for in vitro RNA synthesis. For example, the promoter sequence can be a T7, T3, or SP6 promoter sequence or a variation of a T7, T3, or SP6 promoter sequence. The DNA encoding the engineered protein can be part of a vector, as detailed below. In such embodiments, the in vitro-transcribed RNA can be purified, capped, and/or polyadenylated. In other embodiments, the RNA encoding the engineered Cas9 protein can be part of a self-replicating RNA (Yoshioka et al., Cell Stem Cell, 2013, 13:246-254). The self-replicating RNA can be derived from a noninfectious, self-replicating Venezuelan equine encephalitis (VEE) virus RNA replicon, which is a positive-sense, single-stranded RNA that is capable of self-replicating for a limited number of cell divisions, and which can be modified to code proteins of interest (Yoshioka et al., Cell Stem Cell, 2013, 13:246-254).

In other embodiments, the nucleic acid encoding the engineered Cas9 protein can be DNA. The DNA coding sequence can be operably linked to at least one promoter control sequence for expression in the cell of interest. In certain embodiments, the DNA coding sequence can be operably linked to a promoter sequence for expression of the engineered Cas9 protein in bacterial (e.g., *E. coli*) cells or eukaryotic (e.g., yeast, insect, or mammalian) cells. Suitable bacterial promoters include, without limit, T7 promoters, lac operon promoters, trp promoters, tac promoters (which are hybrids of trp and lac promoters), variations of any of the foregoing, and combinations of any of the foregoing. Non-limiting examples of suitable eukaryotic promoters include constitutive, regulated, or cell- or tissue-specific promoters. Suitable eukaryotic constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable eukaryotic regulated promoter control sequences include without limit those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter. The promoter sequence can be wild type or it can be modified for more efficient or efficacious expression. In some embodiments, the DNA coding sequence also can be linked to a polyadenylation signal (e.g., SV40 polyA signal, bovine growth hormone (BGH) polyA signal, etc.) and/or at least one transcriptional termination sequence. In some situations, the engineered Cas9 protein can be purified from the bacterial or eukaryotic cells.

In still other embodiments, the engineered guide RNA can be encoded by DNA. In some instances, the DNA encoding the engineered guide RNA can be operably linked to a promoter sequence that is recognized by a phage RNA polymerase for in vitro RNA synthesis. For example, the promoter sequence can be a T7, T3, or SP6 promoter sequence or a variation of a T7, T3, or SP6 promoter sequence. In other instances, the DNA encoding the engineered guide RNA can be operably linked to a promoter sequence that is recognized by RNA polymerase III (Pol III) for expression in eukaryotic cells of interest. Examples of suitable Pol III promoters include, but are not limited to, mammalian U6, U3, H1, and 7SL RNA promoters.

In various embodiments, the nucleic acid encoding the engineered Cas9 protein can be present in a vector. In some embodiments, the vector can further comprise nucleic acid encoding the engineered guide RNA. Suitable vectors include plasmid vectors, viral vectors, and self-replicating RNA (Yoshioka et al., Cell Stem Cell, 2013, 13:246-254). In some embodiments, the nucleic acid encoding the complex or fusion protein can be present in a plasmid vector. Non-limiting examples of suitable plasmid vectors include pUC, pBR322, pET, pBluescript, and variants thereof. In other embodiments, the nucleic acid encoding the complex or fusion protein can be part of a viral vector (e.g., lentiviral vectors, adeno-associated viral vectors, adenoviral vectors, and so forth). The plasmid or viral vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information about vectors and use thereof can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

(III) Eukaryotic Cells

Another aspect of the present disclosure comprises eukaryotic cells comprising at least one engineered Cas9 system as detailed above in section (I) and/or at least one nucleic acid encoding an engineered Cas9 protein and/or engineered guide RNA as detailed above in section (II).

The eukaryotic cell can be a human cell, a non-human mammalian cell, a non-mammalian vertebrate cell, an invertebrate cell, a plant cell, or a single cell eukaryotic organism. Examples of suitable eukaryotic cells are detailed below in section (IV)(c). The eukaryotic cell can be in vitro, ex vivo, or in vivo.

(IV) Methods for Modifying Chromosomal Sequences

A further aspect of the present disclosure encompasses methods for modifying a chromosomal sequence in eukaryotic cells. In general, the methods comprise introducing into the eukaryotic cell of interest at least one engineered Cas9 system as detailed above in section (I) and/or at least one nucleic acid encoding said engineered Cas9 system as detailed above in section (II).

In embodiments in which the engineered Cas9 protein comprises nuclease or nickase activity, the chromosomal sequence modification can comprise a substitution of at least one nucleotide, a deletion of at least one nucleotide, an insertion of at least one nucleotide. In some iterations, the method comprises introducing into the eukaryotic cell one engineered Cas9 system comprising nuclease activity or two engineered Cas9 systems comprising nickase activity and no donor polynucleotide, such that the engineered Cas9 system or systems introduce a double-stranded break in the target site in the chromosomal sequence and repair of the double-stranded break by cellular DNA repair processes introduces at least one nucleotide change (i.e., indel), thereby inactivating the chromosomal sequence (i.e., gene knock-out). In other iterations, the method comprises introducing into the eukaryotic cell one engineered Cas9 system comprising nuclease activity or two engineered Cas9 systems comprising nickase activity, as well as the donor polynucleotide, such that the engineered Cas9 system or systems introduce a double-stranded break in the target site in the chromosomal sequence and repair of the double-stranded break by cellular DNA repair processes leads to insertion or exchange of sequence in the donor polynucleotide into the target site in the chromosomal sequence (i.e., gene correction or gene knock-in).

In embodiments, in which the engineered Cas9 protein comprises epigenetic modification activity or transcriptional regulation activity, the chromosomal sequence modification can comprise a conversion of at least one nucleotide in or near the target site, a modification of at least one nucleotide in or near the target site, a modification of at least one histone protein in or near the target site, and/or a change in transcription in or near the target site in the chromosomal sequence.

(a) Introduction into the Cell

As mentioned above, the method comprises introducing into the eukaryotic cell at least one engineered Cas9 system and/or nucleic acid encoding said system (and optional donor polynucleotide). The at least one system and/or nucleic acid/donor polynucleotide can be introduced into the cell of interest by a variety of means.

In some embodiments, the cell can be transfected with the appropriate molecules (i.e., protein, DNA, and/or RNA). Suitable transfection methods include nucleofection (or electroporation), calcium phosphate-mediated transfection, cationic polymer transfection (e.g., DEAE-dextran or polyethylenimine), viral transduction, virosome transfection, virion transfection, liposome transfection, cationic liposome transfection, immunoliposome transfection, nonliposomal lipid transfection, dendrimer transfection, heat shock transfection, magnetofection, lipofection, gene gun delivery, impalefection, sonoporation, optical transfection, and proprietary agent-enhanced uptake of nucleic acids. Transfection methods are well known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001). In other embodiments, the molecules can be introduced into the cell by microinjection. For example, the molecules can be injected into the cytoplasm or nuclei of the cells of interest. The amount of each molecule introduced into the cell can vary, but those skilled in the art are familiar with means for determining the appropriate amount.

The various molecules can be introduced into the cell simultaneously or sequentially. For example, the engineered Cas9 system (or its encoding nucleic acid) and the donor polynucleotide can be introduced at the same time. Alternatively, one can be introduced first and then the other can be introduced later into the cell.

In general, the cell is maintained under conditions appropriate for cell growth and/or maintenance. Suitable cell culture conditions are well known in the art and are described, for example, in Santiago et al., Proc. Natl. Acad. Sci. USA, 2008, 105:5809-5814; Moehle et al. Proc. Natl. Acad. Sci. USA, 2007, 104:3055-3060; Urnov et al., Nature, 2005, 435:646-651; and Lombardo et al., Nat. Biotechnol., 2007, 25:1298-1306. Those of skill in the art appreciate that methods for culturing cells are known in the art and can and will vary depending on the cell type. Routine optimization may be used, in all cases, to determine the best techniques for a particular cell type.

(b) Optional Donor Polynucleotide

In embodiments in which the engineered Cas9 protein comprises nuclease or nickase activity, the method can further comprise introducing at least one donor polynucleotide into the cell. The donor polynucleotide can be single-stranded or double-stranded, linear or circular, and/or RNA or DNA. In some embodiments, the donor polynucleotide can be a vector, e.g., a plasmid vector.

The donor polynucleotide comprises at least one donor sequence. In some aspects, the donor sequence of the donor polynucleotide can be a modified version of an endogenous or native chromosomal sequence. For example, the donor sequence can be essentially identical to a portion of the chromosomal sequence at or near the sequence targeted by the engineered Cas9 system, but which comprises at least one nucleotide change. Thus, upon integration or exchange with the native sequence, the sequence at the targeted chromosomal location comprises at least one nucleotide change. For example, the change can be an insertion of one or more nucleotides, a deletion of one or more nucleotides, a substitution of one or more nucleotides, or combinations thereof. As a consequence of the "gene correction" integration of the modified sequence, the cell can produce a modified gene product from the targeted chromosomal sequence.

In other aspects, the donor sequence of the donor polynucleotide can be an exogenous sequence. As used herein, an "exogenous" sequence refers to a sequence that is not native to the cell, or a sequence whose native location is in a different location in the genome of the cell. For example, the exogenous sequence can comprise protein coding sequence, which can be operably linked to an exogenous promoter control sequence such that, upon integration into the genome, the cell is able to express the protein coded by the integrated sequence. Alternatively, the exogenous sequence can be integrated into the chromosomal sequence such that its expression is regulated by an endogenous promoter control sequence. In other iterations, the exogenous sequence can be a transcriptional control sequence, another expression control sequence, an RNA coding sequence, and so forth. As noted above, integration of an exogenous sequence into a chromosomal sequence is termed a "knock in."

As can be appreciated by those skilled in the art, the length of the donor sequence can and will vary. For example, the donor sequence can vary in length from several nucleotides to hundreds of nucleotides to hundreds of thousands of nucleotides.

Typically, the donor sequence in the donor polynucleotide is flanked by an upstream sequence and a downstream sequence, which have substantial sequence identity to sequences located upstream and downstream, respectively, of the sequence targeted by the engineered Cas9 system. Because of these sequence similarities, the upstream and downstream sequences of the donor polynucleotide permit homologous recombination between the donor polynucleotide and the targeted chromosomal sequence such that the donor sequence can be integrated into (or exchanged with) the chromosomal sequence.

The upstream sequence, as used herein, refers to a nucleic acid sequence that shares substantial sequence identity with a chromosomal sequence upstream of the sequence targeted by the engineered Cas9 system. Similarly, the downstream sequence refers to a nucleic acid sequence that shares substantial sequence identity with a chromosomal sequence downstream of the sequence targeted by the engineered Cas9 system. As used herein, the phrase "substantial sequence identity" refers to sequences having at least about 75% sequence identity. Thus, the upstream and downstream sequences in the donor polynucleotide can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% A sequence identity with sequence upstream or downstream to the target sequence. In an exemplary embodiment, the upstream and downstream sequences in the donor polynucleotide can have about 95% or 100% sequence identity with chromosomal sequences upstream or downstream to the sequence targeted by the engineered Cas9 system.

In some embodiments, the upstream sequence shares substantial sequence identity with a chromosomal sequence located immediately upstream of the sequence targeted by the engineered Cas9 system. In other embodiments, the upstream sequence shares substantial sequence identity with a chromosomal sequence that is located within about one hundred (100) nucleotides upstream from the target sequence. Thus, for example, the upstream sequence can share substantial sequence identity with a chromosomal sequence that is located about 1 to about 20, about 21 to about 40, about 41 to about 60, about 61 to about 80, or about 81 to about 100 nucleotides upstream from the target sequence. In some embodiments, the downstream sequence shares substantial sequence identity with a chromosomal sequence located immediately downstream of the sequence targeted by the engineered Cas9 system. In other embodiments, the downstream sequence shares substantial sequence identity with a chromosomal sequence that is located within about one hundred (100) nucleotides downstream from the target sequence. Thus, for example, the downstream sequence can share substantial sequence identity with a chromosomal sequence that is located about 1 to about 20, about 21 to about 40, about 41 to about 60, about 61 to about 80, or about 81 to about 100 nucleotides downstream from the target sequence.

Each upstream or downstream sequence can range in length from about 20 nucleotides to about 5000 nucleotides. In some embodiments, upstream and downstream sequences can comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. In specific embodiments, upstream and downstream sequences can range in length from about 50 to about 1500 nucleotides.

(c) Cell Types

A variety of eukaryotic cells are suitable for use in the methods disclosed herein. For example, the cell can be a human cell, a non-human mammalian cell, a non-mammalian vertebrate cell, an invertebrate cell, an insect cell, a plant cell, a yeast cell, or a single cell eukaryotic organism. In some embodiments, the cell can be a one cell embryo. For example, a non-human mammalian embryo including rat, hamster, rodent, rabbit, feline, canine, ovine, porcine, bovine, equine, and primate embryos. In still other embodiments, the cell can be a stem cell such as embryonic stem cells, ES-like stem cells, fetal stem cells, adult stem cells, and the like. In one embodiment, the stem cell is not a human embryonic stem cell. Furthermore, the stem cells may include those made by the techniques disclosed in WO2003/046141, which is incorporated herein in its entirety, or Chung et al. (Cell Stem Cell, 2008, 2:113-117). The cell can be in vitro (i.e., in culture), ex vivo (i.e., within tissue isolated from an organism), or in vivo (i.e., within an organism). In exemplary embodiments, the cell is a mammalian cell or mammalian cell line. In particular embodiments, the cell is a human cell or human cell line.

Non-limiting examples of suitable mammalian cells or cell lines include human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells; Chinese hamster ovary (CHO) cells, baby hamster kidney (BHK) cells;

mouse myeloma NSO cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Nepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells. An extensive list of mammalian cell lines may be found in the American Type Culture Collection catalog (ATCC, Manassas, Va.).

(V) Applications

The compositions and methods disclosed herein can be used in a variety of therapeutic, diagnostic, industrial, and research applications. In some embodiments, the present disclosure can be used to modify any chromosomal sequence of interest in a cell, animal, or plant in order to model and/or study the function of genes, study genetic or epigenetic conditions of interest, or study biochemical pathways involved in various diseases or disorders. For example, transgenic organisms can be created that model diseases or disorders, wherein the expression of one or more nucleic acid sequences associated with a disease or disorder is altered. The disease model can be used to study the effects of mutations on the organism, study the development and/or progression of the disease, study the effect of a pharmaceutically active compound on the disease, and/or assess the efficacy of a potential gene therapy strategy.

In other embodiments, the compositions and methods can be used to perform efficient and cost effective functional genomic screens, which can be used to study the function of genes involved in a particular biological process and how any alteration in gene expression can affect the biological process, or to perform saturating or deep scanning mutagenesis of genomic loci in conjunction with a cellular phenotype. Saturating or deep scanning mutagenesis can be used to determine critical minimal features and discrete vulnerabilities of functional elements required for gene expression, drug resistance, and reversal of disease, for example.

In further embodiments, the compositions and methods disclosed herein can be used for diagnostic tests to establish the presence of a disease or disorder and/or for use in determining treatment options. Examples of suitable diagnostic tests include detection of specific mutations in cancer cells (e.g., specific mutation in EGFR, HER2, and the like), detection of specific mutations associated with particular diseases (e.g., trinucleotide repeats, mutations in β-globin associated with sickle cell disease, specific SNPs, etc.), detection of hepatitis, detection of viruses (e.g., Zika), and so forth.

In additional embodiments, the compositions and methods disclosed herein can be used to correct genetic mutations associated with a particular disease or disorder such as, e.g., correct globin gene mutations associated with sickle cell disease or thalassemia, correct mutations in the adenosine deaminase gene associated with severe combined immune deficiency (SCID), reduce the expression of HTT, the disease-causing gene of Huntington's disease, or correct mutations in the rhodopsin gene for the treatment of retinitis pigmentosa. Such modifications may be made in cells ex vivo.

In still other embodiments, the compositions and methods disclosed herein can be used to generate crop plants with improved traits or increased resistance to environmental stresses. The present disclosure can also be used to generate farm animal with improved traits or production animals. For example, pigs have many features that make them attractive as biomedical models, especially in regenerative medicine or xenotransplantation.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd Ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about" when used in relation to a numerical value, x, for example means x±5%.

As used herein, the terms "complementary" or "complementarity" refer to the association of double-stranded nucleic acids by base pairing through specific hydrogen bonds. The base pairing may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some (e.g., 70%) of the bases are complementary. The bases that are not complementary are "mismatched." Complementarity may also be complete (i.e., 100%), if all the bases in the duplex region are complementary.

As used herein, the term "CRISPR/Cas system" or "Cas9 system" refers to a complex comprising a Cas9 protein (i.e., nuclease, nickase, or catalytically dead protein) and a guide RNA.

The term "endogenous sequence," as used herein, refers to a chromosomal sequence that is native to the cell.

As used herein, the term "exogenous" refers to a sequence that is not native to the cell, or a chromosomal sequence whose native location in the genome of the cell is in a different chromosomal location.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not endogenous or native to the cell of interest. For example, a heterologous protein refers to a protein that is derived from or was originally derived from an exogenous source, such as an exogenously introduced nucleic acid sequence. In some instances, the heterologous protein is not normally produced by the cell of interest.

The term "nickase" refers to an enzyme that cleaves one strand of a double-stranded nucleic acid sequence (i.e., nicks a double-stranded sequence). For example, a nuclease with double strand cleavage activity can be modified by mutation and/or deletion to function as a nickase and cleave only one strand of a double-stranded sequence.

The term "nuclease," as used herein, refers to an enzyme that cleaves both strands of a double-stranded nucleic acid sequence.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine), nucleotide isomers, or nucleotide analogs. A nucleotide analog refers to a nucleotide having a modified purine or pyrimidine base or a modified ribose moiety. A nucleotide analog may be a naturally occurring nucleotide (e.g., inosine, pseudouridine, etc.) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

The terms "target sequence," "target chromosomal sequence," and "target site" are used interchangeably to refer to the specific sequence in chromosomal DNA to which the engineered Cas9 system is targeted, and the site at which the engineered Cas9 system modifies the DNA or protein(s) associated with the DNA.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GENBANK+EMBL+DDBJ+PDB+GENBANK CDS translations+Swiss protein+Spupdate+PIR. Details of these programs can be found on the GENBANK NIH genetic sequence database website.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the disclosure.

Example 1: Determination of PAM Requirements for Target DNA Cleavage by Cas9 Orthologs Cas9 orthologs from *Bacillus smithfi, Lactobacillus rhamnosus, Parasutterella excrementihominis, Mycoplasma canis, Mycoplasma gallisepticum, Akkermansia glycaniphila, Akkermansia muciniphila, Oenococcus kitaharae, Bifidobacterium bombi, Acidothermus cellulolyticus, Alicyclobacillus hesperidum, Wolinella succinogenes, Nitratifractor salsuginis, Ralstonia syzygfi,* and *Corynebacterium diphtheria* were codon optimized for expression in human cells and tagged with a SV40 large T antigen nuclear localization (NLS) on the C terminus (SEQ ID NOs:1-30; see Table 6 below). The expression of each ortholog was driven by a human cytomegalovirus (CMV) immediate early enhancer and promoter. CRISPR RNA (crRNA) and putative trans-activating crRNA (tracrRNA) for each ortholog were joined together to form a single guide RNA (sgRNA) (SEQ ID NOs:31-45; see Table 6 below). The expression of each sgRNA was driven by a human U6 promoter. In vitro transcribed sgRNA was prepared from a T7 promoter tagged PCR template as a supplement for in vitro digestion.

Human K562 cells were transfected with Cas9 encoding plasmid and sgRNA expression plasmid by nucleofection. Each transfection consisted of 2 million cells, 5 μg of Cas9 encoding plasmid DNA, and 3 μg of sgRNA expression plasmid DNA. Cells were harvested approximately 24 hr post transfection, washed with ice cold PBS buffer, and lysed with 150 μL of lysis solution (20 mM HEPES, pH 7.5; 100 mM KCl; 5 mM MgCl2, 1 mM DTT, 5% glycerol, 0.1% Triton X-100, 1×Protease inhibitor) with constant agitation for 30 minutes in a 4° C. cold room. Supernatant was prepared by removing residual cellular debris with centrifugation at 16,000×g for 2 minutes at 4° C. and used as a source of Cas9 RNP for in vitro digestion of a plasmid DNA PAM library. The library contained $4^8$ degenerate PAMs, each immediately preceded by a protospacer with the following configuration: 5'-GTACAAACGGCAGAAGCTG-GNNNNNNNN-3' (SEQ ID NO:46). Each in vitro digestion consisted of 10 μL of cell lysate supernatant, 2 μL of 5× digestion buffer (100 mM HEPES, pH 7.5; 500 mM KCl; 25 mM MgCl2; 5 mM DTT; 25% glycerol), 800 ng of PAM library DNA, and 20 pmol of in vitro transcribed sgRNA supplement in a 20 μL reaction volume. Reaction was maintained at 37° C. for 30 minutes and then purified with PCR purification kit. Illumina NextSeq sequencing libraries were prepared from digested products and subjected to deep sequencing. Deep sequencing data were analyzed using a Weblogo program to deduce the PAM requirement for each Cas9 ortholog.

Results are summarized in FIG. 1. The results revealed several Cas9 orthologs that use A and/or T containing PAMs for in vitro target DNA cleavage. These Cas9 orthologs could provide a means to target AT rich genomic sites. The results also revealed several Cas9 orthologs that use a PAM suitable for targeting GC rich genomic sites. These Cas9 orthologs could provide alternative targeting schemes to SpyCas9 in GC rich genomic sites to increase targeting resolution and specificity.

Example 2: Genome Modification Using *Bacillus smithii* Cas9 (BsmCas9) and *Lactobacillus rhamnosus* Cas9 (LrhCas9)

As shown in FIG. 1 and Table A (above), the small BsmCas9 (1095 aa) (SEQ ID NO: 2) and the LrhCas9 (SEQ ID NO: 4) use a 5'-NNNNCAAA-3' PAM and a 5'-NGAAA-3' PAM for target DNA binding, respectively. These novel PAM usages provide a means to target AT rich genomic sites. To demonstrate gene editing, human K562 cells ($1\times10^6$) were nucleofected with 5 μg of Cas9 encoding plasmid DNA and 3 μg of sgRNA expression plasmid DNA. Targeted genomic sites include the human tyrosine-protein phosphatase non-receptor type 2 (PTN2) locus, the human empty spiracles homeobox 1 (EMX1) locus, the human programmed cell death 1 ligand 1 (PD1L1) locus, the human AAVS1 safe harbor locus, the human cytochrome p450 oxidoreductase (POR) locus, and the human nuclear receptor subfamily 1 group I member 3(CAR) locus. Genomic DNA was prepared using a DNA extraction solution (QuickExtract™) three days post transfection and targeted genomic regions were each PCR amplified (JumpStart Taq™ ReadyMix™). The PCR primers are listed in Table 1.

TABLE 1

PCR Primers.

| Locus | Forward primer (5'-3') | Reverse primer (5'-3') | Size (bp) |
|---|---|---|---|
| PTN2 | CTGTTTCCTGGGTTCCA ATAACAAGAC (SEQ ID NO: 47) | ACAAGGGCTCAAGTGGAGT G (SEQ ID NO: 48) | 290 |
| EMX1 | ATGGGAGCAGCTGGTCA GAG (SEQ ID NO: 49) | CAGCCCATTGCTTGTCCCT (SEQ ID NO: 50) | 507 |
| PD1L1 | CTCGCCATTCCAGCCAC TCAAAC (SEQ ID NO: 51) | GGTTAAGTCGGGTTTCCTT GCAG (SEQ ID NO: 52) | 341 |
| AAVS1 | TTCGGGTCACCTCTCAC TCC (SEQ ID NO: 53) | GGCTCCATCGTAAGCAAAC C (SEQ ID NO: 54) | 469 |
| POR | CTCCCCTGCTTCTTGTC GTAT (SEQ ID NO: 55) | ACAGGTCGTGGACACTCAC A (SEQ ID NO: 56) | 380 |
| CAR | GGATCAAGTCAAGGGCA TGT (SEQ ID NO: 57) | ATGTAGCTGGACAGGCTTG G (SEQ ID NO: 58) | 347 |

Amplification was carried out using the following condition: 1 cycle of 98° C. for 2 minutes for initial denaturation; 34 cycles of 98° C. for 15 seconds, 62° C. for 30 seconds, and 72° C. for 45 seconds; 1 cycle of 72° C. for 5 minutes; and hold at 4° C. PCR products were digested with Cel-1 nuclease and resolved on a 10% acrylamide gel. Targeted mutation rates were measured using ImageJ and expressed as percent insertions and/or deletions (% Indel). Results are summarized in Table 2. These results demonstrate that both Cas9 orthologs were able to edit endogenous genomic sites in human cells using a 5'-NNNNCAAA-3' PAM (BsmCas9) or a 5'-NGAAA-3' PAM (LrhCas9).

TABLE 2

Gene Editing with BsmCas9 and LrhCas9 in Human K562 Cells.

| Cas9 | Locus/Target # | Protospacer sequence (5'-3') | PAM (5'-3') | Indel (%) |
|---|---|---|---|---|
| BsmCas9 | PTN2 | CTCATACATGGCTATAATAGAA (SEQ ID NO: 59) | GGAG<u>CAAA</u> | 11.9 |
| | EMX1/Target 1 | GAAGGTGTGGTTCCAGAACCGG (SEQ ID NO: 60) | AGGA<u>CAAA</u> | 6.8 |
| | EMX1/Target 2 | TGGTTCCAGAACCAGGAGGACAA (SEQ ID NO: 61) | AGTA<u>CAAA</u> | 10.9 |

TABLE 2-continued

Gene Editing with BsmCas9 and LrhCas9 in Human K562 Cells.

| Cas9 | Locus/Target # | Protospacer sequence (5'-3') | PAM (5'-3') | Indel (%) |
|---|---|---|---|---|
| | EMX1/Target 3 | CCCAGGTGAAGGTGTGGTTCCA (SEQ ID NO: 62) | GAAC<u>CGGA</u> | 0 |
| | EMX1/Target 4 | AGAACCGGAGGACAAAGTACAA (SEQ ID NO: 63) | ACGG<u>CAGA</u> | 0 |
| LrhCas9 | PD1L1 | CCTCTGGCACATCCTCCAAA (SEQ ID NO: 64) | T<u>GAAA</u> | 38.9 |
| | AAVS1 | CTAGGGACAGGATTGGTGAC (SEQ ID NO: 65) | A<u>GAAA</u> | 32.78 |
| | POR/Target 1 | GCTCGTACTGGCGAATGCT (SEQ ID NO: 66) | G<u>GAAA</u> | 26.7 |
| | POR/Target 2 | GCTGAAGAGCTACGAGAACC (SEQ ID NO: 67) | A<u>GAAG</u> | 0 |
| | POR/Target 3 | CATGGGGGAGATGGGCCGGC (SEQ ID NO: 68) | T<u>GAAG</u> | 0 |
| | CAR/Target 1 | AGAGACTCTCTAGAAGGGAC (SEQ ID NO: 69) | A<u>GAAA</u> | 31.7 |
| | CAR/Target 2 | GTGAGAGTCTCCTCCCCAATG (SEQ ID NO: 70) | G<u>GAAA</u> | 27.0 |
| | CAR/Target 3 | GGGAGGAGACTCTCACCTGA (SEQ ID NO: 71) | A<u>GAAA</u> | 0 |

*The determinant nucleotides of the PAM are underlined.

Example 3: Improvement of *Parasutterella Excrementihominis* Cas9 (PexCas9) by Fusion with Chromatin Modulating Motifs

*Parasutterella excrementihominis* Cas9 (PexCas9-NLS) (SEQ ID NO:6) was modified by fusion with a human HMGN1 peptide (SEQ ID NO:72) on the N terminus using a TGSG linker (SEQ ID NO:109) and with either a human HMGB1 box A peptide (PexCas9-HN1HB1 fusion; SEQ ID NO:117) or a human histone H1 central globular domain peptide (PexCas9-HN1H1G; SEQ ID NO:118) on the C terminus using a LEGGGS linker (SEQ ID NO:108).

TABLE 3

Chromatin Modulating Motifs

| Name | Peptide Sequence | SEQ ID NO: |
|---|---|---|
| HMGN1 (HN1) | MPKRKVSSAEGAAKEEPKRRSARLSAKPPAKV EAKPKKAAAKDKSSDKKVQTKGKRGAKGKQAE VANQETKEDLPAENGETKTEESPASDEAGEKE AKSD | 72 |
| Human HMGB1 box A (HB1) | MGKGDPKKPRGKMSSYAFFVQTCREEHKKKHP DASVNFSEFSKKCSERWKTMSAKEKGKFEDMA KADKARYEREMKTYIPPKGE | 73 |
| Human histone H1 central globular domain (H1G) | STDHPKYSDMIVAAIQAEKNRAGSSRQSIQKY IKSHYKVGENADSQIKLSIKRLVTTGVLKQTK GVGASGSFRLAKSDEP | 74 |

Human K562 cells (1×10⁶) were transfected with plasmid DNA encoding PexCas9-NLS, PexCas9-HN1HB1 fusion, or PexCas9-HN1H1G fusion in molar equivalent amounts (5 and 5.4 μg, respectively) and 3 μg of sgRNA plasmid for targeting a genomic site in the human cytochrome p450 oxidoreductase (POR) locus. Genomic DNA was prepared using DNA extraction solution (QuickExtract™) three days post transfection and the targeted genomic region was PCR amplified using the forward primer 5'-CTCCCCTGCTTCT-TGTCGTAT-3' (SEQ ID NO:55) and the reverse primer 5'-ACAGGTCGTGGACACTCACA-3' (SEQ ID NO:56). Amplification was carried out with the following condition: 1 cycle of 98° C. for 2 minutes for initial denaturation; 34 cycles of 98° C. for 15 seconds, 62° C. for 30 seconds, and 72° C. for 45 seconds; 1 cycle of 72° C. for 5 minutes; and hold at 4° C. PCR products were digested with Cel-1 nuclease and resolved on a 10% acrylamide gel. Targeted mutation rates were measured using ImageJ and expressed as percent insertions and/or deletions (% Indel). Results are summarized in Table 4. The results demonstrate that Cas9 fusion with at least one chromatin modulating motif enhances its gene editing efficiency on endogenous targets in human cells.

TABLE 4

Gene editing using PexCas9 and PexCas9
fusion proteins in human K562 cells.

| Cas9 nuclease | Locus | Protospacer (5'-3') | PAM (5'-3')* | Indel (%) |
|---|---|---|---|---|
| PexCas9-NLS | POR | TGTACATGGGGGAGATGGGC | C<u>GG</u> | 22.9 |
| PexCas9-HN1HB1 fusion | | (SEQ ID NO: 75) | | 36.8 |
| PexCas9HN1H1G fusion | | | | 43.7 |

*The determinant nucleotides of the PAM are underlined.

Example 4. Improvement of *Mycoplasma canis* Cas9 (McaCas9) System by sgRNA Modification The wild type crRNA coding sequence of McaCas9 contains four consecutive thymidine residues in the repeat region, and three of the four thymidine residues are predicted to pair with three adenosine residues in the putative tracrRNA sequence when the crRNA and tracrRNA are joined together to form a sgRNA. Human RNA polymerase (Pol) III is known to use four or more consecutive thymidine residues on the coding RNA strand as a transcription termination signal. To prevent an early transcriptional termination of McaCas9 sgRNA in human cells, a T to C mutation and a corresponding A to G mutation were introduced into the sgRNA scaffold to form a modified sgRNA scaffold with the following sequence: 5'-GUU<u>C</u>UAGUGUUGUACAAUAU-UUGGGUGAAAACCCAAAUAUUGUACAUCCUA<u>G</u>AU CAAGGCGCUUAAUUGCUGCCGUAAUUG-CUGAAAGCGUAGCUUUCAGUUUUUUU-3' (SEQ ID NO:76), where the mutated nucleotides are underlined. This modification is also predicted to increase the sgRNA scaffold thermodynamic stability.

Human K562 cells (1×10⁶) were transfected with 5.5 µg of plasmid DNA encoding a McaCas9 fusion protein, which contains a HMGN1 peptide on the N terminus and a histone H1 globular domain peptide on the C terminus, and 3 µg of sgRNA plasmid DNA encoding the control sgRNA scaffold or the modified sgRNA scaffold. Genomic DNA was prepared using a DNA extraction solution (QuickExtract™) three days post transfection and the targeted genomic region was PCR amplified using the forward primer 5'-CTCCCCT-GCTTCTTGTCGTAT-3' (SEQ ID NO:55) and the reverse primer 5'-ACAGGTCGTGGACACTCACA-3' (SEQ ID NO:56). Amplification was carried out with the following condition: 1 cycle of 98° C. for 2 minutes for initial denaturation; 34 cycles of 98° C. for 15 seconds, 62° C. for 30 seconds, and 72° C. for 45 seconds; 1 cycle of 72° C. for 5 minutes; and hold at 4° C. PCR products were digested with Cel-1 nuclease and resolved on a 10% acrylamide gel. Targeted mutation rates were measured using ImageJ and expressed as percent insertions and/or deletions (% Indel). Results are summarized in Table 5. The results demonstrate that the activity of a Cas9 ortholog in mammalian cells can be enhanced by modifying its sgRNA scaffold.

TABLE 5

Gene editing using McaCas9 in combination with
control sgRNA scaffold or modified sgRNA scaffold.

| sgRNA scaffold | Locus | Protospacer (5'-3') | PAM (5'-3') | Indel (%) |
|---|---|---|---|---|
| Control sgRNA scaffold | POR | ATAGATGCGGCCAAGGTGTACA (SEQ ID NO: 77) | T<u>GGG</u> | 25.5 |
| Modified sgRNA scaffold | | | | 36.2 |

*The determinant nucleotides of the PAM are underlined.

Example 5. Improvement of McaCas9, BsmCas9, PexCas9, and LrhCas9 Activity by Fusion with Chromatin Modulating Motifs Additional Cas9-CMM fusion proteins were prepared by linking McaCas9-NLS, BsmCas9-NLS, and LrhCas9-NLS proteins with HMGN1 (HN1) at the amino terminus and either HMGB1 box A (HB1) or histone H1 central globular motif (H1 G) at the carboxyl terminus to yield McaCas9-HN1HB1 (SEQ ID NO:123), McaCas9-HN1H1G (SEQ ID NO:124), BsmCas9-HN1HB1 (SEQ ID NO:119), Bsm-HN1H1G (SEQ ID NO:120), Lrh-HN1HB1 (SEQ ID NO:121), LrhCas9-HN1H1G (SEQ ID NO:122). The nuclease activity of these fusions and the PexCas9-CMM fusions described above in Example 3 were compared to the activity of the corresponding engineered Cas9 protein essentially as described above in Examples 2 and 3. Table 6 presents the target site (i.e., protospacer+PAM, which is shown in bold with the determinate nucleotides underlined) in specific loci for each Cas9 nuclease.

TABLE 6

Gene Editing Target Sites

| Cas9 | Locus | Target site (5'-3') | SEQ ID NO |
|---|---|---|---|
| Mca | POR11 | ATAGATGCGGCCAAGGTGTACAT<u>GG</u> | 125 |
| | POR2 | CTACGAGAACCAGAAGCCGTGA<u>GT</u>GG | 126 |
| Bsm | PTN2 | CTCATACATGGCTATAATAGAAGGAG<u>CAAA</u> | 127 |
| | EMX1 | GAAGGTGTGGTTCCAGAACCGGAGGA<u>CAAA</u> | 128 |
| | EMX2 | TGGTTCCAGAACCGGAGGACAAAGTA<u>CAAA</u> | 129 |
| Pex | POR1 | TGTACATGGGGGAGATGGGCC<u>GG</u> | 130 |
| | AAVS1 | GGGGCCACTAGGGACAGGATT<u>GG</u> | 131 |

TABLE 6-continued

Gene Editing Target Sites

| Cas9 | Locus | Target site (5'-3') | SEQ ID NO |
|------|-------|---------------------|-----------|
| Lrh | POR11 | AGCTCGTACTGGCGAATGCTGGAAA | 132 |
| | PD1L1 | CCTCTGGCACATCCTCCAAATGAAA | 133 |

Figure 2A:
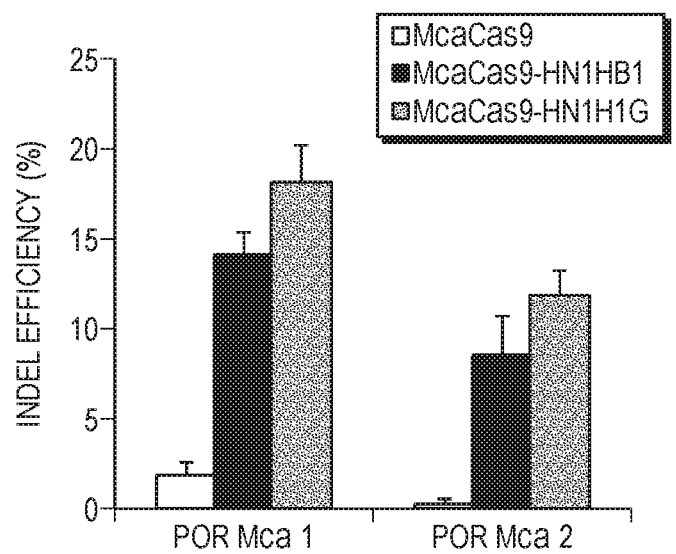
FIG. 2A presents the cleavage efficiency (as the percent of indels) of McaCas9, McaCas9-HN1HB1 fusion (i.e., HMGN1 at the amino terminus and HMGB1 box A at the carboxyl terminus), and McaCas9-HN1H1G fusion (i.e., HMGN1 at the amino terminus and histone H1 central globular motif at the carboxyl terminus). The target site of each locus is presented in Table 6. Error bars show mean±SD (n=3 biological replicates).
Figure 2B:
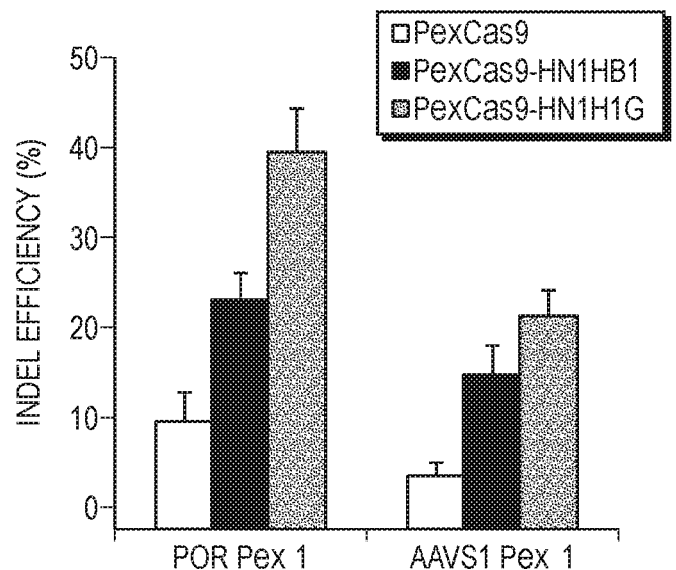
FIG. 2B presents the cleavage efficiency (as the percent of indels) of PexCas9, PexCas9-HN1HB1 fusion (i.e., HMGN1 at the amino terminus and HMGB1 box A at the carboxyl terminus), and PexCas9-HN1H1G fusion (i.e., HMGN1 at the amino terminus and histone H1 central globular motif at the carboxyl terminus). The target site of each locus is presented in Table 6. Error bars show mean±SD (n=3 biological replicates).
Figure 2C:
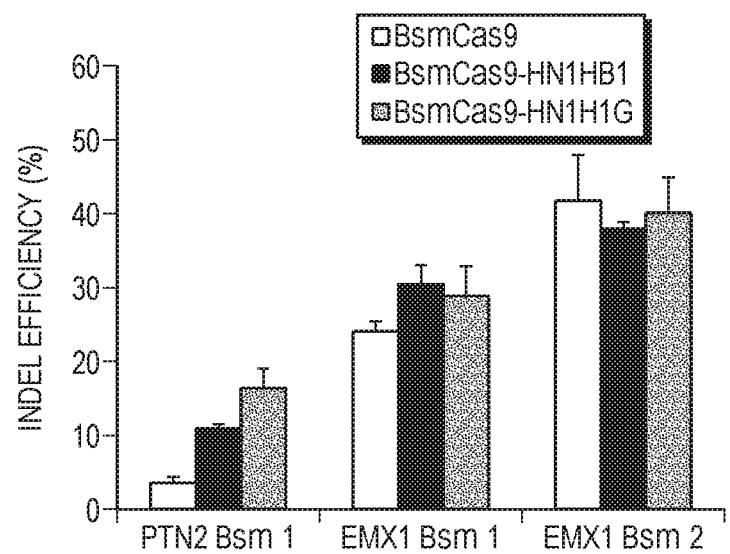
FIG. 2C presents the cleavage efficiency (as the percent of indels) of BsmCas9, BsmCas9-HN1HB1 fusion (i.e., HMGN1 at the amino terminus and HMGB1 box A at the carboxyl terminus), and BsmCas9-HN1H1G fusion (i.e., HMGN1 at the amino terminus and histone H1 central globular motif at the carboxyl terminus). The target site of each locus is presented in Table 6. Error bars show mean±SD (n=3 biological replicates).
Figure 2D:
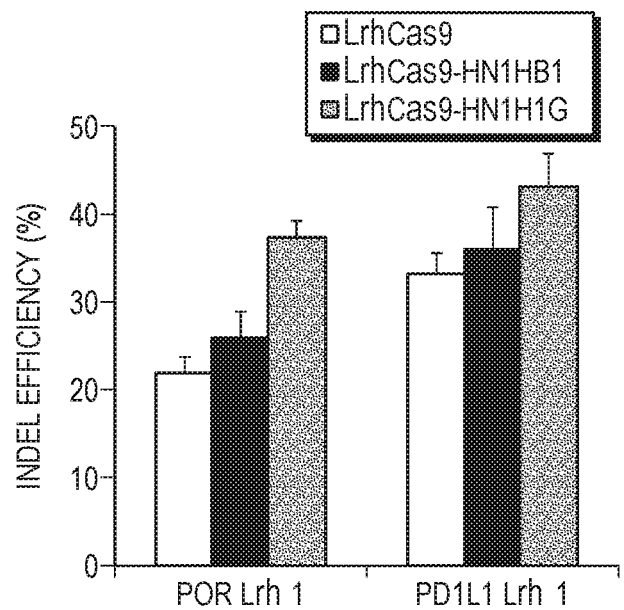
FIG. 2D presents the cleavage efficiency (as the percent of indels) of LrhCas9, LrhCas9-HN1HB1 fusion (i.e., HMGN1 at the amino terminus and HMGB1 box A at the carboxyl terminus), and LrhCas9-HN1H1G fusion (i.e., HMGN1 at the amino terminus and histone H1 central globular motif at the carboxyl terminus). The target site of each locus is presented in Table 6. Error bars show mean±SD (n=3 biological replicates).

The percent of indels under each condition are plotted in FIGS. 2A-D. Both the HN1HB1 and HN1H1G combinations significantly enhanced the four Cas9 orthologs on at least one site. Based on the fold change magnitude, the CMM fusion modification provided the largest enhancement on McaCas9, increasing its activity by at least five-fold on the two sites tested (FIG. 2A). CMM fusion provided more than two-fold enhancement on PexCas9 (FIG. 2B). BsmCas9 activity was enhanced by more than three-fold on one site, but there was only 20% increase on the second site and no effect on the third site (FIG. 2C). It should be noted, however, that all three BsmCas9 nucleases were highly efficient (>35% indels). LrhCas9 was highly efficient on the two sites tested (22% and 33% indels) even without the fusion modification (FIG. 2D). However, the HN1H1G combination still provided a significant enhancement on both sites, with 70% and 28% increase in activity. These results demonstrate that the CMM fusion strategy enhances gene editing efficiency.

Example 6. Off-Target Effects of Cas9-CMM Fusions

Figure 3:
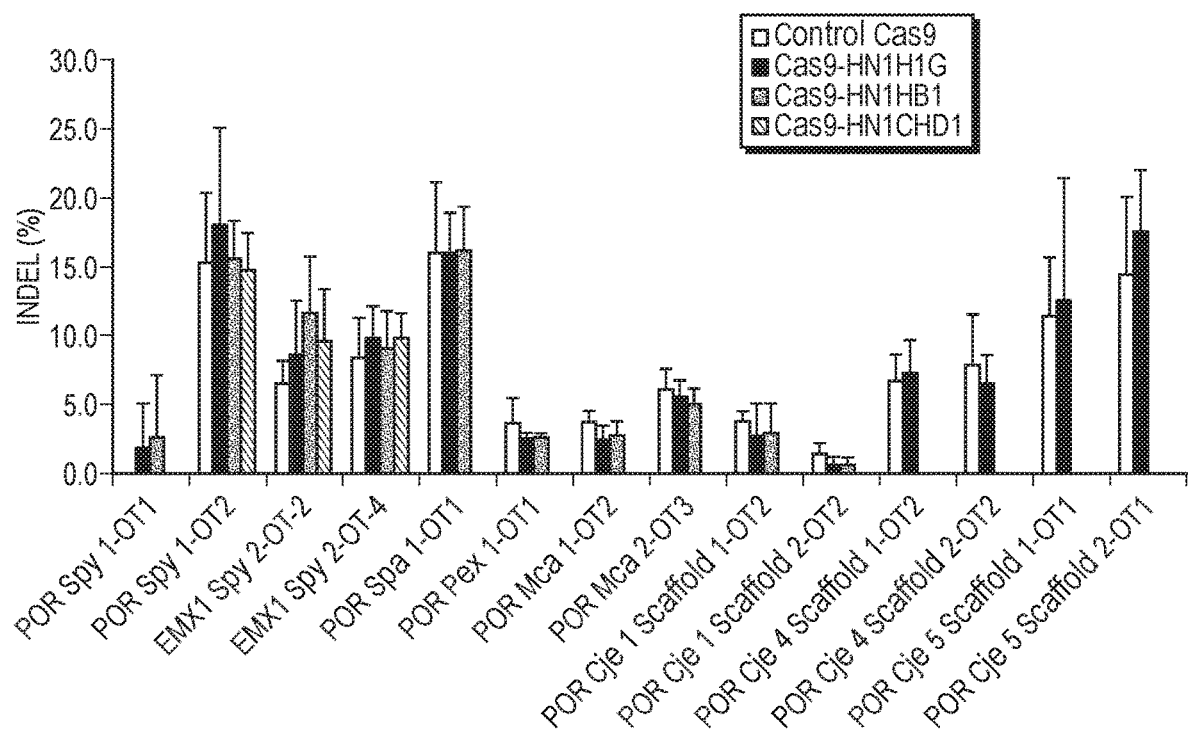
FIG. 3 shows off-target activities (as the percent of indels) of control Cas9 and Cas9-CMM fusion nucleases. Error bars show mean±SD (n=3 biological replicates).

To assess the off-target activity of the Cas9-CMM fusions, 1 to 5 top ranked potential off-target sites for each target site were analyzed using the Surveyor Nuclease assay. In addition to the Cas9 and Cas9-CMM fusion data described above in Example 5, data from *Streptococcus pyogenes* Cas9 (SpyCas9), SpyCas9-CMM fusions, *Streptococcus pasteurianus* Cas9 (SpaCas9), Spa-CMM fusions, *Campylobacter jejuni* Cas9 (CjeCas9), and CjeCas9-SMM fusions were also analyzed. From a total of 64 potential off-target sites assayed, off-target cleavage was detected on 11 sites, contributed by 9 guide sequences out of total 21 guide sequences tested. On the 11 off-target sites, the control Cas9 and the fusion nucleases were concurrent, with the exception of the POR Spy 1-OT1 site, where no off-target cleavage was detected on the control SpyCas9. Overall, there was no significant difference between the fusion nucleases and the control Cas9 (FIG. 3). For example, across all the 11 off-target sites, the HN1H1G fusion combination averaged 8.0±6.0% indels and the control Cas9 averaged 7.5±5.1% indels. Likewise, across the 10 off-target sites relevant to the HN1HB1 fusion combination, there was no significant difference between the fusion combination and the control Cas9 (6.9±5.7% vs. 6.5±5.4% indels). Taken together, these results show that the on-target activity enhancement by the HN1H1B and HN1H1G fusion combinations generally does not result in an increase in off-target activity.

Engineered Cas9 Systems

Table 7 presents the human codon optimized DNA and protein sequences of engineered Cas9/NLS proteins (SEQ ID NOS:1-30, wherein the NLS sequence is underlined) and the DNA sequences of engineered sgRNAs (SEQ ID NOS: 31-45; the N residues at the 5' end indicate the programmable target sequence). Also presented are the Cas9-CMM fusions (SEQ ID NOS:117-124).

TABLE 7

Engineered Cas9 Systems

```
BsmCas9/NLS DNA sequence (SEQ ID NO: 1)
ATGAACTACAAGATGGGCCTCGACATCGGAATCGCCTCTGTTGGATGGGCCGTGATCAACCTG
GACCTGAAGAGAATCGAGGACCTCGGCGTGCGGATCTTCGACAAGGCTGAGCATCCTCAGAAC
GGCGAGTCTCTGGCCCTGCCTAGAAGAATTGCCAGAAGCGCCAGACGGCGGCTGCGGAGAAGA
AAGCACAGACTGGAACGGATCAGACGGCTGCTGGTGTCCGAGAACGTGCTGACCAAAGAAGAG
ATGAACCTGCTGTTCAAGCAGAAAAAGCAGATCGACGTGTGGCAGCTGAGAGTGGACGCCCTG
GAAAGAAAGCTGAACAACGACGAGCTGGCCAGAGTGCTGCTGCACCTGGCCAAGAGAAGAGGC
TTCAAGAGCAACAGAAAGAGCGAGCGGAACAGCAAAGAGAGCAGCGAGTTCCTGAAGAACATC
GAAGAGAACCAGAGCATTCTGGCCCAGTACAGATCCGTGGGCGAGATGATCGTGAAGGACAGC
AAGTTCGCCTACCACAAGCGGAACAAGCTGGACAGCTACAGCAACATGATCGCCAGGGACGAT
CTGGAAAGAGAGATCAAGCTGATCTTCGAGAAGCAGCGCGAGTTCAACAACCCCGTGTGCACC
GAGAGACTGGAAGAGAAGTACCTGAACATCTGGTCCAGCCAGCGGCCTTTCGCCTCCAAAGAG
GACATCGAGAAAAAGTGGGCTTCTGCACCTTCGAGCCCAAAGAGAAAGAGCCCCTAAGGCC
ACCTACACCTTCCAGAGCTTCATCGTGTGGGAGCACATCAACAAGCTGCGGCTGGTGTCTCCC
GACGAGACAAGAGCCCTGACCGAGATCGAGCGGAATCTGCTGTATAAGCAGGCCTTCAGCAAG
AACAAGATGACCTACTACGACATCCGGAAGCTGCTGAACCTGAGCGACGACATCCACTTCAAG
GGCCTGCTGTACGACCCCAAGAGCAGCCTGAAGCAGATTGAGAACATCCGGTTTCTGGAACTG
GACTCTTACCACAAGATCCGGAAGTGCATCGAGAATGTGTACGGCAAGGACGGCATCCGCATG
TTCAACGAGACAGACATCGACACCTTCGGCTACGCCCTGACCATCTTCAAGGACGACGAGGAT
ATCGTGGCCTACCTGCAGAACGAGTACATCACCAAGAACGGCAAGCGGGTGTCCAATCTGGCC
AACAAGGTGTACGACAAGTCCCTGATCGACGAACTGCTGAATCTGTCCTTCTCCAAATTCGCC
CACCTGAGCATGAAGGCCATCCGGAACATCCTGCCTTACATGGAACAGGGCGAAATCTACAGC
AAGGCCTGCGAACTGGCCGGCTACAACTTCACAGGCCCCAAGAAGAAAGAGAAGGCCCTGCTG
CTGCCTGTGATCCCCAATATCGCCAATCCTGTGGTCATGCGGGCCCTGACACAGAGCAGAAAG
GTGGTCAACGCCATCATCAAGAAATACGGATCCCCCGTGTCCATCCACATCGAGCTGGCTAGG
GATCTGAGCCACAGCTTCGACGAGCGGAAGAAGATCCAGAAGGACCAGACCGAGAACCGCAAG
AAGAACGAAACCGCCATCAAGCAGCTGATCGAGTACGAGCTGACTAAGAACCCCACCGGCCTG
GACATCGTGAAGTTCAAACTTTGGAGCGAGCAGCAAGGCAGATGCATGTACTCCCTGAAGCCT
ATTGAGCTGGAAAGACTGCTGGAACCCGGCTACGTGGAAGTGGACCACATTCTGCCCTACAGC
AGAAGCCTGGACGACAGCTACGCCAACAAAGTGCTGGTCCTGACAAAAGAGAACCGCGAAAAG
GGCAATCACACCCCTGTGGAATATCTCGGCCTGGGCTCTGAGCGGTGGAAGAAATTCGAGAAG
TTCGTGCTGGCTAACAAGCAGTTCTCTAAGAAGAAGAAGCAGAACCTGCTCCGGCTGAGATAC
GAGGAAACCGAGGAAAAAGAGTTCAAAGAGCGGAACCTGAACGACACCCGGTACATCTCCAAG
TTCTTCGCCAACTTCATCAAAGAGCATCTGAAGTTCGCCGACGGCGACGGCGGCCAGAAAGTG
TACACAATCAACGGCAAGATCACCGCTCACCTGAGAAGCAGATGGGACTTCAACAAGAACCGG
```

TABLE 7-continued

Engineered Cas9 Systems

GAAGAGAGCGACCTGCACCACGCTGTGGATGCTGTGATTGTGGCCTGTGCCACACAGGGCATG
ATCAAGAAGATTACCGAGTTCTACAAGGCCCGCGAGCAGAACAAAGAGTCCGCCAAGAAAAAA
GAACCCATCTTTCCCCAGCCTTGGCCTCACTTCGCCGATGAGCTGAAGGCTCGGCTGAGCAAG
TTCCCTCAAGAGTCCATCGAGGCCTTCGCTCTGGGCAACTACGACAGAAAGAAGCTGGAATCC
CTGCGGCCTGTGTTCGTGTCCAGAATGCCCAAGAGATCCGTGACAGGCGCTGCCCACCAAGAG
ACACTGAGAAGATGCGTGGGCATCGACGAGCAGTCTGGCAAGATTCAGACCGCCGTGAAAACA
AAGCTGAGCGACATCAAGCTGGATAAGGACGGACACTTCCCCATGTACCAGAAAGAGTCTGAC
CCCAGAACCTACGAGGCCATCAGACGAGGCTGCTCGAACACAACAACGACCCTAAGAAGGCC
TTTCAAGAGCCACTGTACAAGCCCAAAAAGAATGGCGAGCCCGGACCAGTGATCCGGACCGTG
AAGATCATCGACACAAAGAACAAGGTGGTGCACCTGGACGGCAGCAAGACAGTGGCCTACAAC
TCCAACATCGTGCGGACCGACGTGTTCGAGAAGGATGGCAAGTACTACGTGCCCGTGTAC
ACTATGGATATCATGAAGGGCACCCTGCCTAACAAGGCCATCGAAGCCAACAAGCCCTACTCC
GAGTGGAAAGAGATGACCGAAGAGTACACGTTCCAGTTCAGTCTGTTCCCCAACGACCTCGTG
CGCATCGTGCTGCCAAGAGAGAAAACCATCAAGACCAGCACCAACGAGGAAATCATCATTAAG
GACATCTTTGCCTACTACAAGACCATCGACAGCGCCACAGGCGGCCTGGAACTGATCTCCCAC
GATCGGAACTTCAGCCTGAGAGGCGTGGGCTCTAAGACACTGAAGCGCTTTGAGAAGTATCAG
GTGGACGTGCTGGGCAACATCCACAAAGTGAAGGGCGAGAAGAGAGTCGGCCTGGCCGCTCCT
ACCAACCAGAAAAAGGGAAAGACCGTGGACAGCCTGCAGAGCGTGTCCGATCCCAAGAAGAAG
AGGAAGGTG

BsmCas9/NLS protein sequence (SEQ ID NO: 2)
MNYKMGLDIGIASVGWAVINLDLKRIEDLGVRIFDKAEHPQNGESLALPRRIARSARRRLRRR
KHRLERIRRLLVSENVLTKEEMNLLFKQKKQIDVWQLRVDALERKLNNDELARVLLHLAKRRG
FKSNRKSERNSKESSEFLKNIEENQSILAQYRSVGEMIVKDSKFAYHKRNKLDSYSNMIARDD
LEREIKLIFEKQREFNNPVCTERLEEKYLNIWSSQRPFASKEDIEKKVGFCTFEPKEKRAPKA
TYTFQSFIVWEHINKLRLVSPDETRALTEIERNLLYKQAFSKNKMTYYDIRKLLNLSDDIHFK
GLLYDPKSSLKQIENIRFLELDSYHKIRKCIENVYGKDGIRMFNETDIDTFGYALTIFKDDED
IVAYLQNEYITKNGKRVSNLANKVYDKSLIDELLNLSFSKFAHLSMKAIRNILPYMEQGEIYS
KACELAGYNFTGPKKKEKALLLPVIPNIANPVVMRALTQSRKVVNAIIKKYGSPVSIHIELAR
DLSHSFDERKKIQKDQTENRKKNETAIKQLIEYELTKNPTGLDIVKFKLWSEQQGRCMYSLKP
IELERLLEPGYVEVDHILPYSRSLDDSYANKVLVLTKENREKGNHTPVEYLGLGSERWKKFEK
PVLANKQFSKKKKQNLLRLRYEETEEKEFKERNLNDTRYISKFFANFIKEHLKFADGDGGQKV
YTINGKITAHLRSRWDFNKNREESDLHHAVDAVIVACATQGMIKKITEFYKAREQNKESAKKK
EPIFPQPWPHFADELKARLSKFPQESIEAFALGNYDRKKLESLRPVFVSRMPKRSVTGAAHQE
TLRRCVGIDEQSGKIQTAVKTKLSDIKLDKDGHFPMYQKESDPRTYEAIRQRLLEHNNDPKKA
FQEPLYKPKKNGEPGPVIRTVKIIDTKNKVVHLDGSKTVAYNSNIVRTDVFEKDGKYYCPVY
TMDIMKGTLPNKAIEANKPYSEWKEMTEEYTFQFSLFPNDLVRIVLPREKTIKTSTNEEIIIK
DIFAYYKTIDSATGGLELISHDRNFSLRGVGSKTLKRFEKYQVDVLGNIHKVKGEKRVGLAAP
TNQKKGKTVDSLQSVSDPKKKRKV LrhCas9/NLS DNA sequence (SEQ ID NO: 3)
ATGACCAAGCTGAACCAGCCTTACGGCATCGGCCTGGACATCGGCAGCAATAGCATCGGCTTT
GCCGTGGTGGACGCCAACAGCCATCTGCTGAGACTGAAGGGCGAGACAGCCATCGGCGCCAGA
CTGTTTAGAGAGGGACAGAGCGCCGCTGACAGACGGGGAAGCAGAACCACAAGAAGGCGGCTG
TCCAGAACCAGATGGCGGCTGAGCTTCCTGCGGGATTTCTTCGCCCCTCACATCACCAAGATC
GACCCCGACTTCTTTCTGCGGCAAAAATACTCCGAGATCAGCCCCAAGGACAAGGACAGGTTT
AAGTACGAGAAGCGGCTGTTCAACGACCGGACCGACGCCGAGTTCTACGAGGACTACCCCAGC
ATGTACCACCTGAGACTGCACCTGATGACCCACACACACAAGGCCGATCCTCGGGAAATCTTC
CTGGCCATCCACCACATCCTGAAGTCCAGAGGCCACTTTCTGACACCCGGCGCTGCCAAGGAC
TTCAACACCGACAAAGTGGACCTTGAGGACATCTTCCCCGCTCTGACAGAGGCTTACGCCCAG
GTGTACCCCGATCTGGAACTGACCTTCGATCTGGCCAAGGCCGACGACTTCAAGGCCAAGCTG
CTGGACGAACAGGCCACACCTAGCGACACACAGAAAGCCCTGGTCAACCTGCTGCTGTCTAGC
GACGGCGAGAAGAAATCGTGAAGAAGCGGAAGCAGGTCCTGACCGAGTTCGCCAAGGCCATC
ACCGGCTGAAAACAAAGTTCAATCTGGCCCTGGGCACCGAGGTGGACAAGCTGATGCTTCC
AACTGGCAGTTCAGCATGGGCCAGCTGGACGACAAGTGGTCCAACATCGAAACCAGCATGACC
GACCAGGGCACCGAAATCTTCGAGCAGATCAAGAGCTGTACCGGGCCAGACTGCTGAACGGA
ATTGTGCCTGCCGGCATGAGCCTGTCTCAGGCCAAAGTGGCCGATTACGGCCAGCACAAAGAG
GACCTGGAACTGTTCAAGACCTACCTGAAGAAGCTGAACGACCACGAGCTGGCCAAGACCATC
AGGGGCCTGTACGATCGGTACATCAACGGCGACGACGCCAAGCCTTTCCTGCGCGAGGATTTT
GTGAAGGCCCTGACCAAAGAAGTGACAGCTCACCCCAACGAGGTGTCCGAACAGCTGCTGAAC
AGGATGGGCCAAGCCAACTTCATGCTGAAGCAGCGGACCAAGGCCAACGGCGCCATTCCTATT
CAGCTGCAGCAGAGAGAGCTGGACCAGATCATTGCCAACCAGAGCAAGTACTACGACTGGCTG
GCCGCTCCTAATCCTGTGGAAGCCCACAGATGGAAGATGCCCTACCAGCTGGATGAGCTGCTC
AACTTTCACATCCCCTACTACGTGGGCCCTCTGATCACCCCTAAACAGCAGGCCGAGAGCGGC
GAGAATGTGTTCGCTTGGATGGTCCGAAAGGACCCCAGCGGCAACATCACCCCTTACAACTTC
GACGAGAAGGTGGACAGAGAGGCCAGCGCCAACACCTTCATCCAGAGAATGAAGACCACCGAC
ACATACCTGATCGGCGAGGACGTGCTGCCTAAGCAGAGCCTGCTGTACCAGAAATACGAGGTG
CTGAACGAGCTGAACAACGTGCGGATCAACAACGAGTGCCTGGGCACAGACCAGAAGCAGAGA
CTGATCAGAGAGGTGTTCGAGCGGCACAGCAGCGTGACCATCAACAGGTGGCCGACAATCTG
GTGGCCCACGGCGATTTTGCCAGACGGCCTGAGATTAGAGGACTGGCCGATGAGAAGCGGTTC
CTGAGCAGCCTGAGCACCTACCACCAGCTGAAAGAGATCCTGCACGAGGCCATCGACGACCCC
ACCAAACTGCTGGATATCGAGAACATCATCACCTGGTCCACCGTGTTCGAGGACCACACCATC
TTCGAGACAAAGCTGGCCGAGATCGAGTGGCTGGACCCCAAGAAGATCAACGAGCTGTCTGC
ATCAGATACAGAGGCTGGGGCCAGTTCTCCCGGAAGCTGCTCGATGGACTGAAGCTTGGCAAT
GGCCACACCGTGATTCAAGAACTGATGCTGAGCAACCACAACCTGATGCAGATCCTGGCCGAC
GAGACACTGAAAGAAACCATGACAGAGCTGAATCAGGACAAGCTGAAAACCGACGACATCGAG
GATGTGATCAACGACGCCTACACAAGCCCAGCAACAAAAAGGCCCTCAGACAGGTGCTGAGA
GTGGTCGAGGATATCAAGCACGCCGCCAACGGACAGGACCCTAGCTGGCTGTTTATCGAAACC TABLE 7-continued Engineered Cas9 Systems

```
GCCGATGGAACAGGCACCGCCGGCAAGAGAACACAGAGCCGGCAGAAACAGATCCAGACCGTG
TACGCCAACGCCGCTCAAGAGCTGATCGATTCTGCCGTGCGGGCGAGCTGGAAGATAAGATT
GCTGACAAGGCCAGCTTCACCGACCGGCTGGTGCTGTACTTTATGCAAGGCGGCAGAGACATC
TACACAGGCGCCCCTCTGAACATCGACCAGCTGAGCCACTACGATATCGACCACATTCTGCCC
CAGAGCCTGATCAAGGACGACAGCCTGGACAACGGGTGCTCGTGAACGCCACCATCAACCGC
GAGAAGAACAATGTGTTTGCCAGCACACTGTTCGCCGGAAAGATGAAGGCCACCTGGCGGAAA
TGGCACGAAGCCGGACTGATCTCTGGCAGAAAGCTGCGGAATCTGATGCTGCGGCCCGACGAG
ATCGACAAGTTTGCCAAGGGCTTCGTGGCCCGGCAGCTGGTTGAGACAAGACAGATCATCAAG
CTGACAGAGCAGATTGCCGCCGCTCAGTACCCCAACACCAAGATTATTGCCGTGAAGGCCGGA
CTGTCCCATCAGCTGAGAGAGGAACTGGACTTCCCCAAGAACCGGGACGTGAACCACTACCAC
CACGCCTTCGATGCCTTTCTGGCCGCTAGAATCGGCACCTACCTGCTGAAGAGATACCCCAAG
CTGGCCCCATTCTTCACCTACGGCGAGTTTGCTAAGGTGGACGTCAAGAAGTTCCGCGAGTTC
AACTTCATCGGAGCCCTGACACACGCCAAGAAGAACATTATCGCCAAGGACACCGGCGAGATC
GTGTGGGACAAAGAGCGGGACATCAGAGAACTGGACCGCATCTACAACTTCAAGCGGATGCTG
ATCACACACGAGGTGTACTTCGAGACTGCCGACCTGTTCAAGCAGACCATCTACGCCGCTAAG
GACAGCAAAGAGAGAGGCGGCAGCAAGCAGCTGATCCCTAAGAAGCAGGGCTACCCCACTCAG
GTGTACGGCGGCTACACACAAGAGAGCGGCTCTTACAACGCCCTCGTCGAGTGGCCGAGGCC
GATACAACAGCCTACCAAGTGATCAAGATCAGCGCCCAGAACGCCAGCAAGATCGCCTCCGCC
AACCTGAAAAGCCGCGAGAAAGGCAAACAGCTCCTGAATGAGATCGTCGTGAAGCAGCTGGCT
AAGCGGCGGAAGAACTGGAAGCCTAGCGCCAATAGCTTCAAGATCGTGATCCCCAGATTCGGC
ATGGGCACCCTGTTCCAGAACGCTAAGTACGGCCTGTTCATGGTCAACAGCGACACCTACTAC
CGGAACTACCAAGAACTCTGGCTGAGCCGGGAAAACCAGAAACTGCTGAAAAAGCTGTTCTCC
ATCAAATACGAGAAAACCCAGATGAACCACGACGCCCTGCAGGTCTACAAGGCCATTATCGAC
CAGGTGGAAAAGTTCTTCAAGCTGTACGACATCAACCAGTTCCGCGCCAAGCTGAGCGACGCC
ATCGAGAGATTTGAGAAGCTGCCCATCAATACCGACGGCAACAAGATCGGCAAGACCGAGACT
CTGAGACAGATCCTGATCGGACTGCAGGCCAATGGCACCCGGTCCAACGTGAAGAACCTGGGC
ATCAAGACCGATCTGGGCCTGCTGCAAGTCGGCAGCGGAATCAAGCTGGACAAGGATACCCAG
ATCGTGTATCAGAGCCCCTCCGGCCTGTTTAAGCGGAGAATCCCACTGGCTGACCTGCCCAAG
AAGAAGAGGAAGGTG
```

LrhCas9/NLS protein sequence (SEQ ID NO: 4)
MTKLNQPYGIGLDIGSNSIGFAVVDANSHLLRLKGETAIGARLFREGQSAADRRGSRTTRRRL
SRTRWRLSFLRDFFAPHITKIDPDFFLRQKYSEISPKDKDRFKYEKRLFNDRTDAEFYEDYPS
MYHLRLHLMTHTHKADPREIFLAIHHILKSRGHFLTPGAAKDFNTDKVDLEDIFPALTEAYAQ
VYPDLELTFDLAKADDFKAKLLDEQATPSDTQKALVNLLLSSDGEKEIVKKRKQVLTEFAKAI
TGLKTKFNLALGTEVDEADASNWQFSMGQLDDKWSNIETSMTDQGTEIFEQIQELYRARLLNG
IVPAGMSLSQAKVADYGQHKEDLELFKTYLKKLNDHELAKTIRGLYDRYINGDDAKPFLREDF
VKALTKEVTAHPNEVSEQLLNRMGQANFMLKQRTKANGAIPIQLQQRELDQIIANQSKYYDWL
AAPNPVEAHRWKMPYQLDELLNFHIPYYVGPLITPKQQAESGENVFAWMVRKDPSGNITPYNF
DEKVDREASANTFIQRMKTITTYLIGEDVLPKQSLLYQKYEVLNELNNVRINNECLGTDQKQR
LIREVFERHSSVTIKQVADNLVAHGDFARRPEIRGLADEKRFLSSLSTYHQLKEILHEAIDDP
TKLLDIENIITWSTVFEDHTIFETKLAEIEWLDPKKINELSGIRYRGWGQFSRKLLDGLKLGN
GHTVIQELMLSNHNLMQILADETLKETMTELNQDKLKTDDIEDVINDAYTSPSNKKALRQVLR
VVEDIKHAANGQDPSWLFIETADGIGTAGKRTQSRQKQIQTVYANAAQELIDSAVRGELEDKI
ADKASFTDRLVLYFMQGGRDIYTGAPLNIDQLSHYDIDHILPQSLIKDDSLDNRVLVNATINR
EKNNVFASTLFAGKMKATWRKWHEAGLISGRKLRNLMLRPDEIDKFAKGFVARQLVETRQIIK
LTEQIAAAQYPNTKIIAVKAGLSHQLREELDFPKNRDVNHYHHAFDAFLAARIGTYLLKRYPK
LAPFFTYGEFAKVDVKKFREFNFIGALTHAKKNITAKDTGEIVWDKERDIRELDRIYNFKRML
ITHEVYFETADLFKQTIYAAKDSKERGGSKQLIPKKQGYPTQVYGGYTQESGSYNALVRVAEA
DTTAYQVIKISAQNASKIASANLKSREKGKQLLNEIVVKQLAKRRKNWKPSANSFKIVIPRFG
MGTLFQNAKYGLFMVNSDTYYRNYQELWLSRENQKLLKKLFSIKYEKTQMNHDALQVYKAIID
QVEKFFKLYDINQFRAKLSDAIERFEKLPINTDGNKIGKTETLRQILIGLQANGTRSNVKNLG
IKTDLGLLQVGSGIKLDKDTQIVYQSPSGLFKRRIPLADLPKKKRKV PexCas9/NLS DNA sequence (SEQ ID NO: 5)
```
ATGGGCAAGACCCACATCATCGGCGTTGGCCTGGATCTCGGCGGCACATACACAGGCACCTTC
ATCACCAGCCATCCTAGCGACGAAGCCGAGCACAGAGATCACGCAGCGCCTTCACCGTGGTC
AACAGCGAGAAGCTGAGCTTCAGCAGCAAGAGCAGAACAGCCGTGCGGCACAGAGTGCGGAGC
TACAAGGGCTTCGACCTGCGTAGAAGGCTGCTGCTTCTGGTGGCCGAGTATCAGCTGCTGCAG
AAGAGCAGACACTGGCCCCTGAGGAAAGAGAGAACCTGAGAATCGCCCTGAGCGGCTACCTG
AAGAGAAGAGGCTACGCCAGAACCGAGGCCGAGACAGATACAAGCGTGCTGGAATCTCTGGA
CCCAGCGTGTTCAGCAGCGCTCCCAGCTTCACCAATTTCTTCAACGACAGCGAGCCCCTGAAC
ATCCAGTGGAAGCCATTGCCAACTCTCCCGAGACAACAAAGGCCCTGAACAAAGAGCTGAGC
GGCCAGAAAGAGGCCGACTTCAAGAAGTACATCAAGACCAGCTTTCCCGAGTACAGCGCCAAA
GAGATTCTGGCCAACTACGTGAAGGCAGACGGGCCATTCTGGACGCCAGTATATCGCC
AACCTGCAGAGCCTGGCCACAAGCACAGAAGCAAGTACCTGAGCGACATTCTGCAGGACATG
AAGCGGGACAGCCGGATCACCAGACTGAGCGAAGCCTTTGGCAGCACCGACAACCTGTGGCGG
ATCATCGGCAACATCAGCAATCTGCAAGAACGGGCCGTGCGGTGGTACTTCAACGATGCCAAG
TTCGAGCAGGGCCAAGAGCAGCTGGATGCCGTGAAGCTGAAGAATGTGCTCGTGCGGGCCCTG
AAGTATCTGCGGAGTGACGACAAAGAGTGGAGCGCCTCTCAGAAGCAGATCATCCAGTCTCTG
GAACAGAGCGGCGACGTGCTGGATGTGCTGGCTGGACTCGACCCCGACGAGACAATCCCTCCA
TACGAGGACCAGAACAACAGACGGCCTCCTGAGGATCAGACCCTGTATCTGAACCCCAAGGCT
CTGAGCAGCGAGTACGGCGAGAAGTGGAAGTCTTGGGCCAACAGTTTGCCGGCGTTACCCT
CTGCTGACCGAGGATCTGACCGAGATCCTGAAGAACACCGACAGAAAGTCCCGGATCAAGATC
AGATCCGATGTGCTGCCCGACAGCGACTACAGACTGGCCTACATCCTGCAGAGAGCCTTCGAT
CGGTCTATCGCCCTGGACGAGTGCAGCATCAGAAGAACCGCCGAGGACTTCGAGAACGGCGTG
GTCATCAAGAACGAGAAACTGGAAGATGTGCTGAGCGGACACCAGCTGGAAGAGTTTCTGGAA
TTTGCCAATCGGTACTACCAAGAGACAGCCAAGGCCAAGAACGGCCTGTGGTTCCCAGAGAAC
```

TABLE 7-continued

Engineered Cas9 Systems

GCCCTGCTGGAAAGAGCCGATCTGCACCCTCCTATGAAGAACAAGATTCTGAACGTGATCGTC
GGACAGGCCCTGGGAGTGTCTCCTGCTGAGGGCACCGATTTCATCGAGGAAATTTGGAACAGC
AAAGTGAAAGGCCGGTCCACCGTGCGGAGCATCTGTAACGCCATCGAGAATGAGAGAAAGACC
TACGGACCCTACTTCAGCGAGGACTACAAGTTCGTGAAAACGGCCCTGAAAGAGGGCAAAACC
GAGAAAGAGCTGTCCAAGAAATTCGCCGCCGTGATCAAGGTGCTGAAGATGGTGTCTGAGGTG
GTGCCCTTTATCGGAAAAGAGCTGCGGCTGTCTGACGAGGCCCAGAGCAAGTTCGACAATCTG
TACTCTCTGGCCCAGCTGTACAACCTGATCGAGACAGAGCGGAACGGCTTCAGCAAGGTGTCA
CTGGCTGCCCACCTGGAAAATGCCTGGCGGATGACCATGACAGATGGATCCGCCCAGTGCTGT
AGACTGCCTGCCGATTGTGTGCGGCCCTTCGACGGCTTTATCCGGAAGGCCATCGACCGGAAC
TCTTGGGAAGTCGCCAAGCGGATTGCCGAGGAAGTGAAGAAGTCCGTCGACTTCACCAACGGC
ACCGTGAAGATCCCTGTGGCCATCGAGGCCAACAGCTTCAACTTTACCGCCAGCCTGACCGAC
CTGAAGTACATTCAGCTCAAAGAACAGAAGCTCAAGAAGAAGTTGGAGGACATCCAGCGGAAC
GAAGAGAATCAAGAGAAGCGGTGGCTGAGCAAAGAGGAACGGATCAGAGCCGACAGCCACGGC
ATCTGTGCCTATACTGGCAGACCCCTGGATGACGTGGGCGAGATCGATCACATCATCCCCAGA
AGCCTGACACTGAAGAAAAGCGAGAGCATCTACAACTCCGAAGTGAACCTGATCTTCGTGTCT
GCCCAGGGCAATCAAGAAAAGAAGAACAACATCTACCTGCTGAGCAACCTCGCCAAGAACTAC
CTGGCCGCCGTGTTTGGCACAAGCGACCTGAGCCAGATCACCAACGAGATCGAGAGCACCGTG
CTGCAGCTGAAAGCTGCTGGCAGACTGGGCTACTTCGATCTGCTGAGCGAAAAGAGCGGGCC
TGCGCCAGACATGCCCTGTTTCTGAATAGCGACTCCGAGGCCAGACGCGCCGTGATTGATGTT
CTTGGCTCTCGGAGAAAGGCCAGCGTGAACGGAACCCAGGCTTGGTTTGTGCGGTCCATCTTC
TCCAAAGTGCGGCAGGCACTGGCCGCTTGGACACAAGAAACAGGCAACGAGCTGATCTTTGAC
GCCATCAGCGTGCCAGCCGCCGATAGCTCTGAGATGAGGAAGAGATTCGCCGAGTACCGGCCT
GAGTTCAGAAAGCCCAAAGTGCAGCCTGTGGCCTCTCACAGCATCGACGCCATGTGCATCTAT
CTGGCCGCCTGCAGCGACCCCTTCAAGACCAAGAGAATGGGCTCTCAGCTGGCCATCTACGAG
CCCATCAACTTCGATAACCTGTTCACCGGCAGCTGTCAAGTGATCCAGAACACCCCTCGGAAC
TTCTCCGACAAGACCAATATCGCTAACAGCCCCATCTTCAAAGAGACAATCTACGCCGAGCGG
TTCCTGGACATCATCGTGTCCAGAGGCGAGATTTTCATCGGCTACCCCAGCAACATGCCCTTC
GAGGAAAAGCCCAACCGGATCAGCATCGGCGGCAAGGACCCTTTCAGCATCCTGTCTGTGCTG
GGCGCCTACCTGGATAAGGCCCCTAGCAGCGAGAAAGAAAAGCTCACCATCTACCGGGTCGTC
AAGAACAAAGCCTTCGAGCTGTTCTCCAAGGTGGCCGGCAGCAAGTTTACCGCCGAAGAAGAT
AAGGCCGCCAAGATCCTGGAAGCCCTGCACTTCGTGACCGTGAAACAGGATGTGGCCGCCACC
GTGTCCGATCTGATCAAGAGCAAGAAAGAACTGAGCAAGGATAGCATCGAGAACCTGGCCAAG
CAGAAGGGCTGCCTGAAGAAGGTGGAATACTCCAGCAAAGAGTTCAAGTTCAAGGGCAGCCTG
ATCATCCCTGCCGCCGTGGAATGGGGAAAAGTGCTGTGGAACGTGTTCAAAGAAAACACGGCC
GAAGAACTGAAGGACGAGAACGCTCTGAGGAAGGCCCTGGAAGCTGCCTGGCCTAGCTCTTTC
GGCACCAGAAACCTGCACTCTAAGGCCAAGCGGGTGTTCAGCCTGCCTGTGGTGGCTACACAA
TCTGGCGCCGTGCGGATCAGACGCAAGACAGCCTTCGGCGACTTCGTGTACCAGAGCCAGGAC
ACAAACAACCTGTACAGCAGCTTCCCCGTGAAGAACGGCAAGCTGGATTGGAGCAGCCCTATC
ATTCACCCCGCTCTGCAGAACCGGAACCTGACCGCCTACGGCTACAGATTCGTGGACCACGAC
AGATCCATCAGCATGAGCGAGTTCAGAGAGGTGTACAACAAGGACCTGATGAGGATCGAG
CTGGCCCAGGGAACAAGCAGCAGACGCTACCTGAGAGTGGAAATGCCCGGCGAGAAATTCCTC
GCTTGGTTTGGCGAGAACAGCATCAGCCTGGGCTCCAGCTTCAAGTTCTCTGTGTCCGAGGTG
TTCGACAACAAAATCTACACCGAGAACGCCGAGTTTACCAAGTTCCTGCCTAAGCCTAGAGAG
GACAACAAGCACAACGGGACCATCTTTTTCGAACTCGTGGGCCCCAGAGTGATCTTCAACTAC
ATCGTTGGCGGAGCCGCCAGCAGCCTGAAAGAAATCTTTAGCGAGGCCGGCAAAGAGCGGAGC
CCCAAGAAGAAGAGGAAGGTG

PexCas9/NLS protein sequence (SEQ ID NO: 6)
MGKTHIIGVGLDLGGTYTGTFITSHPSDEAEHRDHSSAFTVVNSEKLSFSSKSRTAVRHRVRS
YKGFDLRRRLLLLVAEYQLLQKKQTLAPEERENLRIALSGYLKRRGYARTEAETDTSVLESLD
PSVFSSAPSFTNFFNDSEPLNIQWEAIANSPETTKALNKELSGQKEADFKKYIKTSFPEYSAK
EILANYVEGRRAILDASKYIANLQSLGHKHRSKYLSDILQDMKRDSRITRLSEAFGSTDNLWR
IIGNISNLQERAVRWYFNDAKFEQGQEQLDAVKLKNVLVRALKYLRSDDKEWSASQKQIIQSL
EQSGDVLDVLAGLDPDRTIPPYEDQNNRRPPEDQTLYLNPKALSSEYGEKWKSWANKFAGAYP
LLTEDLTEILKNTDRKSRIKIRSDVLPDSDYRLAYILQRAFDRSIALDECSIRRTAEDFENGV
VIKNEKLEDVLSGHQLEEFLEFANRYYQETAKAKNGLWFPENALLERADLHPPMKNKILNVIV
GQALGVSPAEGTDFIEEIWNSKVKGRSTVRSICNAIENERKTYGPYFSEDYKFVKTALKEGKT
EKELSKKFAAVIKVLKMVSEVVPFIGKELRLSDEAQSKFDNLYSLAQLYNLIETERNGFSKVS
LAAHLENAWRMTMTDGSAQCCRLPADCVRPFDGFIRKAIDRNSWEVAKRIAEEVKKSVDFTNG
TVKIPVAIEANSFNFTASLTDLKYIQLKEQKLKKKLEDIQRNEENQEKRWLSKEERIRADSHG
ICAYTGRPLDDVGEIDHIIPRSLTLKKSESIYNSEVNLIFVSAQGNQEKKNNIYLLSNLAKNY
LAAVFGTSDLSQITNEIESTVLQLKAAGRLGYFDLLSEKERACARHALFLNSDSEARRAVIDV
LGSRRKASVNGTQAWFVRSIFSKVRQALAAWTQETGNELIFDAISVPAADSSEMRKRFAEYRP
EFRKPKVQPVASHSIDAMCIYLAACSDPFKTKRMGSQLAIYEPINFDNLFTGSCQVIQNTPRN
FSDKTNIANSPIFKETIYAERFLDIIVSRGEIFIGYPSNMPFEEKPNRISIGGKDPFSILSVL
GAYLDKAPSSEKEKLTIYRVVKNKAFELFSKVAGSKFTAEEDKAAKILEALHFVTVKQDVAAT
VSDLIKSKKELSKDSIENLAKQKGCLKKVEYSSKEFKFKGSLIIPAAVEWGKVLWNVFKENTA
EELKDENALRKALEAAWPSSFGTRNLHSKAKRVFSLPVVATQSGAVRIRRKTAFGDFVYQSQD
TNNLYSSFPVKNGKLDWSSPIIHPALQNRNLTAYGYRFVDHDRSISMSEFREVYNKDDLMRIE
LAQGTSSRRYLRVEMPGEKFLAWFGENSISLGSSFKFSVSEVFDNKIYTENAEFTKFLPKPRE
DNKHNGTIFFELVGPRVIFNYIVGGAASSLKEIFSEAGKERSPKKKRKV McaCas9/NLS DNA sequence (SEQ ID NO: 7)
ATGGAAAAGAAGCGGAAAGTCACCCTGGGCTTCGACCTGGGAATCGCCTCTGTTGGATGGGCC
ATCGTGGACAGCGAGACAAACCAGGTGTACAAGCTGGGCAGCAGACTGTTCGACGCCCCTGAC
ACCAACCTGGAAAGAAGAACCCAGCGGGGCACCAGAAGGCTGCTGCGGAAGAAAGTACCGG
AACCAGAAATTCTACAACCTGGTCAAGCGGACCGAGGTGTTCGGCCTGTCTAGCAGAGAGGCC
ATCGAGAACAGATTCAGAGAGCTGAGCATCAAGTACCCCAACATCATCGAGCTGAAAACAAAG

TABLE 7-continued

Engineered Cas9 Systems

```
GCCCTGAGCCAAGAAGTGTGCCCCGACGAGATTGCCTGGATTCTGCACGACTACCTGAAGAAC
CGGGGCTACTTCTACGACGAGAAAGAGACAAAAGAGGACTTCGACCAGCAGACCGTGGAATCC
ATGCCTAGCTACAAGCTGAACGAGTTCTACAAGAAGTACGGCTACTTCAAAGGCGCCCTGTCT
CAGCCTACCGAGAGCGAGATGAAGGACAACAAGGACCTGAAAGAGGCATTCTTCTTCGACTTC
TCCAACAAAGAGTGGCTGAAAGAGATCAACTACTTCTTCAACGTGCAGAAGAACATCCTGAGC
GAGACATTCATCGAAGAGTTCAAGAAGATTTTCAGCTTCACCCGGGACATCAGCAAAGGCCCA
GGCAGCGACAATATGCCCTCTCCTTACGGCATCTTCGGCGAGTTCGGCGACAATGGCCAAGGC
GGCAGATACGAGCACATCTGGGACAAGAACATCGGCAAGTGCAGCATCTTCACCAACGAGCAG
AGAGCCCCTAAGTACCTGCCTAGCGCTCTGATCTTCAACTTCCTGAACGAGCTGGCCAACATC
AGACTGTACAGCACCGACAAGAAGAATATCCAGCCTCTGTGGAAGCTGAGCAGCATCGATAAG
CTGAATATCCTGCTGAACCTGTTCAACCTGCCTATCAGCGAGAAGAAGAAAAAGCTGACCAGC
ACCAACATCAACGACATCGTGAAGAAAGAGTCCATCAAGAGCATCATGCTGAGCGTCGAGGAC
ATCGACATGATCAAGGATGAGTGGGCCGGCAAAGAACCCAACGTGTACGGCGTTGGACTGAGC
GGCCTGAACATCGAGGAAAGCGCCAAAGAGAACAAGTTCAAGTTCCAAGACCTGAAGATCCTG
AACGTCCTGATCAATCTGCTGGACAACGTGGGCATCAAGTTCGAGTTCAAGGACCGCAGCGAC
ATCATCAAGAACCTGGAACTGCTGGATAACCTGTACCTGTTCCTGATCTACCAGAAAGAGAGC
AACAACAAAGACAGCTCCATCGACCTGTTTATCGCCAAGAACAAGTCCCTGAATATCGAGAAC
CTGAAGCTCAAGCTCAAAGAGTTCCTGCTCGGAGCCGGCAACGAGTTCGAGAACCACAACAGC
AAGACCCACAGCCTGTCCAAGAAGGCCATTGACGCCATCCTGCCTAAGCTGCTCGACAACAAC
GAAGGCTGGAATCTGGAAGCCATCAAGAATTACGACGAGGAAATCAAGAGCCAGATCGAGGAC
AACTCCAGCCTGATGGCCAAGCAGGATAAGAAGTACCTGAACGACAACTTCCTCAAGGATGCC
ATTCTGCCGCCAAACGTGAAAGTGACCTTCCAGCAGGCCATCCTCATCTTCAACAAGATCATC
CAGAAGTTCAGCAAGGATTTCGAGATCGACAAGGTCGTGATCGAACTGGCCAGAGAGATGACC
CAGGACCAAGAGAACGACGCCCTGAAGGGAATCGCTAAGGCCCAGAAGTCCAAGAAAAGCCTG
GTGGAAGAGAGACTCGAAGCCAACAACATCGACAAGAGCGTGTTCAACGATAAGTACGAGAAG
CTTATCTACAAGATTTTCCTGTGGATCAGCCAGGACTTTAAGGACCCCTACACCGGCGCCAAG
ATCAGCGCCAATGAGATCGTGGATAACAAGGTGGAAATCGACCACATCATCCCTTACAGCCTG
TGCTTCGACGACAGCAGCGCCAACAAAGTGCTGGTGCACAAGCAGAGCAATCAAGAGAAGTCT
AACAGCCTGCCGTACGAGTACATCAAGCAGGGCCACTCCGGCTGGAACTGGGACGAGTTCACC
AAATACGTGAAGCGGGTGTTCGTGAACAACGTGGACTCTATCCTGAGCAAGAAAGAGCGCCTG
AAGAAGTCCGAGAATCTGCTGACCACCAGCTACGACGGCTATGAGAAGCTGGGCTTCCTGGCC
AGAAACCTGAATGACACCAGATACGCCACCATCCTGTTCCGGGACCAGCTGAACAATTACGCC
GAGCACCACCTGATCGATAACAAGAAAATGTTCAAAGTGATCGCCATGAACGGGGCCGTGACC
AGCTTCATCCGGAAGAACATGAGCTACGACAACAAGCTGCGGCTGAAGGACAGAAGCGACTTC
AGCCACCACGCCTACGACGCCGCCATCATTGCCCTGTTCAGCAACAAGACCAAGACGCTGTAC
AACCTGATTGACCCCAGCCTGAACGGCATCATCAGCAAGAGAAGCGAAGGCTATTGGGTCATC
GAGGATCGGTACACAGGCGAGATCAAAGAGCTTAAGAAAGAGGATTGGACCTCTATCAAGAAC
AATGTGCAGGCCCGGAAGATCGCCAAAGAAATCGAGGAATATCTGATCGACCTGGACGATGAG
GTGTTCTTCAGCCGGAAAACTAAGCGCAAGACCAACCGGCAGCTGTACAATGAGACAATCTAC
GGAATCGCCGCCAAGACCGACGAGGACGGCATCACCAACTACTACAAGAAAGAAAAGTTCTCC
ATCCTGGACGACAAGGACATCTACCTGCGGCTGCTGAGAGAACGCGAGAAGTTCGTGATCAAC
CAGAGCAACCCCAGCGATCGACCAGATTATCGAGATCATCGAGAGCTACGGGAAGAAAAC
AACATCCCCAGCCGCGACGAGGCCATCAATATCAAGTACACGAAGAACAAGATTAACTACAAC
CTCTACCTCAAGCAGTACATGCGGAGCCTGACCAAGAGCCTGGACCAGTTCAGCGAGGGCTTC
ATCAATCAGATGATCGCCAACAAGACGTTCGTGCTGTATAACCCCACCAAGAACACAACGCGG
AAGATCAAGTTCCTGCGGCTCGTGAACGATGTGAAGATCAACGATATTCGCAAGAATCAAGTG
ATCAACAAGTTTAACGGGAAGAACAACGAGCCCAAGGCCTTCTACGAGAATATCAACAGCCTG
GGCGCCATCGTGTTCAAGTCCTCCGCCAACAACTTCAAGACCCTGTCCATCAACCACCCAGATC
GCCATCTTCGGAGACAAGAACTGGGATATCGAGGATTTCAAGACCTACAACATGGAAAAAATC
GAGAAGTACAAAGAGATATACGGCATCGACAAAACCTACAACTTCCACAGCTTTATCTTCCCC
GGCACAATCCTGCTCGATAAGCAGAACAAAGAGTTCTACTACATCAGCAGCATCCAGACCGTG
AACGACCAAATTGAGCTGAAGTTTCTGAACAAGATCGAGTTTAAGAACGACGACAACACCTCC
GGGGCCAACAAGCCTCCTCGGAGACTGAGATTCGGCATTAAGTCCATCATGAACAACTACGAG
CAGGTCGACATCAGCCCCTTCGGCATCAACAAGAAGATATTCGAGCCCAAGAAGAAGAGGAAG
GTG
```

McaCas9/NLS protein sequence (SEQ ID NO: 8)
MEKKRKVTLGFDLGIASVGWAIVDSETNQVYKLGSRLFDAPDTNLERRTQRGTRRLLRRRKYR
NQKFYNLVKRTEVFGLSSREATENRFRELSIKYPNIIELKTKALSQEVCPDEIAWILHDYLKN
RGYFYDEKETKEDFDQQTVESMPSYKLNEFYKKYGYFKGALSQPTESEMKDNKDLKEAFFFDF
SNKEWLKEINYFFNVQKNILSETFIEEFKKIFSFTRDISKGPGSDNMPSPYGIFGEFGDNGQG
GRYEHIWDKNIGKCSIFTNEQRAPKYLPSALIFNFLNELANIRLYSTDKKNIQPLWKLSSIDK
LNILLNLFNLPISEKKKKLTSTNINDIVKKESIKSIMLSVEDIDMIKDEWAGKEPNVYGVGLS
GLNIEESAKENKFKFQDLKILNVLINLLDNVGIKFEFKDRSDIIKNLELLDNLYLFLIYQKES
NNKDSSIDLFIAKNKSLNIENLKLKLKEFLLGAGNEFENHNSKTHSLSKKAIDAILPKLLDNN
EGWNLEAIKNYDEEIKSQIEDNSSLMAKQDKKYLNDNFLKDAILPPNVKVTFQQAILIFNKII
QKFSKDFEIDKVVIELAREMTQDQENDALKGIAKAQKSKKSLVEERLEANNIDKSVFNDKYEK
LIYKIFLWISQDFKDPYTGAKISANEIVDNKVEIDHIIPYSLCFDDSSANKVLVHKQSNQEKS
NSLPYEYIKQGHSGWNWDEFTKYVKRVFVNNVDSILSKKERLKKSENLLTTSYDGYEKLGFLA
RNLNDTRYATILFRDQLNNYAEHHLIDNKKMFKVIAMNGAVISFIRKNMSYDNKLRLKDRSDF
SHHAYDAAIIALFSNKTKTLYNLIDPSLNGIISKRSEGYWVIEDRYTGEIKELKKEDWTSIKN
NVQARKIAKEIEEYLIDLDDEVFFSRKTKRKTNRQLYNETIYGIAAKTDEDGITNYYKKEKFS
ILDDKDIYLRLLREREKFVINQSNPEVIDQIIETIESYGKENNIPSRDEAINIKYTKNKINYN
LYLKQYMRSLTKSLDQFSEGFINQMIANKTFVLYNPTKNTTRKIKFLRLVNDVKINDIRKNQV
INKFNGKNNEPKAFYENINSLGAIVFKSSANNFKILSINTQTAIFGDKNWDIEDFKTYNMEKI
EKYKEIYGIDKTYNPHSFIFPGTILLDKQNKEFYYISSIQTVNDQIELKFLNKIEFKNDDNTS
GANKPPRRLRFGIKSIMNNYEQVDISPFGINKKIFEPKKKRKVPKKKRKV TABLE 7-continued Engineered Cas9 Systems MgaCas9/NLS DNA sequence (SEQ ID NO: 9)
ATGAACAACAGCATCAAGAGCAAGCCCGAAGTGACCATCGGCCTGGATCTCGGCGTTGGCTCT
GTTGGATGGGCCATCGTGGACAACGAGACAAACATCATCCACCACCTGGGCAGCAGACTGTTC
AGCCAGGCCAAGACAGCTGAGGACAGGCGGTCTTTCAGAGGCGTGCGGAGACTGATCCGGCGG
AGAAAGTACAAGCTGAAGAGATTCGTGAACCTGATCTGGAAGTACAACAGCTACTTCGGCTTC
AAGAACAAAGAGGACATCCTGAACAACTACCAAGAGCAGCAGAAACTGCACAACACCGTGCTG
AACCTGAAGCTCGAAGCCCTGAACGCCAAGATCGACCCCAAGGCTCTGAGCTGGATTCTGCAC
GACTACCTGAAGAACCGGGGCCACTTCTACGAGGACAACCGGGACTTCAACGTGTACCCCACA
GAGGAACTGGCCAACTACTTCGACGAGTTCGGCTACTACAAGGGCATCATCGACAGCAAGAAC
GACGACGATGATAAGCTGGAAGAGGGCCTGACCAAGTACAAGTTCAGCAACCAGCACTGGCTG
GAAGAAGTGAAGAAGGTCCTGAGCAACCAGACCGGCCTGCCTGAGAAGTTCAAGAGGAATAC
GAGAGCCTGTTCAGCTACGTGCGGAACTACTCTGAAGGCCCTGGCAGCATCAACAGCGTGTCC
CCATACGGCATCTATCACCTGGACGAGAAGAGGGCAAAGTCGTCCAGAAGTATAACAACATC
TGGGACAAGACCATCGGGAAGTGCAGCATCTTCCCCGACGAGTACAGAGCCCCTAAGAACAGC
CCTATCGCCATGATCTTCAACGAGATCAACGAGCTGAGCACCATCCGGTCCTACAGCATCTAC
CTGACCGGCTGGTTCATCAATCAAGAGTTCAAGAAGGCCTACCTGAACAAGCTGCTGGACCTG
CTGATCAAGACCAACAGCGAGAAGCCCATCGACGCCCGGCAGTTTAAGAAGCTGCGGGAAGAG
ACAATCGCCGAGAGCATCGGCAAGAAACCCTGAAGGACGTGGAAAGCGAGGAAAAGCTGGAA
AAGGACGACCACAAGTGGAAGCTGAAGGGCCTGAAGCTGAACACCAACGGCAAGATCCAGTAC
AACGACCTGTCTAGCCTGGCCAAGTTCGTGCACAAACTGAAGCAGCACCTGAAACTGGACTTT
CTGCTGGAAGATCAGTACACCCCTCTGGACAAGATCAACTTCCTGCAGAGCCTGTACGTGTAC
CTGGGCAAGCACCTGAGATACAGCAACAGAGTGGACAGCGCCAACCTGAAAGAGTTCAGCGAC
AGCTCCCGGCTGTTCGAGAGAGTGCTGCAAGAGCAGAAGGACGGCCTGTTCAAGCTGTTTGAG
CAGACCGACAAGGACGACGAGAAGATCCTGACACAGACCCACAGCCTGTCCACCAAGGCTATG
CTGCTGGCCATCACCAGAATGACCAACCTGGACAATGACGAGGATAACCAGAAGAACAACGAC
AAAGGCTGGAACTTCGAGGCCATCAAGAACTTCGACCAGAAGTTCATCGACATCACCAAGACG
AACAACAACCTGAGCCTGAAGCAGGACAAGCGCTACCTGGATGACCAGTTCATCAACGACGCC
ATTCTGAGCCCTGGCGTGAAGAGAATCCTGCGCGAGGCCACCAAGGTGTTCAACGCCATCCTC
AAGCAGTTCTCCGAAGAGTACGACGTGACCAAGGTGGTCATCGAGCTGGCCAGAGAGCTGAGC
GAAGAGAAAGAACTGGAAAACACCAAGAACTACAAGAAGCTTATCAAGAAGAACGGCGATAAG
ATCAGCGAGGGACTGAAAGCCCTGGGGATCGCCGAGGATAAGATCGAAGAGATCCTGAAGTCT
CCCACCAAGTCCTACAAAGTGCTGCTGTGGCTGCAGCAGGACCACATCGATCCCTACAGCCAG
AAAGAGATCGCCTTCGACGATATCCTGACCAAAACCGAAAAGACCGAGATCGACCACATCATT
CCTTACTCCATCAGCTTCGACGACAGCAGCAGCAACAAACTGCTGGTGCTGGCCGAGTCCAAT
CAGGCCAAGTCCAACCAGACACCTTACGAGTTTATCAACTCCGGCAAGGCCGAGATCACCTGG
GAAGTGTACGAGGCCTACTGCCACAAGTTCAAAAACGGCGACTCCAGCCTGCTGGACAGCACC
CAGAGAAGCAAGAAATTCGCCAAGATGATGAAGACCGACACCAGCTCTAAGTACGACATCGGC
TTTCTGGCCCGGAACCTGAACGACACCAGATACGCCACCATCGTGTTCCGGGACGCTCTGAAG
GACTACGCCAACAACCACCTGGTGGAAGATAAGCCCATGTTCAAGGTCGTGTGCATCAACGGC
GGCGTGACCAGCTTCCTGCGGAAGAACTTTGACCCCAAGTCTTGGTACGCCAAGAAGGACAGA
GACAAGAACATTCACCACGCCGTGGACGCCAGCATCATCTCCATCTTCAGCAACGAGACTAAG
ACCCTGTTCAACCAGCTGACAAAGTTCGCCGACTACAAGCTGTTCAAGAATACCGACGGCTCT
TGGAAGAAGATCGATCCTAAGACAGGCGTGGTGTCAGAAGTGACCGACGAGAATTGGAAGCAG
ATCCGCGTGCGCAACCAGGTGTCCGAGATCGCCAAAGTGATCGACAAGTACATCCAGGACAGC
AACATCGAGCGGAAGGCCAGATACAGCCGGAAGATCGAGAACAAGACCAATATCAGCCTGTTT
AACGACACCGTGTACTCCGCCAAGAAAGTGGGCTACGAGGATCAGATCAAGCGCAAGAACCTG
AAAACCCTGGACATCCACGAGAGCGCCGAGGAAAACAAGAACAGCAAAGTGAAAAAGCAGTTC
GTGTACCGGAAGCTCGTGAACGTGTCCCTGCTGAACAATGACAAGCTGGCCGACCTGTTCGCC
GAGAAAGAAGATATTCTGATGTACCGGGCCAATCCGTGGGTCATCAACCTGGCCGAGCAGATT
TTCAACGAGTACACCGAGAACAAAAGATCAAGAGCCAGAACGTGTTCGAGAAGTACATGCTG
GATCTGACCAAAGAGTTCCCCGAGAAGTTTAGCGAGGCCTTCGTGAAGTCCATGATCAGAAAC
AAGACCGCCATCATCTACAACGTCGAGAAGGATGTGGTGCACCGGATCAAGCGGCTGAAGATT
CTGAGCAGCGAGCTGAAAGAAAACAAGTGGTCCAACGTGATCATCCGCTCCAAGAACGAGAGC
GGCACCAAGCTGAGCTACCAGGACACCATCACTCTATCGCCCTGATGATCATGCGGAGCATC
GACCCAACCGCCAAAAAACAGTACATCAGGGTGCCCCTGAACACCCTGAATCTGCACCTGGGC
GACCAGGACTTCGACCTGCACAATATCGACGCCTATCTGAAGAAGCCTAAGTTCGTCAAGTAC
CTGAAGGCCAATGAGATCGGCGACGAGTATAAGCCTTGGCGCGTGCTGACAAGCGGCACACTG
CTGATCCACAAGAAAGACAAGAAACTCATGTACATCAGCAGCTTCCAGAACCTCAACGACCTC
ATCGAGATCAAGAATCTGATCGAGACAGAGTACAAAGAAAACGTGGACTCAGACCCCAAGAAG
AAGAAAAAGGCCAGCCAGATCCTGAGAAGCCTGAGCGTGATCCTGAACGATTACATCCTGCTG
GATGCCAAGTATAACTTCGACATCCTGGGCCTGTCTAAGAACAAGATTGACGAGATCCTCAAC
AGCAAGCTGGACCTCGACAAGATTGCCAAGCCCAAGAAGAAGAGGAAGGTG MgaCas9/NLS protein sequence (SEQ ID NO: 10)
MNNSIKSKPEVTIGLDLGVGSVGWAIVDNETNIIHHLGSRLFSQAKTAEDRRSFRGVRRLIRR
RKYKLKRFVNLIWKYNSYFGFKNKEDILNNYQEQQKLHNTVLNLKLEALNAKIDPKALSWILH
DYLKNRGHFYEDNRDFNVYPTEELANYFDEFGYYKGIIDSKNDDDDKLEEGLTKYKFSNQHWL
EEVKKVLSNQTGLPEKFKEEYESLFSYVRNYSEGPGSINSVSPYGIYHLDEKEGKVVQKYNNI
WDKTIGKCSIFPDEYRAPKNSPIAMIFNEINELSTIRSYSTYLTGWFINQEFKKAYLNKLLDL
LIKTNSEKPIDARQFKKLREETIAESIGKETLKDVESEEKLEKDDHKWKLKGLKLNTNGKIQY
NDLSSLAKFVHKLKQHLKLDFLLEDQYTPLDKINFLQSLYVYLGKHLRYSNRVDSANLKEFSD
SSRLFERVLQEQKDGLFKLFEQTDKDDEKILTQTHSLSTKAMLLAITRMTNLDNDEDNQKNND
KGWNFEAIKNFDQKFIDITKTNNNLSLKQDKRYLDDQFINDAILSPGVKRILREATKVFNAIL
KQFSEEYDVTKVVIELARELSEEKELENTKNYKKLIKKNGDKISEGLKALGIAEDKIEEILKS
PTKSYKVLLWLQQDHIDPYSQKEIAFDDILTKTEKTEIDHIIPYSISFDDSSSNKLLVLAESN
QAKSNQTPYEFINSGKAEITWEVYEAYCHKFKNGDSSLLDSTQRSKKFAKMMKTDTSSKYDIG
FLARNLNDTRYATIVFRDALKDYANNHLVEDKPMFKVVCINGGVTSFLRKNFDPKSWYAKKDR
DKNIHHAVDASIISIFSNETKTLFNQLTKFADYKLFKNTDGSWKKIDPKTGVVSEVTDENWKQ TABLE 7-continued Engineered Cas9 Systems IRVRNQVSEIAKVIDKYIQDSNIERKARYSRKIENKTNISLFNDTVYSAKKVGYEDQIKRKNL
KTLDIHESAEENKNSKVKKQFVYRKLVNVSLLNNDKLADLFAEKEDILMYRANPWVINLAEQI
FNEYTENKKIKSQNVFEKYMLDLTKEFFKEFSEAFVKSMIRNKTAITYNVEKDVVHRIKRLKI
LSSELKENKWSNVIIRSKNESGTKLSYQDTINSIALMIMRSIDPTAKKQYIRVPLNTLNLHLG
DQDFDLHNIDAYLKKPKFVKYLKANEIGDEYKPWRVLTSGTLLIHKKDKKLMYISSFQNLNDL
IEIKNLIETEYKENVDSDPKKKKKASQILRSLSVILNDYILLDAKYNFDILGLSKNKIDEILN
SKLDLDKIAK<u>PKKKRKV</u>

Ag1Cas9/NLS DNA sequence (SEQ ID NO: 11)
ATGCAGAACATCACCTTCAGCTTCGACGTGGGCTACGCCTCTATCGGATGGGCTGTTGTTCAG
GCCCCTGCTCAGCCAGAGCAGGACCCTGGAATAGTGGCCTGTGGCACCGTGCTGTTCCCTAGC
GACGATTGCCAGGCCTTCCAGCGGAGAAACTACCGGCGGCTGCGGAGGAACATCCGGTCCAGA
AGAGTGCGGATCGAGCGGATCGGAAAGCTGCTGGTTCAGGCCGGAATCCTGACACCTGAGGAA
AAGGCCACACCTGGACACCCCGCTCCATTCTTTTTGGCAGCCCAGGCTTGGCAGGGCATCAGA
CAACTGTCTCCACTGGAAGTGTGGCACATCCTGCGTTGGTACGCCCACAACAGAGGCTACGAC
AACAATGCCGCCTGGGCCACCGTGTCCACCAAAGAGGATACCGAGAAAGTCAACAACGCCCGG
CACCTGATGCAGAAGTTTGGCGCCGAGACAATGTGCGCCACACTGTGCCATGCTATGGAACTG
GACATGGACGTGCCCGATGCCGCCATGACAGTGTCTACACCAGCCTACAGAACCCTGAACAGC
GCCTTTCCTAGAGATGTGGTGCAGAGAGAGGTGCTGGACATCCTGAGACACAGCGCCAGCCAC
ATCAAAGAGCTGACCCCTGAGATCATCCGGCTGATCGCCCAGCAAGAGGATCTGAGCACAGAG
CAGAGAAGCGAGCTGGCCGCCAAGGGAATTAGACTGGCCAGAAGATACCGGGGCAGCCTGCTG
TTTGGACAGCTGCTGCCCAGATTCGACAACCGGATCATCAGACGGTGCCCCATCATCTGGGCC
CACACATTTGAGCAGGCCAAGACCAGCGGCATGAGCGAGAAAGAAGCTCAGGCCCTGGCTGAC
AAGGTGGCCAAAGTGCCTACAGCCGACTGTCCCGAGTTCTACGCCTACAGATTCGCCCGCATC
CTGAACAATCTGAGAGCCAACGGACTGCCCCTGCCTGTGGAAGTTCGCTGTGAACTGATGCAG
GCCGCCAGAGCCGAGGGAAAACTGACAGCCGCCAAGATCAAGAAAGAAATCATGAGGCTGATG
GGCGACGTCGAGAGCAACATCGACCACTACTTCCATCTGCACCCCGACAGCGAGGAAGCCCTG
ATTCTCGATCCCGCTATGGAATGCCTGCACCGGACCGGACTGTACGATGCCCTCAGCTCTGTC
GTGCGAAGAGTGGCCCTGACCAGACTGCGGAGAGGCAAAATCTGTACCCCTGCCTACCTGCGG
GACATGATGCTGAGACACGGCGAGGATACCCAGGCTCTGGATCTGGCCATTGCCAAGCAGCAG
GGAAGAAAGGCCCCTCGGCCTAGAAAGAACGACACAGATGCCAGCGCCGACTCTGCAGCATTGCA
TGGCAAGATAAGCCCCTGGCTCCTAAGACAGCCTCTGGCAGAGCCCCTTATGCCAGACCAGTT
CTGAGACAGGCCGTGGACGAGATCATGAATGGCGAGGACCCTACCAGGCCAGCTCTGGATGAA
CAGCATCCCGACGGCGAGGACAAGCCTTCTCACGGCTGTCTGTATGGCCTGCTGGACCCTGCC
AGCAAAGAGAACGAGTACCTGAACAAGCTTCCCCTGGACGCCCTGACAAACAATCACCTCGTG
CGGCACCGGATGCTGATCCTGGATAGACTGACCCAGGACCTCGTCAGAGAGTTCGCTGACGGC
GATCCCAGCAGAGTGGAACGGTTCTGTATCGAAGTGGGCAGAGAGCTGAGCGCCTTCTCTGGC
ATGACCAGCAAGCAGATCCAGTCCGAGCTGAACGAGCGGATGAAGCACTTCAAGAGCGCCGTG
GCCTATCTGGCCAAACACGCCCCTGATATGGCCACATCTGCCGGCCTGATCCGGAAGTGCAGA
ATCGCTATGGACATGAACTGGCAGTGCCCTTTCACCGGCCAGACCTACATGCCCTACGACCTG
CCTAAGCTGGAACGCGAGCACATCGTGCCCTACGCCAACAGAAAGACAGATGCCCTGTCTGCC
CTGGTGCTGACATGGCTGGCCGTGAACAAGATGAAGGGCAAGAGAACCGCCTACCAGTTTATC
AAAGAGTGCGAGGGCCAGAGCGTGCCCGGCAGAAATCAGAATATCGTGTCCGTGAAGCAGTAC
GAGACATTCGTGGAAAAGCTGGACACCAAGGGCCACGCCGACGCCAAGAGAAAAAAGACC
CGGAAGAAACTGATGATGGTGGACAGACTGAGCAGCCAGGGAACAAACGGCGAGTCTGAGCTG
GATTTCACCGAGGGCATGATGACCCAGAGCAGCCACTCTGATGAAGATCGCCGCTAGAGGCGTG
CGGAAGAACTTTCCTCACGCCACCGTGGACATGATCCCTGGCGCTATTACTGGCACTGTGCGC
AAGGCTTGGAAGGTGGCAGGATGCCTGGCCGGCATTTGTCCTGAAGCCGTCGATCCCGTGACA
CACAGAATCCAGGACAAAGAGACACTGCGGCGGCTGACCCATCTGCATCATGCACTGGATGCC
TGCGTGCTGGGACTGATCCCTCACCTGATTCCAGAGCACAGATCCGGCCTGCTGAGAAAAGCT
CTGGCCGCTAGAAGGCTGCCCGAGAATGTTCGGCAAGAGGTGGAAAGCGCCGTGTCCAAGCGG
TACTACACCATCACAAAAGAGAGCAAACTGGAACTGCGGGATCTGCCCACCACACTGAAGAAC
TCTATCGCCGCCAAGCTGAGCGAGGGCAGAGTGGTGCAACACATCCCTGCCGATATGAGCGGA
GCCAAGCTGAAGAGACAATCTGGGGAATTGCCCCTGGCCAGCACATCGACGACAATAGCGAG
GTGGTCATCCGGCAGAAGTCCCTGAGCATCGGCAAGGACGGCAACAGAATCAGAACCAGAAAG
ACCGACAAGCAGGGCAACCCCATCACCGAGAAGGCCTCTAAGCTCGTGGGCATCAAGCCTACC
GGCACCAGCAAACTGCAGCCCATCAGAGGCGTGATCATCATCAAGGACAACTTCGCCATTGCT
CTGGACCCCGTGCCAACCATGATTCCCCACCACAACGTGTACAAGCGGCTGGAAGACTGCGG
AAGCTGAACCACGGTAGACATGTGCGGCTGCTGAAAAAGGGCATGCTGATCAGGCTGAGCCAC
CAGAAGTCCGGCGACAAGAACGGCATGTGGAAAGTGCGGAGCATCCAGGACCAGGGCTCCTCT
GGCCTGAAAGTGAATCTGCAGAGGCCCTACTACGCCGGCAAGATCGAGGACACCAGAACCGAG
AATTGGAAGAACGTGTCCATCAAGGCCCTGCTGAGCCAAGGCATGGAAATCCTGCCAACCACC
TACTGCGGCACCACACCT<u>CCCAAGAAGAAGAGGAAGGTG</u>

Ag1Cas9/NLS protein sequence (SEQ ID NO: 12)
MQNITFSFDVGYASIGWAVVQAPAQPEQDPGIVACGTVLFPSDDCQAFQRRNYRRLRRNIRSR
RVRIERIGKLLVQAGILTPEEKATPGHPAPFFLAAQAWQGIRQLSPLEVWHILRWYAHNRGYD
NNAAWATVSTKEDTEKVNNARHLMQKFGAETMCATLCHAMELDMDVPDAAMTVSTPAYRTLNS
APPRDVVQREVLDILRHSASHIKELTPEIIRLIAQQEDLSTEQRSELAAKGIRLARRYRGSLL
FGQLLPRFDNRIIRRCPIIWAHTFEQAKTSGMSEKEAQALADKVAKVPTADCPEFYAYRFARI
LNNLRANGLPLPVEVRCELMQAARAEGKLTAAKIKKEIMRLMGDVESNIDHYFHLHPDSEEAL
ILDPAMECLHRTGLYDALSSVVRRVALTRLRRGKICTPAYLRDMMLRHGEDTQALDLAIAKQQ
GRKAPRPRKNDTDASADASIAWQDKPLAPKTASGRAPYARPVLRQAVDEIMNGEDPIRPALDE
QHPDGEDKPSHGCLYGLLDPASKENEYLNKLPLDALTNNHLVRHRMLILDRLTQDLVREFADG
DPSRVERFCIEVGRELSAFSGMTSKQIQSELNERMKHFKSAVAYLAKHAPDMATSAGLIRKCR
IAMDMNWQCPFTGQTYMPYDLPKLEREHIVPYANRKTDALSALVLTWLAVNKMKGKRTAYQFI
KECEGQSVPGRNQNIVSVKQYETFVEKLDTKGHADDAKRKKTRKKLMMVDRLSSQGTNGESEL
DFTEGMMTQSSHLMKIAARGVRKNFPHATVDMIPGAITGTVRKAWKVAGCLAGICPEAVDPVT TABLE 7-continued Engineered Cas9 Systems HRIQDKETLRRLTHLHHALDACVLGLIPHLIPEHRSGLLRKALAARRLPENVRQEVESAVSKR
YYTITKESKLELRDLPTTLKNSIAAKLSEGRVVQHIPADMSGAKLEETIWGIAPGQHIDDNSE
VVIRQKSLSIGKDGNRIRTRKTDKQGNPITEKASKLVGIKPIGTSKLQPIRGVIIIKDNFAIA
LDPVPTMIPHHNVYKRLEELRKLNHGRHVRLLKKGMLIRLSHQKSGDKNGMWKVRSIQDQGSS
GLKVNLQRPYYAGKIEDTRTENWKNVSIKALLSQGMEILPTTYCGTTPPKKKRKV AmuCas9/NLS DNA sequence (SEQ ID NO: 13)
ATGAGCAGAAGCCTGACCTTCAGCTTCGACATCGGCTACGCCTCTATCGGCTGGGCCGTGATT
GCCTCTGCCAGCCACGATGATGCCGATCCTAGCGTGTGTGGCTGTGGCACCGTGCTGTTCCCC
AAGGATGATTGCCAGGCCTTCAAGCGGAGAGAGTACCGGCGGCTGCGGAGAAACATCCGGTCC
AGAAGAGTGCGGATCGAGCGGATTGGTAGACTGCTGGTGCAGGCCCAGATCATCACCCCTGAG
ATGAAGGAAACCAGCGGACACCCCGCTCCATTCTACCTGGCATCTGAGGCCCTGAAGGGCCAC
AGAACACTGGCCCCTATTGAACTGTGGCATGTGCTGCGTTGGTACGCCCACAACAGAGGCTAC
GACAACAACGCCAGCTGGTCCAACAGCCTGTCTGAGGATGGTGGCAACGGCGAGGATACCGAG
AGAGTGAAACACGCCCAGGACCTGATGGACAAGCACGGCACAGCTACAATGGCCGAGACAATC
TGCAGAGAGCTGAAGCTGGAAGAGGGCAAAGCCGACGCTCCTATGGAAGTGTCTACCCCTGCC
TACAAGAACCTGAACACCGCCTTTCCACGGCTGATCGTGGAAAAAGAAGTGCGGAGAATCCTG
GAACTGAGCGCCCCTCTGATCCCTGGACTGACAGCCGAGATCATCGAGCTGATCGCCCAGCAT
CACCCTCTGACCACTGAACAGAGAGGCGTGCTGCTCCAGCACGGCATTAAGCTGGCCAGAAGA
TACAGAGGCAGCCTGCTGTTCGGCCAGCTGATCCCTAGATTCGACAACAGGATCATCAGCAGA
TGCCCCGTGACATGGGCCCAAGTGTATGAGGCCGAGCTGAAGAAGGGCAACAGCGAGCAGTCT
GCCAGAGAGAGAGCCGAGAAGCTGAGCAAGGTGCCCACCGCCAATTGTCCCGAGTTCTACGAG
TACCGGATGGCCAGAATCCTGTGCAACATCAGAGCCGACGGCGAGCCTCTGAGCGCCGAGATT
AGACGCGAGCTGATGAACCAGGCCAGACAAGAGGGAAAGCTGACCAAGGCCAGCCTGGAAAAG
GCCATCTCTAGCCGGCTGGGCAAAGAAACCGAGACAAACGTGTCCAACTACTTCACACTGCAC
CCCGACAGCGAGGAAGCCCTGTATCTGAATCCTGCCGTGGAAGTGCTGCAGAGAAGCGGCATC
GGCCAGATTCTGAGCCCCAGCGTGTACAGAATCGCCGCCAACAGACTGCGGAGAGGCAAGAGC
GTGACCCCTAACTACCTGCTGAATCTGCTGAAGTCCAGAGGCGAGTCTGGCGAGGCCCTGGAA
AAAAAGATCGAGAAAGAGTCCAAGAAGAAAGAGGCCGACTACGCCGACACACCCCTGAAGCCT
AAGTACGCCACAGGCAGAGCCCCTTACGCCAGAACCGTGCTGAAGAAAGTGGTGGAAGAGATC
CTGGATGGCGAGGACCCTACCAGACCTGCTAGAGGCGAAGCTCACCCTGACGGCGAACTGAAA
GCCCACGATGGCTGCCTGTACTGCCTGCTGGATACCGACAGCAGCGTGAACCAGCACCAGAAA
GAGCGGAGACTGGACACCATGACCAACAACCACCTCGTGCGGCACCGGATGCTGATCCTGGAC
AGACTCCTGAAGGATCTGATCCAGGACTTCGCCGACGGCCAGAAGGACAGAATCAGCAGAGTG
TGCGTGGAAGTCGGCAAAGAGCTGACCACCTTCAGCGCTATGGACAGCAAGAAGATCCAGCGG
GAACTGACCCTGCGGCAGAAGTCTCATACCGACGCCGTGAACAGACTGAAGAGAAAGCTTCCA
GGCAAGGCCCTGAGCGCCAACCTGATCAGAAAGTGCAGAATCGCAATGGACATGAACTGGACA
TGCCCCTTCACCGGCGCCACATATGGCGATCACGAGCTGGAAAATCTGGAACTGGAACACATC
GTGCCCCACAGCTTCAGACAGAGCAATGCCCTGTCTAGCCTGGTGCTGACATGGCCTGGCGTG
AACAGGATGAAGGGACAGAGAACCGGCTACGACTTCGTGGAACAAGAGCAAGAGAACCCCGTG
CCTGACAAGCCCAACCTGCACATCTGCAGCCTGAACAACTATCGCGAGCTGGTGGAAAAGCTG
GACGACAAGAAGGGACACGAGGACGACAGACGGCGGAAGAAGAAAGAAAGGCCCTGCTGATG
GTCCGAGGCCTGTCTCACAAACACCAGAGCCAGAACCACGAGGCCATGAAAGAAATCGGCATG
ACCGAGGGCATGATGACCCAGAGCAGCCACCTGATGAAGCTGGCCTGCAAGAGCATCAAGACC
AGCCTGCCTGACGCTCACATCGACATGATTCCAGGCGCCGTGACTGCCGAAGTTCGCAAAGCC
TGGGATGTGTTCGGCGTGTTCAAAGAACTGTGCCCCGAAGCCGCCGATCCTGACTCTGGCAAG
ATCCTGAAAGAGAACCTGCGGAGCCTGACTCATCTGCATCACGCCCTGGATGCCGTGTGCTG
GGACTGATCCCCTACATCATCCCCGCTCACCACAATGGCCTGCTGAGAAGAGTCCTGGCCATG
CGCAGAATCCCCGAGAAACTGATCCCTCAAGTGCGGCCCGTGGCCAACCAGAGACACTACGTG
CTGAACGACGACGGCCGGATGATGCTGAGGGATCTGAGTGCCAGCCTGAAAGAAAACATCCGC
GAGCAGCTGATGGAACAGCGAGTGATCCAGCACGTGCCCGCTGATATGGGCGGAGCACTGCTC
AAAGAAACAATGCAGCGGGTGCTGAGCGTGGACGGCTCTGGCGAAGATGCTATGGTGTCCTG
TCTAAGAAGAAGGACGGCAAGAAAGAAGAATCAAGTCAAGGCCTCCAAGCTCGTGGGAGTG
TTTCCTGAGGGCCCCAGCAAGCTGAAAGCTCTGAAGGCCGCCATCGAGATCGACGGCAATTAT
GGCGTGGCACTGGACCCCAAGCCTGTGGTCATCAGACACATCAAGGTGTTCAAGAGGATCATG
GCCCTCAAAGAGCAGAACGGCGGCAAGCCAGTGCGCATCCTGAAAAAGGGCATGCTGATTCAC
CTGACCAGCAGCAAGGACCCTAAGCACGCTGGCGTTTGGAGAATCGAGAGCATCCAGGACAGC
AAAGGCGGCGTGAAACTGGACCTGCAGAGGGCTCATTGCGCCGTGCCTAAGAACAAGACCCAC
GAGTGCAATTGGAGAGAGGTGGACCTGATCTCCCTGCTGAAAAAGTACCAGATGAAGCGCTAC
CCCACCAGCTACACCGGCACACCTAGACCCAAGAAGAAGAGGAAGGTG AmuCas9/NLS protein sequence (SEQ ID NO: 14)
MSRSLTFSFDIGYASIGWAVIASASHDDADPSVCGCGTVLFPKDDCQAFKRREYRRLRRNIRS
RRVRIERIGRLLVQAQIITPEMKETSGHPAPFYLASEALKGHRTLAPIELWHVLRWYAHNRGY
DNNASWSNSLSEDGNGEDTERVKHAQDLMDKHGTATMAETICRELKLEEGKADAPMEVSTPA
YKNLNTAFPRLIVEKEVRRILELSAPLIPGLTAEIIELIAQHHPLTTEQRGVLLQHGIKLARR
YRGSLLFGQLIPRFDNRIISRCPVTWAQVYEAELKKGNSEQSAREREAEKLSKVPTANCPEFYE
YRMARILCNIRADGEPLSAEIRRELMNQARQEGKLTKASLEKAISSRLGKETETNVSNYFTLH
PDSEEALYLNPAVEVLQRSGIGQILSPSVYRIAANRLRRGKSVTPNYLLNLLKSRGESGEALE
KKIEKESKKKEADYADTPLKPKYATGRAPYARTVLKKVVEEILDGEDPTRPARGEAHPDGELK
AHDGCLYCLLDTDSSVNQHQKERRLDTMTNNHLVRHRMLILDRLLKDLIQDFADGQKDRISRV
CVEVGKELTTFSAMDSKKIQRELTLRQKSHTDAVNRLKRKLPGKALSANLIRKCRIAMDMNWT
CPFTGATYGDHELENLELEHIVPHSFRQSNALSSLVLTWPGVNRMKGQRTGYDFVEQEQENPV
PDKPNLHICSLNNYRELVEKLDDKKGHEDDRRRKKKRKALLMVRGLSHKHQSQNHEAMKEIGM
TEGMMTQSSHLMKLACKSIKTSLPDAHIDMIPGAVTAEVRKAWDVFGVFKELCPEAADPDSGK
ILKENLRSLTHLHHALDACVLGLIPYIIPAHHNGLLRRVLAMRRIPEKLIPQVRPVANQRHYV
LNDDGRMMLRDLSASLKENIREQLMEQRVIQHVPADMGGALLKETMQRVLSVDGSGEDAMVSL
SKKKDGKKEKNQVKASKLVGVFPEGPSKLKALKAAIEIDGNYVALDPKPVVIRHIKVFKRIM TABLE 7-continued Engineered Cas9 Systems ALKEQNGGKPVRILKKGMLIHLTSSKDPKHAGVWRIESIQDSKGGVKLDLQRAHCAVPKNKTH
ECNWREVDLISLLKKYQMKRYPTSYTGTPR<u>PKKKRKV</u>

SEQ ID NO: 15. OkiCas9/NLS DNA
ATGGCCAGAGATTACAGCGTCGGCCTGGATATCGGCACCTCTTCTGTTGGATGGGCCGCCATC
GACAACAAGTACCACCTGATCCGGGCCAAGAGCAAGAACCTGATTGGCGTGCGGCTGTTCGAT
AGCGCCGTGACCGCCGAGAAGAGAAGAGGCTACAGAACCACCAGACGGCGGCTGAGCAGACGG
CATTGGAGACTGAGACTGCTGAACGACATCTTCGCCGGACCTCTGACCGATTTCGGCGACGAG
AATTTCCTGGCCAGACTGAAGTACAGCTGGGTTCACCCTCAAGACCAGAGCAATCAGGCCCAC
TTTGCCGCCGGACTGCTGTTCGACAGCAAAGAGCAGGACAAGGACTTCTACCGGAAGTACCCC
ACCATCTATCACCTGAGACTGGCCCTGATGAACGACGACCAGAAGCACGACCTGAGAGAGGTG
TACCTGGCCATCCACCACCTGGTCAAGTACAGAGGCCACTTCCTGATCGAGGGCGACGTGAAA
GCCGACAGCGCCTTTGATGTGCACACCTTCGCCGACGCCATCCAGAGATACGCCGAGAGCAAC
AACTCCGACGAGAACCTGCTGGGCAAGATCGACGAGAAGAAGCTGAGCGCTGCCCTGACCGAT
AAGCACGGCAGCAAAAGCCAGAGAGCCGAGACAGCCGAAACCGCCTTCGACATCCTGGACCTG
CAGTCCAAGAAGCAGATCCAGGCCATCCTGAAGTCCGTCGTGGGCAACCAGGCCAATCTGATG
GCCATTTTTGGCCTGGACAGCAGCGCCATCAGCAAGGACGAGCAGAAGAACTACAAGTTCAGC
TTCGACGACGCCGACATCGATGAGAAGATCGCCGATTCTGAGGCCCTGCTGAGCGATACCGAG
TTCGAGTTCCTGTGCGATCTGAAGGCCGCCTTTGACGGCCTGACACTGAAAATGCTGCTGGGC
GACGACAAGACCGTGTCCGCTGCTATGGTTCGACGGTTCAACGAGCACCAGAAGGACTGGGAG
TACATCAAGAGCCACATCCGGAACGCCAAGAACGCCGGCAATGGCCTGTACGAGAAGTCTAAG
AAGTTCGACGGCATCAACGCCGCCTATCTGGCTCTGCAGTCCGACAACGAGGACGACAGAAAG
AAGGCCAAGAAGATTTTCCAGGACGAGATCAGCTCCGCCGACATTCCCGATGATGTGAAGGCC
GATTTCCTGAAGAAGATTGACGACGATCAGTTCCTGCCTATCCAGCGGACCAAGAACAACGGC
ACAATCCCTCACCAGCTGCACCGGAACGAGCTGGAACAGATCATCGAGAAGCAGGGGATCTAC
TACCCATTCCTGAAGGACACCTACCAAGAGAACAGCCACGAGCTGAACAAAATCACAGCCCTG
ATCAACTTCAGGGTGCCCTACTACGTGGGCCCTCTGGTGGAAGAGGAACAGAAAATCGCCGAC
GACGGCAAGAACATCCCCGATCCTACCAACCACTGGATGGTCCGAAAGTCCAACGACACCATC
ACACCCTGGAACCTGAGCCAGGTGGTCGACCTGGATAAGAGCGGCAGAAGATTCATCGAGCGG
CTGACCGGCACCGATACCTATCTGATCGGAGAGCCCACACTGCCCAAGAACAGCCTGCTGTAC
CAGAAATTCGACGTGCTGCAAGAACTGAACAACATCCGCGTGTCCGGCAGACGGCTGGACATT
AGAGCCAAGCAGGATGCCTTCGAGCACCTGTTCAAGGTGCAGAAAACCGTGTCTGCTACCAAT
CTGAAGGACTTCCTGGTGCAAGCCGGCTACATCAGCGAGGACACCCAGATTGAAGGACTCGCC
GACGTGAACGGAAAGAACTTCAACAACGCCCTGACCACCTACAACTACCTGGTGTCTGTGCTG
GGCCGCGAGTTCGTGGAAAACCCCAGCAACGAGGAACTGCTGGAAGAGATTACCGAGCTGCAG
ACCGTGTTCGAGGACAAGAAGGTGCTGCGGAGACAGCTGGATCAGCTGGACGGACTGAGCGAC
CACAACAGAGAGAAGCTTTCCCGGAAGCACTACACCGGCTGGGGCAGAATCAGCAAGAAGCTG
CTGACCACCAAGATCGTGCAGAACGCCGACAAGATCGATAACCAGACCTTCGATGTGCCCCGG
ATGAACCAGAGCATCATCGACACCCTGTACAACACCAAGATGAACCTGATGGAAATCATCAAC
AATGCCGAGGATGACTTCGGCGTCAGAGCCTGGATCGACAAGCAGAACACCATCCGATGGCAC
GAGCAGGACGTGTACAGCCTGATCGATGAACTGGCTGGCCCCAAAGATGATCAAGCGGGGCATC
GTGCAGTCCTTTAGAATCCTGGACGACATCACCAAGGCCGTGGGCTACGCCCCTAAACGGGTG
TACCTCGAATTTGCCAGAAAGACCCAAGAGAGCCACCTGACCAACAGCCGGAAGAACCAGCTG
AGCACCCTGCTGAAGAATGCCGGCCTGTCTGAGCTGGTCACAAGGTGTCCCAGTATGATGCC
GCCGCTCTGCAGAACGACCGGCTGTATCTTTACTTCCTGCAGCAAGGCAAGGACATGTACTCC
GGCGAGAAGCTGAATCTGGACAACCTGAGCAACTACGACATCGACCACATCATCCCTCAGGCT
TACACCAAGGACAACAGCCTGGACAACAGAGTGCTGGTGTCCAATATCACCAACCGGCGGAAG
TCCGACAGCAGCAACTATCTGCCCGCTCTGATCGATAAGATGCGGCCCTTTTGGAGCGTGCTG
AGCAAGCAGGGGCTGCTGTCTAAGCACAAGTTCGCCAACCTGACCAGAACCAGAGACTTCGAC
GATATGAAAAGAGCGGTTTATCGCCCGCAGCCTGGTGGAAACCCGGCAGATCATTAAGAAC
GTGGCCAGCCTGATTGACAGCCACTTCGGCGGAGAGACAAAAGCCGTGGCCATTAGAAGCAGC
CTGACAGCCGACATGCGGAGATACGTGGACATCCCCAAGAACCGGGACATCAACGACTACCAC
CACGCCTTCGATGCCCTGCTGTTAGCACAGTGGGCCAGTACACCGAGAACAGCGGCCTGATG
AAGAAGGGCCAGCTGTCCGATTCTGCCGGCAACCAGTACAATCGGTACATCAAAGAGTGGATT
CACGCCGCCAGGCTGAACGCACAGTCCCAGAGAGTGAACCCCTTCGGCTTTGTCGTGGGCTCC
ATGAGAAATGCTGCCCCTGGCAAGCTGAACCCCGAGACAGGGGAGATCACCCCAGAGGAAAAC
GCCGACTGGTCTATCGCCGACCTGGACTACCTGCACAAAGTGATGAATTTCCGGAAGATCACC
GTGACCAGGCGGCTGAAGGATCAGAAGGACAGCTGTACGACGAGAGCAGATACCCCTCCGTG
CTGCACGACGCCAAGTCTAAGGCCAGCATCAACTTTGACAAGCACAAGCCCGTGGACCTGTAC
GGCGGCTTTAGCTCTGCCAAGCCTGCCTATGCCGCACTGATCAAGTTCAAGAACAAGTTCCGG
CTGGTCAACGTGCTGCGGCAGTGGACCTACAGCGACAAGAACTCCAGGACTATATCCTTGAG
CAGATCAGAGGCAAGTACCCTAAGGCCGAGATGGTGCTGTCTCACATCCCTTACGGCCAGCTG
GTCAAGAAAGATGGCGCCCTGGTCACCATCTCTAGCGCCACAGAGCTGCACAACTTTGAGCAG
CTGTGGCTGCCTCTGGCCGACTACAAGCTGATCAACACACTGCTTAAGACCAAAGAGGACAAC
CTCGTCGATATCCTGCACAACCGGCTGGATCTCCCCGAGATGACAATCGAGAGCGCCTTCTAT
AAAGCCTTCGACTCCATCCTGAGCTTCGCCTTCAACAGATACGCCCTGCACCAGAACGCCCTC
GTGAACTGCAGGCCCACAGGGACGATTTCAATGCCCTGAACTACGAGGATAAGCAGCAGACC
CTGGAAAGGATTCTGGACGCTCTGCATGCCTCTCCAGCCAGCAGCGACCTGAAGAAAATCAAC
CTGTCCAGCGGCTTCGGCCGGCTGTTTTCCCCTAGCCACTTTACCCTGGCCGACACCGACGAG
TTCATCTTCCAGAGCGTGACCGGCCTGTTCAGCACCCAGAAACAGTGGCCAGCTGTATCAA
GAGACAAAG<u>CCCAAGAAGAAGAGGAAGGTG</u>

OkiCas9/NLS protein sequence (SEQ ID NO: 16)
MARDYSVGLDIGTSSVGWAAIDNKYHLIRAKSKNLIGVRLFDSAVTAEKRRGYRTTRRRLSRR
HWRLRLLNDIFAGPLTDFGDENFLARLKYSWVHPQDQSNQAHFAAGLLFDSKEQDKDFYRKYP
TIYHLRLALMNDDQKHDLREVYLAIHHLVKYRGHFLIEGDVKADSAFDVHTFADAIQRYAESN
NSDENLLGKIDEKKLSAALTDKHGSKSQRAETAETAFDILDLQSKKQIQAILKSVVGNQANLM
AIFGLDSSAISKDEQKNYKFSFDDADIDEKIADSEALLSDTEFEFLCDLKAAFDGLTLKMLLG TABLE 7-continued Engineered Cas9 Systems DDKTVSAAMVRRFNEHQKDWEYIKSHIRNAKNAGNGLYEKSKKFDGINAAYLALQSDNEDDRK
KAKKIFQDEISSADIPDDVKADFLKKIDDDQFLPIQRTKNNGTIPHQLHRNELEQIIEKQGIY
YPFLKDTYQENSHELNKITALINFRVPYYVGPLVEEEQKIADDGKNIPDPTNHWMVRKSNDTI
TPWNLSQVVDLDKSGRRFIERLTGTDTYLIGEPTLPKNSLLYQKFDVLQELNNIRVSGRRLDI
RAKQDAFEHLFKVQKTVSATNLKDFLVQAGYISEDTQIEGLADVNGKNFNNALTTYNYLVSVL
GREFVENPSNEELLEEITELQTVFEDKKVLRRQLDQLDGLSDHNREKLSRKHYTGWGRISKKL
LTTKIVQNADKIDNQTFDVPRMNQSIIDTLYNTKMNLMEIINNAEDDFGVRAWIDKQNTTDGD
EQDVYSLIDELAGPKEIKRGIVQSFRILDDITKAVGYAPKRVYLEFARKTQESHLTNSRKNQL
STLLKNAGLSELVTQVSQYDAAALQNDRLYLYFLQQGKDMYSGEKLNLDNLSNYDIDHIIPQA
YTKDNSLDNRVLVSNITNRRKSDSSNYLPALIDKMRPFWSVLSKQGLLSKHKFANLTRTRDFD
DMEKERFIARSLVETRQIIKNVASLIDSHFGGETKAVAIRSSLTADMRRYVDIPKNRDINDYH
HAFDALLFSTVGQYTENSGLMKKGQLSDSAGNQYNRYIKEWIHAARLNAQSQRVNPFGFVVGS
MRNAAPGKLNPETGEITPEENADWSIADLDYLHKVMNFRKITVTRRLKDQKGQLYDESRYPSV
LHDAKSKASINFDKHKPVDLYGGFSSAKPAYAALIKFKNKFRLVNVLRQWTYSDKNSEDYILE
QIRGKYPKAEMVLSHIPYGQLVKKDGALVTISSATELHNFEQLWLPLADYKLINTLLKTKEDN
LVDILHNRLDLPEMTIESAFYKAFDSILSFAFNRYALHQNALVKLQAHRDDFNALNYEDKQQT
LERILDALHASPASSDLKKINLSSGFGRLFSPSHFTLADTDEFIFQSVTGLFSTQKTVAQLYQ
ETKPKKKRKV BboCas9/NLS DNA sequence (SEQ ID NO: 17)
ATGAGCCAGCACCGGCGGTATAGAATCGGCATCGACGTGGGCCTGAATAGCGTTGGACTGGCC
GCCGTGGAAATCGACGCCAACCACGACAATCCTCTGGACGAGATCCCCATCAGCATCCTGAAT
GCCCAGAGCGTGATCCACGATGGCGGAGTGGACCCTGATGAGCCAAGTCTGCTACAAGCAGA
CGGGCTTCTGCTGGCGTGGCCAGAAGAACAAGACGGCTGCCAAGAGCAAGCGGCAGAGACTG
GCCAAGCTGGACGAGGTGCTGAATGAGCTGGGCTACCCCGTGGAAGATGAGAGCCAGTTTCCA
GCCGGCAGCAACCCCTATATCGCTTGGCAAGTGCGGGCCAAACTGGCCGAGACATTCATCCCC
GACGTGGAAACCCGGAAGCGGATGATCTCTATCGCCATCCGGCACATTGCCCGGCATAGAGGA
TGGCGGAATCCCTACTCTTCTGTGGCCGACGCCGAGCGGATGAGCCATACACCTTCTCCATTC
ATGGTGGAATACGCCAAGAAGCTGGACTTCGAGATCAACGACAGACGGACCAACGGCTTCTAT
CACAGCCCTTGGCAGAGCGTGGACGAGGAAGGCAAGAGACTGAGCAAGAGCGAGCTGGAAAAG
CAGCCCAAGATCGAGGACTGGAACGACAACCCCATCAACGGCAAGACAATCGCCCAGCTGGTC
GTGTCCTCTCTGGAACCCCAGACCAAGATCAGACGGGATCTGACACACGGCCTGCAGACCGAG
AGCACCCTGAATATCCAGACAGAGAAGCTGCACCAGAGCGACTACATCCACGAACTGGAAACC
ATCTTCGAGCGGCAGCACGTGGACCAGACAACCCAAGAACAGCTGCTGGAAGCCACCTTCCAC
ACCAAGAATCCTAAGGCCGTGGGAGCCGCCGCTAAGCTCGTTGGAAAAGATGCCCTGGACAGC
CGGTACTACAGAGCCAGCAGAGCCACACCAGCCTTCGAAGAGTACAGAGTGATGGCCGCCATC
GACACCCTGCGATTAGAGAGCACGGCACCGAGAGACAGCTGACCACCGACGAGAGAAGAAG
CTGTTCGACTTCATCAAGGGGCTGCCCAGCAAAAAGACCAAGAACGAGCCCAGCATCAGCTCC
CTGACCTGGGGAGATGTGGCCGATTTTCTGGGCATCCAGCGGATCGATCTGAGAGGCCTGGGC
TCTCTGAAAGACGGCGAACCTGTGTCTGCCAAGCAGCCTCCTGTGATCGAGACAAACGACATC
ATGCAGAAGGCCCCTGATCCAATCGCTGCCTGGTGGTCACAGGCCAACACCAAAGAACGGGAC
AGATTCGTCGAGTTCATGAGCAACGCTGGCGCCATCAAGGACACCTCCGACGAAGTGCGGAAC
ATTGACGCCGAGATCAGCCAGCTGCTCGAAGAACTGACCGGCTCTGAGCTGGAATCCCTGGAT
AAGATCACCCTGACCTCTGGCAGAGCCGCCTACAGCTCTCAGACCCTGAGAACATCACCAAC
TATATGTACGAGACAGGCTGCGACCTGACCACAGCCAGACAAGAGCTGTACCACGTGGGCAAG
AATTGGGCCCCTCCTGCTCCTCCTATCTACGAGCACACAGGCAACCCCAGCGTGGACAGAACC
TTCAGCATCATCCACAGATGGCTGTGCAACATGCGGGACCAGTACGGCGAGCCCGAGACAGTG
AATATCGAGTACGTCCGCGACGGCTTCAGCAGCACATCTACACAGCTGGCCGAGCAGCGCGAG
CGGGATAGAAGATACGCCGACAACCTGAAGATGCTGAGCAACTACGAGGGCGCCAGCAGCAGA
TCAGATGTGCGGAGAATCAAGGCCCTGCAGAGACAGAACTGCCAGTGCATCTACTGCGGCCGG
ACCATCACCTTCGAGACATGCCAGATGGACCATGTGCTGCCCCGGAAAGGCCCTGGATCCGAT
AGCAAGTTCGAGAACCTGGTGGCCACATGCGGCGAGTGCAACAAGTCCAAGAGCGATACCCTG
TACATGAACTGGGCCAAGACATACCCCAATACCAACCTGCAGGACGTGCTGAGAAGAATCCAA
GAGTGGTCCAAGGACGGCTGGATGACCGACAAAAGATGGCGGCAGTACAAAGAGGCCCTGATC
CTGAGACTGGAAGCTACCGAGAAGCAAGAGCCCCTGGACAATCGGAGCATGGAAAGCGTGTCC
TACATGGCCAGAGAGCTGCGGAACCGGATCTACGGCTTTACGGCTGGCACGACCAGGACGAC
GCCCTGAAACAAGGCAGACAGAGGGTGTTCGTGTCCAGCGGCAGTATGACAGCCGCTGCCAGA
AGGACCCCTTTCGAGTCCCCACTGATTAAGGGCGCCGATGAGGAAACCTACGAGAGCAGCCTG
CCTTGGCTGGATGGCATGAAGGGCAAGACCAGACTGGATCGGAGACACCATGCCGTGGACGCC
AGCATCATTGCCATGATGAGGCCCCAGATCGTGAAGATCCTGACAGAGGCCCAAGAGATCAGA
AGCGAGCAGCACGACAAGTACCGGAAGGGCCAGACACCTGACTACGTGTGCAAGCGGCGGGAC
TACTGGCGGAATTGGAGAGGCACCCCTGACACCAGAGATGAGGAAGTGTTCAACTACTGGGCT
GGGGAGCAGCTGAGAACCCTGACCGATCTGGTGTCCCAGAAGATGGCCGACGACGAAATCCCC
GTGATCTACCCCACCAGACTGAGACTCGGCAATGGCAGCGCCCACAAGGATACCGTGGTGTCC
ATGATGACCCGGAAAGTGGGCGACGAGCTGAGCATCACCGCCATCAACAAAGCCGAAAGCGGA
GCCCTGTACACAGCCCTGACCAGAGACAGCGACTTCGACTGGAAAACCGGCCTGAGCGCCAAT
CCTAACCGGCGATCAGAGTGCACGATAAGTGGTTCGAGGCCGACGATACCATCAAGTTTCTG
GAACCTGCCGTGGAAGTGGTGCTGAAGAACAACACCAGAGCCAGAATCGACCCCGAGGCTCTG
GATAAGGTGCACAGCACACTGTACGTGCCCGTCAGAGGCGAGGATCGCCGAAGCCGGAAATAGC
ATTCACCACGTGCGGTTCTACAAGATCCCCAAGCTGAACAGCAAGGGCAAGCAGACCGGCAGC
ATCTACGCCATGCTGAGAGTGCTGACCATCGACCTGGCCATGAACAGTACGACAAAGAGACA
GGCAAGAAGCAGGACCTGTTCACCCTGCCACTGCCTGAAAGCAGCCTGAGCAGAAGATTCAGC
GAGCCCAAACTGCGGCAGGCTCTGATCGATGGCACAGCCGAATATCTCGGATGGGCCGTCGTG
GACGATGAGCTTGAGATCCCCGCCTTCGCCAACGCCAGAATCACAGAGGAACAGGCCATTAAC
GGCAGCTTCACCGACAGACTGCTGCACAGCTTTCCCGGCACACACAAGTTCAGATTCGCCGGC
TTCTCCCGGAACACCGAGATCGCCATTAGACCTGTGCAGCTGGCCTCTGAGGGCCTGATCGAA
ACCGATGAGAACCGGAAGAGACAGCAGCTGCGGCTGACCCAGCCTAACACCGAGTACAGCAAC
AGCATCAAGAACGTGCTGAAGTCCGGCCTGCACCTGAAAGTGAACACCCTGTTCCAGACAGGC TABLE 7-continued Engineered Cas9 Systems ATCCTGGTCACCAGGGCCAATAGCCAGGGAAAGCAGAGCATCCGGTTCAGCACAGTGGAAGAG
CCCAAGAAGAAGAGGAAGGTG BboCas9/NLS protein sequence (SEQ ID NO: 18)
MSQHRRYRIGIDVGLNSVGLAAVEIDANHDNPLDEIPISILNAQSVIHDGGVDPDEAKSATSR
RASAGVARRTRRLHKSKRQRLAKLDEVLNELGYPVEDESQFPAGSNPYIAWQVRAKLAETFIP
DVETRKRMISIAIRHIARHRGWRNPYSSVADAERMSHIPSPFMVEYAKKLDFEINDRRINGFY
HSPWQSVDEEGKRLSKSELEKQPKIEDWNDNPINGKTIAQLVVSSLEPQTKIRRDLTHGLQTE
STLNIQTEKLHQSDYIHELETIFERQHVDQTTQEQLLEATFHTKNPKAVGAAAKLVGKDALDS
RYYRASRATPAFEEYRVMAAIDTLRIREHGTERQLTTDERRKLFDFIKGLPSKKTKNEPSISS
LTWGDVADFLGIQRIDLRGLGSLKDGEPVSAKQPPVIETNDIMQKAPDPIAAWWSQANTKERD
RFVEFMSNAGAIKDTSDEVRNIDAEISQLLEELTGSELESLDKITLTSGRAAYSSQTLRNITN
YMYETGCDLTTARQELYHVGKNWAPPAPPIYEHIGNPSVDRIFSIIHRWLCNMRDQYGEPETV
NIEYVRDGFSSTSTQLAEQRERDRRYADNLKMLSNYEGASSRSDVRRIKALQRQNCQCIYCGR
TITFETCQMDHVLPRKGPGSDSKFENLVATCGECNKSKSDTLYMNWAKTYPNTNLQDVLRRIQ
EWSKDGWMTDKRWRQYKEALILRLEATEKQEPLDNRSMESVSYMARELRNRIYGFYGWHDQDD
ALKQGRQRVFVSSGSMTAAARRTPFESPLIKGADEETYESSLPWLDGMKGKTRLDRRHHAVDA
SIIAMMRPQIVKILTEAQEIRSEQHDKYRKGQTPDYVCKRRDYWRNWRGTPDTRDEEVFNYWA
GEQLRILTDLVSQKMADDEIPVIYPTRLRLGNGSAHKDTVVSMMTRKVGDELSITAINKAESG
ALYTALTRDSDFDWKTGLSANPNRRIRVHDKWFEADDTIKFLEPAVEVVLKNNTRARIDPEAL
DKVHSTLYVPVRGGIAEAGNSIHHVRFYKIPKLNSKGKQTGSIYAMLRVLTIDLAMNQYDKET
GKKQDLFTLPLPESSLSRRFSEPKLRQALIDGTAEYLGWAVVDDELEIPAFANARITEEQAIN
GSFTDRLLHSFPGTHKFRFAGFSRNTEIAIRPVQLASEGLIETDENRKRQQLRLTQPNTEYSN
SIKNVLKSGLHLKVNTLFQTGILVTRANSQGKQSIRFSTVEEPKKKRKV AceCas9/NLS DNA sequence (SEQ ID NO: 19)
ATGGGCGGATCTGAAGTGGGAACCGTGCCTGTGACTGGAGACTGGGAGTCGATGTGGGCGAG
AGATCCATTGGACTGGCCGCCGTGTCCTACGAAGAGGACAAGCCCAAAGAAATCCTGGCTGCT
GTGTCCTGGATTCACGATGGCGGAGTGGGCGACGAAAGAAGCGGAGCTAGTAGACTGGCCCTG
AGAGGCATGGCCAGAAGGGCTAGACGGCTGCGGAGATTCCGTAGAGCCAGACTGCGCGACCTG
GACATGCTGCTGTCTGAACTCGGATGGACCCCTCTGCCTGACAAGAACGTGTCCACCTGTGGAT
GCCTGGCTGGCCAGAAAGAGACTGGCCGAGGAATACGTGGTGGACGAGACAGAGAGAAGAAGG
CTGCTGGGCTACGCCGTGTCTCACATGGCTAGACATAGAGGCTGGCGGAACCCCTGGACCACC
ATCAAGGACCTGAAGAACCTGCCTCAGCCTAGCGACAGCTGGGAGAGAACCAGAGAAAGCCTG
GAAGCCCGGTACTCCGTGTCTCTGGAACCTGGCACAGTTGGACAGTGGGCCGGATACCTGCTG
CAGAGAGCCCCTGGCATCAGACTGAACCCTACACAGCAGAGCGCCGGAAGAAGGGCCGAACTG
TCTAATGCCACCGCCTTCGAGACAAGACTGCGGCAAGAGGATGTGCTGTGGGAGCTGAGATGT
ATCGCCGACGTTCAGGGCCTGCCTGAGGACGTGGTGTCCAATGTGATCGACGCCGTGTTCTGC
CAGAAAAGACCTAGCGTGCCCGCCGAGAGAATCGGCAGAGATCCTCTCGATCCCAGCCAGCTG
AGAGCCAGCAGAGCCTGCCTGGAATTTCAAGAGTACCGGATCTGGCCGCTGTGGCCAACCTG
AGAATCAGAGATGGCAGCGGCAGCAGACCCCTGAGTCTGGAAGAAAGAAACGCCGTGATCGAG
GCCCTGCTGGCCCAGACAGAAAGAAGCCTCACTTGGAGCGACATTGCCCTGGAAATCCTGAAG
CTGCCCAACGAGAGCGACCTGACCTCTGTGCCTGAAGAGGATGGCCCAAGCAGCCTGGCCTAC
TCTCAGTTCGCCCCCTTTCGATGAGACAAGCGCCCGGATCGCCAGTTTATCGCCAAGAACAGA
CGGAAGATCCCCACATTCGCCCAGTGGTGGCAAGAGCAGGATCGGACCAGTAGAAGCGATCTG
GTGGCTGCCCTGGCCGACAATTCTATTGCCGGCGAGGAAGAACAAGAGCTGCTGGTGCATCTG
CCCGACGCCGAACTTGAAGCTCTGGAAGGACTGGCTCTGCCCTCTGGCAGAGTGGCCTATAGC
AGACTGACACTGAGCGGCCTGACCAGAGTGATGAGAGATGATGGCGTGGACGTGCACAACGCC
CGCAAGACATGCTTCGGAGTGGACGACAATTGGCGGCCTCCACTGCCTGCTCTGCATGAAGCT
ACAGGACACCCCGTGGTGGATAGAAACCTGGCTATCCTGCGGAAGTTCCTGAGCAGCGCCACC
ATGAGATGGGGCCCTCCACAGTCTATCGTGGTGGAACTTGCCAGAGGCGCCAGCGAGAGCAGA
GAAAGGCAGGCCGAAGAAGAAGCGCTCGGAGAGCCCACAGAAAGGCCAACGACAGAATTAGA
GCCGAACTCAGAGCCTCCGGCCTGAGCGATCCTTCTCCTGCCGATCTTGTTAGAGCCCGGCTG
CTGGAACTGTACGACTGCCACTGTATGTACTGTGGCGCCCCTATCTCCTGGGAGAACAGCGAG
CTGGATCACATCGTGCCCAGAACAGATGGCGGATCCAACAGACACGAGAACCTGGCCATTACA
TGCGGCGCCTGCAACAAAGAAAAAGGCAGAAGGCCCTTCGCCAGCTGGGCCGAGACAAGCAAT
AGAGTGCAGCTGCGGGACGTGATCGACCGGGTGCAGAAGCTGAAGTACAGCGGCAACATGTAC
TGGACCCGGGACGAGTTCAGCCGGTACAAGAAAAGCGTGGTGGCCCGGCTGAAGCGGAGAACC
TCTGATCCTGAAGTGATCCAGAGCATCGAGAGCACCGGCTATGCTGCCGTGGCTCTGAGAGAT
AGACTGCTGAGCTACGGCGAGAAGAATGGCGTGGCACAGGTGGCCGTTTTTAGAGGCGGAGTG
ACAGCCGAGGCCAGAAGATGGCTGGACATCTCCATCGAGCGGCTGTTCAGTAGAGTGGCCATC
TTCGCCCAGAGCACCTCCACCAAGAGGCTGGATAGAAGGCACCACGCCGTGGATGCTGTGGTG
CTGACAACACTGACACCCGGCGTGGCCAAGACACTGGCTGATCTAGAAGCAGAAGAGTGTCC
GCCGAGTTCTGCGCAGACCAAGCGACGTGAACAGACACAGCACCGAGGAACCTCAGAGCCCC
GCCTACAGACAGTGGAAAGAGAGCTGTTCTGGCCTGGGCGACCTGCTGATTTCTACCGCCGCC
AGAGATTCTATCGCCGTGGCTGCTCCTCTGAGACTGAGGCCAACAGGCGCACTGCACGAGGAA
ACCCTGAGAGCCTTTAGCGAGCACACAGTGGGAGCCGCTTGAAGGGCGCTGAGCTGAGAAGA
ATCGTGGAACCCGAAGTGTACGCCGCCTTCCTGGCACTTACAGATCCTGGCGGCAGATTCCTG
AAGGTGTCCCCTAGCGAAGATGTGCTGCCTGCCGACGAGAACAGGCACATTGTCTGAGCGAC
AGAGTGCTGGGCCCAGAGACAGAGTGAAACTGTTCCCCGACGACCGGGGCAGCATCAGAGTC
AGAGGTGGCGCAGCCTATATCGCCAGCTTTCACCACGCCAGAGTGTTCAGATGGGGAAGCAGC
CACTCTCCTAGCTTCGCCCTGCTGAGAGTCTCTCGGCTGATCTGGCTGTGGCTGGCCTGCTT
AGAGATGGGGTCGACGTGTTCACAGCCGAGCTGCCACCTTGGACTCCCGCTTGGAGATATGCC
TCTATCGCCCTGGTCAAGGCCGTGGAAAGCGGCGACGCTAAGCAAGTTGGATGGCTGGTGCCT
GGCGACGAACTGGATTTTGGACCTGAGGGCGTGACAACCGCTGCCGGCGATCTGAGCATGTTC
CTGAAGTACTTTCCCGAGCGGCACTGGGTCGTGACCGGCTTCGAAGATGACAAGAGGATCAAC
CTGAAGCCTGCCTTCCTGTCTGCCGAACAGGCTGAGGTGCTGAGGACTGAGAGAAGCGACAGA
CCCGACACACTGACAGAGGCCGGCGAAATTCTGGCCCAGTTCTTCCCTAGATGTTGGCGGGCC TABLE 7-continued Engineered Cas9 Systems ACAGTGGCTAAGGTGCTGTGCCATCCTGGCCTGACCGTGATCAGAAGAACAGCCCTGGGACAG
CCTAGGTGGCGGAGAGGACATCTGCCTTATTCATGGCGGCCTTGGAGCGCCGATCCTTGGAGT
GGCGGAACACCT<u>CCCAAGAAGAAGAGGAAGGTG</u>

AceCas9/NLS protein sequence (SEQ ID NO: 20)
MGGSEVGTVPVTWRLGVDVGERSIGLAAVSYEEDKPKEILAAVSWIHDGGVGDERSGASRLAL
RGMARRARRLRRFRRARLRDLDMLLSELGWTPLPDKNVSPVDAWLARKRLAEEYVVDETERRR
LLGYAVSHMARHRGWRNPWTTIKDLKNLPQPSDSWERTRESLEARYSVSLEPGTVGQWAGYLL
QRAPGIRLNPTQQSAGRRAELSNATAFETRLRQEDVLWELRCIADVQGLPEDVVSNVIDAVFC
QKRPSVPAERIGRDPLDPSQLRASRACLEFQEYRIVAAVANLRIRDGSGSRPLSLEERNAVIE
ALLAQTERSLTWSDIALEILKLPNESDLTSVPEEDGPSSLAYSQFAPFDETSARIAEFIAKNR
RKIPTFAQWWQEQDRTSRSDLVAALADNSIAGEEEQELLVHLPDAELEALEGLALPSGRVAYS
RLTLSGLTRVMRDDGVDVHNARKTCFGVDDNWRPPLPALHEATGHPVVDRNLAILRKFLSSAT
MRWGPPQSIVVELARGASESRERQAEEEAARRAHRKANDRIRAELRASGLSDPSPADLVRARL
LELYDCHCMYCGAPISWENSELDHIVPRTDGGSNRHENLAITCGACNKEKGRRPFASWAETSN
RVQLRDVIDRVQKLKYSGNMYWTRDEFSRYKKSVVARLKRRTSDPEVIQSIESTGYAAVALRD
RLLSYGEKNGVAQVAVFRGGVTAEARRWLDISIERLFSRVAIFAQSTSTKRLDRRHHAVDAVV
LTTLTPGVAKTLADARSRRVSAEFWRRPSDVNRHSTEEPQSPAYRQWKESCSGLGDLLISTAA
RDSIAVAAPLRLRPTGALHEETLRAFSEHTVGAAWKGAELRRIVEPEVYAAFLALTDPGGRFL
KVSPSEDVLPADENRHIVLSDRVLGPRDRVKLFPDDRGSIRVRGGAAYIASFHHARVFRWGSS
HSPSFALLRVSLADLAVAGLLRDGVDVFTAELPPWTPAWRYASIALVKAVESGDAKQVGWLVP
GDELDFGPEGVTTAAGDLSMFLKYFPERHWVVTGFEDDKRINLKPAFLSAEQAEVLRTERSDR
PDTLTEAGEILAQFFPRCWRATVAKVLCHPGLTVIRRTALGQPRWRRGHLPYSWRPWSADPWS
GGTP<u>PKKKRKV</u>

AheCas9/NLS DNA sequence (SEQ ID NO: 21)
ATGGCCTATAGACTGGGCCTCGACATCGGCATCACATCTGTTGGATGGGCCGTCGTGGCCCTG
GAAAAGGATGAGTCTGGACTGAAGCCCGTGCGCATCCAGGATCTGGGCGTCAGAATCTTCGAC
AAGGCCGAGGATAGCAAGACCGGCGCTTCTCTGGCTCTGCCCAGAAGAGAAGCCAGAAGCGCC
AGAAGAAGAACCCGGCGGAGAAGGCACAGACTGTGGCGCGTGAAAAGACTGCTGGAACAGCAC
GGCATCCTGAGCATGGAACAGATCGAGGCCCTGTACGCCCAGAGAACAAGCAGCCCTGATGTG
TATGCCCTGAGAGTGGCCGGCCTGGACAGATGTCTGATCGCCGAAGAGATCGCCCGGGTGCTG
ATTCACATTGCCCACGAAGAGGCTTCCAGAGCAACAGAAAGAGCGAGATCAAGGACAGCGAC
GCCGGCAAGCTGCTGAAGGCCGTGCAAGAGAACGAGAACCTGATGCAGAGCAAGGGCTACAGA
ACCGTGGCCGAGATGCTGGTGTCTGAGGCCACAAAGACAGACGCCGAGGGAAAGCTGGTGCAC
GGCAAGAAGCACGGCTACGTCAGCAACGTGCGGAACAAGGCCGGCGAGTACAGACACACAGTG
TCCAGACAGGCCATCGTGGACGAAGTGCGGAAGATTTTCGCCGCTCAGAGAGCCCTGGGCAAC
GACGTGATGAGCGAGGAACTGGAAGATAGCTACCTGAAGATCCTGTGCAGCCAGCGGAACTTC
GATGATGGCCCTGGCGGCGATTCTCCTTATGGACACGGAAGCGTTAGCCCCGACGGCGTCAGA
CAGAGCATCTACGAGAGAATGGTCGGAAGCTGCACCTTCGACAGGCAGGCGAAGAGAGCCCCT
AGAAGCAGCTACAGCTTCGAGCGGTTTCAGCTGCTGACCAAGGTGGTCAACCTGCGGATCTAC
CGGCAGCAAGAGGATGGCGGCAGATACCCTTGTGAACTGACCCAGACCGAGCGGGCCAGAGTG
ATCGATTGTGCCTACGAGCAGACCAAGATCACCTACGGAAAGCTGAGAAAGCTGCTGGACATG
AAGGACACCGAGAGCTTTGCCGGCCTGACCTACGGCCTGAACAGAAGCAGAACAAGACCGAG
GACACCGTGTTCGTGGAAATGAAGTTCTACCACGAAGTCCGCAAGGCCCTGCAGAGAGCCGGG
GTTTTCATTCAGGACCTGAGCATCGAGACACTGGACCAGATCGGCTGGATTCTGAGCGTGTGG
AAGTCCGACGACAACCGGCGGAAGAAGCTGTCTACACTGGGCCTGAGCGACAACGTGATCGAA
GAACTGCTGCCCCTGAACGGCTCCAAGTTTGGCCACCTGAGCCTGAAGGCCATCAGAAAGATC
CTGCCTTTCCTGGAAGATGGGTACAGCTACGACGTGGCCTGTGAACTGGCCGGCTATCAGTTT
CAGGGCAAGACAGAGTACGTGAAGCAGCGGCTGCTGCCTCCACTTGGAGAAGGCGAAGTGACA
AACCCCGTTGTGCGCAGAGCACTGAGCCAGGCCATCAAGGTTGTGAACGCCGTGATCAGAAAG
CACGGCAGCCCAGAGAGCATCCACATCGAACTGGCCAGAGAGCTGAAGCAAGAACCTGGACGAG
CGGAGAAAGATCGAGAAGGCCCAGAAAGAAAATCAGAAGAACAACGAGCAGATTAAGGACGAG
ATCCGCGAGATCCTGGGATCCGCCCATGTGACCGGAAGAGACATCGTGAAGTACAAGCTGTTC
AAACAGCAACAAGAGTTCTGCATGTACAGCGGCGAGAAGCTGGACGTGACCAGACTGTTTGAG
CCTGGCTATGCCGAGGTGGACCACATCATCCCTTACGGCATCAGCTTCGACGACTCCTACGAC
AACAAGGTGCTGGTTAAGACCGAGCAGAACCGGCAGAAGGGCAATAGAACCCCTCTGGAATAC
CTGCGGGACAAGCCTGAGCAGAAGGCCAAGTTTATCGCCCTGGTGGAATCTATCCCTCTGAGC
CAGAAAAAGAAAAACCACCTCCTGATGGACAAGCGGGCCATCGACCTGGAACAAGAGGGCTTC
AGAGAGCGGAACCTGAGCGATACCCGGTACATCACACGGGCCCTGATGAACCACATCCAGGCT
TGGCTGCTGTTCGACGAGACAGCCAGCACCAGATCCAAGAGGGTCGTGTGTGTGAATGGCGCC
GTGACCGCCTACATGAGAGCTAGATGGGGCCTGACAAAGGATAGAGATGCCGGCGATAAGCAC
CACGCCGCTGATGCTGTGGTGGTGGCCTGTATCGGAGACAGCCTGATCCAGAGAGTGACCAAA
TACGACAAGTTCAAGCGGAACGCCCTGGCCGACCGGAACAGATATGTGCAGCAGGTTTCCAAG
AGCGAGGGCATCACCCAGTACGTGGACAAAGAAACCGGCGAGGTGTTCACCTGGGAGTCCTTC
GATGAGCGGAAGTTCCTGCCTAACGAGCCCCTGGAACCTTGGCCATTCTTCAGGGATGAGCTG
CTGGCCAGACTGAGCGACGACCCCTCCAAGAACATCAGAGCCATCGGCCTGCTGACCTACAGC
GAGACTGAGCAGATCGATCCCATCTTCGTGTCCAGAATGCCCACCAGAAAGTGACCGGCGCA
GCCCACAAAGAGACAATCGATCCCCACGGATCGTGAAGGTGGACGATAACAAGGGCACCGAG
ATCCAGGTGGTGGTGTCTAAGGTGGCCCTGACCGAGCTGAAGCTGACCAAAGACGGCGAAATC
AAGGATTACTTCAGGCCCGAGGACGACCCCAGACTGTACAACACCCTGAGAGAACGGCTGGTG
CAGTTCGGCGGAGATGCCAAGGCCGCCTTCAAAGAACCCGTGTACAAGATCAGCAAGGACGGC
TCTGTGCGGACCCCTGTGCGGAAAGTGAAGATTCAAGAGAACGTGACACTGGACGTGCCAGTG
CATGGCGGAAGAGGAATTGCCGAGAATGGCGGCATGGTCCGAATCGACGTGTTCGCCAAAGGC
GGCAAGTACTACTTCGTGCCCATCTACGTGGCCGACGTGCTGAAGAGAGAGCTGCCCAACAGA
CTGGCCACCGCTCACAAGCCTTACAGCGAATGGCGCGTGGTGGACGACAGCTACCAGTTCAAG
TTCTCTCTGTACCCCAACGATGCCGTGATGATCAAGCCCAGCAGAGAGGTGGACATCACCTAC
AAGGACCGGAAAGAGCCCGTCGGCTGCCGGATCATGTACTTTGTGTCCGCCAATATCGCCAGC TABLE 7-continued Engineered Cas9 Systems

```
GCCTCCATCAGCCTGAGAACCCACGATAACTCCGGCGAGCTGGAAGGACTGGGCATCCAAGGA
CTGGAAGTGTTCGAGAATACGTCGTGGGCCCTCTGGGCGACACACACCCTGTGTACAAAGAA
CGGCGGATGCCCTTCAGAGTGGAACGGAAGATGAACCCCAAGAAGAAGAGGAAGGTG
```

AheCas9/NLS protein sequence (SEQ ID NO: 22)

```
MAYRLGLDIGITSVGWAVVALEKDESGLKPVRIQDLGVRIFDKAEDSKTGASLALPRREARSA
RRRTRRRRHRLWRVKRLLEQHGILSMEQIEALYAQRTSSPDVYALRVAGLDRCLIAEEIARVL
IHIAHRRGFQSNRKSEIKDSDAGKLLKAVQENENLMQSKGYRTVAEMLVSEATKTDAEGKLVH
GKKHGYVSNVRNKAGEYRHTVSRQAIVDEVRKIFAAQRALGNDVMSEELEDSYLKILCSQRNF
DDGPGGDSPYGHGSVSPDGVRQSIYERMVGSCTFETGEKRAPRSSYSFERFQLLTKVVNLRIY
RQQEDGGRYPCELTQTERARVIDCAYEQTKITYGKLRKLLDMKDTESFAGLTYGLNRSRNKTE
DTVFVEMKFYHEVRKALQRAGVFIQDLSIETLDQIGWILSVWKSDDNRRKKLSTLGLSDNVIE
ELLPLNGSKFGHLSLKAIRKILPFLEDGYSYDVACELAGYQFQGKTEYVKQRLLPPLGEGEVT
NPVVRRALSQAIKVVNAVIRKHGSPESIHIELARELSKNLDERRKIEKAQKENQKNNEQIKDE
IREILGSAHVTGRDIVKYKLFKQQQEFCMYSGEKLDVTRLFEPGYAEVDHIIPYGISFDDSYD
NKVLVKTEQNRQKGNRTPLEYLRDKPEQKAKFIALVESIPLSQKKKNHLLMDKRAIDLEQEGF
RERNLSDTRYITRALMNHIQAWLLFDETASTRSKRVVCVNGAVTAYMRARWGLTKDRDAGDKH
HAADAVVVACIGDSLIQRVTKYDKFKRNALADRNRYVQQVSKSEGITQYVDKETGEVFTWESF
DERKFLPNEPLEPWPFFRDELLARLSDDPSKNIRAIGLLTYSETEQIDPIFVSRMPTRKVTGA
AHKETIRSPRIVKVDDNKGTEIQVVVSKVALTELKLTKDGEIKDYFRPEDDPRLYNTLRERLV
QFGGDAKAAFKEPVYKISKDGSVRTPVRKVKIQEKLTLGVPVHGGRGIAENGGMVRIDVFAKG
GKYYFVPIYVADVLKRELPNRLATAHKPYSEWRVVDDSYQFKFSLYPNDAVMIKPSREVDITY
KDRKEPVGCRIMYFVSANIASASISLRTHDNSGELEGLGIQGLEVFEKYVVGPLGDTHPVYKE
RRMPFRVERKMNPKKKRKV
```

WsuCas9/NLS DNA sequence (SEQ ID NO: 23)

```
ATGCTGGTGTCCCCTATCTCTGTGGATCTCGGCGGCAAGAATACCGGCTTCTTCAGCTTCACC
GACAGCCTGGACAATAGCCAGAGCGGCACCGTGATCTACGACGAGAGCTTCGTGCTGAGCCAA
GTGGGCAGAAGAAGCAAGCGGCACAGCAAGCGGAACAACCTGAGAAACAAGCTGGTCAAGCGG
CTGTTCCTGCTGATCCTGCAAGAGCACCACGGCCTGAGCATCGACGTTCTGCCCGATGAGATC
CGGGGCCTGTTCAACAAGAGAGGCTACACCTACGCCGGCTTCGAGCTGGACGAGAAGAAGAAG
GACGCCCTGGAAAGCGATACCCTGAAAGAGTTCCTGAGCGAGAAGCTGCAGTCCATCGACAGA
GACAGCGACGTGGAAGATTTCCTGAACCAGATCGCCAGCAACGCCGAGAGCTTTAAGGACTAC
AAGAAAGGCTTCGAGGCCGTGTTCGCCAGCGCCACACACAGCCCCAACAAGAAGCTGGAACTG
AAGGACGAGCTGAAGTCCGAGTACGGCGAGAACGCCCAAAGAACTGCTGGCCGGCCTGAGAGTG
ACCAAAGAGATCCTGGACGAGTTCGACAAGCAAGAGAACCAGGGCAACCTGCCTCGGGCCAAG
TACTTTGAGGAACTGGGCGAGTATATCGCCACCAACGAGAAAGTCAAGAGCTTCTTCGACAGC
AACAGCCTGAAGCTGACCGACATGACCAAGCTGATCGGCAACATCAGCAACTACCAGCTGAAA
GAGCTGCGGCGGTACTTCAACGACAAAGAGATGGAAAAGGGCGACATCTGGATTCCCAACAAG
CTGCACAAGATCACCGAGAGATTTGTGCGGAGCTGGCACCCCAAGAACGACGCCGATAGACAG
AGAAGGGCCGAGCTGATGAAGGACCTGAAGTCCAAAGAAATCATGGAACTGCTGACCACCACC
GAGCCTGTGATGACAATCCCTCCTTACGACGACATGAACAACAGAGGCGCCGTGAAGTGTCAG
ACCCTGCGGCTGAATGAGGAATACCTGGACAAACATCTGCCCAACTGGCGGGATATCGCCAAG
AGACTGAACCACGGCAAGTTCAACGACGACCTGGCCGACTCTACCGTGAAGGGCTACAGCGAG
GATAGCACCCTGCTGCACAGACTGCTGGACACCTCTAAAGAGATCGACATCTACGAGCTGCGG
GGCAAGAAGCCCAACGAGCTGCTGGTTAAGACACTGGGCCAGAGCGACGCCAACAGACTGTAT
GGCTTCGCCCAGAACTACTATGAGCTGATCCGGCAGAAAGTGCGCGCTGGCATTTGGGTGCCC
GTGAAGAACAAGGATGACTCCCTGAACCTGGAAGATAACTCCAACATGCTGAAGCGGTGCAAC
CACAATCCTCCACACAAGAAGAATCAGATCCACAACCTGGTGGCCGGCATCCTGGGAGTGAAA
CTGGATGAGGCCAAGTTCGCCGAGTTCGAGAAGAGCTTTGAGCGCCAAAGTGGGCAACAAG
AAACTGAGCGCCTACTGCAAGAACATCGAGGAACTGAGAAAGACCCACGGCAACACCTTCAAG
ATCGATATAGAGGAACTGCGCCAAGAAGGACCCCGCCGAGCTGTCCAAAGAGGAAAAGGCCAAG
CTGAGACTGACCGACGACGTGATCCTGAATGAGTGGTCCCAGAAGATCGCCAACTTCTTTGAC
ATCGACGACAAGCACCGGCAGCGGTTCAACAACCTGTTCAGCATGGCCCAGCTGCACACAGTG
ATCGACACACCCAGAAGCGGCTTCAGCTCTACCTGCAAAAGATGCACCGCCGAGAACAGGTTC
AGAAGCGAGACAGCCTTCTACAACGACGAGACAGGCGAGTTCACAGAAGGCCACAGCCACC
TGTCAGAGACTGCCCGCTGATACCCAGAGGCCTTTCAGCGGAAAGATCGAGCGGTACATCGAC
AAGCTGGGATACGAGCTGGCCAAGATCAAGGCTAAAGAACTGGAAGGCATGGAAGCTAAAGAA
ATCAAGGTGCCCATCATCCTGGAACAGAACGCCTTCGAGTACGAGGAAAGCCTGCGGAAGTCT
AAGACCGGATCCAACGACAGAGTGATCAACTCCAAGAAAGACCGCGACGGAAAGAAACTGGCC
AAGGCCAAAGAGAACGCCGAGGACAGGCTGAAGGACAAGGACAAGCGGATCAAGGCCTTCAGC
AGCGGCATCTGCCCTTACTGCGGAGATACCATCGGAGATGACGGCGAGATCGACCACATCCTG
CCTAGAAGCCACACACTGAAAATCTACGGGACCGTGTTCAACCCCGAGGGCAATCTGATCTAC
GTGCACCAGAAGTGCAACCAGGCCAAAGCCGACAGCATCTACAAGCTGAGCGATATCAAGGCC
GGCGTGTCAGCCCAGTGGATTGAAGAACAGGTGGCCAACATTAAGGGGTACAAGACCTTCGAG
GTGCTGTCCGCCGAACAGCAGAAGGCCTTTAGATACGCCCTGTTCCTCCAGAACGACAACGAG
GCCTACAAAAAGGTGGTGGACTGGCTGCGGACCGACCAGTCTGCTAGAGTGAACGGCACACAG
AAGTACCTGGCCAAAAAGATCCAAGAGAAGCTCACCAAGATGCTGCCTAACAAGCACCTGAGC
TTCGAGTTCATCCTGGCCGATGCCACCGAGGTGTCAGAGCTGGAAAGGCAGTACGCCAGACAG
AACCCTCTGCTGGCTAAGGCCGAGAAGCAGGCCCCTTCTTCTCACGCCATTGATGCCGTGATG
GCCTTCGTGGCCAGATACCAGAAGGTGTTCAAGGACGGCACCCCCTCCTAACGCCGATGAGGTG
GCAAAACTGGCTATGCTGGACAGCTGGAACCCCGCCTCTAATGAGCCTCTGACAAAGGGCCTG
TCCACGAACCAGAAAATCGAGAAGATGATCAAGAGCGGCGACTACGGCCAGAAAACATGAGA
GAGGTGTTCGGCAAGTCCATCTTCGGAGAGAATGCCATCGGCGAGAGATACAAGCCCATCGTG
GTTCAAGAAGGCGGCTACTACATCGGCTACCCCGCCACAGTGAAAAAGGGCTACGAACTGAAG
AACTGCAAGGTGGTCACCAGCAAGAACGATATTGCCAAGCTGGAAAAGATCATCAAGAACCAG
GACCTGATCTCTCTGAAAGAGAATCAGTACATCAAAATCTTCTCCATCAACAAGCAGACCATC
AGCGAGCTGAGCAACCGCTACTTCAACATGAATTACAAGAACCTGGTCGAGCGGGACAAAGAA
```

TABLE 7-continued

Engineered Cas9 Systems

```
ATTGTGGGACTGCTTGAGTTTATCGTCGAGAACTGCCGGTACTACACCAAGAAAGTGGACGTG
AAGTTCGCCCCTAAGTACATCCACGAGACAAAGTACCCCTTCTACGATGACTGGCGGAGATTC
GACGAGGCCTGGCGGTATCTGCAAGAAAACCAGAACAAGACCAGCTCCAAGGACCGCTTCGTG
ATCGATAAGAGCAGCCTGAACGAGTACTACCAGCCAGACAAGAATGAGTACAAGCTGGACGTG
GACACCCAGCCTATCTGGGACGACTTCTGCCGGTGGTACTTCCTGGACAGATACAAGACCGCC
AACGACAAGAAGTCCATCCGCATCAAGGCCCGCAAGACATTCTCCCTGCTGGCTGAGTCTGGC
GTGCAGGGCAAAGTGTTCCGGGCCAAGAGAAAGATCCCTACCGGCTACGCCTATCAGGCCCTG
CCTATGGACAACAACGTGATCGCTGGCGATTACGCCAACATTCTGCTGGAAGCCAACAGCAAG
ACCCTGAGCCTGGTGCCTAAGAGCGGCATCAGCATTGAGAAGCAGCTGGACAAAAAGCTCGAC
GTCATCAAAAAGACCGACGTGCGCGGCCTGGCAATCGACAACAACTCCTTCTTCAACGCCGAC
TTCGACACACACGGCATCCGGCTGATCGTGGAAAACACCAGCGTGAAAGTGGGAAACTTCCCC
ATCAGCGCCATCGATAAGTCCGCCAAGCGGATGATCTTCAGAGCCCTGTTTGAGAAAGAGAAG
GGGAAGCGCAAGAAAAAGACCACCATCAGCTTCAAAGAAAGCGGCCCTGTGCAGGACTACCTC
AAGGTGTTCCTGAAAAAGATCGTGAAGATCCAGCTGAGAACCGACGGCTCCATCTCCAACATC
GTCGTGCGGAAGAATGCCGCCGATTTCACCCTGAGCTTTAGAAGCGAGCACATCCAGAAACTG
CTGAAGCCCAAGAAGAGGAAGGTG
```

WsuCas9/NLS protein sequence (SEQ ID NO: 24)
MLVSPISVDLGGKNTGFFSFTDSLDNSQSGTVIYDESFVLSQVGRRSKRHSKRNNLRNKLVKR
LFLLILQEHHGLSIDVLPDEIRGLFNKRGYTYAGFELDEKKKDALESDTLKEFLSEKLQSIDR
DSDVEDFLNQIASNAESFKDYKKGFEAVFASATHSPNKKLELKDELKSEYGENAKELLAGLRV
TKEILDEFDKQENQGNLPRAKYFEELGEYIATNEKVKSFFDSNSLKLTDMTKLIGNISNYQLK
ELRRYFNDKEMEKGDIWIPNKLHKITERFVRSWHPKNDADRQRRAELMKDLKSKEIMELLTTT
EPVMTIPPYDDMNNRGAVKCQTLRLNEEYLDKHLPNWRDIAKRLNHGKFNDDLADSTVKGYSE
DSTLLHRLLDTSKEIDIYELRGKKPNELLVKTLGQSDANRLYGFAQNYYELIRQKVRAGIWVP
VKNKDDSLNLEDNSNMLKRCNHNPPHKKNQIHNLVAGILGVKLDEAKFAEFEKELWSAKVGNK
KLSAYCKNIEELRKTHGNTFKIDIEELRKKDPAELSKEEKAKLRLTDDVILNEWSQKIANFFD
IDDKHRQRFNNLFSMAQLHTVIDTPRSGFSSTCKRCTAENRFRSETAFYNDETGEFHKKATAT
CQRLPADTQRPFSGKIERYIDKLGYELAKIKAKELEGMEAKEIKVPIILEQNAFEYEESLRKS
KTGSNDRVINSKKDRDGKKLAKAKENAEDRLKDKDKRIKAFSSGICPYCGDTIGDDEIDHIL
PRSHTLKIYGTVFNPEGNLIYVHQKCNQAKADSIYKLSDIKAGVSAQWIEEQVANIKGYKTFS
VLSAEQQKAFRYALFLQNDNEAYKKVVDWLRTDQSARVNGTQKYLAKKIQEKLTKMLPNKHLS
FEFILADATEVSELRRQYARQNPLLAKAEKQAPSSHAIDAVMAFVARYQKVFKDGTPPNADEV
AKLAMLDSWNPASNEPLTKGLSTNQKIEKMIKSGDYGQKNMREVFGKSIFGENAIGERYKPIV
VQEGGYYIGYPATVKKGYELKNCKVVTSKNDIAKLEKIIKNQDLISLKENQYIKIFSINKQTI
SELSNRYFNMNYKNLVERDKEIVGLLEFIVENCRYYTKKVDVKFAPKYIHETKYPFYDDWRRF
DEAWRYLQENQNKTSSKDRFVIDKSSLNEYYQPDKNEYKLDVDTQPIWDDFCRWYFLDRYKTA
NDKKSIRIKARKTFSLLAESGVQGKVFRAKRKIPTGYAYQALPMDNNVIAGDYANILLEANSK
TLSLVPKSGISIEKQLDKKLDVIKKTDVRGLAIDNNSFFNADFDTHGIRLIVENTSVKVGNFP
ISAIDKSAKRMIFRALFEKEKGKRKKKTTISFKESGPVQDYLKVFLKKIVKIQLRTDGSISNI
VVRKNAADFTLSFRSEHIQKLLKPKKKRKV NsaCas9/NLS DNA sequence (SEQ ID NO: 25)
```
ATGAAGAAGATCCTGGGCGTCGACCTGGGCATCACCAGCTTTGGATACGCCATCCTGCAAGAG
ACAGGCAAGGACCTGTACAGATGCCTGGACAACAGCGTGGTCATGCGGAACAACCCCTACGAC
GAGAAGTCTGGCGAGAGCAGCCAGAGCATCCGCAGCACCCAGAAATCCATGCGGCGGCTGATC
GAGAAGCGGAAGAAACGGATCAGATGCGTGGCCCAGACAATGGAACGCTACGGCATCCTGGAC
TACTCCGAGACAATGAAGATCAACGACCCCAAGAACAACCCGATCAAGACAGATGGCAGCTG
AGAGCCGTGGACGCCTGGAAAAGACCTCTGAGCCCTCAAGAGCTGTTCGCCATCTTTGCCCAC
ATGGCCAAGCACCGGGGCTACAAGTCTATCGCCACCGAGGACCTGATCTACGAGCTGGAACTG
GAACTCGGCCTGAACGACCCTGAGAAAGAGTCCGAGAAGAAGGCCGACGAGCGGAGACAGGTG
TACAACGCCCTGAGCACCTGGAAGAACTGCGGAAGAAGTACGGCCGGCAGACAATCGCCCAG
ACCATCCACAGAGCTGTGGAAGCCGGCGACCTGCGGAGCTACAGAAACCACGACGACTACGAG
AAGATGATCCGCAGAGAGGACATCGAGGAAGAGATTGAGAAGGTCCTGCTGCGGCAGGCTGAA
CTGGGAGCACTTGGACTGCCTGAGGAACAGGTGTCCGAGCTGATCGATGAGCTGAAGGCCTGC
ATCACCGACCAAGAGATGCCCACCATCGACGAGAGCCTGTTCGGCAAGTGCACCTTCTACAAG
GACGAGCTGGCCGCTCCTGCCTACAGCTACCTGTACGACCTGTACCGGCTGTACAAGAAGCTG
GCCGACCTGAACATCGACGGCTACGAAGTGACCCAAGAGGACCGCGAGAAAGTGATCGAGTGG
GTCGAGAAAAGATCGCCCAGGGCAAGAACCTGAAGAAAATCACCCACAAGGACCTCCGGAAG
ATCCTCGGACTGGCCCCTGAGCAGAAGATTTTCGGCGTCGAGGACGAGAATCGTCAAGGGA
AAGAAAGAACCCCGGACCTTCGTGCCCTTCTTCTTCCTGGCCGATATCGCCAAGTTCAAAGAA
CTGTTTGCCAGCATCCAGAAGCACCCCGACGCTCTGCAGATTTTCAGAGAACTGGCCGAGATC
CTGCAGCGGAGCAAGACACCTCAAGAGGGCCCTGGATAGACTGAGAGCCCTGATGGCCGGCAAG
GGCATCGACACCGATGACAGAGAGCTGCTGGAACTCTTCAAGAACAAGCGGAGCGGCACAAGA
GAGCTGAGCCACCGCTATATCCTGGAAGCCCTGCCTCTGTTCCTGGAAGGCTATGACGAGAAA
GAGGTGCAGAGAATCCTGGGCTTTGACGACCGCGAGGACTACAGCAGATACCCCAAGAGCCTG
CGGCATCTGCACCTGAGAGAGGGCAACCTGTTCGAGAAAGAAGAGAATCCCATCAACAACCAC
GCCGTGAAGTCCCTGGCTTCTTGGGCCCTGGGACTGATCGCTGACCTGTCTTGGAGATACGGC
CCCTTCGATGAGATCATCCTGGAAACCACCAGGGACGCCCTGCCTCTGCAAGAAGATCCGGAAAGAA
ATCGACAAGGCCATGCGCGAGAGAGAAAGCCCTGGACAAGATCATCGGCAAGTACAAGAAA
GAGTTCCCCAGCATCGACAAGCGGCTGGCCAGAAAGATTCAGCTGTGGGAGAGACAGAAAGGC
CTCGATCTGTACTCCGGCAAAGTGATCAACCTGAGCCAGCTGCTCGATGGATCCGCCGACATC
GAGCACATCGTGCCTCAGTCTCTCGGCGGCCTGAGCACCGACTACAATACCATCGTGACCCTG
AAGTCCGTGAACGCCGCCAAGGGCAATAGACTGCCTGGCGATTGGCTGGCCGGAAATCCCGAC
TACAGAGAACGGATCGGCATGCTGTCTGAGAAGGGCCTGATCGACTGGAAGAAGAGGAAGAAC
CTGCTGGCCCAGAGCCTGGACGAAATCTACACCGAGAACACCCACAGCAAAGGCATCCGGGCC
ACAAGCTACCTGGAAGCTCTGGTTGCCCAGGTGCTGAAGCGGTACTACCCATTTCCTGATCCT
GAGCTGCGCAAGAATGGCATCGGCGTGCGGATGATCCCCGGAAAAGTGACCAGCAAGACCAGA
```

TABLE 7-continued

Engineered Cas9 Systems

AGCCTGCTGGGAATCAAGAGCAAGAGCCGCGAGACAAACTTCCACCACGCCGAGGATGCCCTG
ATTCTGAGCACACTGACCAGAGGCTGGCAGAACCGGCTGCACAGAATGCTGAGAGACAACTAC
GGCAAGAGCGAGGCCGAGCTGAAAGAACTCTGGAAAAAGTACATGCCCCACATCGAGGGCCTG
ACACTGGCCGACTATATCGATGAGGCCTTCCGGCGGTTCATGAGCAAGGGCGAAGAGTCCCTG
TTCTACCGGGACATGTTCGACACCATCCGGTCCATCAGCTACTGGGTCGACAAGAAGCCTCTG
AGCGCCAGCAGCCACAAAGAAACCGTGTACAGCAGCAGACAGGAGGTGCCCACACTGAGGAAA
AACATTCTGGAAGCCTTCGACAGCCTGAACGTGATCAAGGACCGGCACAAGCTGACCACCGAA
GAGTTCATGAAGCGCTACGACAAAGAGATCCGGCAGAAGCTGTGGCTGCACCGCATCGGCAAC
ACCAACGACGAGTCTTACCGCGCCGTGGAAGAGAGAGCCACACAGATTGCCCAGATCCTGACC
AGATACCAGCTCATGGACGCCCAGAATGACAAAGAAATTGATGAGAAGTTTCAGCAGGCCCTG
AAAGAGCTGATCACAAGCCCCATCGAAGTGACTGGCAAGCTGCTGCGGAAAATGAGATTCGTG
TACGACAAGCTGAACGCCATGCAGATCGACAGAGGCCTGGTGGAAACCGACAAGAACATGCTG
GGCATCCACATCAGCAAGGGCCCCAATGAGAAGCTGATCTTCAGACGGATGGACGTGAACAAC
GCCCACGAGCTGCAAAAAGAACGCAGCGGAATCCTGTGCTACCTGAACGAGATGCTGTTCATC
TTCAACAAGAAGGGGCTGATTCACTACGGCTGCCTGCGGTCTTACCTCGAAAAAGGCCAGGGC
AGCAAGTATATCGCCCTGTTCAACCCTCGGTTCCCCGCCAATCCTAAGGCTCAGCCTAGCAAG
TTCACCAGCGACAGCAAGATCAAGCAAGTCGGCATCGGCAGCGCCACCGGAATCATTAAGGCC
CACCTGGATCTGGATGGCCACGTGCGCTCTTATGAGGTGTTCGGAACACTGCCCGAGGGCAGC
ATCGAGTGGTTCAAAGAGGAAAGCGGCTACGGCAGAGTGGAAGATGACCCTCA<u>CCACCCCAAG
AAGAAGAGGAAGGTG</u>

NsaCas9/NLS protein sequence (SEQ ID NO: 26)
MKKILGVDLGITSFGYAILQETGKDLYRCLDNSVVMRNNPYDEKSGESSQSIRSTQKSMRRLI
EKRKKRIRCVAQTMERYGILDYSETMKINDPKNNPIKNRWQLRAVDAWKRPLSPQELFAIFAH
MAKHRGYKSIATEDLIYELELELGLNDPEKESEKKADERRQVYNALRHLEELRKKYGGETIAQ
TIHRAVEAGDLRSYRNHDDYEKMIRREDIEEEIEKVLLRQAELGALGLPEEQVSELIDELKAC
ITDQEMPTIDESLFGKCTFYKDELAAPAYSYLYDLYRLYKKLADLNIDGYEVTQEDREKVIEW
VEKKIAQGKNLKKITHKDLRKILGLAPEQKIFGVEDERIVKGKKEPRTFVPFFFLADIAKFKE
LFASIQKHPDALQIFRELAEILQRSKTPQEALDRLRALMAGKGIDTDDRELLELFKNKRSGTR
ELSHRYILEALPLFLEGYDEKEVQRILGFDDREDYSRYPKSLRHLHLREGNLFEKEENPINNH
AVKSLASWALGLIADLSWRYGPFDEIILETTRDALPEKIRKEIDKAMREREKALDKIIGKYKK
EFPSIDKRLARKIQLWERQKGLDLYSGKVINLSQLLDGSADIEHIVPQSLGGLSTDYNTIVTL
KSVNAAKGNRLPGDWLAGNPDYRERIGMLSEKGLIDWKKRKNLLAQSLDEIYTENTHSKGIRA
TSYLEALVAQVLKRYYPFPDPELRKNGIGVRMIPGKVTSKTRSLLGIKSKSRETNFHHAEDAL
ILSTLTRGWQNRLHRMLRDNYGKSEAELKELWKKYMPHIEGLTLADYIDEAFRRFMSKGEESL
FYRDMFDTIRSISYWVDKKPLSASSHKETVYSSRHEVPTLRKNILEAFDSLNVIKDRHKLTTE
EFMKRYDKEIRQKLWLHRIGNTNDESYRAVEERATQIAQILTRYQLMDAQNDKEIDEKFQQAL
KELITSPIEVTGKLLRKMRFVYDKLNAMQIDRGLVETDKNMLGIHISKGPNEKLIFRRMDVNN
AHELQKERSGILCYLNEMLFIFNKKGLIHYGCLRSYLEKGQGSKYIALFNPRFPANPKAQPSK
FTSDSKIKQVGIGSATGIIKAHLDLDGHVRSYEVFGTLPEGSIEWFKEESGYGRVEDDPHH<u>PK
KKRKV</u>

RsyCas9/NLS DNA sequence (SEQ ID NO: 27)
ATGGCCGAGAAGCAGCACAGATGGGGACTCGACATCGGCACCAATTCTATCGGCTGGGCCGTG
ATCGCCCTGATCGAAGGCAGACCTGCTGGACTGGTGGCCTACCGGCAGCAGAATCTTTAGCGAC
GGCAGAAACCCCAAGGACGGCAGCTCTCTGGCCGTCGAGAGAAGAGGACCTCGGCAGATGCGG
CGGAGAAGAGACAGATATCTCCGGCGGAGGGACAGATTCATGCAGGCCCTGATCAACGTGGGC
CTGATGCCTGGGGATGCCGCCGTAGAAAAGCCCTGGTCACCGAGAATCCCTACGTGCTGAGA
CAGAGAGGCCTGGACCAAGCTCTGACCCTGCCTGAATTTGGCAGAGCCCTGTTCCACCTGAAC
CAGCGGAGAGGCTTCCAGAGCAACAGAAAGACCGATCGGGCCACCGCCAAAGAAAGCGGCAAA
GTGAAGAACGCCATTGCCGCCTTCAGAGCCGGCATGGGCAATGCCAGAACAGTGGGAGAAGCC
CTGGCCAGACGACTGGAAGATGGCAGACCAGTGCGGGCCAGAATGGTCGGACAGGGCAAAGAT
GAGCACTACGAGCTGTATATCGCCAGAGAGTGGATCGCCCAAGAGTTCGATGCCCTGTGGGCC
AGCCAGCAGAGATTTCATGCTGAGGTGCTGGCCGACGCCGCCAGAGATAGACTGAGAGCCATC
CTGCTGTTCCAGCGGAAGCTGCTGCCTGTGCCTGTGGGCAAGTGCTTCCTGGAACCTAACCAG
CCTAGAGTGGCCGCTGCTCTGCCTAGCGCTCAGAGATTCAGACTGATGCAAGAGCTGAACCAC
CTGAGAGTGATGACCCTGGCCGACAAGAGAGAGAGGCCCCTGAGCTTCAAGAGAGAAACGAT
CTGCTGGCCCAGCTGGTGGCCAGACCTAAGTGCGGCTTCGACATGCTGCGGAAGATCGTGTTC
GGCGCCAACAAAGAGGCCTACAGATTCACCATCGAGAGCGAGCGGCGGAAAGAACTGAAGGGC
TGTGATACAGCCGCCAAGCTGGCCAAAGTGAATGCCCTGGGAACTAGATGGCAGGCTCTGTCC
CTGGACGAGCAGGATAGACTCGTGTGCCTGCTGCTGGACGGCGAGAATGATGCTGTGCTGGCT
GATGCCCTGCGGGAACACTATGGACTGACAGACGCCCAGATCGACACACTGCTGGGCCTGTCT
TTTGAGGACGGCCACATGAGACTGGGGAGAAGCGCTCTGCTGAGAGTCCTGGATGCCCTGGAA
TCCGGAAGAGATGAGCAGGGACTGCCCCTGTCCTACGATAAGGCTGTTGTGGCTGCCGGCTAT
CCAGCTCACACAGCCGATCTGGAAAACGGCGAGAGAGATGCACTGCCCTACTACGGCGAGCTG
CTGTGGCGGTATACACAGGATGCCCCTACCGCCAAGAACGACGCCGAGAGAAAGTTCGGCAAG
ATCGCCAATCCTACCGTGCACATCGGCCTGAATCAGCTGAGAAAGTTGTCAATGCCCTGATC
CAGAGATACGGCAAGCCCGCTCAGATCGTGGTGGAACTGGCCAGAAATCTGAAGGCTGGCCTG
GAAGAGAAAGAGCGGATCAAGAACAGCAGACGCCAACCTGGAACGAGAACGAGAGAATCCGG
CAGAAGCTGCAGGACGCTGGCGTGCCCGACAACAGAGAAAACCGGCTGCGGATGCGGCTGTTC
GAGGAACTCGGACAAGGCAATGGACTGGGCACCCCTTGCATCTACTCCGGCAGACAGATCAGC
CTGCAGAGACTGTTCAGCAACGACGTGCAGGTCGACCACATCCTGCCTTTCAGCAAGACCCTG
GATGACAGCTTCGCCAACAAGGTGCTCGCCCAGCACGACGTGCAACAGATACAAGGGCAACAGA
GGCCCTTTCGAGGGCCTTCGGAGCCAACAGAGATGGCTACGCCTGGGACGACATTAGAGCCAGA
GCAGCCGTGCTGCCCCGGAACAAGAGAAACAGATTTGCCGAGACAGCCATGCAGGACTGGCTG
CACAACGAGACTGACTTTCTGGCTCGGCAGCTGACCGATACCGCCTACCTTAGCAGAGTGGCC
AGGCAGTACCTGACCGCCATCTGCAGCAAGGACGACGTGTACGTTAGCCCCGGCAGACTGACT
GCCATGCTGAGAGCTAAGTGGGGCCTGAACAGAGTGCTGGATGGCGTGATGGAAGAACAGGGC TABLE 7-continued Engineered Cas9 Systems AGACCCGCCGTGAAGAACCGGGATGATCACAGACACCACGCCATCGACGCCGTGGTTATTGGC
GCCACAGATAGAGCCATGCTGCAACAGGTGGCCACACTGGCCGCTAGAGCTAGAGAACAGGAC
GCCGAAAGGCTGATCGGCGACATGCCTACGCCTTGGCCTAATTTCCTTGAGGACGTGCGGGCT
GCCGTGGCCAGATGTGTGGTTTCTCACAAGCCCGACCACGGACCAGAAGGCGGCCTGCATAAC
GATACAGCCTACGGCATTGTGGCCGGACCATTCGAGGATGGCAGATACAGAGTGCGGCACCGG
GTGTCCCTGTTCGATCTGAAACCTGGCGACCTGAGCAACGTCCGCTGTGATGCTCCTCTGCAA
GCCGAGCTGGAACCCATCTTCGAGCAGGACGATGCCAGGGCCAGAGAAGTGGCTCTTACAGCC
CTGGCTGAGCGGTACAGACAGCGGAAAGTGTGGCTGGAAGAACTGATGAGCGTGCTGCCTATC
AGACCCAGAGGCGAGGACGGAAAGACCCTGCCAGATAGCGCTCCTTACAAGGCCTACAAGGGC
GACTCCAACTACTGCTATGAGCTGTTCATCAATGAGCGCGGCAGATGGGATGGCGAGCTGATC
TCTACCTTCCGGGCCAATCAGGCCGCTTACCGGCGGTTCAGAAATGACCCAGCCAGGTTCAGA
AGATACACCGCTGGCGGTAGACCCCTGCTGATGAGACTGTGTATCAACGACTATATCGCCGTG
GGCACAGCCGCCGAGAGGACCATCTTTAGAGTGGTCAAGATGAGCGAGAACAAGATCACTCTG
GCCGAGCACTTCGAAGGCGGAACCCTGAAACAGAGGGATGCCGACAAGGACGATCCCTTCAAG
TATCTGACAAAGAGCCCTGGCGCTCTGCGCGATCTGGGAGCTAGAAGAATCTTCGTGGACCTG
ATCGGCCGCGTGCTGGACCCAGGCATTAAGGGCGAT<u>CCCAAGAAGAAGAGGAAGGTG</u>

RsyCas9/NLS protein sequence (SEQ ID NO: 28)
MAEKQHRWGLDIGTNSIGWAVIALIEGRPAGLVATGSRIFSDGRNPKDGSSLAVERRGPRQMR
RRRDRYLRRRDRPMQALINVGLMPGDAAARKALVTENPYVLRQRGLDQALTLPEFGRALFHLN
QRRGFQSNRKTDRATAKESGKVKNAIAAFRAGMGNARTVGEALARRLEDGRPVRARMVGQKD
EHYELYIAREWIAQEFDALWASQQRFHAEVLADAARDRLRAILLFQRKLLPVPVGKCFLEPNQ
PRVAAALPSAQRFRLMQELNHLRVMTLADKRERPLSFQERNDLLAQLVARPKCGFDMLRKIVF
GANKEAYRFTIESERRKELKGCDTAAKLAKVNALGTRWQALSLDEQDRLVCLLLDGENDAVLA
DALREHYGLTDAQIDTLLGLSFEDGHMRLGRSALLRVLDALESGRDEQGLPLSYDKAVVAAGY
PAHTADLENGERDALPYYGELLWRYTQDAPTAKNDAERKFGKIANPTVHIGLNQLRKLVNALI
QRYGKPAQIVVELARNLKAGLEEKERIKKQQTANLERNERIRQKLQDAGVPDNRENRLRMRLF
EELGQGNGLGTPCIYSGRQISLQRLFSNDVQVDHILPFSKTLDDSFANKVLAQHDANRYKGNR
GPFEAFGANRDGYAWDDIRARAAVLPRNKRNRFAETAMQDWLHNETDFLARQLTDTAYLSRVA
RQYLTAICSKDDVYVSPGRLTAMLRAKWGLNRVLDGVMEEQGRPAVKNRDDHRHHAIDAVVIG
ATDRAMLQQVATLAARAREQDAERLIGDMPTPWPNFLEDVRAAVARCVVSHKPDHGPEGGLHN
DTAYGIVAGPFEDGRYRVRHRVSLFDLKPGDLSNVRCDAPLQAELEPIFEQDDARAREVALTA
LAERYRQRKVWLEELMSVLPIRPRGEDGKTLPDSAPYKAYKGDSNYCYELFINERGRWDGELI
STFRANQAAYRRFRNDPARFRRYTAGGRPLLMRLCINDYIAVGTAAERTIFRVVKMSENKITL
AEHFEGGTLKQRDADKDDPFKYLTKSPGALRDLGARRIFVDLIGRVLDPGIKGD<u>PKKKRKV</u>

CdiCas9/NLS DNA sequence (SEQ ID NO: 29)
ATGAAGTACCACGTGGGCATCGACGTGGGCACCTTTTCTGTTGGACTGGCCGCCATCGAAGTG
GACGATGCCGGAATGCCTATCAAGACCCTGAGCCTGGTGTCCCACATCCACGATTCTGGACTG
GACCCCGACGAGATCAAGAGCGCCGTTACAAGACTGGCCAGCAGCGGCGAATCGCCAGAAGAACC
AGACGGCTGTACCGGCGGAAGAGAAGAAGGCTGCAGCAGCTGGACAAGTTCATCCAGAGACAA
GGCTGGCCCGTGATCGAGCTGGAAGATTACAGCGACCCTCTGTACCCCTGGAAAGTGCGGGCT
GAACTGGCTGCCAGCTATATCGCCGATGAGAAAGAGCGGGCGAGAAGCTGTCTGTGGCCCTG
AGACACATTGCCAGACACAGAGGATGGCGGAACCCCTACGCCAAGGTGTCCTCTCTGTATCTG
CCTGACGGCCCTAGCGACGCCTTCAAGGCCATCAGAGAGGAAATCAAGAGAGCCAGCGGCCAG
CCTGTGCCTGAAACAGCTACAGTGGGCCAGATGGTCACCCTGTGTGAACTGGGCACCCTGAAG
TTGAGAGGCGAAGGCGGAGTGCTGTCTGCCAGACTCCAGCAGAGCGATTACGCCAGAGAGATC
CAAGAGATTTGCCGGATGCAAGAGATCGGCCAAGAGCTGTACAGAAAGATCATCGATGTGGTG
TTCGCCGCCGAGTCTCCTAAGGGATCTGCCTCTAGCAGAGTGGGCAAAGACCCTCTGCAGCCC
GGCAAGAATAGAGCCCTGAAAGCCTCCGATGCCTTCCAGAGATACCGGATCGCCGCTCTGATC
GGCAACCTGAGAGTTAGAGTGGACGGCGAGAAGAGGATTCTGAGCGTGGAAGAGAAAAACCTG
GTGTTCGACCACCTGGTCAATCTGACCCCTAAGAAAGAACCCGAGTGGGTCACAATCGCCGAG
ATCCTGGGAATCGACAGAGGCCAGCTGATCGGAACCGCCACCATGACAGATGATGGCGAAAGA
GCCGGCGCTCGGCCTCCTACACATGACACCAATCGGAGCATCGTGAACAGCAGAATCGCCCCT
CTGGTGGACTGGTGGAAAACCGCCTCTGCTCTGGAACAGCACGCTATGGTCAAGGCCCTGTCC
AATGCCGAGGTGGACGACTTCGATTCTCCTGAGGGCGCCAAAGTGCAGGCCTTCTTTGCCGAC
CTGGACGACGATGTGCACGCCAAGCTGGATAGCCTGCATCTGCCTGTTGGCAGAGCCGCCTAC
AGCGAGGATACACTTGTGCGGCTGACCAGACGGATGCTGAGTGATGGCGTGGACCTGTACACC
GCCAGACTGCAAGAGTTTGGCATCGAGCCTAGCTGGACCCCTCCAACACCTAGAATCGGAGAG
CCCGTGGGAAACCCCGCTGTGGACAGAGTGCTGAAAACCGTGTCCAGATGGCTGGAAAGCGCC
ACCAAAAACATGGGGCGCTCCCGAGAGAGTGATCATCGAACACGTGCGCGAGGGCTTCGTGACC
GAGAAAAGGGCCAGAGAAATGGATGGCGACATGCGGAGAAGGGCCGCCAGAAATGCCAAGCTG
TTCCAAGAAATGCAAGAAAAGCTGAACGTGCAGGGCAAGCCCTCCAGAGCCGACCTTTGGAGA
TACCAGAGCGTGCAGAGACAGAACTGCCAGTGCGCCTACTGTGGCAGCCCTATCACCTTCAGC
AACAGCGAGATGGACCACATCGTGCCTAGAGCCGGCCAGGGATCCACCAACACCAGAGAAAAT
CTGGTGGCCGTGTGCCACAGATGCAACCAGACCAAGGGCAACACCCCATTCGCCATCTGGGCC
AAGAACACCTCTATCGAGGGCGTGTCCGTGAAAGAAGCCGTGGAAAGAACCAGGCACTGGGTC
ACCGATACCGGCATGAGAAGCACCGACTTCAAGAAATTCACCAAGGCCGTGGTGGAACGGTTC
CAGAGGGCCACAATGGACGAGGAAATTGACGCCCGCAGCATGGAAAGCGTGGCCTGGATGCCG
AATGAGCTGAGAAGTAGAGTGGCCCAGCACTTCGCCAGCCACGGCACAACAGTCAGAGTGTAC
AGAGGCAGCCTGACCGCCAAGCTCGTAGAGCCTCTGGAATCAGCGGCAAGCTGAAGTTCTTT
GACGGCGTGGGCAAGAGCAGACTGGACAGAAGGCACCACGCCATTGATGCCGCCGTGATCGCC
TTCACCAGCGACTATGTGGCCGAAACACTGGCCGTGCGGAGCAACCTCAAACAGAGCCAGGCT
CACAGACAAGAGGCTCCTCAGTGGCGCGAGTTCACAGGCAAAGATGCCGAACACAGAGCCGCT
TGGAGAGTGTGGTGCCAGAAGATGGAAAAACTGAGCGCCCTGCTGACCGAGGACCTGAGAGAT
GATAGAGTGGTGGTCATGAGCAACGTGCGCCTGAGACTCGGAAATGGCAGCGCCCACAAAGAG
ACAATCGGAAAGCTGAGCGAAAGTGAAGCTGTCCAGCCAGCTGAGCGTGTCCGACATCGATAAG
GCCAGCTCTGAGGCCCCTTTGGTGCGCCCTGACAAGAGAACCTGGCTTCGACCCCAAAGAGGGA TABLE 7-continued Engineered Cas9 Systems

```
CTGCCTGCCAATCCTGAGCGGCACATCAGAGTGAATGGCACCCATGTGTACGCCGGCGACAAC
ATCGGCCTGTTTCCAGTGTCTGCCGGATCTATCGCTCTGAGAGGCGGATATGCCGAGCTGGGC
AGCTCTTTCCATCACGCCAGGGTGTACAAGATCACAAGCGGCAAGAAACCCGCCTTTGCCATG
CTGAGAGTGTATACCATCGACCTGCTGCCTTACCGGAACCAGGACCTGTTCAGCGTGGAACTG
AAGCCCCAGACCATGAGCATGAGACAGGCCGAGAAGAAGCTGAGGGACGCCCTGGCTACAGGC
AACGCCGAATATCTTGGATGGCTGGTGGTGGATGACGAGCTGGTGGTCGATACCAGCAAGATC
GCCACCGACCAAGTGAAGGCTGTGGAAGCCGAACTGGGAACCATCAGACGTTGGCGCGTGGAC
GGCTTTTTCAGCCCCTCTAAGCTGAGACTGCGGCCCCTGCAGATGAGCAAAGAGGGCATCAAG
AAAGAGAGCGCCCCTGAGCTGTCCAAGATCATTGACAGACCTGGCTGGCTGCCCGCCGTGAAC
AAGCTGTTTTCTGACGGCAACGTGACCGTCGTGCGGAGAGATTCTCTGGGCAGAGTGCGCCTG
GAAAGCACAGCACATCTGCCCGTGACATGGAAGGTGCAGCCCAAGAAGAAGAGGAAGGTG

CdiCas9/NLS protein sequence (SEQ ID NO: 30)
MKYHVGIDVGTFSVGLAAIEVDDAGMPIKTLSLVSHIHDSGLDPDKIKSAVTRLASSGIARRT
RRLYRRKRRLQQLDKFIQRQGWPVIELEDYSDPLYPWKVRAELAASYIADEKERGEKLSVAL
RHIARHRGWRNPYAKVSSLYLPDEPSDAFKAIREEIKRASGQPVPETATVGQMVTLCELGTLK
LRGEGGVLSARLQQSDHAREIQEICRMQEIGQELYRKIIDVVFAAESPKGSASSRVGKDPLQP
GKNRALKASDAFQRYRIAALIGNLRVRVDGEKRILSVEEKNLVFDHLVNLAPKKEPEWVTIAE
ILGIDRGQLIGTATMTDDGERAGARPPTHDTNRSIVNSRIAPLVDWWKTASALEQHAMVKALS
NAEVDDFDSPEGAKVQAFFADLDDDVHAKLDSLHLPVGRAAYSEDTLVRLTRRMLADGVDLYT
ARLQEFGIEPSWTPPAPRIGEPVGNPAVDRVLKTVSRWLESATKTWGAPERVIIEHVREGFVT
EKRAREMDGDMRRRAARNAKLFQEMQEKLNVQGKPSRADLWRYQSVQRQNCQCAYCGSPITFS
NSEMDHIVPRAGQGSTNTRENLVAVCHRCNQSKGNTPFAIWAKNTSIEGVSVKEAVERTRHWV
TDTGMRSTDFKKFTKAVVERFQRATMDEEIDARSMESVAWMANELRSRVAQHFASHGTTVRVY
RGSLTAEARRASGISGKLEFLDGVGKSRLDRRHHAIDAAVIAFTSDYVAETLAVRSNLKQSQA
HRQEAPQWREFTGKDAEHRAAWRVWCQKMEKLSALLTEDLRDDRVVVMSNVRLRLGNGSAHEE
TIGKLSKVKLGSQLSVSDIDKASSEALWCALTREPDFDPKDGLPANPERHIRVNGTHVYAGDN
IGLFPVSAGSIALRGGYAELGSSFHHARVYKITSGKKPAFAMLRYRNQDLFSVEL
KPQTMSMRQAEKKLRDALATGNAEYLGWLVVDDELVVDTSKIATDQVKAVEAELGTIRRWVD
GFFGDTRLRLRPLQMSKEGIKKESAPELSKIIDRPGWLPAVNKLFSEGNVTVVRRDSLGRVRL
ESTAHLPVTWKVQPKKKRKV Bsm Cas9 sgRNA (SEQ ID NO: No 31)
NNNNNNNNNNNNNNNNNNNNGUCAUAGUUCCCCUAAGAUUAUUGAAACAAUGAUCUUAGGGUU
ACUAUGAUAAGGGCUUUCUACUUUAGGGGUAGAGAUGUCCCGCGGCGUUGGGGAUCGCCUAUU
GCCCUUAAAGGGCACUCCCCAUUUUAAUUUUUUU Lrh Cas9 sgRNA (SEQ ID NO: 32)
NNNNNNNNNNNNNNNNNNNNGUCUCAGGUAGAUGUCAGAUCAAUCAGAAAUGAUUGAUCUGAC
AUCUACGAGUUGAGAUCAAACAAAGCUUCAGCUGAGUUUCAAUUUCUGAGCCCAUGUUGGGCC
AUACAUAUGCCACCCGAGUGCAAAUCGGGUGGCUUUUUUU Pex Cas9 sgRNA (SEQ ID NO: 33)
NNNNNNNNNNNNNNNNNNNNGUUUCAGUAGUUGUUAGAAGAAUGAAAAUUCUUUUUAACAACGA
AGUCGCCUUCGGGCGAGCUGAAAUCAAUUUGAUUAAAUAUUAGAUCCGGCUACUGAGGUCUUU
GACCUUAUCCGGAUUAACGAAGAGCCUCCGAGGAGGCUUUUUUU Mca Cas9 sgRNA (SEQ ID NO: 34)
NNNNNNNNNNNNNNNNNNNNGUUUAGUGUUGUACAAUAUUGGGUGAAAACCCAAAUAUUGU
ACAUCCUAAAUCAAGGCGCUUAAUUGCUGCCGUAAUUGCUGAAAGCGUAGCUUUCAGUUUUUU
U Mga Cas9 sgRNA (SEQ ID NO: 35)
NNNNNNNNNNNNNNNNNNNNGUUUUAGCACUGUACAAUACUUGUGUAAGCAAUAACGAAAAUU
AUUGCUUACACAAUUAUUGUCGUGCUAAAAUAAGGCGCUGUUAAUGCAGCUGCCGCAUCCGCC
AGAGCAUUUAUGCUCUGGCUUUUUUU Agl Cas9 sgRNA (SEQ ID NO: 36)
NNNNNNNNNNNNNNNNNNNNGUUUUGCCUUGUUCGUGAAUCCAAAGUAAGGCAUGGUAgaaaUAUUAUU
CCUGUGGAUUCAAGACAAAAUUUGAAAUGCAAACCGAUUCCCCGGCUGCAAGCCAGCCACACC
GGUCUUUCAAAGCAUUUUUU Amu Cas9 sgRNA (SEQ ID NO: 37)
NNNNNNNNNNNNNNNNNNNNGUUUUGCCUUGAAUCCAAAACGGAUUCAAGACAAAAUUUGAAA
UGCAAACCGAUUUUCCUGACUGCCAGCCAGUCACACCGGUAACAAAAGCAUUUUUU Oki Cas9 sgRNA (SEQ ID NO: 38)
NNNNNNNNNNNNNNNNNNNNGCUUCAGAUGUGUGUCAGAUCAAUGAgaaaUCAUUGAUCUGAC
ACACAGCAUUGAAGUAAAGCAAGAUUAAUUUCAAGCUUAAUUUUCUUCACAUUUUAUGUGCAG
AAGGGCUUAUGCCCACAAUACAUAAAAAGUCCGCAUUCACUUGCGGACUUUUAUUUUUU Bbo Cas9 sgRNA (SEQ ID NO: 39)
NNNNNNNNNNNNNNNNNNNNGUUUCAAAUUCAAUCUAAAGCGAAAGCUAUACUUAUUAUUGAA
UUUGAAAUAAGGCUGUUCCUUCGUUAGUUCAGUCGAUUGCUCCUCCGGUAUUGCUUAUGCAUG
CCGGAGUUUUUU
```

TABLE 7-continued

Engineered Cas9 Systems

Ace Cas9 sgRNA (SEQ ID NO: 40)
NNNNNNNNNNNNNNNNNNNNNGCUGGGGAGCCUGUCUGAAAAGACAGGCUACCUAGCAAGACCC
CUUCGUGGGGUCGCAUUCUUCACCCCCUCGCAGCAGCGAGGGGGUUCGUUUUUUU

Ahe Cas9 sgRNA (SEQ ID NO: 41)
NNNNNNNNNNNNNNNNNNNNNNGUCAUAGUUCCCUCACAAGCCUCGAUGUGGAAACACAUCAAGG
CUUGCGAGGUUGCUAUGAUAAGGCAACAGGCCGCAAAGCACUGACCCGCAUUCCAAUGAAUGC
GGGUCAUCUACUUUUUUU

Wsu Cas9 sgRNA (SEQ ID NO: 42)
NNNNNNNNNNNNNNNNNNNNNGUUUCACAGGCUAAGCGGAUUUGCgaaaGCAAAUCCGUUCGAU
GCCUUGAAAUCAUCAAAAAGAUAUAAUAGACCCGCCCACUGUAUUGUACAUGGCGGGACUUUU
UUU Nsa Cas9 sgRNA (SEQ ID NO: 43)
NNNNNNNNNNNNNNNNNNNNNGUUAUAAGACCCCUCAAAACCCCACCCUGUUACAAUGUUGUAA
CAGGGUAGGGUUAUUUGAGGGGUCUUAUAAUCAAGAACUGUUACAACAGUUCCAUUCUAGGGC
CCAUCUUCGGACGGGCCUCAGCCUUUUUUU Rsy Cas9 sgRNA (SEQ ID NO: 44)
NNNNNNNNNNNNNNNNNNNNNGUUGUAGCCAGAGCGCAAUUCCCGAUCUGCUGAAAAGCAGAUC
GGGAAUUGCGCUUUGCUACUAACAAGCUGAAUCCGUUAGGAGUAAAUGCACCAAAUGAGAGGG
CCGGCUUAUGCCGGCCCUUUGCUUUUUUU Cdi Cas9 sgRNA (SEQ ID NO: 45)
NNNNNNNNNNNNNNNNNNNNNNACUGGGGUUCAGUUCUCAAAAACCCUGAUAGACUUCGAAAAGU
CACUAACUUAAUUAAAUAGAACUGAACCUCAGUAAGCAUUGGCUCGUUUCCAAUGUUGAUUGC
UCCGCCGGUGCUCCUUAUUAUUAAGGGCGCCGGCUUUCUUUUUUU PexCas9-HN1HB1 fusion (SEQ ID NO: 117)
**MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD**TGSGMGKTHIIGVGLDLGGTYTGTFI
TSHPSDEAEHRDHSSAFTVVNSEKLSFSSKSRTAVRHRVRSYKGFDLRRRLLLLVAEYQLLQK
KQTLAPEERENLRIALSGYLKRRGYARTEAETDTSVLESLDPSVFSSAPSFTNFFNDSEPLNI
QWEAIANSPETTKALNKELSGQKEADFKKYIKTSFPEYSAKEILANYVEGRRAILDASKYIAN
LQSLGHKHRSKYLSDILQDMKRDSRITRLSEAFGSTDNLWRIIGNISNLQERAVRWYFNDAKF
EQGQEQLDAVKLKNVLVRALKYLRSDDKEWSASQKQIIQSLEQSGDVLDVLAGLDPDRTIPPY
EDQNNRRPPEDQTLYLNPKALSSEYGEKWKSWANKFAGAYPLLTEDLTEILKNTDRKSRIKIR
SDVLPDSDYRLAYILQRAFDRSIALDECSIRRTAEDFENGVVIKNEKLEDVLSGHQLEEFLEF
ANRYYQETAKAKNGLWFPENALLERADLHPPMKNKILNVIVGQALGVSPAEGTDFIEEIWNSK
VKGRSTVRSICNAIENERKTYGPYFSEDYKFVKTALKEGKTEKELSKKFAAVIKVLKMVSEVV
PFIGKELRLSDEAQSKFDNLYSLAQLYNLIETERNGFSKVSLAAHLENAWRMTMTDGSAQCCR
LPADCVRPFDGFIRKAIDRNSWEVAKRIAEEVKKSVDFTNGTVKIPVAIEANSFNFTASLTDL
KYIQLKEQKLKKKLEDIQRNEENQEKRWLSKEERIRADSHGICAYTGRPLDDVGEIDHIIPRS
LTLKKSESIYNSEVNLIFVSAQGNQEKKNNIYLLSNLAKNYLAAVFGTSDLSQITNEIESTVL
QLKAAGRLGYFDLLSEKERACARHALFLNSDSEARRAVIDVLGSRRKASVNGTQAWFVRSIFS
KVRQALAAWTQETGNELIFDAISVPAADSSEMRKRFAEYRPEFRKPKVQPVASHSIDAMCIYL
AACSDPFKTKRMGSQLAIYEPINFDNLFTGSCQVIQNTPRNFSDKTNIANSPIFKETIYAERF
LDIIVSRGEIFIGYPSNMPFEEKPNRISIGGKDPFSILVLGAYLDKAPSSEKEKLTIYRVVK
NKAFELFSKVAGSKFTAEEDKAAKILEALHFVTVKQDVAATVSDLIKSKKELSKDSIENLAKQ
KGCLKKVEYSSKEFKFKGSLIIPAAVEWGKVLWNVFKENTAEELKDENALRKALEAAWPSSFG
TRNLHSKAKRVFSLPVVATQSGAVRIRRKTAFGDFVYQSQDTNNLYSSFPVKNGKLDWSSPII
HPALQNRNLTAYGYRFVDHDRSISMSEFREVYNKDDLMRIELAQGTSSRRYLRVEMPGEKFLA
WFGENSISLGSSFKFSVSEVFDNKIYTENAEFTKFLPKPREDNKHNGTIFFELVGPRVIFNYI
VGGAASSLKEIFSEAGKERS<u>PKKKRKV</u>LEGGGGS**GKGDPKKPRGKMSSYAFFVQTCREEHKKK
HPDASVNFSEFSKKCSERWKTMSAKEKGKFEDMAKADKARYEREMKTYIPPKGE**

PexCas9-HN1H1G fusion (SEQ ID NO: 118)
**MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD**TGSGMGKTHIIGVGLDLGGTYTGTFI
TSHPSDEAEHRDHSSAFTVVNSEKLSFSSKSRTAVRHRVRSYKGFDLRRRLLLLVAEYQLLQK
KQTLAPEERENLRIALSGYLKRRGYARTEAETDTSVLESLDPSVFSSAPSFTNFFNDSEPLNI
QWEAIANSPETTKALNKELSGQKEADFKKYIKTSFPEYSAKEILANYVEGRRAILDASKYIAN
LQSLGHKHRSKYLSDILQDMKRDSRITRLSEAFGSTDNLWRIIGNISNLQERAVRWYFNDAKF
EQGQEQLDAVKLKNVLVRALKYLRSDDKEWSASQKQIIQSLEQSGDVLDVLAGLDPDRTIPPY
EDQNNRRPPEDQTLYLNPKALSSEYGEKWKSWANKFAGAYPLLTEDLTEILKNTDRKSRIKIR
SDVLPDSDYRLAYILQRAFDRSIALDECSIRRTAEDFENGVVIKNEKLEDVLSGHQLEEFLEF
ANRYYQETAKAKNGLWFPENALLERADLHPPMKNKILNVIVGQALGVSPAEGTDFIEEIWNSK
VKGRSTVRSICNAIENERKTYGPYFSEDYKFVKTALKEGKTEKELSKKFAAVIKVLKMVSEVV
PFIGKELRLSDEAQSKFDNLYSLAQLYNLIETERNGFSKVSLAAHLENAWRMTMTDGSAQCCR
LPADCVRPFDGFIRKAIDRNSWEVAKRIAEEVKKSVDFTNGTVKIPVAIEANSFNFTASLTDL
KYIQLKEQKLKKKLEDIQRNEENQEKRWLSKEERIRADSHGICAYTGRPLDDVGEIDHIIPRS
LTLKKSESIYNSEVNLIFVSAQGNQEKKNNIYLLSNLAKNYLAAVFGTSDLSQITNEIESTVL
QLKAAGRLGYFDLLSEKERACARHALFLNSDSEARRAVIDVLGSRRKASVNGTQAWFVRSIFS
KVRQALAAWTQETGNELIFDAISVPAADSSEMRKRFAEYRPEFRKPKVQPVASHSIDAMCIYL
AACSDPFKTKRMGSQLAIYEPINFDNLFTGSCQVIQNTPRNFSDKTNIANSPIFKETIYAERF
LDIIVSRGEIFIGYPSNMPFEEKPNRISIGGKDPFSILVLGAYLDKAPSSEKEKLTIYRVVK TABLE 7-continued Engineered Cas9 Systems NKAFELFSKVAGSKFTAEEDKAAKILEALHFVTVKQDVAATVSDLIKSKKELSKDSIENLAKQ
KGCLKKVEYSSKEFKFKGSLIIPAAVEWGKVLWNVFKENTAEELKDENALRKALEAAWPSSFG
TRNLHSKAKRVFSLPVVATQSGAVRIRRKTAFGDFVYQSQDTNNLYSSFPVKNGKLDWSSPII
HPALQNRNLTAYGYRFVDHDRSISMSEFREVYNKDDLMRIELAQGTSSRRYLRVEMPGEKFLA
WFGENSISLGSSFKFSVSEVFDNKIYTENAEFTKFLPKPREDNKHNGTIFFELVGPRVIFNYI
VGGAASSLKEIFSEAGKERS<u>PKKKRKV</u>*LEGGGGS*STDHPKYSDMIVAAIQAEKNRAGSSRQSI
QKYIKSHYKVGENADSQIKLSIKRLVTTGVLKQTKGVGASGSFRLAKSDEP

BsmCas9-HN1HB1 fusion (SEQ ID NO: 119)
MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD*TGSG*MNYKMGLDIGIASVGWAVINLD
LKRIEDLGVRIFDKAEHPQNGESLALPRRIARSARRRLRRRKHRLERIRRLLVSENVLTKEEM
NLLFKQKKQIDVWQLRVDALERKLNNDELARVLLHLAKRRGFKSNRKSERNSKESSEFLKNIE
ENQSILAQYRSVGEMIVKDSKFAYHKRNKLDSYSNMIARDDLEREIKLIFEKQREFNNPVCTE
RLEEKYLNIWSSQRPFASKEDIEKKVGFCTFEPKEKRAPKATYTFQSFIVWEHINKLRLVSPD
ETRALTEIERNLLYKQAFSKNKMTYYDIRKLLNLSDDIHFKGLLYDPKSSLKQIENIRFLELD
SYHKIRKCIENVYGKDGIRMFNETDIDTFGYALTIFKDDEDIVAYLQNEYITKNGKRVSNLAN
KVYDKSLIDELLNLSFSKFAHLSMKAIRNILPYMEQGEIYSKACELAGYNFTGPKKKEKALLL
PVIPNIANPVVMRALTQSRKVVNAIIKKYGSPVSIHIELARDLSHSFDERKKIQKDQTENRKK
NETAIKQLIEYELTKNPTGLDIVKFKLWSEQQGRCMYSLKPIELERLLEPGYVEVDHILPYSR
SLDDSYANKVLVLTKENREKGNHTPVEYLGLGSERWKKFEKFVLANKQFSKKKKQNLLRLRYE
ETEEKEFKERNLNDTRYISKFFANFIKEHLKFADGDGGQKVYTINGKITAHLRSRWDFNKNRE
ESDLHHAVDAVIVACATQGMIKKITEFYKAREQNKESAKKKEPIFPQPWPHFADELKARLSKF
PQESIEAFALGNYDRKKLESLRFVFVSRMPKRSVTGAAHQETLRRCVGIDEQSGKIQTAVKTK
LSDIKLDKDGHFPMYQKESDPRTYEAIRQRLLEHNNDPKKAFQEPLYKPKKNGEPGPVIRTVK
IIDTKNKVVHLDGSKTVAYNSNIVRTDVFEKDGKYYCVPVYTMDIMKGTLPNKAIEANKPYSE
WKEMTEEYTFQFSLFPNDLVRIVLPREKTIKTSTNEEIIKDIFAYYKTIDSATGGLELISHD
RNFSLRGVGSKTLKRFEKYQVDVLGNIHKVKGEKRVGLAAPTNQKKGKTVDSLQSVSD<u>PKKKR</u>
<u>KV</u>*LEGGGGS*GKGDPKKPRGKMSSYAFFVQTCREEHKKKHPDASVNFSEFSKKCSERWKTMSAK
EGKFEDMAKADKARYEREMKTYIPPKGE

BsmCas9-HN1H1G fusion (SEQ ID NO: 120)
MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSDTGSGMNYKMGLDIGIASVGWAVINLD
LKRIEDLGVRIFDKAEHPQNGESLALPRRIARSARRRLRRRKHRLERIRRLLVSENVLTKEEM
NLLFKQKKQIDVWQLRVDALERKLNNDELARVLLHLAKRRGFKSNRKSERNSKESSEFLKNIE
ENQSILAQYRSVGEMIVKDSKFAYHKRNKLDSYSNMIARDDLEREIKLIFEKQREFNNPVCTE
RLEEKYLNIWSSQRPFASKEDIEKKVGFCTFEPKEKRAPKATYTFQSFIVWEHINKLRLVSPD
ETRALTEIERNLLYKQAFSKNKMTYYDIRKLLNLSDDIHFKGLLYDPKSSLKQIENIRFLELD
SYHKIRKCIENVYGKDGIRMFNETDIDTFGYALTIFKDDEDIVAYLQNEYITKNGKRVSNLAN
KVYDKSLIDELLNLSFSKFAHLSMKAIRNILPYMEQGEIYSKACELAGYNFTGPKKKEKALLL
PVIPNIANPVVMRALTQSRKVVNAIIKKYGSPVSIHIELARDLSHSFDERKKIQKDQTENRKK
NETAIKQLIEYELTKNPTGLDIVKFKLWSEQQGRCMYSLKPIELERLLEPGYVEVDHILPYSR
SLDDSYANKVLVLTKENREKGNHTPVEYLGLGSERWKKFEKFVLANKQFSKKKKQNLLRLRYE
ETEEKEFKERNLNDTRYISKFFANFIKEHLKFADGDGGQKVYTINGKITAHLRSRWDFNKNRE
ESDLHHAVDAVIVACATQGMIKKITEFYKAREQNKESAKKKEPIFPQPWPHFADELKARLSKF
PQESIEAFALGNYDRKKLESLRFVFVSRMPKRSVTGAAHQETLRRCVGIDEQSGKIQTAVKTK
LSDIKLDKDGHFPMYQKESDPRTYEAIRQRLLEHNNDPKKAFQEPLYKPKKNGEPGPVIRTVK
IIDTKNKVVHLDGSKTVAYNSNIVRTDVFEKDGKYYCVPVYTMDIMKGTLPNKAIEANKPYSE
WKEMTEEYTFQFSLFPNDLVRIVLPREKTIKTSTNEEIIKDIFAYYKTIDSATGGLELISHD
RNFSLRGVGSKTLKRFEKYQVDVLGNIHKVKGEKRVGLAAPTNQKKGKTVDSLQSVSD<u>PKKKR</u>
<u>KV</u>*LEGGGGS*STDHPKYSDMIVAAIQAEKNRAGSSRQSIQKYIKSHYKVGENADSQIKLSIKRL
VTTGVLKQTKGVGASGSFRLAKSDEP LrhCas9-HN1HB1 fusion (SEQ ID NO: 121)
MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD*TGSG*MTKLNQPYGIGLDIGSNSIGFA
VVDANSHLLRLKGETAIGARLFREGQSAADRRGSRTTRRRLSRTRWRLSFLRDFFAPHITKID
PDFFLRQKYSEISPKDKDRFKYEKRLFNDRTDAEFYEDYPSMYHLRLHLMTHTHKADPREIFL
AIHHILKSRGHFLTPGAAKDFNTDKVDLEDIFPALTEAYAQVYPDLELTFDLAKADDFKAKLL
DEQATPSDTQKALVNLLLSSDGEKEIVKKRKQVLTEFAKAITGLKTKFNLALGTEVDEADASN
WQFSMGQLDDKWSNIETSMTDQGTEIFEQIQELYRARLLNGIVPAGMSLSQAKVADYGQHKED
LELFKTYLKKLNDHELAKTIRGLYDRYINGDDAKPFLREDFVKALTKEVTAHPNEVSEQLLNR
MGQANFMLKQRTKANGAIPIQLQQRELDQIIANQSKYYDWLAAPNVEAHRWKMPYQLDELLN
FHIPYYVGPLITPKQQAESGENVFAWMVRKDPSGNITPYNFDEKVDREASANTFIQRMKTTDT
YLIGEDVLPKQSLLYQKYEVLNELNNVRINNECLGTDQKQRLIREVFERHSSVTIKQVADNLV
AHGDFARRPEIRGLADEKRFLSSLSTYHQLKEILHEAIDDPTKLLDIENIITWSTVFEDHTIF
ETKLAEIEWLDPKKINELSGIRYRGWGQFSRKLLDGLKLGNGHTVIQELMLSNHNLMQILADE
TLKETMTELNQDKLKTDDIEDVINDAYTSPSNKKALRQVLRVVEDIKHAANGQDPSWLFIETA
DGTGTAGKRTQSRQKQIQTVYANAAQELIDSAVRGELEDKIADKASFTDRLVLYFMQGGRDIY
TGAPLNIDQLSHYDIDHILPQSLIKDDSLDNRVLVNATINREKNNVFASTLFAGKMKATWRKW
HEAGLISGRKLRNLMLRPDEIDKFAKGFVARQLVETRQIIKLTEQIAAAQYPNTKIIAVKAGL
SHQLREELDFPKNRDVNHYHHAFDAFLAARIGTYLLKRYPKLAPFFTYGEFAKVDVKKFREFN
FIGALTHAKKNIIAKDTGEIVWDKERDIRELDRIYNFKRMLITHEVYFETADLFKQTIYAAKD
SKERGGSKQLIPKKQGYPTQVYGGYTQESGSYNALVRVAEADTTAYQVIKISAQNASKIASAN
LKSREKGKQLLNEIVVKQLAKRRKNWKPSANSFKIVIPRFGMGTLFQNAKYGLFMVNSDTYYR
NYQELWLSRENQKLLKKLFSIKYEKTQMNHDALQVYKAIIDVEKFFKLYDINQFRAKLSDAI
ERFEKLPINTDGNKIGKTETLRQILIGLQANGTRSNVKNLGIKTDLGLLQVGSGIKLDKDTQI TABLE 7-continued Engineered Cas9 Systems VYQSPSGLFKRRIPLADL<u>PKKKRKV</u>*LEGGGGS***GKGDPKKPRGKMSSYAFFVQTCREEHKKKHP
DASVNFSEFSKKCSERWKTMSAKEKGKFEDMAKADKARYEREMKTYIPPKGE**

LrhCas9-HN1H1G fusion (SEQ ID NO: 122)
**MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD***TGSG*MTKLNQPYGIGLDIGSNSIGFA
VVDANSHLLRLKGETAIGARLFREGQSAADRRGSRTTRRRLSRTRWRLSFLRDFFAPHITKID
PDFFLRQKYSEISPKDKDRFKYEKRLFNDRTDAEFYEDYPSMYHLRLHLMTHTHKADPREIFL
AIHHILKSRGHFLTPGAAKDFNTDKVDLEDIFPALTEAYAQVYPDLELTFDLAKADDFKAKLL
DEQATPSDTQKALVNLLLSSDGEKEIVKKRKQVLTEFAKAITGLKTKFNLALGTEVDEADASN
WQFSMGQLDDKWSNIETSMTDQGTEIFEQIQELYRARLLNGIVPAGMSLSQAKVADYGQHKED
LELFKTYLKKLNDHELAKTIRGLYDRYINGDDAKPFLREDFVKALTKEVTAHPNEVSEQLLNR
MGQANFMLKQRTKANGAIPIQLQQRELDQIIANQSKYYDWLAAPNPVEAHRWKMPYQLDELLN
FHIPYYVGPLITPKQQAESGENVFAWMVRKDPSGNITPYNFDEKVDREASANTFIQRMKTTDT
YLIGEDVLPKQSLLYQKYEVLNELNNVRINNECLGTDQKQRLIREVFERHSSVTIKQVADNLV
AHGDFARRPEIRGLADEKRFLSSLSTYHQLKEILHEAIDDPTKLLDIENIITWSTVFEDHTIF
ETKLAEIEWLDPKKINELSGIRYRGWGQFSRKLLDGLKLGNGHTVIQELMLSNHNLMQILADE
TLKETMTELNQDKLKTDDIEDVINDAYTSPSNKKALRQVLRVVEDIKHAANGQDPSWLFIETA
DGTGTAGKRTQSRQKQIQTVYANAAQELIDSAVRGELEDKIADKASFTDRLVLYFMQGGRDIY
TGAPLNIDQLSHYDIDHILPQSLIKDDSLDNRVLVNATINREKNNVFASTLFAGKMKATWRKW
HEAGLISGRKLRNLMLRPDEIDKFAKGFVARQLVETRQIIKLTEQIAAAQYPNTKIIAVKAGL
SHQLREELDFPKNRDVNHYHHAFDAFLAARIGTYLLKRYPKLAPFFTYGEFAKVDVKKFREFN
FIGALTHAKKNIIAKDTGEIVWDKERDIRELDRIYNFKRMLITHEVYFETADLFKQTIYAAKD
SKERGGSKQLIPKKQGYPTQVYGGYTQESGSYNALVRVAEADTTAYQVIKISAQNASKIASAN
LKSREKGKQLLNEIVVKQLAKRRKNWKPSANSFKIVIPRFGMGTLFQNAKYGLFMVNSDTYYR
NYQELWLSRENQKLLKKLFSIKYEKTQMNHDALQVYKAIIDQVEKFFKLYDINQFRAKLSDAI
ERFEKLPINTDGNKIGKTETLRQILIGLQANGTRSNVKNLGIKTDLGLLQVGSGIKLDKDTQI
VYQSPSGLFKRRIPLADL<u>PKKKRKV</u>*LEGGGGS***STDHPKYSDMIVAAIQAEKNRAGSSRQSIQK
YIKSHYKVGENADSQIKLSIKRLVTTGVLKQTKGVGASGSFRLAKSDEP**

McaCas9-HN1HB1 fusion (SEQ ID NO: 123)
**MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD***TGSG*MEKKRKVTLGFDLGIASVGWAI
VDSETNQVYKLGSRLFDAPDTNLERRTQRGTRRLLRRRKYRNQKFYNLVKRTEVFGLSSREAI
ENRFRELSIKYPNIIELKTKALSQEVCPDEIAWILHDYLKNRGYFYDEKETKEDFDQQTVESM
PSYKLNEFYKKYGYFKGALSQPTESEMKDNKDLKEAFFFDFSNKEWLKEINYFFNVQKNILSE
TFIEEFKKIFSFTRDISKGPGSDNMPSPYGIFGEFGDNGQGGRYEHIWDKNIGKCSIFTNEQR
APKYLPSALIFNFLNELANIRLYSTDKKNIQPLWKLSSIDKLNILLNFLNLPISEKKKKLTST
NINDIVKKESIKSIMLSVEDIDMIKDEWAGKEPNVYGVGLSGLNIEESAKENKFKFQDLKILN
VLINLLDNVGIKFEFKDRSDIIKNLELLDNLYLFLIYQKESNNKDSSIDLFIAKNKSLNIENL
KLKLKEFLLGAGNEFENHNSKTHSLSKKAIDAILPKLLDNNEGWNLEAIKNYDEEIKSQIEDN
SSLMAKQDKKYLNDNFLKDAILPPNVKVTFQQAILIFNKIIQKFSKDFEIDKVVIELAREMTQ
DQENDALKGIAKAQKSKKSLVEERLEANNIDKSVFNDKYEKLIYKIFLWISQDFKDPYTGAKI
SANEIVDNKVEIDHIIPYSLCFDDSSANKVLVHKQSNQEKSNSLPYEYIKQGHSGWNWDEFTK
YVKRVFVNNVDSILSKKERLKKSENLLTTSYDGYEKLGFLARNLNDTRYATILFRDQLNNYAE
HHLIDNKKMFKVIAMNGAVTSFIRKNMSYDNKLRLKDRSDFSHHAYDAAIIALFSNKTKTLYN
LIDPSLNGIISKRSEGYWVIEDRYTGEIKELKKEDWTSIKNNVQARKIAKEIEEYLIDLDDEV
FFSRKTKRKTNRQLYNETIYGIAAKTDEDGITNYYKKEKFSILDDKDIYLRLLREREKFVINQ
SNPEVIDQIIEIIESYGKENNIPSRDEAINIKYTKNKINYNLYLKQYMRSLTKSLDQFSEGFI
NQMIANKTFVLYNPTKNTTRKIKFLRLVNDVKINDIRKNQVINKFNGKNNEPKAFYENINSLG
AIVFKSSANNFKTLSINTQIAIFGDKNWDIEDFKTYNMEKIEKYKEIYGIDKTYNPHSFIFPG
TILLDKQNKEFYYISSIQTVNDQIELKFLNKIEFKNDDNTSGANKPPRRLRFGIKSIMNNYEQ
VDISPFGINKKIFE<u>PKKKRKV</u>*LEGGGGS***GKGDPKKPRGKMSSYAFFVQTCREEHKKKHPDASV
NFSEFSKKCSERWKTMSAKEKGKFEDMAKADKARYEREMKTYIPPKGE**

McaCas9-HN1H1G fusion (SEQ ID NO: 124)
**MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD***TGSG*MEKKRKVTLGFDLGIASVGWAI
VDSETNQVYKLGSRLFDAPDTNLERRTQRGTRRLLRRRKYRNQKFYNLVKRTEVFGLSSREAI
ENRFRELSIKYPNIIELKTKALSQEVCPDEIAWILHDYLKNRGYFYDEKETKEDFDQQTVESM
PSYKLNEFYKKYGYFKGALSQPTESEMKDNKDLKEAFFFDFSNKEWLKEINYFFNVQKNILSE
TFIEEFKKIFSFTRDISKGPGSDNMPSPYGIFGEFGDNGQGGRYEHIWDKNIGKCSIFTNEQR
APKYLPSALIFNFLNELANIRLYSTDKKNIQPLWKLSSIDKLNILLNFLNLPISEKKKKLTST
NINDIVKKESIKSIMLSVEDIDMIKDEWAGKEPNVYGVGLSGLNIEESAKENKFKFQDLKILN
VLINLLDNVGIKFEFKDRSDIIKNLELLDNLYLFLIYQKESNNKDSSIDLFIAKNKSLNIENL
KLKLKEFLLGAGNEFENHNSKTHSLSKKAIDAILPKLLDNNEGWNLEAIKNYDEEIKSQIEDN
SSLMAKQDKKYLNDNFLKDAILPPNVKVTFQQAILIFNKIIQKFSKDFEIDKVVIELAREMTQ
DQENDALKGIAKAQKSKKSLVEERLEANNIDKSVFNDKYEKLIYKIFLWISQDFKDPYTGAKI
SANEIVDNKVEIDHIIPYSLCFDDSSANKVLVHKQSNQEKSNSLPYEYIKQGHSGWNWDEFTK
YVKRVFVNNVDSILSKKERLKKSENLLTTSYDGYEKLGFLARNLNDTRYATILFRDQLNNYAE
HHLIDNKKMFKVIAMNGAVTSFIRKNMSYDNKLRLKDRSDFSHHAYDAAIIALFSNKTKTLYN
LIDPSLNGIISKRSEGYWVIEDRYTGEIKELKKEDWTSIKNNVQARKIAKEIEEYLIDLDDEV
FFSRKTKRKTNRQLYNETIYGIAAKTDEDGITNYYKKEKFSILDDKDIYLRLLREREKFVINQ
SNPEVIDQIIEIIESYGKENNIPSRDEAINIKYTKNKINYNLYLKQYMRSLTKSLDQFSEGFI
NQMIANKTFVLYNPTKNTTRKIKFLRLVNDVKINDIRKNQVINKFNGKNNEPKAFYENINSLG**

TABLE 7-continued

Engineered Cas9 Systems

AIVFKSSANNFKTLSINTQIAIFGDKNWDIEDFKTYNMEKIEKYKEIYGIDKTYNFHSFIFPG
TILLDKQNKEFYYISSIQTVNDQIELKFLNKIEFKNDDNTSGANKPPRRLRFGIKSIMNNYEQ
VDISPFGINKKIFEP*KKKRKV*LEGGGGSSTDHPKYSDMIVAAIQAEKNRAGSSRQSIQKYIKS
HYKVGENADSQIKLSIKRLVTTGVLKQTKGVGASGSFRLAKSDEP

What is claimed is:

1. A system for eukaryotic genome modification comprising (a) an engineered *Bacillus smithii* Cas9 protein comprising a nuclear localization signal (NLS), and (b) an engineered guide RNA, wherein the engineered guide RNA is designed to complex with the engineered *Bacillus smithii* Cas9 protein and the engineered guide RNA comprises a 5' guide sequence designed to hybridize with a target sequence in a double-stranded sequence, and wherein the target sequence is 5' to a protospacer adjacent motif (PAM) comprising the sequence 5'-NNNNCAAA-3', wherein N is A, C, G, or T.

2. The system of claim 1, wherein the engineered *Bacillus smithii* Cas9 protein further comprises at least one heterologous domain and the at least one heterologous domain is a cell-penetrating domain, a marker domain, a chromatin modulating motif, an RNA aptamer binding domain, or combination thereof.

3. The system of claim 1, wherein the engineered *Bacillus smithii* Cas9 protein further comprises (i) at least one modification within a RuvC domain or an HNH domain, such that the engineered *Bacillus smithii* Cas9 protein functions as a nickase; or (ii) at least one modification within a RuvC domain and an HNH domain, such that the engineered *Bacillus smithii* Cas9 protein is catalytically inactive.

4. The system of claim 1, wherein the engineered guide RNA comprises the nucleotide sequence of SEQ ID NO:31.

5. The system of claim 1, wherein the engineered *Bacillus smithii* Cas9 protein further comprises a chromatin modulating motif.

6. The system of claim 1, wherein the engineered *Bacillus smithii* Cas9 protein comprises at least one modification within a RuvC domain or an HNH domain, such that the engineered *Bacillus smithii* Cas9 protein functions as a nickase, and wherein the engineered *Bacillus smithii* Cas9 protein further comprises a cell-penetrating domain, a marker domain, an RNA aptamer binding domain, or combination thereof.

7. The system of claim 1, wherein the engineered *Bacillus smithii* Cas9 protein comprises at least one modification within a RuvC domain and an HNH domain, such that the engineered *Bacillus smithii* Cas9 protein is catalytically inactive, and wherein the engineered *Bacillus smithii* Cas9 protein further comprises a cell-penetrating domain, a marker domain, a chromatin modulating motif, an epigenetic modification domain, a transcriptional regulation domain, an RNA aptamer binding domain, or combination thereof.

8. The system of claim 1, wherein the system is selected from the group consisting of:
(1) a system comprising (a) an engineered *Bacillus smithii* Cas9 protein comprising a NLS, which comprises the amino acid sequence of SEQ ID NO: 2; and (b) an engineered guide RNA, which comprises the nucleotide sequence of SEQ ID NO: 31 designed to hybridize to a target sequence 5' to a PAM comprising the sequence 5'-NNNNCAAA-3', wherein N is A, C, G, or T; and (2) a system comprising (a) an engineered *Bacillus smithii* Cas9 protein comprising a NLS, which comprises the amino acid sequence of SEQ ID NO: 119 or SEQ ID NO: 120; and (b) an engineered guide RNA designed to hybridize to a target sequence 5' to a PAM comprising the sequence 5'-NNNNCAAA-3', wherein N is A, C, G, or T.

9. A plurality of nucleic acids encoding a system for eukaryotic genome modification comprising (a) an engineered *Bacillus smithii* Cas9 protein comprising a nuclear localization signal (NLS); and (b) an engineered guide RNA, wherein the engineered guide RNA is designed to complex with the engineered *Bacillus smithii* Cas9 protein and the engineered guide RNA comprises a 5' guide sequence designed to hybridize with a target sequence in a double-stranded sequence, and wherein the target sequence is 5' to a protospacer adjacent motif (PAM) comprising the sequence 5'-NNNNCAAA-3', wherein N is A, C, G, or T; the plurality of nucleic acids comprising at least one nucleic acid encoding the engineered *Bacillus smithii* Cas9 protein, and at least one nucleic acid encoding the engineered guide RNA.

10. The plurality of nucleic acids of claim 9, wherein the at least one nucleic acid encoding the engineered *Bacillus smithii* Cas9 protein is RNA.

11. The plurality of nucleic acids of claim 9, wherein the at least one nucleic acid encoding the engineered *Bacillus smithii* Cas9 protein is DNA.

12. The plurality of nucleic acids of claim 9, wherein the at least one nucleic acid encoding the engineered *Bacillus smithii* Cas9 protein is codon optimized for expression in a eukaryotic cell.

13. The plurality of nucleic acids of claim 12, wherein the eukaryotic cell is a human cell, a non-human mammalian cell, a non-mammalian vertebrate cell, an invertebrate cell, a plant cell, or a single cell eukaryotic organism.

14. The plurality of nucleic acids of claim 9, wherein the at least one nucleic acid encoding the engineered guide RNA is DNA.

15. The plurality of nucleic acids of claim 9, wherein the at least one nucleic acid encoding the engineered *Bacillus smithii* Cas9 protein is operably linked to a phage promoter sequence for in vitro RNA synthesis or protein expression in a bacterial cell, and the at least one nucleic acid encoding the engineered guide RNA is operably linked to a phage promoter sequence for in vitro RNA synthesis.

16. The plurality of nucleic acids of claim 9, wherein the at least one nucleic acid encoding the engineered *Bacillus smithii* Cas9 protein is operably linked to a eukaryotic promoter sequence for expression in a eukaryotic cell, and the at least one nucleic acid encoding the engineered guide RNA is operably linked to a eukaryotic promoter sequence for expression in a eukaryotic cell.

17. The plurality of nucleic acids of claim 9, wherein the engineered guide RNA comprises the nucleotide sequence of SEQ ID NO:31.

18. At least one vector comprising the plurality of nucleic acids of claim 9, wherein the at least one vector is a plasmid vector, a viral vector, or a self-replicating viral RNA replicon.

19. A eukaryotic cell comprising at least one system comprising (a) an engineered *Bacillus smithii* Cas9 protein comprising a nuclear localization signal (NLS); and (b) an engineered guide RNA, wherein the engineered guide RNA is designed to complex with the engineered *Bacillus smithii* Cas9 protein and the engineered guide RNA comprises a 5' guide sequence designed to hybridize with a target sequence in a double-stranded sequence, and wherein the target sequence is 5' to a protospacer adjacent motif (PAM) comprising the sequence 5'-NNNNCAAA-3', wherein N is A, C, G, or T, wherein the eukaryotic cell is a non-human mammalian cell, a plant cell, a non-mammalian vertebrate cell, an invertebrate cell, or a single cell eukaryotic organism and wherein the eukaryotic cell is in vivo, ex vivo, or in vitro.

20. A human eukaryotic cell comprising at least one system comprising (a) an engineered *Bacillus smithii* Cas9 protein comprising a nuclear localization signal (NLS); and (b) an engineered guide RNA, wherein the engineered guide RNA is designed to complex with the engineered *Bacillus smithii* Cas9 protein and the engineered guide RNA comprises a 5' guide sequence designed to hybridize with a target sequence in a double-stranded sequence, and wherein the target sequence is 5' to a protospacer adjacent motif (PAM) comprising the sequence 5'-NNNNCAAA-3', wherein the human eukaryotic cell is ex vivo, or in vitro.

21. A fusion protein comprising an engineered *Bacillus smithii* Cas9 protein linked to at least one chromatin modulating motif,
wherein the chromatin modulating motif is a high mobility group (HMG) box (HMGB) DNA binding domain, a HMG nucleosome-binding (HMGN) protein, a central globular domain from a histone H1 variant comprising SEQ ID NO: 74, or a combination thereof,
wherein the at least one chromatin modulating motif is linked to the Cas9 protein at its N-terminus, C-terminus, or a combination thereof,
wherein, together with an engineered guide RNA designed to complex with the Cas9 protein, the fusion protein is capable of hybridizing with a target sequence in a double-stranded sequence, and
wherein the target sequence is 5' to a protospacer adjacent motif (PAM) comprising the sequence 5'-NNNNCAAA-3', wherein N is A, C, G, or T.

22. The fusion protein of claim 21, wherein the at least one chromatin modulating motif is a human HMGB1 box A domain, a HMGN1 protein, a human histone H1 central globular domain comprising SEQ ID NO: 74, or a combination thereof.

23. The fusion protein of claim 21, wherein the at least one chromatin modulating motif is linked to the Cas9 protein directly via a chemical bond, indirectly via a linker, or a combination thereof.

24. The fusion protein of claim 21, further comprising at least one nuclear localization signal, at least one cell-penetrating domain, at least one marker domain, or a combination thereof.

25. The fusion protein of claim 21, wherein the fusion protein comprises the amino acid sequence of SEQ ID NO: 119 or SEQ ID NO: 120.

26. A system for eukaryotic genome modification comprising the fusion protein of claim 21 and an engineered guide RNA, wherein the engineered guide RNA comprises the nucleotide sequence of SEQ ID NO:31.

* * * * *

SEQUENCE LISTING

<160> NUMBER OF SEQ ID NOS: 134

<210> SEQ ID NO 1
<211> LENGTH: 3285
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atgaactaca agatgggcct cgacatcgga atcgcctctg ttggatgggc cgtgatcaac      60
ctggacctga agagaatcga ggacctcggc gtgcggatct cgacaaggc tgagcatcct      120
cagaacggcg agtctctggc cctgcctaga agaattgcca aagcgccag acggcggctg      180
cggagaagaa agcacagact ggaacggatc agacggctgc tggtgtccga aacgtgctg      240
accaaagaag agatgaacct gctgttcaag cagaaaaagc agatcgacgt gtggcagctg      300
agagtggacg ccctggaaag aaagctgaac aacgacgagc tggccagagt gctgctgcac      360
ctggccaaga agaggcttc aagagcaac agaaagagcg agcggaacag caaagagagc      420
agcgagttcc tgaagaacat cgaagagaac cagagcattc tggcccagta cagatccgtg      480
ggcgagatga tcgtgaagga cagcaagttc gcctaccaca gcggaacaa gctggacagc      540
tacagcaaca tgatcgccag ggacgatctg aaagagaga tcaagctgat cttcgagaag      600
cagcgcgagt tcaacaaccc cgtgtgcacc gagagactgg aagagaagta cctgaacatc      660
tggtccagcc agcggccttt cgcctccaaa gaggacatcg agaaaaagt gggcttctgc      720
accttcgagc ccaaagagaa aagagcccct aaggccacct acaccttcca gagcttcatc      780
gtgtgggagc acatcaacaa gctgcggctg gtgtctcccg acgagacaag agccctgacc      840
gagatcgagc ggaatctgct gtataagcag gccttcagca gaacaagat gacctactac      900
gacatccgga gctgctgaa cctgagcgac gacatccact tcagggcct gctgtacgac      960
cccaagagca gcctgaagca gattgagaac atccggtttc tggaactgga ctcttaccac      1020
aagatccgga gtgcatcga gaatgtgtac ggcaaggacg gcatccgcat gttcaacgag      1080
acagacatcg acaccttcgg ctacgccctg accatcttca ggacgacga ggatatcgtg      1140
gcctacctgc agaacgagta catcaccaag aacggcaagc gggtgtccaa tctgccaac      1200
aaggtgtacg acaagtccct gatcgacgaa ctgctgaatc tgtccttctc caaattcgcc      1260
cacctgagca tgaaggccat ccggaacatc ctgccttaca tgaacagggg cgaaatctac      1320
agcaaggcct gcgaactggc cggctacaac ttcacaggcc caagaagaa agagaaggcc      1380
ctgctgctgc ctgtgatccc caatatcgcc aatcctgtgg tcatgcgggc cctgacacag      1440
agcagaaagg tggtcaacgc catcatcaag aaatacggat ccccgtgtc catccacatc      1500
gagctggcta gggatctgag ccacagcttc gacgagcgga agaagatcca aggaccag      1560
accgagaacc gcaagaagaa cgaaaccgcc atcaagcagc tgatcgagta cgagctgact      1620
```

-continued

```
aagaacccca ccggcctgga catcgtgaag ttcaaacttt ggagcgagca gcaaggcaga    1680
tgcatgtact ccctgaagcc tattgagctg gaaagactgc tggaacccgg ctacgtggaa    1740
gtggaccaca ttctgcccta cagcagaagc ctggacgaca gctacgccaa caaagtgctg    1800
gtcctgacaa agagaaccg cgaaaagggc aatcacaccc tgtggaata tctcggcctg     1860 ggctctgagc ggtggaagaa attcgagaag ttcgtgctgg ctaacaagca gttctctaag    1920
aagaagaagc agaacctgct ccggctgaga tacgaggaaa ccgaggaaaa agagttcaaa    1980
gagcggaacc tgaacgacac ccggtacatc tccaagttct tcgccaactt catcaaagag    2040
catctgaagt tcgccgacgg cgacggcggc cagaaagtgt acacaatcaa cggcaagatc    2100
accgctcacc tgagaagcag atgggacttc aacaagaacc gggaagagag cgacctgcac    2160
cacgctgtgg atgctgtgat tgtggcctgt gccacacagg gcatgatcaa gaagattacc    2220
gagttctaca aggcccgcga gcagaacaaa gagtccgcca agaaaaaaga acccatcttt    2280
ccccagcctt ggcctcactt cgccgatgag ctgaaggctc ggctgagcaa gttccctcaa    2340
gagtccatcg aggccttcgc tctgggcaac tacgacagaa agaagctgga atccctgcgg    2400
cctgtgttcg tgtccagaat gcccaagaga tccgtgacag cgctgcccca ccaagagaca    2460
ctgagaagat gcgtgggcat cgacgagcag tctggcaaga ttcagaccgc cgtgaaaaca    2520
aagctgagcg acatcaagct ggataaggac ggacacttcc ccatgtacca gaaagagtct    2580
gaccccagaa cctacgaggc catcagacag aggctgctcg aacacaacaa cgaccctaag    2640
aaggcctttc aagagccact gtacaagccc aaaaagaatg gcgagcccgg accagtgatc    2700
cggaccgtga agatcatcga cacaaagaac aaggtggtgc acctggacgg cagcaagaca    2760
gtggcctaca actccaacat cgtgcggacc gacgtgttcg agaaggatgg caagtactac    2820
tgcgtgcccg tgtacactat ggatatcatg aagggcaccc tgcctaacaa ggccatcgaa    2880
gccaacaagc cctactccga gtggaaagag atgaccgaag agtacacgtt ccagttcagt    2940
ctgttcccca cgacctcgt gcgcatcgtg ctgccaagag agaaaaccat caagaccagc    3000
accaacgagg aaatcatcat taaggacatc tttgcctact acaagaccat cgacagcgcc    3060
acaggcggcc tggaactgat ctcccacgat cggaacttca gcctgagagg cgtgggctct    3120
aagacactga gcgctttga aagtatcag gtggacgtgc tgggcaacat ccacaaagtg     3180
aagggcgaga agagagtcgg cctggccgct cctaccaacc agaaaaaggg aaagaccgtg    3240
gacagcctgc agagcgtgtc cgatcccaag aagaaggaga aggtg                   3285
```

<210> SEQ ID NO 2
<211> LENGTH: 1095
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Asn Tyr Lys Met Gly Leu Asp Ile Gly Ile Ala Ser Val Gly Trp
1               5                   10                  15

Ala Val Ile Asn Leu Asp Leu Lys Arg Ile Glu Asp Leu Gly Val Arg
            20                  25                  30

Ile Phe Asp Lys Ala Glu His Pro Gln Asn Gly Glu Ser Leu Ala Leu
        35                  40                  45

Pro Arg Arg Ile Ala Arg Ser Ala Arg Arg Leu Arg Arg Arg Lys
    50                  55                  60
```

-continued

His Arg Leu Glu Arg Ile Arg Arg Leu Leu Val Ser Glu Asn Val Leu
65                  70                  75                  80

Thr Lys Glu Glu Met Asn Leu Leu Phe Lys Gln Lys Lys Gln Ile Asp
                85                  90                  95

Val Trp Gln Leu Arg Val Asp Ala Leu Glu Arg Lys Leu Asn Asn Asp
            100                 105                 110

Glu Leu Ala Arg Val Leu Leu His Leu Ala Lys Arg Arg Gly Phe Lys
        115                 120                 125

Ser Asn Arg Lys Ser Glu Arg Asn Ser Lys Glu Ser Glu Phe Leu
    130                 135                 140

Lys Asn Ile Glu Glu Asn Gln Ser Ile Leu Ala Gln Tyr Arg Ser Val
145                 150                 155                 160

Gly Glu Met Ile Val Lys Asp Ser Lys Phe Ala Tyr His Lys Arg Asn
                165                 170                 175

Lys Leu Asp Ser Tyr Ser Asn Met Ile Ala Arg Asp Asp Leu Glu Arg
            180                 185                 190

Glu Ile Lys Leu Ile Phe Glu Lys Gln Arg Glu Phe Asn Asn Pro Val
        195                 200                 205

Cys Thr Glu Arg Leu Glu Glu Lys Tyr Leu Asn Ile Trp Ser Ser Gln
    210                 215                 220

Arg Pro Phe Ala Ser Lys Glu Asp Ile Glu Lys Lys Val Gly Phe Cys
225                 230                 235                 240

Thr Phe Glu Pro Lys Glu Lys Arg Ala Pro Lys Ala Thr Tyr Thr Phe
                245                 250                 255

Gln Ser Phe Ile Val Trp Glu His Ile Asn Lys Leu Arg Leu Val Ser
            260                 265                 270

Pro Asp Glu Thr Arg Ala Leu Thr Glu Ile Glu Arg Asn Leu Leu Tyr
        275                 280                 285

Lys Gln Ala Phe Ser Lys Asn Lys Met Thr Tyr Tyr Asp Ile Arg Lys
    290                 295                 300

Leu Leu Asn Leu Ser Asp Asp Ile His Phe Lys Gly Leu Leu Tyr Asp
305                 310                 315                 320

Pro Lys Ser Ser Leu Lys Gln Ile Glu Asn Ile Arg Phe Leu Glu Leu
                325                 330                 335

Asp Ser Tyr His Lys Ile Arg Lys Cys Ile Glu Asn Val Tyr Gly Lys
            340                 345                 350

Asp Gly Ile Arg Met Phe Asn Glu Thr Asp Ile Asp Thr Phe Gly Tyr
        355                 360                 365

Ala Leu Thr Ile Phe Lys Asp Asp Glu Asp Ile Val Ala Tyr Leu Gln
    370                 375                 380

Asn Glu Tyr Ile Thr Lys Asn Gly Lys Arg Val Ser Asn Leu Ala Asn
385                 390                 395                 400

Lys Val Tyr Asp Lys Ser Leu Ile Asp Glu Leu Leu Asn Leu Ser Phe
                405                 410                 415

Ser Lys Phe Ala His Leu Ser Met Lys Ala Ile Arg Asn Ile Leu Pro
            420                 425                 430

Tyr Met Glu Gln Gly Glu Ile Tyr Ser Lys Ala Cys Glu Leu Ala Gly
        435                 440                 445

Tyr Asn Phe Thr Gly Pro Lys Lys Lys Glu Lys Ala Leu Leu Leu Pro
    450                 455                 460

Val Ile Pro Asn Ile Ala Asn Pro Val Val Met Arg Ala Leu Thr Gln
465                 470                 475                 480

Ser Arg Lys Val Val Asn Ala Ile Ile Lys Lys Tyr Gly Ser Pro Val

```
                485                 490                 495
Ser Ile His Ile Glu Leu Ala Arg Asp Leu Ser His Ser Phe Asp Glu
            500                 505                 510
Arg Lys Lys Ile Gln Lys Asp Gln Thr Glu Asn Arg Lys Lys Asn Glu
            515                 520                 525
Thr Ala Ile Lys Gln Leu Ile Glu Tyr Glu Leu Thr Lys Asn Pro Thr
            530                 535                 540
Gly Leu Asp Ile Val Lys Phe Lys Leu Trp Ser Glu Gln Gln Gly Arg
545                 550                 555                 560
Cys Met Tyr Ser Leu Lys Pro Ile Glu Leu Glu Arg Leu Leu Glu Pro
                565                 570                 575
Gly Tyr Val Glu Val Asp His Ile Leu Pro Tyr Ser Arg Ser Leu Asp
            580                 585                 590
Asp Ser Tyr Ala Asn Lys Val Leu Val Leu Thr Lys Glu Asn Arg Glu
            595                 600                 605
Lys Gly Asn His Thr Pro Val Glu Tyr Leu Gly Leu Gly Ser Glu Arg
            610                 615                 620
Trp Lys Lys Phe Glu Lys Phe Val Leu Ala Asn Lys Gln Phe Ser Lys
625                 630                 635                 640
Lys Lys Lys Gln Asn Leu Leu Arg Leu Arg Tyr Glu Glu Thr Glu Glu
                645                 650                 655
Lys Glu Phe Lys Glu Arg Asn Leu Asn Asp Thr Arg Tyr Ile Ser Lys
            660                 665                 670
Phe Phe Ala Asn Phe Ile Lys Glu His Leu Lys Phe Ala Asp Gly Asp
            675                 680                 685
Gly Gly Gln Lys Val Tyr Thr Ile Asn Gly Lys Ile Thr Ala His Leu
            690                 695                 700
Arg Ser Arg Trp Asp Phe Asn Lys Asn Arg Glu Glu Ser Asp Leu His
705                 710                 715                 720
His Ala Val Asp Ala Val Ile Val Ala Cys Ala Thr Gln Gly Met Ile
                725                 730                 735
Lys Lys Ile Thr Glu Phe Tyr Lys Ala Arg Glu Gln Asn Lys Glu Ser
            740                 745                 750
Ala Lys Lys Lys Glu Pro Ile Phe Pro Gln Pro Trp Pro His Phe Ala
            755                 760                 765
Asp Glu Leu Lys Ala Arg Leu Ser Lys Phe Pro Gln Glu Ser Ile Glu
            770                 775                 780
Ala Phe Ala Leu Gly Asn Tyr Asp Arg Lys Lys Leu Glu Ser Leu Arg
785                 790                 795                 800
Pro Val Phe Val Ser Arg Met Pro Lys Arg Ser Val Thr Gly Ala Ala
                805                 810                 815
His Gln Glu Thr Leu Arg Arg Cys Val Gly Ile Asp Glu Gln Ser Gly
            820                 825                 830
Lys Ile Gln Thr Ala Val Lys Thr Lys Leu Ser Asp Ile Lys Leu Asp
            835                 840                 845
Lys Asp Gly His Phe Pro Met Tyr Gln Lys Glu Ser Asp Pro Arg Thr
            850                 855                 860
Tyr Glu Ala Ile Arg Gln Arg Leu Leu Glu His Asn Asn Asp Pro Lys
865                 870                 875                 880
Lys Ala Phe Gln Glu Pro Leu Tyr Lys Pro Lys Lys Asn Gly Glu Pro
                885                 890                 895
Gly Pro Val Ile Arg Thr Val Lys Ile Ile Asp Thr Lys Asn Lys Val
            900                 905                 910
```

| | | | | | | | | | | | |
|---|---|---|---|---|---|---|---|---|---|---|---|
Val | His | Leu | Asp | Gly | Ser | Lys | Thr | Val | Ala | Tyr | Asn | Ser | Asn | Ile | Val
    915                 920                 925

Arg | Thr | Asp | Val | Phe | Glu | Lys | Asp | Gly | Lys | Tyr | Tyr | Cys | Val | Pro | Val
    930                 935                 940

Tyr | Thr | Met | Asp | Ile | Met | Lys | Gly | Thr | Leu | Pro | Asn | Lys | Ala | Ile | Glu
945                 950                 955                 960

Ala | Asn | Lys | Pro | Tyr | Ser | Glu | Trp | Lys | Glu | Met | Thr | Glu | Tyr | Thr
                965                 970                 975

Phe | Gln | Phe | Ser | Leu | Phe | Pro | Asn | Asp | Leu | Val | Arg | Ile | Val | Leu | Pro
            980                 985                 990

Arg | Glu | Lys | Thr | Ile | Lys | Thr | Ser | Thr | Asn | Glu | Glu | Ile | Ile | Ile | Lys
        995                 1000                1005

Asp | Ile | Phe | Ala | Tyr | Tyr | Lys | Thr | Ile | Asp | Ser | Ala | Thr | Gly | Gly
    1010                1015                1020

Leu | Glu | Leu | Ile | Ser | His | Asp | Arg | Asn | Phe | Ser | Leu | Arg | Gly | Val
    1025                1030                1035

Gly | Ser | Lys | Thr | Leu | Lys | Arg | Phe | Glu | Lys | Tyr | Gln | Val | Asp | Val
        1040                1045                1050

Leu | Gly | Asn | Ile | His | Lys | Val | Lys | Gly | Glu | Lys | Arg | Val | Gly | Leu
    1055                1060                1065

Ala | Ala | Pro | Thr | Asn | Gln | Lys | Lys | Gly | Lys | Thr | Val | Asp | Ser | Leu
    1070                1075                1080

Gln | Ser | Val | Ser | Asp | Pro | Lys | Lys | Lys | Arg | Lys | Val
    1085                1090                1095

<210> SEQ ID NO 3
<211> LENGTH: 4110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgaccaagc tgaaccagcc ttacggcatc ggcctggaca tcggcagcaa tagcatcggc      60
tttgccgtgg tggacgccaa cagccatctg ctgagactga agggcgagac agccatcggc     120
gccagactgt tagagagggg acagagcgcc gctgacagac ggggaagcag aaccacaaga     180
aggcggctgt ccagaaccag atggcggctg agcttcctgc gggatttctt cgcccctcac     240
atcaccaaga tcgaccccga cttctttctg cggcaaaaat actccgagat cagccccaag     300
gacaaggaca ggtttaagta cgagaagcgg ctgttcaacg accggaccga cgccgagttc     360
tacgaggact accccagcat gtaccacctg agactgcacc tgatgaccca cacacacaag     420
gccgatcctc gggaaatctt cctggccatc accacatccc tgaagtccag aggccacttt     480
ctgacacccg cgctgccaa ggacttcaac accgacaaag tggaccttga ggacatcttc     540
cccgctctga cagaggctta cgcccaggtg taccccgatc tggaactgac cttcgatctg     600
gccaaggccg acgacttcaa ggccaagctg ctggacgaac aggccacacc tagcgacaca     660
cagaaagccc tggtcaacct gctgctgtct agcgacggcg agaaagaaat cgtgaagaag     720
cggaagcagg tcctgaccga gttcgccaag gccatcaccg gcctgaaaac aaagttcaat     780
ctggccctgg caccgaggt ggacgaagct gatgcttcca actggcagtt cagcatgggc     840
cagctggaca caagtggtc caacatcgaa accagcatga ccgaccaggg caccgaaatc     900
ttcgagcaga tccaagagct gtaccgggcc agactgctga acggaattgt gcctgccggc     960
```

```
atgagcctgt ctcaggccaa agtggccgat tacggccagc acaaagagga cctggaactg    1020
ttcaagacct acctgaagaa gctgaacgac cacgagctgg ccaagaccat caggggcctg    1080
tacgatcggt acatcaacgg cgacgacgcc aagccttttc ctgcgcgagga ttttgtgaag    1140 gccctgacca aagaagtgac agctcacccc aacgaggtgt ccgaacagct gctgaacagg    1200
atgggccaag ccaacttcat gctgaagcag cggaccaagg ccaacggcgc cattcctatt    1260
cagctgcagc agagagagct ggaccagatc attgccaacc agagcaagta ctacgactgg    1320
ctggccgctc ctaatcctgt ggaagcccac agatggaaga tgccctacca gctggatgag    1380
ctgctcaact tcacatccc ctactacgtg ggccctctga tcaccc taa acagcaggcc    1440 gagagcggcg agaatgtgtt cgcttggatg gtccgaaagg accccagcgg caacatcacc    1500
ccttacaact tcgacgagaa ggtggacaga gaggccagcg ccaacacctt catccagaga    1560
atgaagacca ccgacacata cctgatcggc gaggacgtgc tgcctaagca gagcctgctg    1620
taccagaaat acgaggtgct gaacgagctg aacaacgtgc ggatcaacaa cgagtgcctg    1680
ggcacagacc agaagcagag actgatcaga gaggtgttcg agcggcacag cagcgtgacc    1740
atcaaacagg tggccgacaa tctggtggcc cacggcgatt ttgccagacg gcctgagatt    1800
agaggactgg ccgatgagaa gcggttcctg agcagcctga gcacctacca ccagctgaaa    1860
gagatcctgc acgaggccat cgacgacccc accaaactgc tggatatcga aacatcatc    1920 acctggtcca ccgtgttcga ggaccacacc atcttcgaga caaagctggc cgagatcgag    1980
tggctggacc ccaagaagat caacgagctg tctggcatca gatacagagg ctggggccag    2040
ttctcccgga agctgctcga tggactgaag cttggcaatg ccacaccgt gattcaagaa    2100 ctgatgctga gcaaccacaa cctgatgcag atcctggccg acgagacact gaaagaaacc    2160
atgacagagc tgaatcagga caagctgaaa accgacgaca tcgaggatgt gatcaacgac    2220
gcctacacaa gccccagcaa caaaaaggcc ctcagacagg tgctgagagt ggtcgaggat    2280
atcaagcacg ccgccaacgg acaggaccct agctggctgt ttatcgaaac cgccgatgga    2340
acaggcaccg ccggcaagag aacacagagc cggcagaaac agatccagac cgtgtacgcc    2400
aacgccgctc aagagctgat cgattctgcc gtgcggggcg agctggaaga taagattgct    2460
gacaaggcca gcttcaccga ccggctggtg ctgtacttta tgcaaggcgg cagagacatc    2520
tacacaggcg cccctctgaa catcgaccag ctgagccact acgatatcga ccacattctg    2580
ccccagagcc tgatcaagga cgacagcctg gacaaccggg tgctcgtgaa cgccaccatc    2640
aaccgcgaga gaacaatgt gtttgccagc acactgttcg ccggaaagat gaaggccacc    2700
tggcggaaat ggcacgaagc cggactgatc tctggcagaa agctgcggaa tctgatgctg    2760
cggcccgacg agatcgacaa gttttgccaag ggcttcgtgg ccggcagct ggttgagaca    2820 agacagatca tcaagctgac agagcagatt gccgccgctc agtaccccaa caccaagatt    2880
attgccgtga aggccggact gtcccatcag ctgagagagg aactggactt ccccaagaac    2940
cgggacgtga accactacca ccacgccttc gatgcctttc tggccgctag aatcggcacc    3000
tacctgctga agagatacc caagctggcc ccattcttca cctacggcga gtttgctaag    3060
gtggacgtca agaagttccg cgagttcaac ttcatcggag ccctgacaca cgccaagaag    3120
aacattatcg ccaaggacac cggcgagatc gtgtgggaca agagcgggga catcagagaa    3180
ctggaccgca tctacaactt caagcggatg ctgatcacac acgaggtgta cttcgagact    3240
gccgacctgt tcaagcagac catctacgcc gctaaggaca gcaaagagag aggcggcagc    3300
```

```
aagcagctga tccctaagaa gcagggctac cccactcagg tgtacggcgg ctacacacaa    3360
gagagcggct cttacaacgc cctcgtcaga gtggccgagg ccgatacaac agcctaccaa    3420
gtgatcaaga tcagcgccca gaacgccagc aagatcgcct ccgccaacct gaaaagccgc    3480
gagaaaggca acagctcctg aatgagatcg tcgtgaagc agctggctaa gcggcggaag    3540
aactggaagc tagcgccaa tagcttcaag atcgtgatcc ccagattcgg catgggcacc    3600
ctgttccaga cgctaagta cggcctgttc atggtcaaca gcgacaccta ctaccggaac    3660
taccaagaac tctggctgag ccgggaaaac cagaaactgc tgaaaaagct gttctccatc    3720
aaatacgaga aacccagat gaaccacgac gccctgcagg tctacaaggc cattatcgac    3780
caggtggaaa agttcttcaa gctgtacgac atcaaccagt tccgcgccaa gctgagcgac    3840
gccatcgaga gatttgagaa gctgcccatc aataccgacg caacaagat cggcaagacc    3900 gagactctga cagatcct gatcggactg caggccaatg gcacccggtc aacgtgaag     3960 aacctgggca tcaagaccga tctgggcctg ctgcaagtcg gcagcggaat caagctggac    4020
aaggataccc agatcgtgta tcagagcccc tccggcctgt ttaagcggag aatcccactg    4080
gctgacctgc ccaagaagaa gaggaaggtg                                    4110
```

<210> SEQ ID NO 4
<211> LENGTH: 1370
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Thr Lys Leu Asn Gln Pro Tyr Gly Ile Gly Leu Asp Ile Gly Ser
1               5                   10                  15

Asn Ser Ile Gly Phe Ala Val Val Asp Ala Asn Ser His Leu Leu Arg
            20                  25                  30

Leu Lys Gly Glu Thr Ala Ile Gly Ala Arg Leu Phe Arg Glu Gly Gln
        35                  40                  45

Ser Ala Ala Asp Arg Arg Gly Ser Arg Thr Thr Arg Arg Arg Leu Ser
    50                  55                  60

Arg Thr Arg Trp Arg Leu Ser Phe Leu Arg Asp Phe Ala Pro His
65                  70                  75                  80

Ile Thr Lys Ile Asp Pro Asp Phe Phe Leu Arg Gln Lys Tyr Ser Glu
                85                  90                  95

Ile Ser Pro Lys Asp Lys Asp Arg Phe Lys Tyr Glu Lys Arg Leu Phe
            100                 105                 110

Asn Asp Arg Thr Asp Ala Glu Phe Tyr Glu Asp Tyr Pro Ser Met Tyr
        115                 120                 125

His Leu Arg Leu His Leu Met Thr His Thr His Lys Ala Asp Pro Arg
    130                 135                 140

Glu Ile Phe Leu Ala Ile His His Ile Leu Lys Ser Arg Gly His Phe
145                 150                 155                 160

Leu Thr Pro Gly Ala Ala Lys Asp Phe Asn Thr Asp Lys Val Asp Leu
                165                 170                 175

Glu Asp Ile Phe Pro Ala Leu Thr Glu Ala Tyr Ala Gln Val Tyr Pro
            180                 185                 190

Asp Leu Glu Leu Thr Phe Asp Leu Ala Lys Ala Asp Phe Lys Ala
        195                 200                 205

Lys Leu Leu Asp Glu Gln Ala Thr Pro Ser Asp Thr Gln Lys Ala Leu
```

-continued

```
                210                 215                 220
Val Asn Leu Leu Leu Ser Ser Asp Gly Glu Lys Glu Ile Val Lys Lys
225                 230                 235                 240

Arg Lys Gln Val Leu Thr Glu Phe Ala Lys Ala Ile Thr Gly Leu Lys
                245                 250                 255

Thr Lys Phe Asn Leu Ala Leu Gly Thr Glu Val Asp Glu Ala Asp Ala
                260                 265                 270

Ser Asn Trp Gln Phe Ser Met Gly Gln Leu Asp Asp Lys Trp Ser Asn
                275                 280                 285

Ile Glu Thr Ser Met Thr Asp Gln Gly Thr Glu Ile Phe Glu Gln Ile
                290                 295                 300

Gln Glu Leu Tyr Arg Ala Arg Leu Leu Asn Gly Ile Val Pro Ala Gly
305                 310                 315                 320

Met Ser Leu Ser Gln Ala Lys Val Ala Asp Tyr Gly Gln His Lys Glu
                325                 330                 335

Asp Leu Glu Leu Phe Lys Thr Tyr Leu Lys Lys Leu Asn Asp His Glu
                340                 345                 350

Leu Ala Lys Thr Ile Arg Gly Leu Tyr Asp Arg Tyr Ile Asn Gly Asp
                355                 360                 365

Asp Ala Lys Pro Phe Leu Arg Glu Asp Phe Val Lys Ala Leu Thr Lys
                370                 375                 380

Glu Val Thr Ala His Pro Asn Glu Val Ser Glu Gln Leu Leu Asn Arg
385                 390                 395                 400

Met Gly Gln Ala Asn Phe Met Leu Lys Gln Arg Thr Lys Ala Asn Gly
                405                 410                 415

Ala Ile Pro Ile Gln Leu Gln Gln Arg Glu Leu Asp Gln Ile Ile Ala
                420                 425                 430

Asn Gln Ser Lys Tyr Tyr Asp Trp Leu Ala Ala Pro Asn Pro Val Glu
                435                 440                 445

Ala His Arg Trp Lys Met Pro Tyr Gln Leu Asp Glu Leu Leu Asn Phe
450                 455                 460

His Ile Pro Tyr Tyr Val Gly Pro Leu Ile Thr Pro Lys Gln Gln Ala
465                 470                 475                 480

Glu Ser Gly Glu Asn Val Phe Ala Trp Met Val Arg Lys Asp Pro Ser
                485                 490                 495

Gly Asn Ile Thr Pro Tyr Asn Phe Asp Glu Lys Val Asp Arg Glu Ala
                500                 505                 510

Ser Ala Asn Thr Phe Ile Gln Arg Met Lys Thr Thr Asp Thr Tyr Leu
                515                 520                 525

Ile Gly Glu Asp Val Leu Pro Lys Gln Ser Leu Leu Tyr Gln Lys Tyr
                530                 535                 540

Glu Val Leu Asn Glu Leu Asn Asn Val Arg Ile Asn Asn Glu Cys Leu
545                 550                 555                 560

Gly Thr Asp Gln Lys Gln Arg Leu Ile Arg Glu Val Phe Glu Arg His
                565                 570                 575

Ser Ser Val Thr Ile Lys Gln Val Ala Asp Asn Leu Val Ala His Gly
                580                 585                 590

Asp Phe Ala Arg Arg Pro Glu Ile Arg Gly Leu Ala Asp Glu Lys Arg
                595                 600                 605

Phe Leu Ser Ser Leu Ser Thr Tyr His Gln Leu Lys Glu Ile Leu His
                610                 615                 620

Glu Ala Ile Asp Asp Pro Thr Lys Leu Leu Asp Ile Glu Asn Ile Ile
625                 630                 635                 640
```

-continued

```
Thr Trp Ser Thr Val Phe Glu Asp His Thr Ile Phe Glu Thr Lys Leu
            645                 650                 655
Ala Glu Ile Glu Trp Leu Asp Pro Lys Lys Ile Asn Glu Leu Ser Gly
            660                 665                 670
Ile Arg Tyr Arg Gly Trp Gly Gln Phe Ser Arg Lys Leu Leu Asp Gly
            675                 680                 685
Leu Lys Leu Gly Asn Gly His Thr Val Ile Gln Glu Leu Met Leu Ser
            690                 695                 700
Asn His Asn Leu Met Gln Ile Leu Ala Asp Glu Thr Leu Lys Glu Thr
705                 710                 715                 720
Met Thr Glu Leu Asn Gln Asp Lys Leu Lys Thr Asp Asp Ile Glu Asp
            725                 730                 735
Val Ile Asn Asp Ala Tyr Thr Ser Pro Ser Asn Lys Lys Ala Leu Arg
            740                 745                 750
Gln Val Leu Arg Val Val Glu Asp Ile Lys His Ala Ala Asn Gly Gln
            755                 760                 765
Asp Pro Ser Trp Leu Phe Ile Glu Thr Ala Asp Gly Thr Gly Thr Ala
            770                 775                 780
Gly Lys Arg Thr Gln Ser Arg Gln Lys Gln Ile Gln Thr Val Tyr Ala
785                 790                 795                 800
Asn Ala Ala Gln Glu Leu Ile Asp Ser Ala Val Arg Gly Glu Leu Glu
            805                 810                 815
Asp Lys Ile Ala Asp Lys Ala Ser Phe Thr Asp Arg Leu Val Leu Tyr
            820                 825                 830
Phe Met Gln Gly Gly Arg Asp Ile Tyr Thr Gly Ala Pro Leu Asn Ile
            835                 840                 845
Asp Gln Leu Ser His Tyr Asp Ile Asp His Ile Leu Pro Gln Ser Leu
            850                 855                 860
Ile Lys Asp Asp Ser Leu Asp Asn Arg Val Leu Val Asn Ala Thr Ile
865                 870                 875                 880
Asn Arg Glu Lys Asn Asn Val Phe Ala Ser Thr Leu Phe Ala Gly Lys
            885                 890                 895
Met Lys Ala Thr Trp Arg Lys Trp His Glu Ala Gly Leu Ile Ser Gly
            900                 905                 910
Arg Lys Leu Arg Asn Leu Met Leu Arg Pro Asp Glu Ile Asp Lys Phe
            915                 920                 925
Ala Lys Gly Phe Val Ala Arg Gln Leu Val Glu Thr Arg Gln Ile Ile
            930                 935                 940
Lys Leu Thr Glu Gln Ile Ala Ala Ala Gln Tyr Pro Asn Thr Lys Ile
945                 950                 955                 960
Ile Ala Val Lys Ala Gly Leu Ser His Gln Leu Arg Glu Glu Leu Asp
            965                 970                 975
Phe Pro Lys Asn Arg Asp Val Asn His Tyr His His Ala Phe Asp Ala
            980                 985                 990
Phe Leu Ala Ala Arg Ile Gly Thr Tyr Leu Leu Lys Arg Tyr Pro Lys
            995                 1000                1005
Leu Ala Pro Phe Phe Thr Tyr Gly Glu Phe Ala Lys Val Asp Val
            1010                1015                1020
Lys Lys Phe Arg Glu Phe Asn Phe Ile Gly Ala Leu Thr His Ala
            1025                1030                1035
Lys Lys Asn Ile Ile Ala Lys Asp Thr Gly Glu Ile Val Trp Asp
            1040                1045                1050
```

| | | | | | | | | | |
|---|---|---|---|---|---|---|---|---|---|
Lys | Glu | Arg | Asp | Ile | Arg | Glu | Leu | Asp | Arg | Ile | Tyr | Asn | Phe | Lys
1055 | | | | | 1060 | | | | | 1065

Arg Met Leu Ile Thr His Glu Val Tyr Phe Glu Thr Ala Asp Leu
 1070                1075               1080

Phe Lys Gln Thr Ile Tyr Ala Ala Lys Asp Ser Lys Glu Arg Gly
 1085                1090               1095

Gly Ser Lys Gln Leu Ile Pro Lys Lys Gln Gly Tyr Pro Thr Gln
 1100                1105               1110

Val Tyr Gly Gly Tyr Thr Gln Glu Ser Gly Ser Tyr Asn Ala Leu
 1115                1120               1125

Val Arg Val Ala Glu Ala Asp Thr Thr Ala Tyr Gln Val Ile Lys
 1130                1135               1140

Ile Ser Ala Gln Asn Ala Ser Lys Ile Ala Ser Ala Asn Leu Lys
 1145                1150               1155

Ser Arg Glu Lys Gly Lys Gln Leu Leu Asn Glu Ile Val Val Lys
 1160                1165               1170

Gln Leu Ala Lys Arg Arg Lys Asn Trp Lys Pro Ser Ala Asn Ser
 1175                1180               1185

Phe Lys Ile Val Ile Pro Arg Phe Gly Met Gly Thr Leu Phe Gln
 1190                1195               1200

Asn Ala Lys Tyr Gly Leu Phe Met Val Asn Ser Asp Thr Tyr Tyr
 1205                1210               1215

Arg Asn Tyr Gln Glu Leu Trp Leu Ser Arg Glu Asn Gln Lys Leu
 1220                1225               1230

Leu Lys Lys Leu Phe Ser Ile Lys Tyr Glu Lys Thr Gln Met Asn
 1235                1240               1245

His Asp Ala Leu Gln Val Tyr Lys Ala Ile Ile Asp Gln Val Glu
 1250                1255               1260

Lys Phe Phe Lys Leu Tyr Asp Ile Asn Gln Phe Arg Ala Lys Leu
 1265                1270               1275

Ser Asp Ala Ile Glu Arg Phe Glu Lys Leu Pro Ile Asn Thr Asp
 1280                1285               1290

Gly Asn Lys Ile Gly Lys Thr Glu Thr Leu Arg Gln Ile Leu Ile
 1295                1300               1305

Gly Leu Gln Ala Asn Gly Thr Arg Ser Asn Val Lys Asn Leu Gly
 1310                1315               1320

Ile Lys Thr Asp Leu Gly Leu Leu Gln Val Gly Ser Gly Ile Lys
 1325                1330               1335

Leu Asp Lys Asp Thr Gln Ile Val Tyr Gln Ser Pro Ser Gly Leu
 1340                1345               1350

Phe Lys Arg Arg Ile Pro Leu Ala Asp Leu Pro Lys Lys Lys Arg
 1355                1360               1365

Lys Val
 1370

<210> SEQ ID NO 5
<211> LENGTH: 4305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgggcaaga cccacatcat cggcgttggc ctggatctcg gcggcacata cacaggcacc    60

```
ttcatcacca gccatcctag cgacgaagcc gagcacagag atcacagcag cgccttcacc      120
gtggtcaaca gcgagaagct gagcttcagc agcaagagca gaacagccgt gcggcacaga      180
gtgcggagct acaagggctt cgacctgcgt agaaggctgc tgcttctggt ggccgagtat      240
cagctgctgc agaagaagca gacactggcc cctgaggaaa gagagaacct gagaatcgcc      300
ctgagcggct acctgaagag aagaggctac gccagaaccg aggccgagac agatacaagc      360
gtgctggaat ctctggaccc cagcgtgttc agcagcgctc ccagcttcac caatttcttc      420
aacgacagcg agccctgaa catccagtgg gaagccattg ccaactctcc cgagacaaca      480
aaggccctga caaagagct gagcggccag aaagaggccg acttcaagaa gtacatcaag      540
accagctttc ccgagtacag cgccaaagag attctggcca actacgtgga aggcagacgg      600
gccattctgg acgccagcaa gtatatcgcc aacctgcaga gcctgggcca acgcacaga      660
agcaagtacc tgagcgacat tctgcaggac atgaagcggg acagccggat caccagactg      720
agcgaagcct ttggcagcac cgacaacctg tggcggatca tcggcaacat cagcaatctg      780
caagaacggg ccgtgcggtg gtacttcaac gatgccaagt cgagcaggg ccaagagcag      840
ctggatgccg tgaagctgaa gaatgtgctc gtgcgggccc tgaagtatct gcggagtgac      900
gacaaagagt ggagcgcctc tcagaagcag atcatccagt ctctggaaca gagcggcgac      960
gtgctggatg tgctggctgg actcgacccc gacagaacaa tccctccata cgaggaccag     1020
aacaacagac ggcctcctga ggatcagacc ctgtatctga ccccaaggc tctgagcagc     1080
gagtacggcg agaagtggaa gtcttgggcc aacaagtttg ccggcgctta ccctctgctg     1140
accgaggatc tgaccgagat cctgaagaac accgacagaa agtcccggat caagatcaga     1200
tccgatgtgc tgcccgacag cgactacaga ctggcctaca tcctgcagag agccttcgat     1260
cggtctatcg ccctggacga gtgcagcatc agaagaaccg ccgaggactt cgagaacggc     1320
gtggtcatca agaacgagaa actggaagat gtgctgagcg acaccagct ggaagagttt     1380
ctggaatttg ccaatcggta ctaccaagag acagccaagg ccaagaacgg cctgtgttc     1440
ccagagaacg ccctgctgga agagccgat ctgcaccctc ctatgaagaa caagattctg     1500
aacgtgatcg tcgacaggc cctgggagtg tctcctgctg agggcaccga tttcatcgag     1560
gaaatttgga cagcaaagt gaaaggccgg tccaccgtgc ggagcatctg taacgccatc     1620
gagaatgaga gaaagaccta cggaccctac ttcagcgagg actacaagtt cgtgaaaacg     1680
gccctgaaag agggcaaaac cgagaaagag ctgtccaaga aattcgccgc cgtgatcaag     1740
gtgctgaaga tggtgtctga ggtggtgccc tttatcggaa agagctgcg gctgtctgac     1800
gaggcccaga gcaagttcga caatctgtac tctctggccc agctgtacaa cctgatcgag     1860
acagagcgga acggcttcag caaggtgtca ctggctgccc acctggaaaa tgcctggcgg     1920
atgaccatga cagatggatc cgcccagtgc tgtagactgc ctgccgattg tgtgcggccc     1980
ttcgacggct ttatccggaa ggccatcgac cggaactctt gggaagtcgc caagcggatt     2040
gccgaggaag tgaagaagtc cgtcgacttc accaacggca ccgtgaagat ccctgtggcc     2100
atcgaggcca acagcttcaa ctttaccgcc agcctgaccg acctgaagta cattcagctc     2160
aaagaacaga agctcaagaa gaagttggag acatccagc ggaacgaaga gaatcaagag     2220
aagcggtggc tgagcaaaga ggaacggatc agagccgaca gccacggcat ctgtgcctat     2280
actggcagac ccctggatga cgtgggcgag atcgatcaca tcatccccag aagcctgaca     2340
ctgaagaaaa gcgagagcat ctacaactcc gaagtgaacc tgatcttcgt gtctgcccag     2400
ggcaatcaag aaaagaagaa caacatctac ctgctgagca acctcgccaa gaactacctg     2460
```

-continued

```
gccgccgtgt tggcacaag cgacctgagc cagatcacca acgagatcga gagcaccgtg    2520
ctgcagctga aagctgctgg cagactgggc tacttcgatc tgctgagcga aaaagagcgg    2580
gcctgcgcca gacatgccct gtttctgaat agcgactccg aggccagacg cgccgtgatt    2640
gatgttcttg gctctcggag aaaggccagc gtgaacggaa cccaggcttg gtttgtgcgg    2700
tccatcttct ccaaagtgcg gcaggcactg gccgcttgga cacaagaaac aggcaacgag    2760
ctgatctttg acgccatcag cgtgccagcc gccgatagct ctgagatgag gaagagattc    2820
gccgagtacc ggcctgagtt cagaaagccc aaagtgcagc tgtggcctc tcacagcatc    2880 gacgccatgt gcatctatct ggccgcctgc agcgacccct tcaagaccaa gagaatgggc    2940
tctcagctgg ccatctacga gcccatcaac ttcgataacc tgttcaccgg cagctgtcaa    3000
gtgatccaga acacccctcg gaacttctcc gacaagacca atatcgctaa cagccccatc    3060
ttcaaagaga caatctacgc cgagcggttc ctggacatca tcgtgtccag aggcgagatt    3120
ttcatcggct accccagcaa catgcccttc gaggaaaagc caaccggat cagcatcggc    3180 ggcaaggacc ctttcagcat cctgtctgtg ctgggcgcct acctggataa ggcccctagc    3240
agcgagaaag aaaagctcac catctaccgg gtcgtcaaga acaaagcctt cgagctgttc    3300
tccaaggtgg ccggcagcaa gtttaccgcc gaagaagata aggccgccaa gatcctggaa    3360
gccctgcact cgtgaccgt gaaacaggat gtggccgcca ccgtgtccga tctgatcaag    3420
agcaagaaag aactgagcaa ggatagcatc gagaacctgg ccaagcagaa gggctgcctg    3480
aagaaggtgg aatactccag caaagagttc aagttcaagg gcagcctgat catccctgcc    3540
gccgtggaat ggggaaaagt gctgtggaac gtgttcaaag aaaacacggc cgaagaactg    3600
aaggacgaga acgctctgag gaaggccctg aagctgcct ggcctagctc tttcggcacc    3660
agaaacctgc actctaaggc caagcgggtg ttcagcctgc ctgtggtggc tacacaatct    3720
ggcgccgtgc ggatcagacg caagacagcc ttcggcgact tcgtgtacca gagccaggac    3780
acaaacaacc tgtacagcag cttccccgtg aagaacggca agctggattg gagcagccct    3840
atcattcacc ccgctctgca gaaccggaac ctgaccgcct acggctacag attcgtggac    3900
cacgacagat ccatcagcat gagcgagttc agagaggtgt acaacaagga cgacctgatg    3960
cggatcgagc tggcccaggg aacaagcagc agacgctacc tgagagtgga aatgcccggc    4020
gagaaattcc tcgcttggtt tggcgagaac agcatcagcc tgggctccag cttcaagttc    4080
tctgtgtccg aggtgttcga aacaaaatc tacaccgaga acgccgagtt taccaagttc    4140
ctgcctaagc ctagagagga caacaagcac aacgggacca tcttttttcga actcgtgggc    4200 cccagagtga tcttcaacta catcgttggc ggagccgcca gcagcctgaa agaaatctt    4260 agcgaggccg gcaaagagcg gagccccaag aagaagagga aggtg              4305
```

<210> SEQ ID NO 6
<211> LENGTH: 1435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Gly Lys Thr His Ile Ile Gly Val Gly Leu Asp Leu Gly Gly Thr
1               5                   10                  15

Tyr Thr Gly Thr Phe Ile Thr Ser His Pro Ser Asp Glu Ala Glu His
            20                  25                  30
```

```
Arg Asp His Ser Ser Ala Phe Thr Val Val Asn Ser Glu Lys Leu Ser
            35                  40                  45

Phe Ser Ser Lys Ser Arg Thr Ala Val Arg His Arg Val Arg Ser Tyr
 50                  55                  60

Lys Gly Phe Asp Leu Arg Arg Arg Leu Leu Leu Val Ala Glu Tyr
 65                  70                  75                  80

Gln Leu Leu Gln Lys Lys Gln Thr Leu Ala Pro Glu Glu Arg Glu Asn
                 85                  90                  95

Leu Arg Ile Ala Leu Ser Gly Tyr Leu Lys Arg Arg Gly Tyr Ala Arg
                100                 105                 110

Thr Glu Ala Glu Thr Asp Thr Ser Val Leu Glu Ser Leu Asp Pro Ser
                115                 120                 125

Val Phe Ser Ser Ala Pro Ser Phe Thr Asn Phe Phe Asn Asp Ser Glu
130                 135                 140

Pro Leu Asn Ile Gln Trp Glu Ala Ile Ala Asn Ser Pro Glu Thr Thr
145                 150                 155                 160

Lys Ala Leu Asn Lys Glu Leu Ser Gly Gln Lys Glu Ala Asp Phe Lys
                165                 170                 175

Lys Tyr Ile Lys Thr Ser Phe Pro Glu Tyr Ser Ala Lys Glu Ile Leu
                180                 185                 190

Ala Asn Tyr Val Glu Gly Arg Arg Ala Ile Leu Asp Ala Ser Lys Tyr
                195                 200                 205

Ile Ala Asn Leu Gln Ser Leu Gly His Lys His Arg Ser Lys Tyr Leu
                210                 215                 220

Ser Asp Ile Leu Gln Asp Met Lys Arg Asp Ser Arg Ile Thr Arg Leu
225                 230                 235                 240

Ser Glu Ala Phe Gly Ser Thr Asp Asn Leu Trp Arg Ile Ile Gly Asn
                245                 250                 255

Ile Ser Asn Leu Gln Glu Arg Ala Val Arg Trp Tyr Phe Asn Asp Ala
                260                 265                 270

Lys Phe Glu Gln Gly Gln Gln Leu Asp Ala Val Lys Leu Lys Asn
                275                 280                 285

Val Leu Val Arg Ala Leu Lys Tyr Leu Arg Ser Asp Asp Lys Glu Trp
290                 295                 300

Ser Ala Ser Gln Lys Gln Ile Ile Gln Ser Leu Glu Gln Ser Gly Asp
305                 310                 315                 320

Val Leu Asp Val Leu Ala Gly Leu Asp Pro Asp Arg Thr Ile Pro Pro
                325                 330                 335

Tyr Glu Asp Gln Asn Asn Arg Arg Pro Pro Glu Asp Gln Thr Leu Tyr
                340                 345                 350

Leu Asn Pro Lys Ala Leu Ser Ser Glu Tyr Gly Glu Lys Trp Lys Ser
                355                 360                 365

Trp Ala Asn Lys Phe Ala Gly Ala Tyr Pro Leu Leu Thr Glu Asp Leu
                370                 375                 380

Thr Glu Ile Leu Lys Asn Thr Asp Arg Lys Ser Arg Ile Lys Ile Arg
385                 390                 395                 400

Ser Asp Val Leu Pro Asp Ser Asp Tyr Arg Leu Ala Tyr Ile Leu Gln
                405                 410                 415

Arg Ala Phe Asp Arg Ser Ile Ala Leu Asp Glu Cys Ser Ile Arg Arg
                420                 425                 430

Thr Ala Glu Asp Phe Glu Asn Gly Val Val Ile Lys Asn Glu Lys Leu
                435                 440                 445
```

-continued

Glu Asp Val Leu Ser Gly His Gln Leu Glu Phe Leu Glu Phe Ala
    450                 455                 460

Asn Arg Tyr Tyr Gln Glu Thr Ala Lys Ala Lys Asn Gly Leu Trp Phe
465                 470                 475                 480

Pro Glu Asn Ala Leu Leu Glu Arg Ala Asp Leu His Pro Pro Met Lys
                485                 490                 495

Asn Lys Ile Leu Asn Val Ile Val Gly Gln Ala Leu Gly Val Ser Pro
            500                 505                 510

Ala Glu Gly Thr Asp Phe Ile Glu Glu Ile Trp Asn Ser Lys Val Lys
        515                 520                 525

Gly Arg Ser Thr Val Arg Ser Ile Cys Asn Ala Ile Glu Asn Glu Arg
530                 535                 540

Lys Thr Tyr Gly Pro Tyr Phe Ser Glu Asp Tyr Lys Phe Val Lys Thr
545                 550                 555                 560

Ala Leu Lys Glu Gly Lys Thr Glu Lys Glu Leu Ser Lys Lys Phe Ala
                565                 570                 575

Ala Val Ile Lys Val Leu Lys Met Val Ser Glu Val Val Pro Phe Ile
            580                 585                 590

Gly Lys Glu Leu Arg Leu Ser Asp Glu Ala Gln Ser Lys Phe Asp Asn
        595                 600                 605

Leu Tyr Ser Leu Ala Gln Leu Tyr Asn Leu Ile Glu Thr Glu Arg Asn
    610                 615                 620

Gly Phe Ser Lys Val Ser Leu Ala Ala His Leu Glu Asn Ala Trp Arg
625                 630                 635                 640

Met Thr Met Thr Asp Gly Ser Ala Gln Cys Cys Arg Leu Pro Ala Asp
                645                 650                 655

Cys Val Arg Pro Phe Asp Gly Phe Ile Arg Lys Ala Ile Asp Arg Asn
            660                 665                 670

Ser Trp Glu Val Ala Lys Arg Ile Ala Glu Glu Val Lys Lys Ser Val
        675                 680                 685

Asp Phe Thr Asn Gly Thr Val Lys Ile Pro Val Ala Ile Glu Ala Asn
    690                 695                 700

Ser Phe Asn Phe Thr Ala Ser Leu Thr Asp Leu Lys Tyr Ile Gln Leu
705                 710                 715                 720

Lys Glu Gln Lys Leu Lys Lys Leu Glu Asp Ile Gln Arg Asn Glu
                725                 730                 735

Glu Asn Gln Glu Lys Arg Trp Leu Ser Lys Glu Arg Ile Arg Ala
                740                 745                 750

Asp Ser His Gly Ile Cys Ala Tyr Thr Gly Arg Pro Leu Asp Asp Val
        755                 760                 765

Gly Glu Ile Asp His Ile Ile Pro Arg Ser Leu Thr Leu Lys Lys Ser
    770                 775                 780

Glu Ser Ile Tyr Asn Ser Glu Val Asn Leu Ile Phe Val Ser Ala Gln
785                 790                 795                 800

Gly Asn Gln Glu Lys Lys Asn Asn Ile Tyr Leu Leu Ser Asn Leu Ala
                805                 810                 815

Lys Asn Tyr Leu Ala Ala Val Phe Gly Thr Ser Asp Leu Ser Gln Ile
            820                 825                 830

Thr Asn Glu Ile Glu Ser Thr Val Leu Gln Leu Lys Ala Ala Gly Arg
        835                 840                 845

Leu Gly Tyr Phe Asp Leu Leu Ser Glu Lys Glu Arg Ala Cys Ala Arg
    850                 855                 860

His Ala Leu Phe Leu Asn Ser Asp Ser Glu Ala Arg Arg Ala Val Ile

```
            865                 870                 875                 880
        Asp Val Leu Gly Ser Arg Arg Lys Ala Ser Val Asn Gly Thr Gln Ala
                        885                 890                 895
        Trp Phe Val Arg Ser Ile Phe Ser Lys Val Arg Gln Ala Leu Ala Ala
                        900                 905                 910
        Trp Thr Gln Glu Thr Gly Asn Glu Leu Ile Phe Asp Ala Ile Ser Val
                        915                 920                 925
        Pro Ala Ala Asp Ser Ser Glu Met Arg Lys Arg Phe Ala Glu Tyr Arg
                        930                 935                 940
        Pro Glu Phe Arg Lys Pro Lys Val Gln Pro Val Ala Ser His Ser Ile
        945                 950                 955                 960
        Asp Ala Met Cys Ile Tyr Leu Ala Ala Cys Ser Asp Pro Phe Lys Thr
                        965                 970                 975
        Lys Arg Met Gly Ser Gln Leu Ala Ile Tyr Glu Pro Ile Asn Phe Asp
                        980                 985                 990
        Asn Leu Phe Thr Gly Ser Cys Gln  Val Ile Gln Asn Thr  Pro Arg Asn
                        995                 1000                1005
        Phe Ser  Asp Lys Thr Asn Ile  Ala Asn Ser Pro Ile  Phe Lys Glu
            1010                1015                1020
        Thr Ile  Tyr Ala Glu Arg Phe  Leu Asp Ile Ile Val  Ser Arg Gly
            1025                1030                1035
        Glu Ile  Phe Ile Gly Tyr Pro  Ser Asn Met Pro Phe  Glu Glu Lys
            1040                1045                1050
        Pro Asn  Arg Ile Ser Ile Gly  Gly Lys Asp Pro Phe  Ser Ile Leu
            1055                1060                1065
        Ser Val  Leu Gly Ala Tyr Leu  Asp Lys Ala Pro Ser  Ser Glu Lys
            1070                1075                1080
        Glu Lys  Leu Thr Ile Tyr Arg  Val Val Lys Asn Lys  Ala Phe Glu
            1085                1090                1095
        Leu Phe  Ser Lys Val Ala Gly  Ser Lys Phe Thr Ala  Glu Glu Asp
            1100                1105                1110
        Lys Ala  Ala Lys Ile Leu Glu  Ala Leu His Phe Val  Thr Val Lys
            1115                1120                1125
        Gln Asp  Val Ala Ala Thr Val  Ser Asp Leu Ile Lys  Ser Lys Lys
            1130                1135                1140
        Glu Leu  Ser Lys Asp Ser Ile  Glu Asn Leu Ala Lys  Gln Lys Gly
            1145                1150                1155
        Cys Leu  Lys Lys Val Glu Tyr  Ser Ser Lys Glu Phe  Lys Phe Lys
            1160                1165                1170
        Gly Ser  Leu Ile Ile Pro Ala  Ala Val Glu Trp Gly  Lys Val Leu
            1175                1180                1185
        Trp Asn  Val Phe Lys Glu Asn  Thr Ala Glu Glu Leu  Lys Asp Glu
            1190                1195                1200
        Asn Ala  Leu Arg Lys Ala Leu  Glu Ala Ala Trp Pro  Ser Ser Phe
            1205                1210                1215
        Gly Thr  Arg Asn Leu His Ser  Lys Ala Lys Arg Val  Phe Ser Leu
            1220                1225                1230
        Pro Val  Val Ala Thr Gln Ser  Gly Ala Val Arg Ile  Arg Arg Lys
            1235                1240                1245
        Thr Ala  Phe Gly Asp Phe Val  Tyr Gln Ser Gln Asp  Thr Asn Asn
            1250                1255                1260
        Leu Tyr  Ser Ser Phe Pro Val  Lys Asn Gly Lys Leu  Asp Trp Ser
            1265                1270                1275
```

| | | | | | | | | | | |
|---|---|---|---|---|---|---|---|---|---|---|
|Ser|Pro|Ile|Ile|His|Pro|Ala|Leu|Gln|Asn|Arg|Asn|Leu|Thr|Ala|
|   |1280|   |   |   |1285|   |   |   |1290|   |

Ser Pro Ile Ile His Pro Ala Leu Gln Asn Arg Asn Leu Thr Ala
    1280            1285            1290

Tyr Gly Tyr Arg Phe Val Asp His Asp Arg Ser Ile Ser Met Ser
    1295            1300            1305

Glu Phe Arg Glu Val Tyr Asn Lys Asp Asp Leu Met Arg Ile Glu
    1310            1315            1320

Leu Ala Gln Gly Thr Ser Ser Arg Arg Tyr Leu Arg Val Glu Met
    1325            1330            1335

Pro Gly Glu Lys Phe Leu Ala Trp Phe Gly Glu Asn Ser Ile Ser
    1340            1345            1350

Leu Gly Ser Ser Phe Lys Phe Ser Val Ser Glu Val Phe Asp Asn
    1355            1360            1365

Lys Ile Tyr Thr Glu Asn Ala Glu Phe Thr Lys Phe Leu Pro Lys
    1370            1375            1380

Pro Arg Glu Asp Asn Lys His Asn Gly Thr Ile Phe Phe Glu Leu
    1385            1390            1395

Val Gly Pro Arg Val Ile Phe Asn Tyr Ile Val Gly Gly Ala Ala
    1400            1405            1410

Ser Ser Leu Lys Glu Ile Phe Ser Glu Ala Gly Lys Glu Arg Ser
    1415            1420            1425

Pro Lys Lys Lys Arg Lys Val
    1430            1435

<210> SEQ ID NO 7
<211> LENGTH: 3720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggaaaaga agcggaaagt caccctgggc ttcgacctgg gaatcgcctc tgttggatgg     60
gccatcgtgg acagcgagac aaaccaggtg tacaagctgg cagcagact gttcgacgcc    120 cctgacacca acctggaaag aagaacccag cggggcacca aaggctgct gcggagaaga    180 aagtaccgga accagaaatt ctacaacctg tcaagcgga ccgaggtgtt cggcctgtct    240
agcagagagg ccatcgagaa cagattcaga gagctgagca tcaagtaccc caacatcatc    300
gagctgaaaa caaggccct gagccaagaa gtgtgccccg acgagattgc ctggattctg    360
cacgactacc tgaagaaccg ggctacttc tacgacgaga agagacaaa agaggacttc    420 gaccagcaga ccgtggaatc catgcctagc tacaagctga cgagttcta caagaagtac    480 ggctacttca aggcgccct gtctcagcct accgagagcg agatgaagga caacaaggac    540
ctgaagaggg cattcttctt cgacttctcc aacaagagt ggctgaaaga gatcaactac    600
ttcttcaacg tgcagaagaa catcctgagc gagacattca tcgaagagtt caagaagatt    660
ttcagcttca cccgggacat cagcaaaggc ccaggcagcg acaatatgcc ctctccttac    720
ggcatcttcg gcgagttcgg cgacaatggc caaggcggca gatacagca catctgggac    780 aagaacatcg gcaagtgcag catcttcacc aacgagcaga gagcccctaa gtacctgcct    840
agcgctctga tcttcaactt cctgaacgag ctggccaaca tcagactgta cagcaccgac    900
aagaagaata tccagcctct gtggaagctg agcagcatcg ataagctgaa atcctgctg    960 aacctgttca acctgcctat cagcgagaag aagaaaaagc tgaccagcac caacatcaac    1020

```
gacatcgtga agaaagagtc catcaagagc atcatgctga gcgtcgagga catcgacatg    1080
atcaaggatg agtgggccgg caaagaaccc aacgtgtacg gcgttggact gagcggcctg    1140
aacatcgagg aaagcgccaa agagaacaag ttcaagttcc aagacctgaa gatcctgaac    1200
gtcctgatca atctgctgga caacgtgggc atcaagttcg agttcaagga ccgcagcgac    1260
atcatcaaga acctggaact gctggataac ctgtacctgt tcctgatcta ccagaaagag    1320
agcaacaaca aagacagctc catcgacctg tttatcgcca agaacaagtc cctgaatatc    1380
gagaacctga agctcaagct caaagagttc ctgctcggag ccggcaacga gttcgagaac    1440
cacaacagca agacccacag cctgtccaag aaggccattg acgccatcct gcctaagctg    1500
ctcgacaaca acgaaggctg gaatctggaa gccatcaaga attacgacga ggaaatcaag    1560
agccagatcg aggacaactc cagcctgatg gccaagcagg ataagaagta cctgaacgac    1620
aacttcctca aggatgccat tctgccgcca aacgtgaaag tgaccttcca gcaggccatc    1680
ctcatcttca acaagatcat ccagaagttc agcaaggatt tcgagatcga caaggtcgtg    1740
atcgaactgg ccagagagat gacccaggac caagagaacg acgccctgaa gggaatcgct    1800
aaggcccaga agtccaagaa aagcctggtg aagagagagc tcaagccaa caacatcgac    1860 aagagcgtgt tcaacgataa gtacgagaag cttatctaca agattttcct gtggatcagc    1920
caggacttta aggaccccta caccggcgcc aagatcagcg ccaatgagat cgtggataac    1980
aaggtggaaa tcgaccacat catcccttac agcctgtgct cgacgacag cagcgccaac    2040 aaagtgctgg tgcacaagca gagcaatcaa gagaagtcta acagcctgcc gtacgagtac    2100
atcaagcagg gccactccgg ctggaactgg acgagttca ccaaatacgt gaagcgggtg    2160
ttcgtgaaca acgtggactc tatcctgagc aagaaagagc gcctgaagaa gtccgagaat    2220
ctgctgacca ccagctacga cggctatgag aagctgggct tcctggccag aaacctgaat    2280
gacaccagat acgccaccat cctgttccgg gaccagctga acaattacgc cgagcaccac    2340
ctgatcgata caagaaaat gttcaaagtg atcgccatga cgggccgt gaccagcttc    2400 atccggaaga acatgagcta cgacaacaag ctgcggctga aggacagaag cgacttcagc    2460
caccacgcct acgacgccgc catcattgcc ctgttcagca caagaccaa gacgctgtac    2520 aacctgattg accccagcct gaacggcatc atcagcaaga aagcgaagg ctattgggtc    2580 atcgaggatc ggtacacagg cgagatcaaa gagcttaaga aagaggattg gacctctatc    2640
aagaacaatg tgcaggcccg gaagatcgcc aaagaaatcg aggaatatct gatcgacctg    2700
gacgatgagg tgttcttcag ccggaaaact aagcgcaaga ccaaccggca gctgtacaat    2760
gagacaatct acggaatcgc cgccaagacc gacgaggacg catcaccaa ctactacaag    2820 aaagaaaagt tctccatcct ggacgacaag gacatctacc tgcggctgct gagagaacgc    2880
gagaagttcg tgatcaacca gagcaacccc gaagtgatcg accagattat cgagatcatc    2940
gagagctacg ggaaagaaa caacatcccc agccgcgacg aggccatcaa tatcaagtac    3000
acgaagaaca agattaacta caacctctac ctcaagcagt acatgcggag cctgaccaag    3060
agcctggacc agttcagcga gggcttcatc aatcagatga tcgccaacaa gacgttcgtg    3120
ctgtataacc ccaccaagaa cacaacgcgg aagatcaagt tcctgcggct cgtgaacgat    3180
gtgaagatca acgatattcg caagaatcaa gtgatcaaca gtttaacgg gaagaacaac    3240 gagcccaagg ccttctacga gaatatcaac agcctgggcg ccatcgtgtt caagtcctcc    3300
gccaacaact tcaagaccct gtccatcaac acccagatcg ccatcttcgg agacaagaac    3360
tgggatatcg aggatttcaa gacctacaac atggaaaaaa tcgagaagta caaagagata    3420
```

```
tacggcatcg acaaaaccta caacttccac agctttatct tccccggcac aatcctgctc    3480
gataagcaga acaaagagtt ctactacatc agcagcatcc agaccgtgaa cgaccaaatt    3540
gagctgaagt ttctgaacaa gatcgagttt aagaacgacg acaacacctc cggggccaac    3600
aagcctcctc ggagactgag attcggcatt aagtccatca tgaacaacta cgagcaggtc    3660
gacatcagcc ccttcggcat caacaagaag atattcgagc ccaagaagaa gaggaaggtg    3720
```

<210> SEQ ID NO 8
<211> LENGTH: 1247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Glu Lys Lys Arg Lys Val Thr Leu Gly Phe Asp Leu Gly Ile Ala
1               5                   10                  15

Ser Val Gly Trp Ala Ile Val Asp Ser Glu Thr Asn Gln Val Tyr Lys
            20                  25                  30

Leu Gly Ser Arg Leu Phe Asp Ala Pro Asp Thr Asn Leu Glu Arg Arg
        35                  40                  45

Thr Gln Arg Gly Thr Arg Arg Leu Leu Arg Arg Lys Tyr Arg Asn
    50                  55                  60

Gln Lys Phe Tyr Asn Leu Val Lys Arg Thr Glu Val Phe Gly Leu Ser
65                  70                  75                  80

Ser Arg Glu Ala Ile Glu Asn Arg Phe Arg Glu Leu Ser Ile Lys Tyr
                85                  90                  95

Pro Asn Ile Ile Glu Leu Lys Thr Lys Ala Leu Ser Gln Glu Val Cys
            100                 105                 110

Pro Asp Glu Ile Ala Trp Ile Leu His Asp Tyr Leu Lys Asn Arg Gly
        115                 120                 125

Tyr Phe Tyr Asp Glu Lys Glu Thr Lys Glu Asp Phe Asp Gln Gln Thr
    130                 135                 140

Val Glu Ser Met Pro Ser Tyr Lys Leu Asn Glu Phe Tyr Lys Lys Tyr
145                 150                 155                 160

Gly Tyr Phe Lys Gly Ala Leu Ser Gln Pro Thr Glu Ser Glu Met Lys
                165                 170                 175

Asp Asn Lys Asp Leu Lys Glu Ala Phe Phe Phe Asp Phe Ser Asn Lys
            180                 185                 190

Glu Trp Leu Lys Glu Ile Asn Tyr Phe Phe Asn Val Gln Lys Asn Ile
        195                 200                 205

Leu Ser Glu Thr Phe Ile Glu Glu Phe Lys Lys Ile Phe Ser Phe Thr
    210                 215                 220

Arg Asp Ile Ser Lys Gly Pro Gly Ser Asp Asn Met Pro Ser Pro Tyr
225                 230                 235                 240

Gly Ile Phe Gly Glu Phe Gly Asp Asn Gly Gln Gly Gly Arg Tyr Glu
                245                 250                 255

His Ile Trp Asp Lys Asn Ile Gly Lys Cys Ser Ile Phe Thr Asn Glu
            260                 265                 270

Gln Arg Ala Pro Lys Tyr Leu Pro Ser Ala Leu Ile Phe Asn Phe Leu
        275                 280                 285

Asn Glu Leu Ala Asn Ile Arg Leu Tyr Ser Thr Asp Lys Lys Asn Ile
    290                 295                 300
```

```
Gln Pro Leu Trp Lys Leu Ser Ser Ile Asp Lys Leu Asn Ile Leu Leu
305                 310                 315                 320

Asn Leu Phe Asn Leu Pro Ile Ser Glu Lys Lys Lys Leu Thr Ser
            325                 330                 335

Thr Asn Ile Asn Asp Ile Val Lys Lys Glu Ser Ile Lys Ser Ile Met
                340                 345                 350

Leu Ser Val Glu Asp Ile Asp Met Ile Lys Asp Glu Trp Ala Gly Lys
            355                 360                 365

Glu Pro Asn Val Tyr Gly Val Gly Leu Ser Gly Leu Asn Ile Glu Glu
            370                 375                 380

Ser Ala Lys Glu Asn Lys Phe Lys Phe Gln Asp Leu Lys Ile Leu Asn
385                 390                 395                 400

Val Leu Ile Asn Leu Leu Asp Asn Val Gly Ile Lys Phe Glu Phe Lys
                405                 410                 415

Asp Arg Ser Asp Ile Ile Lys Asn Leu Glu Leu Leu Asp Asn Leu Tyr
            420                 425                 430

Leu Phe Leu Ile Tyr Gln Lys Glu Ser Asn Asn Lys Asp Ser Ser Ile
            435                 440                 445

Asp Leu Phe Ile Ala Lys Asn Lys Ser Leu Asn Ile Glu Asn Leu Lys
450                 455                 460

Leu Lys Leu Lys Glu Phe Leu Leu Gly Ala Gly Asn Glu Phe Glu Asn
465                 470                 475                 480

His Asn Ser Lys Thr His Ser Leu Ser Lys Lys Ala Ile Asp Ala Ile
                485                 490                 495

Leu Pro Lys Leu Leu Asp Asn Asn Glu Gly Trp Asn Leu Glu Ala Ile
            500                 505                 510

Lys Asn Tyr Asp Glu Glu Ile Lys Ser Gln Ile Glu Asp Asn Ser Ser
            515                 520                 525

Leu Met Ala Lys Gln Asp Lys Lys Tyr Leu Asn Asp Asn Phe Leu Lys
530                 535                 540

Asp Ala Ile Leu Pro Pro Asn Val Lys Val Thr Phe Gln Gln Ala Ile
545                 550                 555                 560

Leu Ile Phe Asn Lys Ile Ile Gln Lys Phe Ser Lys Asp Phe Glu Ile
                565                 570                 575

Asp Lys Val Val Ile Glu Leu Ala Arg Glu Met Thr Gln Asp Gln Glu
            580                 585                 590

Asn Asp Ala Leu Lys Gly Ile Ala Lys Ala Gln Lys Ser Lys Lys Ser
            595                 600                 605

Leu Val Glu Glu Arg Leu Glu Ala Asn Asn Ile Asp Lys Ser Val Phe
610                 615                 620

Asn Asp Lys Tyr Glu Lys Leu Ile Tyr Lys Ile Phe Leu Trp Ile Ser
625                 630                 635                 640

Gln Asp Phe Lys Asp Pro Tyr Thr Gly Ala Lys Ile Ser Ala Asn Glu
                645                 650                 655

Ile Val Asp Asn Lys Val Glu Ile Asp His Ile Ile Pro Tyr Ser Leu
            660                 665                 670

Cys Phe Asp Asp Ser Ser Ala Asn Lys Val Leu Val His Lys Gln Ser
            675                 680                 685

Asn Gln Glu Lys Ser Asn Ser Leu Pro Tyr Glu Tyr Ile Lys Gln Gly
            690                 695                 700

His Ser Gly Trp Asn Trp Asp Glu Phe Thr Lys Tyr Val Lys Arg Val
705                 710                 715                 720

Phe Val Asn Asn Val Asp Ser Ile Leu Ser Lys Lys Glu Arg Leu Lys
```

```
            725                 730                 735
Lys Ser Glu Asn Leu Leu Thr Thr Ser Tyr Asp Gly Tyr Glu Lys Leu
            740                 745                 750
Gly Phe Leu Ala Arg Asn Leu Asn Asp Thr Arg Tyr Ala Thr Ile Leu
            755                 760                 765
Phe Arg Asp Gln Leu Asn Asn Tyr Ala Glu His His Leu Ile Asp Asn
            770                 775                 780
Lys Lys Met Phe Lys Val Ile Ala Met Asn Gly Ala Val Thr Ser Phe
785                 790                 795                 800
Ile Arg Lys Asn Met Ser Tyr Asp Asn Lys Leu Arg Leu Lys Asp Arg
            805                 810                 815
Ser Asp Phe Ser His His Ala Tyr Asp Ala Ala Ile Ile Ala Leu Phe
            820                 825                 830
Ser Asn Lys Thr Lys Thr Leu Tyr Asn Leu Ile Asp Pro Ser Leu Asn
            835                 840                 845
Gly Ile Ile Ser Lys Arg Ser Glu Gly Tyr Trp Val Ile Glu Asp Arg
            850                 855                 860
Tyr Thr Gly Glu Ile Lys Glu Leu Lys Lys Glu Asp Trp Thr Ser Ile
865                 870                 875                 880
Lys Asn Asn Val Gln Ala Arg Lys Ile Ala Lys Glu Ile Glu Glu Tyr
            885                 890                 895
Leu Ile Asp Leu Asp Asp Glu Val Phe Phe Ser Arg Lys Thr Lys Arg
            900                 905                 910
Lys Thr Asn Arg Gln Leu Tyr Asn Glu Thr Ile Tyr Gly Ile Ala Ala
            915                 920                 925
Lys Thr Asp Glu Asp Gly Ile Thr Asn Tyr Tyr Lys Lys Glu Lys Phe
            930                 935                 940
Ser Ile Leu Asp Asp Lys Asp Ile Tyr Leu Arg Leu Leu Arg Glu Arg
945                 950                 955                 960
Glu Lys Phe Val Ile Asn Gln Ser Asn Pro Glu Val Ile Asp Gln Ile
            965                 970                 975
Ile Glu Ile Ile Glu Ser Tyr Gly Lys Glu Asn Asn Ile Pro Ser Arg
            980                 985                 990
Asp Glu Ala Ile Asn Ile Lys Tyr Thr Lys Asn Lys Ile Asn Tyr Asn
            995                 1000                1005
Leu Tyr Leu Lys Gln Tyr Met Arg Ser Leu Thr Lys Ser Leu Asp
            1010                1015                1020
Gln Phe Ser Glu Gly Phe Ile Asn Gln Met Ile Ala Asn Lys Thr
            1025                1030                1035
Phe Val Leu Tyr Asn Pro Thr Lys Asn Thr Thr Arg Lys Ile Lys
            1040                1045                1050
Phe Leu Arg Leu Val Asn Asp Val Lys Ile Asn Asp Ile Arg Lys
            1055                1060                1065
Asn Gln Val Ile Asn Lys Phe Asn Gly Lys Asn Asn Glu Pro Lys
            1070                1075                1080
Ala Phe Tyr Glu Asn Ile Asn Ser Leu Gly Ala Ile Val Phe Lys
            1085                1090                1095
Ser Ser Ala Asn Asn Phe Lys Thr Leu Ser Ile Asn Thr Gln Ile
            1100                1105                1110
Ala Ile Phe Gly Asp Lys Asn Trp Asp Ile Glu Asp Phe Lys Thr
            1115                1120                1125
Tyr Asn Met Glu Lys Ile Glu Lys Tyr Lys Glu Ile Tyr Gly Ile
            1130                1135                1140
```

```
Asp Lys Thr Tyr Asn Phe His Ser Phe Ile Phe Pro Gly Thr Ile
    1145                1150                1155

Leu Leu Asp Lys Gln Asn Lys Glu Phe Tyr Tyr Ile Ser Ser Ile
    1160                1165                1170

Gln Thr Val Asn Asp Gln Ile Glu Leu Lys Phe Leu Asn Lys Ile
    1175                1180                1185

Glu Phe Lys Asn Asp Asp Asn Thr Ser Gly Ala Asn Lys Pro Pro
    1190                1195                1200

Arg Arg Leu Arg Phe Gly Ile Lys Ser Ile Met Asn Asn Tyr Glu
    1205                1210                1215

Gln Val Asp Ile Ser Pro Phe Gly Ile Asn Lys Lys Ile Phe Glu
    1220                1225                1230

Pro Lys Lys Lys Arg Lys Val Pro Lys Lys Lys Arg Lys Val
    1235                1240                1245
```

<210> SEQ ID NO 9
<211> LENGTH: 3831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgaacaaca gcatcaagag caagcccgaa gtgaccatcg gcctggatct cggcgttggc      60
tctgttggat gggccatcgt ggacaacgag acaaacatca tccaccacct gggcagcaga     120
ctgttcagcc aggccaagac agctgaggac aggcggtctt tcagaggcgt gcggagactg     180
atccggcgga gaaagtacaa gctgaagaga ttcgtgaacc tgatctggaa gtacaacagc     240
tacttcggct tcaagaacaa agaggacatc ctgaacaact accaagagca gcagaaactg     300
cacaacaccg tgctgaacct gaagctcgaa gccctgaacg ccaagatcga ccccaaggct     360
ctgagctgga ttctgcacga ctacctgaag aaccggggcc acttctacga ggacaaccgg     420
gacttcaacg tgtaccccac agaggaactg gccaactact cgacgagtt cggctactac     480 aagggcatca tcgacagcaa gaacgacgac gatgataagc tggaagaggg cctgaccaag     540
tacaagttca gcaaccagca ctggctggaa gaagtgaaga ggtcctgag caaccagacc     600 ggcctgcctg agaagttcaa agaggaatac gagagcctgt tcagctacgt gcggaactac     660
tctgaaggcc ctggcagcat caacagcgtg tccccatacg gcatctatca cctggacgag     720
aaagagggca aagtcgtcca gagtataac aacatctggg acaagaccat cgggaagtgc     780
agcatcttcc ccgacgagta cagagcccct aagaacagcc ctatcgccat gatcttcaac     840
gagatcaacg agctgagcac catccggtcc tacagcatct acctgaccgg ctggttcatc     900
aatcaagagt tcaagaaggc ctacctgaac aagctgctgg acctgctgat caagaccaac     960
agcgagaagc ccatcgacgc ccggcagttt aagaagctgc gggaagagac aatcgccgag    1020
agcatcggca agaaacccct gaaggacgtg gaaagcgagg aaaagctgga aaaggacgac    1080
cacaagtgga gctgaaggg cctgaagctg aacaccaacg gcaagatcca gtacaacgac    1140
ctgtctagcc tggccaagtt cgtgcacaaa ctgaagcagc acctgaaact ggactttctg    1200
ctggaagatc agtacacccc tctggacaag atcaacttcc tgcagagcct gtacgtgtac    1260
ctgggcaagc acctgagata cagcaacaga gtggacagcg ccaacctgaa agagttcagc    1320
gacagctccc ggctgttcga gagtgctg caagagcaga aggacggcct gttcaagctg    1380
```

| | |
|---|---|
| tttgagcaga ccgacaagga cgacgagaag atcctgacac agacccacag cctgtccacc | 1440 |
| aaggctatgc tgctggccat caccagaatg accaacctgg acaatgacga ggataaccag | 1500 |
| aagaacaacg acaaaggctg gaacttcgag gccatcaaga acttcgacca gaagttcatc | 1560 |
| gacatcacca agacgaacaa caacctgagc ctgaagcagg acaagcgcta cctggatgac | 1620 |
| cagttcatca acgacgccat tctgagccct ggcgtgaaga gaatcctgcg cgaggccacc | 1680 |
| aaggtgttca cgccatcct caagcagttc tccgaagagt acgacgtgac caaggtggtc | 1740 |
| atcgagctgg ccagagagct gagcgaagag aaagaactgg aaaacaccaa gaactacaag | 1800 |
| aagcttatca agaagaacgg cgataagatc agcgagggac tgaaagccct ggggatcgcc | 1860 |
| gaggataaga tcgaagagat cctgaagtct cccaccaagt cctacaaagt gctgctgtgg | 1920 |
| ctgcagcagg accacatcga tcctacagc cagaaagaga tcgccttcga cgatatcctg | 1980 |
| accaaaaccg aaaagaccga gatcgaccac atcattcctt actccatcag cttcgacgac | 2040 |
| agcagcagca caaactgct ggtgctggcc gagtccaatc aggccaagtc caaccagaca | 2100 |
| ccttacgagt ttatcaactc cggcaaggcc gagatcacct gggaagtgta cgaggcctac | 2160 |
| tgccacaagt tcaaaaacgg cgactccagc ctgctggaca gcacccagag aagcaagaaa | 2220 |
| ttcgccaaga tgatgaagac cgacaccagc tctaagtacg acatcggctt tctggcccgg | 2280 |
| aacctgaacg acaccagata cgccaccatc gtgttccggg acgctctgaa ggactacgcc | 2340 |
| aacaaccacc tggtggaaga taagcccatg ttcaaggtcg tgtgcatcaa cggcggcgtg | 2400 |
| accagcttcc tgcggaagaa ctttgacccc aagtcttggt acgccaagaa ggacagagac | 2460 |
| aagaacattc accgccgt ggacgccagc atcatctcca tcttcagcaa cgagactaag | 2520 |
| accctgttca accagctgac aaagttcgcc gactacaagc tgttcaagaa taccgacggc | 2580 |
| tcttggaaga agatcgatcc taagacaggc gtggtgtcag aagtgaccga cgagaattgg | 2640 |
| aagcagatcc gcgtgcgcaa ccaggtgtcc gagatcgcca agtgatcga caagtacatc | 2700 |
| caggacagca acatcgagcg gaaggccaga tacagccgga agatcgagaa caagaccaat | 2760 |
| atcagcctgt taacgacac cgtgtactcc gccaagaaag tgggctacga ggatcagatc | 2820 |
| aagcgcaaga acctgaaaac cctggacatc acgagagcg ccgaggaaaa caagaacagc | 2880 |
| aaagtgaaaa agcagttcgt gtaccggaag ctcgtgaacg tgtccctgct gaacaatgac | 2940 |
| aagctggccg acctgttcgc cgagaaagaa gatattctga tgtaccgggc caatccgtgg | 3000 |
| gtcatcaacc tggccgagca gattttcaac gagtacaccg agaacaaaaa gatcaagagc | 3060 |
| cagaacgtgt tcgagaagta catgctggat ctgaccaaag agttccccga gaagtttagc | 3120 |
| gaggccttcg tgaagtccat gatcagaaac aagaccgcca tcatctacaa cgtcgagaag | 3180 |
| gatgtggtgc accggatcaa gcggctgaag attctgagca gcgagctgaa agaaaacaag | 3240 |
| tggtccaacg tgatcatccg ctccaagaac gagagcggca ccaagctgag ctaccaggac | 3300 |
| accatcaact ctatcgccct gatgatcatg cggagcatcg acccaaccgc caaaaaacag | 3360 |
| tacatcaggg tgcccctgaa caccctgaat ctgcacctgg cgaccagga cttcgacctg | 3420 |
| cacaatatcg acgcctatct gaagaagcct aagttcgtca agtacctgaa ggccaatgag | 3480 |
| atcggcgacg agtataagcc ttggcgcgtg ctgacaagcg gcactgct gatccacaag | 3540 |
| aaagacaaga aactcatgta catcagcagc ttccagaacc tcaacgacct catcgagatc | 3600 |
| aagaatctga tcgagacaga gtacaaagaa aacgtggact cagacccaa gaagaagaaa | 3660 |
| aaggccagcc agatcctgag aagcctgagc gtgatcctga cgattacat cctgctggat | 3720 |
| gccaagtata acttcgacat cctgggcctg tctaagaaca agattgacga gatcctcaac | 3780 | agcaagctgg acctcgacaa gattgccaag cccaagaaga agaggaaggt g    3831

<210> SEQ ID NO 10
<211> LENGTH: 1277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Asn Asn Ser Ile Lys Ser Lys Pro Glu Val Thr Ile Gly Leu Asp
1               5                   10                  15

Leu Gly Val Gly Ser Val Gly Trp Ala Ile Val Asp Asn Glu Thr Asn
            20                  25                  30

Ile Ile His His Leu Gly Ser Arg Leu Phe Ser Gln Ala Lys Thr Ala
        35                  40                  45

Glu Asp Arg Arg Ser Phe Arg Gly Val Arg Arg Leu Ile Arg Arg Arg
    50                  55                  60

Lys Tyr Lys Leu Lys Arg Phe Val Asn Leu Ile Trp Lys Tyr Asn Ser
65                  70                  75                  80

Tyr Phe Gly Phe Lys Asn Lys Glu Asp Ile Leu Asn Asn Tyr Gln Glu
                85                  90                  95

Gln Gln Lys Leu His Asn Thr Val Leu Asn Leu Lys Leu Glu Ala Leu
            100                 105                 110

Asn Ala Lys Ile Asp Pro Lys Ala Leu Ser Trp Ile Leu His Asp Tyr
        115                 120                 125

Leu Lys Asn Arg Gly His Phe Tyr Glu Asp Asn Arg Asp Phe Asn Val
    130                 135                 140

Tyr Pro Thr Glu Glu Leu Ala Asn Tyr Phe Asp Glu Phe Gly Tyr Tyr
145                 150                 155                 160

Lys Gly Ile Ile Asp Ser Lys Asn Asp Asp Asp Lys Leu Glu Glu
                165                 170                 175

Gly Leu Thr Lys Tyr Lys Phe Ser Asn Gln His Trp Leu Glu Glu Val
            180                 185                 190

Lys Lys Val Leu Ser Asn Gln Thr Gly Leu Pro Glu Lys Phe Lys Glu
        195                 200                 205

Glu Tyr Glu Ser Leu Phe Ser Tyr Val Arg Asn Tyr Ser Glu Gly Pro
    210                 215                 220

Gly Ser Ile Asn Ser Val Ser Pro Tyr Gly Ile Tyr His Leu Asp Glu
225                 230                 235                 240

Lys Glu Gly Lys Val Val Gln Lys Tyr Asn Asn Ile Trp Asp Lys Thr
                245                 250                 255

Ile Gly Lys Cys Ser Ile Phe Pro Asp Glu Tyr Arg Ala Pro Lys Asn
            260                 265                 270

Ser Pro Ile Ala Met Ile Phe Asn Glu Ile Asn Glu Leu Ser Thr Ile
        275                 280                 285

Arg Ser Tyr Ser Ile Tyr Leu Thr Gly Trp Phe Ile Asn Gln Glu Phe
    290                 295                 300

Lys Lys Ala Tyr Leu Asn Lys Leu Leu Asp Leu Leu Ile Lys Thr Asn
305                 310                 315                 320

Ser Glu Lys Pro Ile Asp Ala Arg Gln Phe Lys Lys Leu Arg Glu Glu
                325                 330                 335

Thr Ile Ala Glu Ser Ile Gly Lys Glu Thr Leu Lys Asp Val Glu Ser
            340                 345                 350
```

```
Glu Glu Lys Leu Glu Lys Asp Asp His Lys Trp Lys Leu Lys Gly Leu
            355                 360                 365

Lys Leu Asn Thr Asn Gly Lys Ile Gln Tyr Asn Asp Leu Ser Ser Leu
    370                 375                 380

Ala Lys Phe Val His Lys Leu Lys Gln His Leu Lys Leu Asp Phe Leu
385                 390                 395                 400

Leu Glu Asp Gln Tyr Thr Pro Leu Asp Lys Ile Asn Phe Leu Gln Ser
                405                 410                 415

Leu Tyr Val Tyr Leu Gly Lys His Leu Arg Tyr Ser Asn Arg Val Asp
            420                 425                 430

Ser Ala Asn Leu Lys Glu Phe Ser Asp Ser Ser Arg Leu Phe Glu Arg
            435                 440                 445

Val Leu Gln Glu Gln Lys Asp Gly Leu Phe Lys Leu Phe Glu Gln Thr
    450                 455                 460

Asp Lys Asp Asp Glu Lys Ile Leu Thr Gln Thr His Ser Leu Ser Thr
465                 470                 475                 480

Lys Ala Met Leu Leu Ala Ile Thr Arg Met Thr Asn Leu Asp Asn Asp
                485                 490                 495

Glu Asp Asn Gln Lys Asn Asn Asp Lys Gly Trp Asn Phe Glu Ala Ile
            500                 505                 510

Lys Asn Phe Asp Gln Lys Phe Ile Asp Ile Thr Lys Thr Asn Asn Asn
    515                 520                 525

Leu Ser Leu Lys Gln Asp Lys Arg Tyr Leu Asp Asp Gln Phe Ile Asn
    530                 535                 540

Asp Ala Ile Leu Ser Pro Gly Val Lys Arg Ile Leu Arg Glu Ala Thr
545                 550                 555                 560

Lys Val Phe Asn Ala Ile Leu Lys Gln Phe Ser Glu Glu Tyr Asp Val
                565                 570                 575

Thr Lys Val Val Ile Glu Leu Ala Arg Glu Leu Ser Glu Glu Lys Glu
            580                 585                 590

Leu Glu Asn Thr Lys Asn Tyr Lys Lys Leu Ile Lys Lys Asn Gly Asp
    595                 600                 605

Lys Ile Ser Glu Gly Leu Lys Ala Leu Gly Ile Ala Glu Asp Lys Ile
    610                 615                 620

Glu Glu Ile Leu Lys Ser Pro Thr Lys Ser Tyr Lys Val Leu Leu Trp
625                 630                 635                 640

Leu Gln Gln Asp His Ile Asp Pro Tyr Ser Gln Lys Glu Ile Ala Phe
                645                 650                 655

Asp Asp Ile Leu Thr Lys Thr Glu Lys Thr Glu Ile Asp His Ile Ile
            660                 665                 670

Pro Tyr Ser Ile Ser Phe Asp Asp Ser Ser Asn Lys Leu Leu Val
    675                 680                 685

Leu Ala Glu Ser Asn Gln Ala Lys Ser Asn Gln Thr Pro Tyr Glu Phe
    690                 695                 700

Ile Asn Ser Gly Lys Ala Glu Ile Thr Trp Glu Val Tyr Glu Ala Tyr
705                 710                 715                 720

Cys His Lys Phe Lys Asn Gly Asp Ser Ser Leu Leu Asp Ser Thr Gln
                725                 730                 735

Arg Ser Lys Lys Phe Ala Lys Met Met Lys Thr Asp Thr Ser Ser Lys
            740                 745                 750

Tyr Asp Ile Gly Phe Leu Ala Arg Asn Leu Asn Asp Thr Arg Tyr Ala
    755                 760                 765
```

Thr Ile Val Phe Arg Asp Ala Leu Lys Asp Tyr Ala Asn Asn His Leu
770                 775                 780

Val Glu Asp Lys Pro Met Phe Lys Val Val Cys Ile Asn Gly Gly Val
785                 790                 795                 800

Thr Ser Phe Leu Arg Lys Asn Phe Asp Pro Lys Ser Trp Tyr Ala Lys
            805                 810                 815

Lys Asp Arg Asp Lys Asn Ile His His Ala Val Asp Ala Ser Ile Ile
            820                 825                 830

Ser Ile Phe Ser Asn Glu Thr Lys Thr Leu Phe Asn Gln Leu Thr Lys
            835                 840                 845

Phe Ala Asp Tyr Lys Leu Phe Lys Asn Thr Asp Gly Ser Trp Lys Lys
850                 855                 860

Ile Asp Pro Lys Thr Gly Val Val Ser Glu Val Thr Asp Glu Asn Trp
865                 870                 875                 880

Lys Gln Ile Arg Val Arg Asn Gln Val Ser Glu Ile Ala Lys Val Ile
            885                 890                 895

Asp Lys Tyr Ile Gln Asp Ser Asn Ile Glu Arg Lys Ala Arg Tyr Ser
            900                 905                 910

Arg Lys Ile Glu Asn Lys Thr Asn Ile Ser Leu Phe Asn Asp Thr Val
            915                 920                 925

Tyr Ser Ala Lys Lys Val Gly Tyr Glu Asp Gln Ile Lys Arg Lys Asn
930                 935                 940

Leu Lys Thr Leu Asp Ile His Glu Ser Ala Glu Asn Lys Asn Ser
945                 950                 955                 960

Lys Val Lys Lys Gln Phe Val Tyr Arg Lys Leu Val Asn Val Ser Leu
            965                 970                 975

Leu Asn Asn Asp Lys Leu Ala Asp Leu Phe Ala Glu Lys Glu Asp Ile
            980                 985                 990

Leu Met Tyr Arg Ala Asn Pro Trp Val Ile Asn Leu Ala Glu Gln Ile
        995                 1000                1005

Phe Asn Glu Tyr Thr Glu Asn Lys Lys Ile Lys Ser Gln Asn Val
    1010                1015                1020

Phe Glu Lys Tyr Met Leu Asp Leu Thr Lys Glu Phe Pro Glu Lys
    1025                1030                1035

Phe Ser Glu Ala Phe Val Lys Ser Met Ile Arg Asn Lys Thr Ala
    1040                1045                1050

Ile Ile Tyr Asn Val Glu Lys Asp Val Val His Arg Ile Lys Arg
    1055                1060                1065

Leu Lys Ile Leu Ser Ser Glu Leu Lys Glu Asn Lys Trp Ser Asn
    1070                1075                1080

Val Ile Ile Arg Ser Lys Asn Glu Ser Gly Thr Lys Leu Ser Tyr
    1085                1090                1095

Gln Asp Thr Ile Asn Ser Ile Ala Leu Met Ile Met Arg Ser Ile
    1100                1105                1110

Asp Pro Thr Ala Lys Lys Gln Tyr Ile Arg Val Pro Leu Asn Thr
    1115                1120                1125

Leu Asn Leu His Leu Gly Asp Gln Asp Phe Asp Leu His Asn Ile
    1130                1135                1140

Asp Ala Tyr Leu Lys Lys Pro Lys Phe Val Lys Tyr Leu Lys Ala
    1145                1150                1155

Asn Glu Ile Gly Asp Glu Tyr Lys Pro Trp Arg Val Leu Thr Ser
    1160                1165                1170

Gly Thr Leu Leu Ile His Lys Lys Asp Lys Lys Leu Met Tyr Ile

| | | | | | | | | | | |
|---|---|---|---|---|---|---|---|---|---|---|
| | | 1175 | | | 1180 | | | 1185 | | |

Ser Ser Phe Gln Asn Leu Asn Asp Leu Ile Glu Ile Lys Asn Leu
        1190                1195                1200

Ile Glu Thr Glu Tyr Lys Glu Asn Val Asp Ser Asp Pro Lys Lys
    1205                1210                1215

Lys Lys Lys Ala Ser Gln Ile Leu Arg Ser Leu Ser Val Ile Leu
    1220                1225                1230

Asn Asp Tyr Ile Leu Leu Asp Ala Lys Tyr Asn Phe Asp Ile Leu
    1235                1240                1245

Gly Leu Ser Lys Asn Lys Ile Asp Glu Ile Leu Asn Ser Lys Leu
    1250                1255                1260

Asp Leu Asp Lys Ile Ala Lys Pro Lys Lys Arg Lys Val
    1265                1270                1275

<210> SEQ ID NO 11
<211> LENGTH: 3378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgcagaaca tcaccttcag cttcgacgtg ggctacgcct ctatcggatg ggctgttgtt    60
caggcccctg ctcagccaga gcaggaccct ggaatagtgg cctgtggcac cgtgctgttc   120
cctagcgacg attgccaggc cttccagcgg agaaactacc ggcggctgcg gaggaacatc   180
cggtccagaa gagtgcggat cgagcggatc ggaaagctgc tggttcaggc cggaatcctg   240
acacctgagg aaaaggccac acctggacac cccgctccat tcttttttgg cagcccaggct   300
tggcagggca tcagacaact gtctccactg gaagtgtggc acatcctgcg ttggtacgcc   360
cacaacagag ctacgacaa caatgccgcc tgggccaccg tgtccaccaa agaggatacc   420
gagaaagtca caacgcccg gcacctgatg cagaagtttg gcgccgagac aatgtgcgcc   480
acactgtgcc atgctatgga actggacatg gacgtgcccg atgccgccat gacagtgtct   540
acaccagcct acagaaccct gaacagcgcc tttcctagag atgtggtgca gagagaggtg   600
ctggacatcc tgagacacag cgccagccac atcaagagc tgaccctga gatcatccgg   660
ctgatcgccc agcaagagga tctgagcaca gagcagagaa gcgagctggc cgccaaggga   720
attagactgg ccagaagata ccggggcagc ctgctgtttg acagctgct gcccagattc   780
gacaaccgga tcatcagacg gtgccccatc atctgggccc acacatttga gcaggccaag   840
accagcggca tgagcgagaa agaagctcag gccctggctg acaaggtggc caaagtgcct   900
acagccgact gtcccgagtt ctacgcctac agattcgccc gcatcctgaa caatctgaga   960
gccaacggac tgcccctgcc tgtggaagtt cgctgtgaac tgatgcaggc cgccagagcc  1020
gagggaaaac tgcagccgc caagatcaag aaagaaatca tgaggctgat gggcgacgtc  1080
gagagcaaca tcgaccacta cttccatctg caccccgaca gcgaggaagc cctgattctc  1140
gatcccgcta tggaatgcct gcaccggacc ggactgtacg atgccctcag ctctgtcgtg  1200
cgaagagtgg ccctgaccag actgcggaga ggcaaaatct gtaccctgc ctacctgcgg  1260
gacatgatgc tgagacacgg cgaggatacc caggctctgg atctggccat tgccaagcag  1320
cagggaagaa aggcccctcg gcctagaaag aacgacacag atgccagcgc cgacgccagc  1380
attgcatggc aagataagcc cctggctcct aagacagcct ctggcagagc cccttatgcc  1440
```

| | |
|---|---|
| agaccagttc tgagacaggc cgtggacgag atcatgaatg cgaggaccc taccaggcca | 1500 |
| gctctggatg aacagcatcc cgacggcgag gacaagcctt ctcacggctg tctgtatggc | 1560 |
| ctgctggacc ctgccagcaa agagaacgag tacctgaaca agcttcccct ggacgccctg | 1620 |
| acaaacaatc acctcgtgcg gcaccggatg ctgatcctgg atagactgac ccaggacctc | 1680 |
| gtcagagagt tcgctgacgg cgatcccagc agagtggaac ggttctgtat cgaagtgggc | 1740 |
| agagagctga gcgccttctc tggcatgacc agcaagcaga tccagtccga gctgaacgag | 1800 |
| cggatgaagc acttcaagag cgccgtggcc tatctggcca acacgcccc tgatatggcc | 1860 |
| acatctgccg gcctgatccg gaagtgcaga atcgctatgg acatgaactg cagtgccct | 1920 |
| ttcaccggcc agacctacat gccctacgac ctgcctaagc tggaacgcga gcacatcgtg | 1980 |
| ccctacgcca acagaaagac agatgccctg tctgccctgg tgctgacatg gctggccgtg | 2040 |
| aacaagatga agggcaagag aaccgcctac cagtttatca agagtgcga gggccagagc | 2100 |
| gtgcccggca gaaatcagaa tatcgtgtcc gtgaagcagt acgagacatt cgtggaaaag | 2160 |
| ctggacacca agggccacgc cgacgacgcc aagagaaaaa agacccggaa gaaactgatg | 2220 |
| atggtggaca gactgagcag ccagggaaca aacggcgagt ctgagctgga tttcaccgag | 2280 |
| ggcatgatga cccagagcag ccacctgatg aagatcgccg ctagaggcgt gcggaagaac | 2340 |
| tttcctcacg ccaccgtgga catgatccct ggcgctatta ctggcactgt gcgcaaggct | 2400 |
| tggaaggtgg caggatgcct ggccggcatt tgtcctgaag ccgtcgatcc cgtgacacac | 2460 |
| agaatccagg acaaagagac actgcggcgg ctgacccatc tgcatcatgc actggatgcc | 2520 |
| tgcgtgctgg gactgatccc tcacctgatt ccagagcaca gatccggcct gctgagaaaa | 2580 |
| gctctggccg ctagaaggct gcccgagaat gttcggcaag aggtggaaag cgccgtgtcc | 2640 |
| aagcggtact acaccatcac aaaagagagc aaactggaac tgcgggatct gcccaccaca | 2700 |
| ctgaagaact ctatcgccgc caagctgagc gagggcagag tggtgcaaca catccctgcc | 2760 |
| gatatgagcg gagccaagct ggaagagaca atctggggaa ttgcccctgg ccagcacatc | 2820 |
| gacgacaata gcgaggtggt catccggcag aagtccctga gcatcggcaa ggacggcaac | 2880 |
| agaatcagaa ccagaaagac cgacaagcag ggcaacccca tcaccgagaa ggcctctaag | 2940 |
| ctcgtgggca tcaagcctac cggcaccagc aaactgcagc ccatcagagg cgtgatcatc | 3000 |
| atcaaggaca acttcgccat gctctggac cccgtgccaa ccatgattcc ccaccacaac | 3060 |
| gtgtacaagc ggctggaaga actgcggaag ctgaaccacg gtagacatgt gcggctgctg | 3120 |
| aaaaagggca tgctgatcag gctgagccac cagaagtccg cgacaagaa cggcatgtgg | 3180 |
| aaagtgcgga gcatccagga ccagggctcc tctggcctga agtgaatct gcagaggccc | 3240 |
| tactacgccg gcaagatcga ggacaccaga accgagaatt ggaagaacgt gtccatcaag | 3300 |
| gccctgctga gccaaggcat ggaaatcctg ccaaccacct actgcggcac cacacctccc | 3360 |
| aagaagaaga ggaaggtg | 3378 |

<210> SEQ ID NO 12
<211> LENGTH: 1126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Gln Asn Ile Thr Phe Ser Phe Asp Val Gly Tyr Ala Ser Ile Gly
1               5                   10                  15

```
Trp Ala Val Val Gln Ala Pro Ala Gln Pro Glu Gln Asp Pro Gly Ile
             20                  25                  30

Val Ala Cys Gly Thr Val Leu Phe Pro Ser Asp Cys Gln Ala Phe
         35                  40                  45

Gln Arg Arg Asn Tyr Arg Arg Leu Arg Arg Asn Ile Arg Ser Arg Arg
50                  55                  60

Val Arg Ile Glu Arg Ile Gly Lys Leu Leu Val Gln Ala Gly Ile Leu
65                  70                  75                  80

Thr Pro Glu Glu Lys Ala Thr Pro Gly His Pro Ala Pro Phe Phe Leu
                 85                  90                  95

Ala Ala Gln Ala Trp Gln Gly Ile Arg Gln Leu Ser Pro Leu Glu Val
             100                 105                 110

Trp His Ile Leu Arg Trp Tyr Ala His Asn Arg Gly Tyr Asp Asn Asn
         115                 120                 125

Ala Ala Trp Ala Thr Val Ser Thr Lys Glu Asp Thr Glu Lys Val Asn
         130                 135                 140

Asn Ala Arg His Leu Met Gln Lys Phe Gly Ala Glu Thr Met Cys Ala
145                 150                 155                 160

Thr Leu Cys His Ala Met Glu Leu Asp Met Asp Val Pro Asp Ala Ala
             165                 170                 175

Met Thr Val Ser Thr Pro Ala Tyr Arg Thr Leu Asn Ser Ala Phe Pro
         180                 185                 190

Arg Asp Val Val Gln Arg Glu Val Leu Asp Ile Leu Arg His Ser Ala
         195                 200                 205

Ser His Ile Lys Glu Leu Thr Pro Glu Ile Ile Arg Leu Ile Ala Gln
         210                 215                 220

Gln Glu Asp Leu Ser Thr Glu Gln Arg Ser Glu Leu Ala Ala Lys Gly
225                 230                 235                 240

Ile Arg Leu Ala Arg Arg Tyr Arg Gly Ser Leu Leu Phe Gly Gln Leu
             245                 250                 255

Leu Pro Arg Phe Asp Asn Arg Ile Ile Arg Arg Cys Pro Ile Ile Trp
         260                 265                 270

Ala His Thr Phe Glu Gln Ala Lys Thr Ser Gly Met Ser Glu Lys Glu
         275                 280                 285

Ala Gln Ala Leu Ala Asp Lys Val Ala Lys Val Pro Thr Ala Asp Cys
290                 295                 300

Pro Glu Phe Tyr Ala Tyr Arg Phe Ala Arg Ile Leu Asn Asn Leu Arg
305                 310                 315                 320

Ala Asn Gly Leu Pro Leu Pro Val Glu Val Arg Cys Glu Leu Met Gln
             325                 330                 335

Ala Ala Arg Ala Glu Gly Lys Leu Thr Ala Ala Lys Ile Lys Lys Glu
         340                 345                 350

Ile Met Arg Leu Met Gly Asp Val Glu Ser Asn Ile Asp His Tyr Phe
         355                 360                 365

His Leu His Pro Asp Ser Glu Glu Ala Leu Ile Leu Asp Pro Ala Met
         370                 375                 380

Glu Cys Leu His Arg Thr Gly Leu Tyr Asp Ala Leu Ser Ser Val Val
385                 390                 395                 400

Arg Arg Val Ala Leu Thr Arg Leu Arg Gly Lys Ile Cys Thr Pro
             405                 410                 415

Ala Tyr Leu Arg Asp Met Met Leu Arg His Gly Glu Asp Thr Gln Ala
             420                 425                 430
```

-continued

```
Leu Asp Leu Ala Ile Ala Lys Gln Gln Gly Arg Lys Ala Pro Arg Pro
            435                 440                 445

Arg Lys Asn Asp Thr Asp Ala Ser Ala Asp Ala Ser Ile Ala Trp Gln
450                 455                 460

Asp Lys Pro Leu Ala Pro Lys Thr Ala Ser Gly Arg Ala Pro Tyr Ala
465                 470                 475                 480

Arg Pro Val Leu Arg Gln Ala Val Asp Glu Ile Met Asn Gly Glu Asp
                485                 490                 495

Pro Thr Arg Pro Ala Leu Asp Glu Gln His Pro Asp Gly Glu Asp Lys
            500                 505                 510

Pro Ser His Gly Cys Leu Tyr Gly Leu Leu Asp Pro Ala Ser Lys Glu
        515                 520                 525

Asn Glu Tyr Leu Asn Lys Leu Pro Leu Asp Ala Leu Thr Asn Asn His
    530                 535                 540

Leu Val Arg His Arg Met Leu Ile Leu Asp Arg Leu Thr Gln Asp Leu
545                 550                 555                 560

Val Arg Glu Phe Ala Asp Gly Asp Pro Ser Arg Val Glu Arg Phe Cys
                565                 570                 575

Ile Glu Val Gly Arg Glu Leu Ser Ala Phe Ser Gly Met Thr Ser Lys
            580                 585                 590

Gln Ile Gln Ser Glu Leu Asn Glu Arg Met Lys His Phe Lys Ser Ala
        595                 600                 605

Val Ala Tyr Leu Ala Lys His Ala Pro Asp Met Ala Thr Ser Ala Gly
    610                 615                 620

Leu Ile Arg Lys Cys Arg Ile Ala Met Asp Met Asn Trp Gln Cys Pro
625                 630                 635                 640

Phe Thr Gly Gln Thr Tyr Met Pro Tyr Asp Leu Pro Lys Leu Glu Arg
                645                 650                 655

Glu His Ile Val Pro Tyr Ala Asn Arg Lys Thr Asp Ala Leu Ser Ala
            660                 665                 670

Leu Val Leu Thr Trp Leu Ala Val Asn Lys Met Lys Gly Lys Arg Thr
        675                 680                 685

Ala Tyr Gln Phe Ile Lys Glu Cys Glu Gly Gln Ser Val Pro Gly Arg
    690                 695                 700

Asn Gln Asn Ile Val Ser Val Lys Gln Tyr Glu Thr Phe Val Glu Lys
705                 710                 715                 720

Leu Asp Thr Lys Gly His Ala Asp Asp Ala Lys Arg Lys Lys Thr Arg
                725                 730                 735

Lys Lys Leu Met Met Val Asp Arg Leu Ser Ser Gln Gly Thr Asn Gly
            740                 745                 750

Glu Ser Glu Leu Asp Phe Thr Glu Gly Met Met Thr Gln Ser Ser His
        755                 760                 765

Leu Met Lys Ile Ala Ala Arg Gly Val Arg Lys Asn Phe Pro His Ala
    770                 775                 780

Thr Val Asp Met Ile Pro Gly Ala Ile Thr Gly Thr Val Arg Lys Ala
785                 790                 795                 800

Trp Lys Val Ala Gly Cys Leu Ala Gly Ile Cys Pro Glu Ala Val Asp
                805                 810                 815

Pro Val Thr His Arg Ile Gln Asp Lys Glu Thr Leu Arg Arg Leu Thr
            820                 825                 830

His Leu His His Ala Leu Asp Ala Cys Val Leu Gly Leu Ile Pro His
        835                 840                 845

Leu Ile Pro Glu His Arg Ser Gly Leu Leu Arg Lys Ala Leu Ala Ala
```

```
                    850                 855                 860
Arg Arg Leu Pro Glu Asn Val Arg Gln Glu Val Ser Ala Val Ser
865                 870                 875                 880

Lys Arg Tyr Tyr Thr Ile Thr Lys Glu Ser Lys Leu Glu Leu Arg Asp
                885                 890                 895

Leu Pro Thr Thr Leu Lys Asn Ser Ile Ala Ala Lys Leu Ser Glu Gly
                900                 905                 910

Arg Val Val Gln His Ile Pro Ala Asp Met Ser Gly Ala Lys Leu Glu
            915                 920                 925

Glu Thr Ile Trp Gly Ile Ala Pro Gly Gln His Ile Asp Asp Asn Ser
        930                 935                 940

Glu Val Val Ile Arg Gln Lys Ser Leu Ser Ile Gly Lys Asp Gly Asn
945                 950                 955                 960

Arg Ile Arg Thr Arg Lys Thr Asp Lys Gln Gly Asn Pro Ile Thr Glu
                965                 970                 975

Lys Ala Ser Lys Leu Val Gly Ile Lys Pro Thr Gly Thr Ser Lys Leu
            980                 985                 990

Gln Pro Ile Arg Gly Val Ile Ile Ile Lys Asp Asn Phe Ala Ile Ala
        995                 1000                1005

Leu Asp Pro Val Pro Thr Met Ile Pro His His Asn Val Tyr Lys
    1010                1015                1020

Arg Leu Glu Glu Leu Arg Lys Leu Asn His Gly Arg His Val Arg
    1025                1030                1035

Leu Leu Lys Lys Gly Met Leu Ile Arg Leu Ser His Gln Lys Ser
    1040                1045                1050

Gly Asp Lys Asn Gly Met Trp Lys Val Arg Ser Ile Gln Asp Gln
    1055                1060                1065

Gly Ser Ser Gly Leu Lys Val Asn Leu Gln Arg Pro Tyr Tyr Ala
    1070                1075                1080

Gly Lys Ile Glu Asp Thr Arg Thr Glu Asn Trp Lys Asn Val Ser
    1085                1090                1095

Ile Lys Ala Leu Leu Ser Gln Gly Met Glu Ile Leu Pro Thr Thr
    1100                1105                1110

Tyr Cys Gly Thr Thr Pro Pro Lys Lys Lys Arg Lys Val
    1115                1120                1125

<210> SEQ ID NO 13
<211> LENGTH: 3324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgagcagaa gcctgacctt cagcttcgac atcggctacg cctctatcgg ctgggccgtg      60
attgcctctg ccagccacga tgatgccgat cctagcgtgt gtggctgtgg caccgtgctg     120
ttccccaagg atgattgcca ggccttcaag cggagagagt accggcggct gcggagaaac     180
atccggtcca agagtgcg gatcgagcgg attggtagac tgctggtgca ggcccagatc       240
atcacccctg agatgaagga aaccagcgga caccccgctc cattctacct ggcatctgag     300
gccctgaagg ccacagaac actggcccct attgaactgt ggcatgtgct gcgttggtac     360
gcccacaaca gaggctacga caacaacgcc agctggtcca acagcctgtc tgaggatggt     420
ggcaacggcg aggataccga gagtgaaaa cacgcccagg acctgatgga caagcacggc     480
```

```
acagctacaa tggccgagac aatctgcaga gagctgaagc tggaagaggg caaagccgac    540
gctcctatgg aagtgtctac ccctgcctac aagaacctga acaccgcctt ccacggctg     600 atcgtggaaa aagaagtgcg gagaatcctg gaactgagcg ccctctgat ccctggactg     660 acagccgaga tcatcgagct gatcgcccag catcaccctc tgaccactga acagagaggc    720
gtgctgctcc agcacggcat taagctggcc agaagataca gaggcagcct gctgttcggc    780
cagctgatcc ctagattcga caacaggatc atcagcagat gccccgtgac atgggcccaa    840
gtgtatgagg ccgagctgaa aagggcaac agcgagcagt ctgccagaga gagagccgag    900
aagctgagca aggtgcccac cgccaattgt cccgagttct acgagtaccg gatggccaga    960
atcctgtgca acatcagagc cgacggcgag cctctgagcg ccgagattag acgcgagctg   1020
atgaaccagg ccagacaaga gggaaagctg accaaggcca gcctggaaaa ggccatctct   1080
agccggctgg gcaaagaaac cgagacaaac gtgtccaact acttcacact gcaccccgac   1140
agcgaggaag ccctgtatct gaatcctgcc gtggaagtgc tgcagagaag cggcatcggc   1200
cagattctga gccccagcgt gtacagaatc gccgccaaca gactgcggag aggcaagagc   1260 gtgacccta actacctgct gaatctgctg aagtccagag gcgagtctgg cgaggccctg   1320 gaaaaaaga tcgagaaaga gtccaagaag aaagaggccg actacgccga cacacccctg   1380
aagcctaagt acgccacagg cagagcccct acgccagaa ccgtgctgaa gaaagtggtg    1440
gaagagatcc tggatggcga ggaccctacc agacctgcta gaggcgaagc tcaccctgac    1500
ggcgaactga agcccacga tggctgcctg tactgcctgc tggataccga cagcagcgtg    1560
aaccagcacc agaaagagcg gagactggac accatgacca caaccacct cgtgcggcac    1620 cggatgctga tcctggacag actcctgaag gatctgatcc aggacttcgc cgacggccag   1680
aaggacagaa tcagcagagt gtgcgtggaa gtcggcaaag agctgaccac cttcagcgct   1740
atggacagca gaagatcca gcgggaactg accctgcggc agaagtctca taccgacgcc    1800
gtgaacagac tgaagagaaa gcttccaggc aagggcctga gcgccaacct gatcagaaag    1860
tgcagaatcg caatggacat gaactggaca tgccccttca ccggcgccac atatggcgat    1920
cacgagctgg aaaatctgga actggaacac atcgtgcccc acagcttcag acagagcaat    1980
gccctgtcta gcctggtgct gacatggcct ggcgtgaaca ggatgaaggg acagagaacc    2040
ggctacgact tcgtggaaca agagcaagag acccccgtgc tgacaagcc caacctgcac    2100 atctgcagcc tgaacaacta tcgcgagctg gtggaaaagc tggacgacaa gaagggacac    2160
gaggacgaca cacggcggaa gaagaaaaga aaggccctgc tgatggtccg aggcctgtct    2220
cacaaacacc agagccagaa ccacgaggcc atgaagaaa tcggcatgac cgagggcatg    2280
atgacccaga gcagccacct gatgaagctg gcctgcaaga gcatcaagac cagcctgcct    2340
gacgctcaca tcgacatgat tccaggcgcc gtgactgccg aagttcgcaa agcctgggat    2400
gtgttcggcg tgttcaaaga actgtgcccc gaagccgccg atcctgactc tggcaagatc    2460
ctgaaagaga acctgcggag cctgactcat ctgcatcacg ccctggatgc ctgtgtgctg    2520
ggactgatcc cctacatcat ccccgctcac cacaatggcc tgctgagaag agtcctggcc    2580
atgcgcagaa tccccgagaa actgatccct caagtgcggc cgtggccaa ccagagacac    2640 tacgtgctga cgacgacgg ccggatgatg ctgagggatc tgagtgccag cctgaaagaa    2700
aacatccgcg agcagctgat ggaacagcga gtgatccagc acgtgcccgc tgatatgggc    2760
ggagcactgc tcaaagaaac aatgcagcgg gtgctgagcg tggacggctc tggcgaagat    2820
```

```
gctatggtgt ccctgtctaa gaagaaggac ggcaagaaag agaagaatca agtcaaggcc    2880
tccaagctcg tgggagtgtt tcctgagggc cccagcaagc tgaaagctct gaaggccgcc    2940
atcgagatcg acggcaatta tggcgtggca ctggacccca agcctgtggt catcagacac    3000
atcaaggtgt tcaagaggat catggccctc aaagagcaga acggcggcaa gccagtgcgc    3060
atcctgaaaa agggcatgct gattcacctg accagcagca aggaccctaa gcacgctggc    3120
gtttggagaa tcgagagcat ccaggacagc aaaggcggcg tgaaactgga cctgcagagg    3180
gctcattgcg ccgtgcctaa gaacaagacc cacgagtgca attggagaga ggtggacctg    3240
atctcccctg ctgaaaaagta ccagatgaag cgctacccca ccagctacac cggcacacct    3300
agacccaaga agaagaggaa ggtg                                            3324
```

<210> SEQ ID NO 14
<211> LENGTH: 1108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Ser Arg Ser Leu Thr Phe Ser Phe Asp Ile Gly Tyr Ala Ser Ile
1               5                   10                  15

Gly Trp Ala Val Ile Ala Ser Ala Ser His Asp Asp Ala Asp Pro Ser
            20                  25                  30

Val Cys Gly Cys Gly Thr Val Leu Phe Pro Lys Asp Asp Cys Gln Ala
        35                  40                  45

Phe Lys Arg Arg Glu Tyr Arg Arg Leu Arg Arg Asn Ile Arg Ser Arg
    50                  55                  60

Arg Val Arg Ile Glu Arg Ile Gly Arg Leu Val Gln Ala Gln Ile
65                  70                  75                  80

Ile Thr Pro Glu Met Lys Glu Thr Ser Gly His Pro Ala Pro Phe Tyr
                85                  90                  95

Leu Ala Ser Glu Ala Leu Lys Gly His Arg Thr Leu Ala Pro Ile Glu
            100                 105                 110

Leu Trp His Val Leu Arg Trp Tyr Ala His Asn Arg Gly Tyr Asp Asn
        115                 120                 125

Asn Ala Ser Trp Ser Asn Ser Leu Ser Glu Asp Gly Gly Asn Gly Glu
    130                 135                 140

Asp Thr Glu Arg Val Lys His Ala Gln Asp Leu Met Asp Lys His Gly
145                 150                 155                 160

Thr Ala Thr Met Ala Glu Thr Ile Cys Arg Glu Leu Lys Leu Glu Glu
                165                 170                 175

Gly Lys Ala Asp Ala Pro Met Glu Val Ser Thr Pro Ala Tyr Lys Asn
            180                 185                 190

Leu Asn Thr Ala Phe Pro Arg Leu Ile Val Glu Lys Glu Val Arg Arg
        195                 200                 205

Ile Leu Glu Leu Ser Ala Pro Leu Ile Pro Gly Leu Thr Ala Glu Ile
    210                 215                 220

Ile Glu Leu Ile Ala Gln His His Pro Leu Thr Thr Glu Gln Arg Gly
225                 230                 235                 240

Val Leu Leu Gln His Gly Ile Lys Leu Ala Arg Arg Tyr Arg Gly Ser
                245                 250                 255

Leu Leu Phe Gly Gln Leu Ile Pro Arg Phe Asp Asn Arg Ile Ile Ser
            260                 265                 270
```

```
Arg Cys Pro Val Thr Trp Ala Gln Val Tyr Glu Ala Glu Leu Lys Lys
        275                 280                 285

Gly Asn Ser Glu Gln Ser Ala Arg Glu Arg Ala Glu Lys Leu Ser Lys
        290                 295                 300

Val Pro Thr Ala Asn Cys Pro Glu Phe Tyr Glu Tyr Arg Met Ala Arg
305                 310                 315                 320

Ile Leu Cys Asn Ile Arg Ala Asp Gly Glu Pro Leu Ser Ala Glu Ile
                325                 330                 335

Arg Arg Glu Leu Met Asn Gln Ala Arg Gln Glu Gly Lys Leu Thr Lys
                340                 345                 350

Ala Ser Leu Glu Lys Ala Ile Ser Ser Arg Leu Gly Lys Glu Thr Glu
                355                 360                 365

Thr Asn Val Ser Asn Tyr Phe Thr Leu His Pro Asp Ser Glu Ala
        370                 375                 380

Leu Tyr Leu Asn Pro Ala Val Glu Val Leu Gln Arg Ser Gly Ile Gly
385                 390                 395                 400

Gln Ile Leu Ser Pro Ser Val Tyr Arg Ile Ala Ala Asn Arg Leu Arg
                405                 410                 415

Arg Gly Lys Ser Val Thr Pro Asn Tyr Leu Leu Asn Leu Leu Lys Ser
                420                 425                 430

Arg Gly Glu Ser Gly Glu Ala Leu Glu Lys Lys Ile Glu Lys Glu Ser
                435                 440                 445

Lys Lys Lys Glu Ala Asp Tyr Ala Asp Thr Pro Leu Lys Pro Lys Tyr
                450                 455                 460

Ala Thr Gly Arg Ala Pro Tyr Ala Arg Thr Val Leu Lys Val Val
465                 470                 475                 480

Glu Glu Ile Leu Asp Gly Glu Asp Pro Thr Arg Pro Ala Arg Gly Glu
                485                 490                 495

Ala His Pro Asp Gly Glu Leu Lys Ala His Asp Gly Cys Leu Tyr Cys
                500                 505                 510

Leu Leu Asp Thr Asp Ser Ser Val Asn Gln His Gln Lys Glu Arg Arg
                515                 520                 525

Leu Asp Thr Met Thr Asn Asn His Leu Val Arg His Arg Met Leu Ile
                530                 535                 540

Leu Asp Arg Leu Leu Lys Asp Leu Ile Gln Asp Phe Ala Asp Gly Gln
545                 550                 555                 560

Lys Asp Arg Ile Ser Arg Val Cys Val Glu Val Gly Lys Glu Leu Thr
                565                 570                 575

Thr Phe Ser Ala Met Asp Ser Lys Lys Ile Gln Arg Glu Leu Thr Leu
                580                 585                 590

Arg Gln Lys Ser His Thr Asp Ala Val Asn Arg Leu Lys Arg Lys Leu
                595                 600                 605

Pro Gly Lys Ala Leu Ser Ala Asn Leu Ile Arg Lys Cys Arg Ile Ala
        610                 615                 620

Met Asp Met Asn Trp Thr Cys Pro Phe Thr Gly Ala Thr Tyr Gly Asp
625                 630                 635                 640

His Glu Leu Glu Asn Leu Glu Leu Glu His Ile Val Pro His Ser Phe
                645                 650                 655

Arg Gln Ser Asn Ala Leu Ser Ser Leu Val Leu Thr Trp Pro Gly Val
                660                 665                 670

Asn Arg Met Lys Gly Gln Arg Thr Gly Tyr Asp Phe Val Glu Gln Glu
                675                 680                 685
```

```
Gln Glu Asn Pro Val Pro Asp Lys Pro Asn Leu His Ile Cys Ser Leu
690                 695                 700

Asn Asn Tyr Arg Glu Leu Val Glu Lys Leu Asp Asp Lys Lys Gly His
705                 710                 715                 720

Glu Asp Asp Arg Arg Lys Lys Lys Arg Lys Ala Leu Leu Met Val
            725                 730                 735

Arg Gly Leu Ser His Lys His Gln Ser Gln Asn His Glu Ala Met Lys
                740                 745                 750

Glu Ile Gly Met Thr Glu Gly Met Met Thr Gln Ser Ser His Leu Met
            755                 760                 765

Lys Leu Ala Cys Lys Ser Ile Lys Thr Ser Leu Pro Asp Ala His Ile
770                 775                 780

Asp Met Ile Pro Gly Ala Val Thr Ala Glu Val Arg Lys Ala Trp Asp
785                 790                 795                 800

Val Phe Gly Val Phe Lys Glu Leu Cys Pro Glu Ala Ala Asp Pro Asp
                805                 810                 815

Ser Gly Lys Ile Leu Lys Glu Asn Leu Arg Ser Leu Thr His Leu His
            820                 825                 830

His Ala Leu Asp Ala Cys Val Leu Gly Leu Ile Pro Tyr Ile Ile Pro
                835                 840                 845

Ala His His Asn Gly Leu Leu Arg Arg Val Leu Ala Met Arg Arg Ile
850                 855                 860

Pro Glu Lys Leu Ile Pro Gln Val Arg Pro Val Ala Asn Gln Arg His
865                 870                 875                 880

Tyr Val Leu Asn Asp Asp Gly Arg Met Met Leu Arg Asp Leu Ser Ala
                885                 890                 895

Ser Leu Lys Glu Asn Ile Arg Glu Gln Leu Met Glu Gln Arg Val Ile
            900                 905                 910

Gln His Val Pro Ala Asp Met Gly Gly Ala Leu Leu Lys Glu Thr Met
            915                 920                 925

Gln Arg Val Leu Ser Val Asp Gly Ser Gly Glu Asp Ala Met Val Ser
            930                 935                 940

Leu Ser Lys Lys Lys Asp Gly Lys Lys Glu Lys Asn Gln Val Lys Ala
945                 950                 955                 960

Ser Lys Leu Val Gly Val Phe Pro Glu Gly Pro Ser Lys Leu Lys Ala
                965                 970                 975

Leu Lys Ala Ala Ile Glu Ile Asp Gly Asn Tyr Gly Val Ala Leu Asp
            980                 985                 990

Pro Lys Pro Val Val Ile Arg His Ile Lys Val Phe Lys Arg Ile Met
            995                 1000                1005

Ala Leu Lys Glu Gln Asn Gly Gly Lys Pro Val Arg Ile Leu Lys
    1010                1015                1020

Lys Gly Met Leu Ile His Leu Thr Ser Ser Lys Asp Pro Lys His
    1025                1030                1035

Ala Gly Val Trp Arg Ile Glu Ser Ile Gln Asp Ser Lys Gly Gly
    1040                1045                1050

Val Lys Leu Asp Leu Gln Arg Ala His Cys Ala Val Pro Lys Asn
    1055                1060                1065

Lys Thr His Glu Cys Asn Trp Arg Glu Val Asp Leu Ile Ser Leu
    1070                1075                1080

Leu Lys Lys Tyr Gln Met Lys Arg Tyr Pro Thr Ser Tyr Thr Gly
    1085                1090                1095

Thr Pro Arg Pro Lys Lys Lys Arg Lys Val
```

<210> SEQ ID NO 15
<211> LENGTH: 4188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | | | | | |
|---|---|---|---|---|---|
| atggccagag | attacagcgt | cggcctggat | atcggcacct | cttctgttgg | atgggccgcc | 60 |
| atcgacaaca | agtaccacct | gatccgggcc | aagagcaaga | acctgattgg | cgtgcggctg | 120 |
| ttcgatagcg | ccgtgaccgc | cgagaagaga | agaggctaca | gaaccaccag | acggcggctg | 180 |
| agcagacggc | attggagact | gagactgctg | aacgacatct | cgccggacc | tctgaccgat | 240 |
| ttcggcgacg | agaatttcct | ggccagactg | aagtacagct | gggttcaccc | tcaagaccag | 300 |
| agcaatcagg | cccactttgc | cgccggactg | ctgttcgaca | gcaaagagca | ggacaaggac | 360 |
| ttctaccgga | agtaccccac | catctatcac | ctgagactgg | ccctgatgaa | cgacgaccag | 420 |
| aagcacgacc | tgagagaggt | gtacctggcc | atccaccacc | tggtcaagta | cagaggccac | 480 |
| ttcctgatcg | agggcgacgt | gaaagccgac | agcgcctttg | atgtgcacac | cttcgccgac | 540 |
| gccatccaga | gatacgccga | gagcaacaac | tccgacgaga | acctgctggg | caagatcgac | 600 |
| gagaagaagc | tgagcgctgc | cctgaccgat | aagcacggca | gcaaaagcca | gagagccgag | 660 |
| acagccgaaa | ccgccttcga | catcctggac | ctgcagtcca | agaagcagat | ccaggccatc | 720 |
| ctgaagtccg | tcgtgggcaa | ccaggccaat | ctgatggcca | tttttggcct | ggacagcagc | 780 |
| gccatcagca | aggacgagca | gaagaactac | aagttcagct | cgacgacgc | cgacatcgat | 840 |
| gagaagatcg | ccgattctga | ggccctgctg | agcgataccg | agttcgagtt | cctgtgcgat | 900 |
| ctgaaggccg | cctttgacgg | cctgacactg | aaaatgctgc | tgggcgacga | caagaccgtg | 960 |
| tccgctgcta | tggttcgacg | gttcaacgag | caccagaagg | actgggagta | catcaagagc | 1020 |
| cacatccgga | cgccaagaa | cgccggcaat | ggcctgtacg | agaagtctaa | gaagttcgac | 1080 |
| ggcatcaacg | ccgcctatct | ggctctgcag | tccgacaacg | aggacgacag | aaagaaggcc | 1140 |
| aagaagattt | tccaggacga | gatcagctcc | gccgacattc | ccgatgatgt | gaaggccgat | 1200 |
| ttcctgaaga | agattgacga | cgatcagttc | ctgcctatcc | agcggaccaa | gaacaacggc | 1260 |
| acaatccctc | accagctgca | ccggaacgag | ctggaacaga | tcatcgagaa | gcagggatc | 1320 |
| tactacccat | tcctgaagga | cacctaccaa | gagaacagcc | acgagctgaa | caaaatcaca | 1380 |
| gccctgatca | acttcagggt | gcctactac | gtgggccctc | tggtggaaga | ggaacagaaa | 1440 |
| atcgccgacg | acgcaagaa | catccccgat | cctaccaacc | actggatggt | ccgaaagtcc | 1500 |
| aacgacacca | tcacaccctg | gaacctgagc | caggtggtcg | acctggataa | gagcggcaga | 1560 |
| agattcatcg | agcggctgac | cggcaccgat | acctatctga | tcggagagcc | cacactgccc | 1620 |
| aagaacagcc | tgctgtacca | gaaattcgac | gtgctgcaag | aactgaacaa | catccgcgtg | 1680 |
| tccggcagac | ggctggacat | tagagccaag | caggatgcct | tcgagcacct | gttcaaggtg | 1740 |
| cagaaaaccg | tgtctgctac | caatctgaag | gacttcctgg | tgcaagccgg | ctacatcagc | 1800 |
| gaggacaccc | agattgaagg | actcgccgac | gtgaacggaa | agaacttcaa | caacgccctg | 1860 |
| accacctaca | actacctggt | gtctgtgctg | ggccgcgagt | tcgtgaaaaa | ccccagcaac | 1920 |
| gaggaactgc | tggaagagat | taccgagctg | cagaccgtgt | cgaggacaa | gaaggtgctg | 1980 |

```
cggagacagc tggatcagct ggacggactg agcgaccaca acagagagaa gctttcccgg    2040
aagcactaca ccggctgggg cagaatcagc aagaagctgc tgaccaccaa gatcgtgcag    2100
aacgccgaca agatcgataa ccagaccttc gatgtgcccc ggatgaacca gagcatcatc    2160
gacaccctgt acaacaccaa gatgaacctg atggaaatca tcaacaatgc cgaggatgac    2220
ttcggcgtca gagcctggat cgacaagcag aacaccaccg atggcgacga gcaggacgtg    2280
tacagcctga tcgatgaact ggctggcccc aaagagatca gcggggcat cgtgcagtcc    2340 tttagaatcc tggacgacat caccaaggcc gtgggctacg cccctaaacg ggtgtacctc    2400
gaatttgcca gaaagaccca agagagccac ctgaccaaca gccggaagaa ccagctgagc    2460
accctgctga agaatgccgg cctgtctgag ctggtcacac aggtgtccca gtatgatgcc    2520
gccgctctgc agaacgaccg gctgtatctt tacttcctgc agcaaggcaa ggacatgtac    2580
tccggcgaga agctgaatct ggacaacctg agcaactacg acatcgacca catcatccct    2640
caggcttaca ccaaggacaa cagcctggac aacagagtgc tggtgtccaa tatcaccaac    2700
cggcggaagt ccgacagcag caactatctg cccgctctga tcgataagat gcggcccttt    2760
tggagcgtgc tgagcaagca ggggctgctg tctaagcaca agttcgccaa cctgaccaga    2820
accagagact tcgacgatat ggaaaaagag cggtttatcg cccgcagcct ggtggaaacc    2880
cggcagatca ttaagaacgt ggccagcctg attgacagcc acttcggcgg agagacaaaa    2940
gccgtggcca tttagaagcag cctgacagcc gacatgcgga gatacgtgga catccccaag    3000
aaccgggaca tcaacgacta ccaccacgcc ttcgatgccc tgctgtttag cacagtgggc    3060
cagtacaccg agaacagcgg cctgatgaag aagggccagc tgtccgattc tgccggcaac    3120
cagtacaatc ggtacatcaa agagtggatt cacgccgcca ggctgaacgc acagtcccag    3180
agagtgaacc ccttcggctt tgtcgtgggc tccatgagaa atgctgcccc tggcaagctg    3240
aaccccgaga caggggagat caccccagag gaaaacgccg actggtctat cgccgacctg    3300
gactacctgc acaaagtgat gaatttccgg aagatcaccg tgaccaggcg gctgaaggat    3360
cagaaaggac agctgtacga cgagagcaga taccccctccg tgctgcacga cgccaagtct    3420
aaggccagca tcaactttga caagcacaag cccgtggacc tgtacggcgg ctttagctct    3480
gccaagcctg cctatgccgc actgatcaag ttcaagaaca gttccggct ggtcaacgtg    3540 ctgcggcagt ggacctacag cgacaagaac tccgaggact atatccttga gcagatcaga    3600
ggcaagtacc ctaaggccga gatggtgctg tctcacatcc cttacggcca gctggtcaag    3660
aaagatggcg ccctggtcac catctctagc gccacagagc tgcacaactt tgagcagctg    3720
tggctgcctc tggccgacta caagctgatc aacacactgc ttaagaccaa agaggacaac    3780
ctcgtcgata tcctgcacaa ccggctggat ctccccgaga tgacaatcga gagcgccttc    3840
tacaaagcct tcgactccat cctgagcttc gccttcaaca gatacgccct gcaccagaac    3900
gccctcgtga aactgcaggc ccacagggac gatttcaatg ccctgaacta cgaggataag    3960
cagcagaccc tggaaaggat tctggacgct ctgcatgcct ctccagccag cagcgacctg    4020
aagaaaatca acctgtccag cggcttcggc cggctgtttt cccctagcca ctttacccctg    4080 gccgacaccg acgagttcat cttccagagc gtgaccggcc tgttcagcac ccagaaaaca    4140
gtggctcagc tgtatcaaga gacaaagccc aagaagaaga ggaaggtg               4188
```

<210> SEQ ID NO 16
<211> LENGTH: 1396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Arg Asp Tyr Ser Val Gly Leu Asp Ile Gly Thr Ser Ser Val
1               5                   10                  15

Gly Trp Ala Ala Ile Asp Asn Lys Tyr His Leu Ile Arg Ala Lys Ser
            20                  25                  30

Lys Asn Leu Ile Gly Val Arg Leu Phe Asp Ser Ala Val Thr Ala Glu
        35                  40                  45

Lys Arg Arg Gly Tyr Arg Thr Thr Arg Arg Leu Ser Arg Arg His
50                  55                  60

Trp Arg Leu Arg Leu Leu Asn Asp Ile Phe Ala Gly Pro Leu Thr Asp
65                  70                  75                  80

Phe Gly Asp Glu Asn Phe Leu Ala Arg Leu Lys Tyr Ser Trp Val His
                85                  90                  95

Pro Gln Asp Gln Ser Asn Gln Ala His Phe Ala Ala Gly Leu Leu Phe
            100                 105                 110

Asp Ser Lys Glu Gln Asp Lys Asp Phe Tyr Arg Lys Tyr Pro Thr Ile
        115                 120                 125

Tyr His Leu Arg Leu Ala Leu Met Asn Asp Asp Gln Lys His Asp Leu
    130                 135                 140

Arg Glu Val Tyr Leu Ala Ile His His Leu Val Lys Tyr Arg Gly His
145                 150                 155                 160

Phe Leu Ile Glu Gly Asp Val Lys Ala Asp Ser Ala Phe Asp Val His
                165                 170                 175

Thr Phe Ala Asp Ala Ile Gln Arg Tyr Ala Glu Ser Asn Asn Ser Asp
            180                 185                 190

Glu Asn Leu Leu Gly Lys Ile Asp Glu Lys Leu Ser Ala Ala Leu
        195                 200                 205

Thr Asp Lys His Gly Ser Lys Ser Gln Arg Ala Glu Thr Ala Glu Thr
    210                 215                 220

Ala Phe Asp Ile Leu Asp Leu Gln Ser Lys Lys Gln Ile Gln Ala Ile
225                 230                 235                 240

Leu Lys Ser Val Val Gly Asn Gln Ala Asn Leu Met Ala Ile Phe Gly
                245                 250                 255

Leu Asp Ser Ser Ala Ile Ser Lys Asp Glu Gln Lys Asn Tyr Lys Phe
            260                 265                 270

Ser Phe Asp Asp Ala Asp Ile Asp Glu Lys Ile Ala Asp Ser Glu Ala
        275                 280                 285

Leu Leu Ser Asp Thr Glu Phe Glu Phe Leu Cys Asp Leu Lys Ala Ala
    290                 295                 300

Phe Asp Gly Leu Thr Leu Lys Met Leu Leu Gly Asp Lys Thr Val
305                 310                 315                 320

Ser Ala Ala Met Val Arg Arg Phe Asn Glu His Gln Lys Asp Trp Glu
                325                 330                 335

Tyr Ile Lys Ser His Ile Arg Asn Ala Lys Asn Ala Gly Asn Gly Leu
            340                 345                 350

Tyr Glu Lys Ser Lys Lys Phe Asp Gly Ile Asn Ala Ala Tyr Leu Ala
        355                 360                 365

Leu Gln Ser Asp Asn Glu Asp Asp Arg Lys Lys Ala Lys Lys Ile Phe
    370                 375                 380

Gln Asp Glu Ile Ser Ser Ala Asp Ile Pro Asp Asp Val Lys Ala Asp

-continued

```
            385                 390                 395                 400
        Phe Leu Lys Lys Ile Asp Asp Gln Phe Leu Pro Ile Gln Arg Thr
                        405                 410                 415

Lys Asn Asn Gly Thr Ile Pro His Gln Leu His Arg Asn Glu Leu Glu
                        420                 425                 430

Gln Ile Ile Glu Lys Gln Gly Ile Tyr Tyr Pro Phe Leu Lys Asp Thr
                        435                 440                 445

Tyr Gln Glu Asn Ser His Glu Leu Asn Lys Ile Thr Ala Leu Ile Asn
                    450                 455                 460

Phe Arg Val Pro Tyr Tyr Val Gly Pro Leu Val Glu Glu Gln Lys
        465                 470                 475                 480

Ile Ala Asp Asp Gly Lys Asn Ile Pro Asp Pro Thr Asn His Trp Met
                                485                 490                 495

Val Arg Lys Ser Asn Asp Thr Ile Thr Pro Trp Asn Leu Ser Gln Val
                        500                 505                 510

Val Asp Leu Asp Lys Ser Gly Arg Arg Phe Ile Glu Arg Leu Thr Gly
                        515                 520                 525

Thr Asp Thr Tyr Leu Ile Gly Glu Pro Thr Leu Pro Lys Asn Ser Leu
                    530                 535                 540

Leu Tyr Gln Lys Phe Asp Val Leu Gln Glu Leu Asn Asn Ile Arg Val
        545                 550                 555                 560

Ser Gly Arg Arg Leu Asp Ile Arg Ala Lys Gln Asp Ala Phe Glu His
                            565                 570                 575

Leu Phe Lys Val Gln Lys Thr Val Ser Ala Thr Asn Leu Lys Asp Phe
                        580                 585                 590

Leu Val Gln Ala Gly Tyr Ile Ser Glu Asp Thr Gln Ile Glu Gly Leu
                    595                 600                 605

Ala Asp Val Asn Gly Lys Asn Phe Asn Asn Ala Leu Thr Thr Tyr Asn
                    610                 615                 620

Tyr Leu Val Ser Val Leu Gly Arg Glu Phe Val Glu Asn Pro Ser Asn
        625                 630                 635                 640

Glu Glu Leu Leu Glu Glu Ile Thr Glu Leu Gln Thr Val Phe Glu Asp
                            645                 650                 655

Lys Lys Val Leu Arg Arg Gln Leu Asp Gln Leu Asp Gly Leu Ser Asp
                        660                 665                 670

His Asn Arg Glu Lys Leu Ser Arg Lys His Tyr Thr Gly Trp Gly Arg
                    675                 680                 685

Ile Ser Lys Lys Leu Leu Thr Thr Lys Ile Val Gln Asn Ala Asp Lys
                    690                 695                 700

Ile Asp Asn Gln Thr Phe Asp Val Pro Arg Met Asn Gln Ser Ile Ile
        705                 710                 715                 720

Asp Thr Leu Tyr Asn Thr Lys Met Asn Leu Met Glu Ile Ile Asn Asn
                        725                 730                 735

Ala Glu Asp Asp Phe Gly Val Arg Ala Trp Ile Asp Lys Gln Asn Thr
                        740                 745                 750

Thr Asp Gly Asp Glu Gln Asp Val Tyr Ser Leu Ile Asp Glu Leu Ala
                    755                 760                 765

Gly Pro Lys Glu Ile Lys Arg Gly Ile Val Gln Ser Phe Arg Ile Leu
                    770                 775                 780

Asp Asp Ile Thr Lys Ala Val Gly Tyr Ala Pro Lys Arg Val Tyr Leu
        785                 790                 795                 800

Glu Phe Ala Arg Lys Thr Gln Glu Ser His Leu Thr Asn Ser Arg Lys
                        805                 810                 815
```

-continued

Asn Gln Leu Ser Thr Leu Leu Lys Asn Ala Gly Leu Ser Glu Leu Val
            820                 825                 830

Thr Gln Val Ser Gln Tyr Asp Ala Ala Leu Gln Asn Asp Arg Leu
            835                 840                 845

Tyr Leu Tyr Phe Leu Gln Gln Gly Lys Asp Met Tyr Ser Gly Glu Lys
            850                 855                 860

Leu Asn Leu Asp Asn Leu Ser Asn Tyr Asp Ile Asp His Ile Ile Pro
865                     870                 875                 880

Gln Ala Tyr Thr Lys Asp Asn Ser Leu Asp Asn Arg Val Leu Val Ser
                885                 890                 895

Asn Ile Thr Asn Arg Arg Lys Ser Asp Ser Ser Asn Tyr Leu Pro Ala
            900                 905                 910

Leu Ile Asp Lys Met Arg Pro Phe Trp Ser Val Leu Ser Lys Gln Gly
            915                 920                 925

Leu Leu Ser Lys His Lys Phe Ala Asn Leu Thr Arg Thr Arg Asp Phe
            930                 935                 940

Asp Asp Met Glu Lys Glu Arg Phe Ile Ala Arg Ser Leu Val Glu Thr
945                 950                 955                 960

Arg Gln Ile Ile Lys Asn Val Ala Ser Leu Ile Asp Ser His Phe Gly
                965                 970                 975

Gly Glu Thr Lys Ala Val Ala Ile Arg Ser Ser Leu Thr Ala Asp Met
            980                 985                 990

Arg Arg Tyr Val Asp Ile Pro Lys Asn Arg Asp Ile Asn Asp Tyr His
            995                 1000                1005

His Ala Phe Asp Ala Leu Leu Phe Ser Thr Val Gly Gln Tyr Thr
        1010                1015                1020

Glu Asn Ser Gly Leu Met Lys Lys Gly Gln Leu Ser Asp Ser Ala
        1025                1030                1035

Gly Asn Gln Tyr Asn Arg Tyr Ile Lys Glu Trp Ile His Ala Ala
        1040                1045                1050

Arg Leu Asn Ala Gln Ser Gln Arg Val Asn Pro Phe Gly Phe Val
        1055                1060                1065

Val Gly Ser Met Arg Asn Ala Ala Pro Gly Lys Leu Asn Pro Glu
        1070                1075                1080

Thr Gly Glu Ile Thr Pro Glu Glu Asn Ala Asp Trp Ser Ile Ala
        1085                1090                1095

Asp Leu Asp Tyr Leu His Lys Val Met Asn Phe Arg Lys Ile Thr
        1100                1105                1110

Val Thr Arg Arg Leu Lys Asp Gln Lys Gly Gln Leu Tyr Asp Glu
        1115                1120                1125

Ser Arg Tyr Pro Ser Val Leu His Asp Ala Lys Ser Lys Ala Ser
        1130                1135                1140

Ile Asn Phe Asp Lys His Lys Pro Val Asp Leu Tyr Gly Gly Phe
        1145                1150                1155

Ser Ser Ala Lys Pro Ala Tyr Ala Ala Leu Ile Lys Phe Lys Asn
        1160                1165                1170

Lys Phe Arg Leu Val Asn Val Leu Arg Gln Trp Thr Tyr Ser Asp
        1175                1180                1185

Lys Asn Ser Glu Asp Tyr Ile Leu Glu Gln Ile Arg Gly Lys Tyr
        1190                1195                1200

Pro Lys Ala Glu Met Val Leu Ser His Ile Pro Tyr Gly Gln Leu
        1205                1210                1215

| | | | | | | | | | | |
|---|---|---|---|---|---|---|---|---|---|---|
|Val|Lys 1220|Lys|Asp|Gly|Ala 1225|Leu|Val|Thr|Ile 1230|Ser|Ser|Ala|Thr|Glu|

Leu His Asn Phe Glu Gln Leu Trp Leu Pro Leu Ala Asp Tyr Lys
1235                1240                1245

Leu Ile Asn Thr Leu Leu Lys Thr Lys Glu Asp Asn Leu Val Asp
1250                1255                1260

Ile Leu His Asn Arg Leu Asp Leu Pro Glu Met Thr Ile Glu Ser
1265                1270                1275

Ala Phe Tyr Lys Ala Phe Asp Ser Ile Leu Ser Phe Ala Phe Asn
1280                1285                1290

Arg Tyr Ala Leu His Gln Asn Ala Leu Val Lys Leu Gln Ala His
1295                1300                1305

Arg Asp Asp Phe Asn Ala Leu Asn Tyr Glu Asp Lys Gln Gln Thr
1310                1315                1320

Leu Glu Arg Ile Leu Asp Ala Leu His Ala Ser Pro Ala Ser Ser
1325                1330                1335

Asp Leu Lys Lys Ile Asn Leu Ser Ser Gly Phe Gly Arg Leu Phe
1340                1345                1350

Ser Pro Ser His Phe Thr Leu Ala Asp Thr Asp Glu Phe Ile Phe
1355                1360                1365

Gln Ser Val Thr Gly Leu Phe Ser Thr Gln Lys Thr Val Ala Gln
1370                1375                1380

Leu Tyr Gln Glu Thr Lys Pro Lys Lys Lys Arg Lys Val
1385                1390                1395

<210> SEQ ID NO 17
<211> LENGTH: 3738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atgagccagc accggcggta tagaatcggc atcgacgtgg gcctgaatag cgttggactg      60
gccgccgtgg aaatcgacgc caaccacgac aatcctctgg acgagatccc catcagcatc     120
ctgaatgccc agagcgtgat ccacgatggc ggagtggacc ctgatgaggc caagtctgct     180
acaagcagac gggcttctgc tggcgtggcc agaagaacaa gacggctgca aagagcaag     240 cggcagagac tggccaagct ggacgaggtg ctgaatgagc tgggctaccc cgtggaagat     300
gagagccagt ttccagccgg cagcaacccc tatatcgctt ggcaagtgcg ggccaaactg     360
gccgagacat tcatccccga cgtggaaacc cggaagcgga tgatctctat cgccatccgg     420
cacattgccc ggcatagagg atggcggaat ccctactctt ctgtggccga cgccgagcgg     480
atgagccata caccttctcc attcatggtg aatacgcca agaagctgga cttcgagatc     540
aacgacagac ggaccaacgg cttctatcac agcccttggc agagcgtgga cgaggaaggc     600
aagagactga gcaagagcga gctggaaaag cagcccaaga tcgaggactg aacgacaac     660 cccatcaacg gcaagacaat cgcccagctg gtcgtgtcct ctctggaacc ccagaccaag     720
atcagacggg atctgacaca cggcctgcag accgagagca ccctgaatat ccagacagag     780
aagctgcacc agagcgacta catccacgaa ctggaaacca tcttcgagcg cagcacgtg     840 gaccagacaa cccaagaaca gctgctggaa gccaccttcc acaccaagaa tcctaaggcc     900
gtgggagccg ccgctaagct cgttggaaaa gatgccctgg acagccggta ctacagagcc     960
```

-continued

```
agcagagcca caccagcctt cgaagagtac agagtgatgg ccgccatcga caccctgcgg    1020
attagagagc acggcaccga gagacagctg accaccgacg agagaagaaa gctgttcgac    1080
ttcatcaagg ggctgcccag caaaaagacc aagaacgagc ccagcatcag ctccctgacc    1140
tggggagatg tggccgattt tctgggcatc cagcggatcg atctgagagg cctgggctct    1200
ctgaaagacg gcgaacctgt gtctgccaag cagcctcctg tgatcgagac aaacgacatc    1260
atgcagaagc cccctgatcc aatcgctgcc tggtggtcac aggccaacac caaagaacgg    1320
gacagattcg tcgagttcat gagcaacgct ggcgccatca aggacacctc cgacgaagtg    1380
cggaacattg acgccgagat cagccagctg ctcgaagaac tgaccggctc tgagctggaa    1440
tccctggata agatcaccct gacctctggc agagccgcct acagctctca gaccctgaga    1500
aacatcacca actatatgta cgagacaggc tgcgacctga ccacagccag acaagagctg    1560
taccacgtgg gcaagaattg ggcccctcct gctcctccta tctacgagca cacaggcaac    1620
cccagcgtgg acagaacctt cagcatcatc cacagatggc tgtgcaacat gcgggaccag    1680
tacggcgagc ccgagacagt gaatatcgag tacgtccgcg acggcttcag cagcacatct    1740
acacagctgg ccgagcagcg cgagcgggat agaagatacg ccgacaacct gaagatgctg    1800
agcaactacg agggcgccag cagcagatca gatgtgcgga gaatcaaggc cctgcagaga    1860
cagaactgcc agtgcatcta ctgcggccgg accatcacct tcgagacatg ccagatggac    1920
catgtgctgc cccggaaagg ccctggatcc gatagcaagt cgagaaccct ggtggccaca    1980
tgcggcgagt gcaacaagtc caagagcgat accctgtaca tgaactgggc caagacatac    2040
cccaatacca acctgcagga cgtgctgaga gaatccaag agtggtccaa ggacggctgg    2100
atgaccgaca aaagatggcg gcagtacaaa gaggccctga tcctgagact ggaagctacc    2160
gagaagcaag agcccctgga caatcggagc atggaaagcg tgtcctacat ggccagagag    2220
ctgcggaacc ggatctacgg ctttttacggc tggcacgacc aggacgacgc cctgaaacaa    2280
ggcagacaga gggtgttcgt gtccagcggc agtatgacag ccgctgccag aaggacccct    2340
ttcgagtccc cactgattaa gggcgccgat gaggaaacct acgagagcag cctgccttgg    2400
ctggatggca tgaagggcaa gaccagactg gatcggagac accatgccgt ggacgccagc    2460
atcattgcca tgatgaggcc ccagatcgtg aagatcctga cagaggccca agagatcaga    2520
agcgagcagc acgacaagta ccggaagggc cagacacctg actacgtgtg caagcggcgg    2580
gactactggc ggaattggag aggcaccccct gacaccagag atgaggaagt gttcaactac    2640
tgggctgggg agcagctgag aaccctgacc gatctggtgt cccagaagat ggccgacgac    2700
gaaatccccg tgatctaccc caccagactg agactcggca atggcagcgc ccacaaggat    2760
accgtggtgt ccatgatgac ccggaaagtg ggcgacgagc tgagcatcac cgccatcaac    2820
aaagccgaaa gcggagccct gtacacagcc ctgaccagag acagcgactt cgactggaaa    2880
accggcctga cgccaatcc taaccggcgg atcagagtgc acgataagtg gttcgaggcc    2940
gacgatacca tcaagtttct ggaacctgcc gtggaagtgg tgctgaagaa caacaccaga    3000
gccagaatcg accccgaggc tctggataag gtgcacagca cactgtacgt gcccgtcaga    3060
ggcggaatcg ccgaagccgg aaatagcatt caccacgtgc ggttctacaa gatccccaag    3120
ctgaacagca agggcaagca gaccggcagc atctacgcca tgctgagagt gctgaccatc    3180
gacctggcca tgaaccagta cgacaaagag acaggcaaga agcaggacct gttcaccctg    3240
ccactgcctg aaagcagcct gagcagaaga ttcagcgagc ccaaactgcg gcaggctctg    3300
atcgatggca cagccgaata tctcggatgg gccgtcgtgg acgatgagct tgagatcccc    3360
```

-continued

```
gccttcgcca acgccagaat cacagaggaa caggccatta acggcagctt caccgacaga      3420
ctgctgcaca gctttcccgg cacacacaag ttcagattcg ccggcttctc ccggaacacc      3480
gagatcgcca ttagacctgt gcagctggcc tctgagggcc tgatcgaaac cgatgagaac      3540
cggaagagac agcagctgcg gctgacccag cctaacaccg agtacagcaa cagcatcaag      3600
aacgtgctga agtccggcct gcacctgaaa gtgaacaccc tgttccagac aggcatcctg      3660
gtcaccaggg ccaatagcca gggaaagcag agcatccggt tcagcacagt ggaagagccc      3720
aagaagaaga ggaaggtg                                                    3738
```

<210> SEQ ID NO 18
<211> LENGTH: 1246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Met Ser Gln His Arg Arg Tyr Arg Ile Gly Ile Asp Val Gly Leu Asn
1               5                   10                  15

Ser Val Gly Leu Ala Ala Val Glu Ile Asp Ala Asn His Asp Asn Pro
            20                  25                  30

Leu Asp Glu Ile Pro Ile Ser Ile Leu Asn Ala Gln Ser Val Ile His
        35                  40                  45

Asp Gly Gly Val Asp Pro Asp Glu Ala Lys Ser Ala Thr Ser Arg Arg
    50                  55                  60

Ala Ser Ala Gly Val Ala Arg Arg Thr Arg Arg Leu His Lys Ser Lys
65                  70                  75                  80

Arg Gln Arg Leu Ala Lys Leu Asp Glu Val Leu Asn Glu Leu Gly Tyr
                85                  90                  95

Pro Val Glu Asp Glu Ser Gln Phe Pro Ala Gly Ser Asn Pro Tyr Ile
            100                 105                 110

Ala Trp Gln Val Arg Ala Lys Leu Ala Glu Thr Phe Ile Pro Asp Val
        115                 120                 125

Glu Thr Arg Lys Arg Met Ile Ser Ile Ala Ile Arg His Ile Ala Arg
    130                 135                 140

His Arg Gly Trp Arg Asn Pro Tyr Ser Ser Val Ala Asp Ala Glu Arg
145                 150                 155                 160

Met Ser His Thr Pro Ser Pro Phe Met Val Glu Tyr Ala Lys Lys Leu
                165                 170                 175

Asp Phe Glu Ile Asn Asp Arg Arg Thr Asn Gly Phe Tyr His Ser Pro
            180                 185                 190

Trp Gln Ser Val Asp Glu Glu Gly Lys Arg Leu Ser Lys Ser Glu Leu
        195                 200                 205

Glu Lys Gln Pro Lys Ile Glu Asp Trp Asn Asp Asn Pro Ile Asn Gly
    210                 215                 220

Lys Thr Ile Ala Gln Leu Val Val Ser Ser Leu Glu Pro Gln Thr Lys
225                 230                 235                 240

Ile Arg Arg Asp Leu Thr His Gly Leu Gln Thr Glu Ser Thr Leu Asn
                245                 250                 255

Ile Gln Thr Glu Lys Leu His Gln Ser Asp Tyr Ile His Glu Leu Glu
            260                 265                 270

Thr Ile Phe Glu Arg Gln His Val Asp Gln Thr Thr Gln Glu Gln Leu
        275                 280                 285
```

```
Leu Glu Ala Thr Phe His Thr Lys Asn Pro Lys Ala Val Gly Ala Ala
            290                 295                 300

Ala Lys Leu Val Gly Lys Asp Ala Leu Asp Ser Arg Tyr Tyr Arg Ala
305                 310                 315                 320

Ser Arg Ala Thr Pro Ala Phe Glu Glu Tyr Arg Val Met Ala Ala Ile
                    325                 330                 335

Asp Thr Leu Arg Ile Arg Glu His Gly Thr Glu Arg Gln Leu Thr Thr
                340                 345                 350

Asp Glu Arg Arg Lys Leu Phe Asp Phe Ile Lys Gly Leu Pro Ser Lys
            355                 360                 365

Lys Thr Lys Asn Glu Pro Ser Ile Ser Ser Leu Thr Trp Gly Asp Val
370                 375                 380

Ala Asp Phe Leu Gly Ile Gln Arg Ile Asp Leu Arg Gly Leu Gly Ser
385                 390                 395                 400

Leu Lys Asp Gly Glu Pro Val Ser Ala Lys Gln Pro Val Ile Glu
                405                 410                 415

Thr Asn Asp Ile Met Gln Lys Ala Pro Asp Pro Ile Ala Ala Trp Trp
                420                 425                 430

Ser Gln Ala Asn Thr Lys Glu Arg Asp Arg Phe Val Glu Phe Met Ser
            435                 440                 445

Asn Ala Gly Ala Ile Lys Asp Thr Ser Asp Glu Val Arg Asn Ile Asp
450                 455                 460

Ala Glu Ile Ser Gln Leu Leu Glu Glu Leu Thr Gly Ser Glu Leu Glu
465                 470                 475                 480

Ser Leu Asp Lys Ile Thr Leu Thr Ser Gly Arg Ala Ala Tyr Ser Ser
                485                 490                 495

Gln Thr Leu Arg Asn Ile Thr Asn Tyr Met Tyr Glu Thr Gly Cys Asp
            500                 505                 510

Leu Thr Thr Ala Arg Gln Glu Leu Tyr His Val Gly Lys Asn Trp Ala
            515                 520                 525

Pro Pro Ala Pro Pro Ile Tyr Glu His Thr Gly Asn Pro Ser Val Asp
530                 535                 540

Arg Thr Phe Ser Ile Ile His Arg Trp Leu Cys Asn Met Arg Asp Gln
545                 550                 555                 560

Tyr Gly Glu Pro Glu Thr Val Asn Ile Glu Tyr Val Arg Asp Gly Phe
                565                 570                 575

Ser Ser Thr Ser Thr Gln Leu Ala Glu Gln Arg Glu Arg Asp Arg Arg
                580                 585                 590

Tyr Ala Asp Asn Leu Lys Met Leu Ser Asn Tyr Glu Gly Ala Ser Ser
            595                 600                 605

Arg Ser Asp Val Arg Arg Ile Lys Ala Leu Gln Arg Gln Asn Cys Gln
610                 615                 620

Cys Ile Tyr Cys Gly Arg Thr Ile Thr Phe Glu Thr Cys Gln Met Asp
625                 630                 635                 640

His Val Leu Pro Arg Lys Gly Pro Gly Ser Asp Ser Lys Phe Glu Asn
                645                 650                 655

Leu Val Ala Thr Cys Gly Glu Cys Asn Lys Ser Lys Ser Asp Thr Leu
                660                 665                 670

Tyr Met Asn Trp Ala Lys Thr Tyr Pro Asn Thr Asn Leu Gln Asp Val
            675                 680                 685

Leu Arg Arg Ile Gln Glu Trp Ser Lys Asp Gly Trp Met Thr Asp Lys
690                 695                 700
```

-continued

Arg Trp Arg Gln Tyr Lys Glu Ala Leu Ile Leu Arg Leu Glu Ala Thr
705                 710                 715                 720

Glu Lys Gln Glu Pro Leu Asp Asn Arg Ser Met Glu Ser Val Ser Tyr
            725                 730                 735

Met Ala Arg Glu Leu Arg Asn Arg Ile Tyr Gly Phe Tyr Gly Trp His
            740                 745                 750

Asp Gln Asp Asp Ala Leu Lys Gln Gly Arg Gln Arg Val Phe Val Ser
            755                 760                 765

Ser Gly Ser Met Thr Ala Ala Arg Arg Thr Pro Phe Glu Ser Pro
770                 775                 780

Leu Ile Lys Gly Ala Asp Glu Thr Tyr Glu Ser Ser Leu Pro Trp
785                 790                 795                 800

Leu Asp Gly Met Lys Gly Lys Thr Arg Leu Asp Arg Arg His His Ala
            805                 810                 815

Val Asp Ala Ser Ile Ile Ala Met Met Arg Pro Gln Ile Val Lys Ile
            820                 825                 830

Leu Thr Glu Ala Gln Glu Ile Arg Ser Glu Gln His Asp Lys Tyr Arg
            835                 840                 845

Lys Gly Gln Thr Pro Asp Tyr Val Cys Lys Arg Arg Asp Tyr Trp Arg
850                 855                 860

Asn Trp Arg Gly Thr Pro Asp Thr Arg Asp Glu Val Phe Asn Tyr
865                 870                 875                 880

Trp Ala Gly Glu Gln Leu Arg Thr Leu Thr Asp Leu Val Ser Gln Lys
                885                 890                 895

Met Ala Asp Asp Glu Ile Pro Val Ile Tyr Pro Thr Arg Leu Arg Leu
            900                 905                 910

Gly Asn Gly Ser Ala His Lys Asp Thr Val Val Ser Met Met Thr Arg
            915                 920                 925

Lys Val Gly Asp Glu Leu Ser Ile Thr Ala Ile Asn Lys Ala Glu Ser
930                 935                 940

Gly Ala Leu Tyr Thr Ala Leu Thr Arg Asp Ser Asp Phe Asp Trp Lys
945                 950                 955                 960

Thr Gly Leu Ser Ala Asn Pro Asn Arg Arg Ile Arg Val His Asp Lys
            965                 970                 975

Trp Phe Glu Ala Asp Asp Thr Ile Lys Phe Leu Glu Pro Ala Val Glu
            980                 985                 990

Val Val Leu Lys Asn Asn Thr Arg Ala Arg Ile Asp Pro Glu Ala Leu
                995                 1000                1005

Asp Lys Val His Ser Thr Leu Tyr Val Pro Val Arg Gly Gly Ile
    1010                1015                1020

Ala Glu Ala Gly Asn Ser Ile His His Val Arg Phe Tyr Lys Ile
    1025                1030                1035

Pro Lys Leu Asn Ser Lys Gly Lys Gln Thr Gly Ser Ile Tyr Ala
    1040                1045                1050

Met Leu Arg Val Leu Thr Ile Asp Leu Ala Met Asn Gln Tyr Asp
    1055                1060                1065

Lys Glu Thr Gly Lys Lys Gln Asp Leu Phe Thr Leu Pro Leu Pro
    1070                1075                1080

Glu Ser Ser Leu Ser Arg Arg Phe Ser Glu Pro Lys Leu Arg Gln
    1085                1090                1095

Ala Leu Ile Asp Gly Thr Ala Glu Tyr Leu Gly Trp Ala Val Val
    1100                1105                1110

Asp Asp Glu Leu Glu Ile Pro Ala Phe Ala Asn Ala Arg Ile Thr

Glu Glu Gln Ala Ile Asn Gly Ser Phe Thr Asp Arg Leu Leu His
1130               1135                    1140

Ser Phe Pro Gly Thr His Lys Phe Arg Phe Ala Gly Phe Ser Arg
1145               1150                    1155

Asn Thr Glu Ile Ala Ile Arg Pro Val Gln Leu Ala Ser Glu Gly
1160               1165                    1170

Leu Ile Glu Thr Asp Glu Asn Arg Lys Arg Gln Gln Leu Arg Leu
1175               1180                    1185

Thr Gln Pro Asn Thr Glu Tyr Ser Asn Ser Ile Lys Asn Val Leu
1190               1195                    1200

Lys Ser Gly Leu His Leu Lys Val Asn Thr Leu Phe Gln Thr Gly
1205               1210                    1215

Ile Leu Val Thr Arg Ala Asn Ser Gln Gly Lys Gln Ser Ile Arg
1220               1225                    1230

Phe Ser Thr Val Glu Glu Pro Lys Lys Lys Arg Lys Val
1235               1240                    1245

<210> SEQ ID NO 19
<211> LENGTH: 3435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atgggcggat ctgaagtggg aaccgtgcct gtgacttgga gactgggagt cgatgtgggc      60
gagagatcca ttggactggc cgccgtgtcc tacgaagagg acaagcccaa agaaatcctg     120
gctgctgtgt cctggattca cgatggcgga gtgggcgacg aaagaagcgg agctagtaga     180
ctggccctga gaggcatggc cagaagggct agacggctgc ggagattccg tagagccaga     240
ctgcgcgacc tggacatgct gctgtctgaa ctcggatgga cccctctgcc tgacaagaac     300
gtgtcacctg tggatgcctg gctggccaga aagagactgg ccgaggaata cgtggtggac     360
gagacagaga agaaggct gctgggctac gccgtgtctc acatggctag acatagaggc     420
tggcggaacc cctggaccac catcaaggac ctgaagaacc tgcctcagcc tagcgacagc     480
tgggagagaa ccagagaaag cctggaagcc cggtactccg tgtctctgga acctggcaca     540
gttggacagt gggccggata cctgctgcag agagccctg gcatcagact gaaccctaca     600
cagcagagcg ccggaagaag ggccgaactg tctaatgcca ccgccttcga cacagactg     660 cggcaagagg atgtgctgtg ggagctgaga tgtatcgccg acgttcaggg cctgcctgag     720
gacgtggtgt ccaatgtgat cgacgccgtg ttctgccaga aaagacctag cgtgcccgcc     780
gagagaatcg gcagagatcc tctcgatccc agccagctga gagccagcag agcctgcctg     840
gaatttcaag agtaccggat cgtggccgct gtggccaacc tgagaatcag agatggcagc     900
ggcagcagac ccctgagtct ggaagaaaga aacgccgtga tcgaggccct gctggcccag     960
acagaaagaa gcctcacttg gagcgacatt gccctggaaa tcctgaagct gcccaacgag    1020
agcgacctga cctctgtgcc tgaagaggat ggccaagca gcctggccta ctctcagttc    1080
gcccctttcg atgagacaag cgcccggatc gccgagttta cgccaagaa cagacggaag    1140 atccccacat cgcccagtg gtggcaagag caggatcgga ccagtagaag cgatctggtg    1200
gctgccctgg ccgacaattc tattgccggc gaggaagaac aagagctgct ggtgcatctg    1260
```

```
cccgacgccg aacttgaagc tctggaagga ctggctctgc cctctggcag agtggcctat    1320
agcagactga cactgagcgg cctgaccaga gtgatgagag atgatggcgt ggacgtgcac    1380
aacgcccgca agacatgctt cggagtggac gacaattggc ggcctccact gcctgctctg    1440
catgaagcta caggacaccc cgtggtggat agaaacctgg ctatcctgcg aagttcctg     1500 agcagcgcca ccatgagatg gggccctcca cagtctatcg tggtggaact tgccagaggc    1560
gccagcgaga gcagagaaag gcaggccgaa gaagaagccg ctcggagagc ccacagaaag    1620
gccaacgaca gaattagagc cgaactcaga gcctccggcc tgagcgatcc ttctcctgcc    1680
gatcttgtta gagcccggct gctggaactg tacgactgcc actgtatgta ctgtggcgcc    1740
cctatctcct gggagaacag cgagctggat cacatcgtgc cagaacaga tggcggatcc     1800 aacagacacg agaacctggc cattacatgc ggcgcctgca caaagaaaa aggcagaagg      1860 cccttcgcca gctgggccga acaagcaat agagtgcagc tgcgggacgt gatcgaccgg     1920
gtgcagaagc tgaagtacag cggcaacatg tactggaccc gggacgagtt cagccggtac    1980
aagaaaagcg tggtggcccg gctgaagcgg agaacctctg atcctgaagt gatccagagc    2040
atcgagagca ccggctatgc tgccgtggct ctgagagata gactgctgag ctacggcgag    2100
aagaatggcg tggcacaggt ggccgttttt agaggcggag tgacagccga ggccagaaga    2160
tggctggaca tctccatcga gcggctgttc agtagagtgg ccatcttcgc cagagcacc     2220 tccaccaaga ggctggatag aaggcaccac gccgtggatg ctgtggtgct gacaacactg    2280
acacccggcg tggccaagac actggctgat gctagaagca aagagtgtc cgccgagttc     2340 tggcgcagac caagcgacgt gaacagacac agcaccgagg aacctcagag ccccgcctac    2400
agacagtgga agagagctg ttctggcctg gcgacctgc tgatttctac cgccgccaga       2460
gattctatcg ccgtggctgc tcctctgaga ctgaggccaa caggcgcact gcacgaggaa    2520
accctgagag cctttagcga gcacacagtg ggagccgctt ggaagggcgc tgagctgaga    2580
agaatcgtgg aacccgaagt gtacgccgcc ttcctggcac ttacagatcc tggcggcaga    2640
ttcctgaagg tgtcccctag cgaagatgtg ctgcctgccg acgagaacag gcacattgtg    2700
ctgagcgaca gagtgctggg ccccagagac agagtgaaac tgttccccga cgaccggggc    2760
agcatcagag tcagaggtgg cgcagcctat atcgccagct tcaccacgc cagagtgttc      2820 agatggggaa gcagccactc tcctagcttc gccctgctga gagtctctct ggctgatctg    2880
gctgtggctg gcctgcttag agatggggtc gacgtgttca cagccgagct gccaccttgg    2940
actcccgctt ggagatatgc ctctatcgcc ctggtcaagg ccgtggaaag cggcgacgct    3000
aagcaagttg gatggctggt gcctggcgac gaactggatt ttggacctga gggcgtgaca    3060
accgctgccg cgatctgag catgttcctg aagtactttc cgagcggca ctgggtcgtg       3120 accggcttcg aagatgacaa gaggatcaac ctgaagcctg ccttcctgtc tgccgaacag    3180
gctgaggtgc tgaggactga gagaagcgac agacccgaca cactgacaga ggccggcgaa    3240
attctggccc agttcttccc tagatgttgg cgggccacag tggctaaggt gctgtgccat    3300
cctggcctga ccgtgatcag aagaacagcc ctgggacagc ctaggtggcg gagaggacat    3360 ctgcctatt catggcggcc ttggagcgcc gatccttgga gtggcggaac acctcccaag     3420
aagaagagga aggtg                                                     3435
```

<210> SEQ ID NO 20
<211> LENGTH: 1145
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Gly Gly Ser Glu Val Gly Thr Val Pro Val Thr Trp Arg Leu Gly
1               5                   10                  15

Val Asp Val Gly Glu Arg Ser Ile Gly Leu Ala Ala Val Ser Tyr Glu
            20                  25                  30

Glu Asp Lys Pro Lys Glu Ile Leu Ala Ala Val Ser Trp Ile His Asp
        35                  40                  45

Gly Gly Val Gly Asp Glu Arg Ser Gly Ala Ser Arg Leu Ala Leu Arg
    50                  55                  60

Gly Met Ala Arg Arg Ala Arg Arg Leu Arg Arg Phe Arg Arg Ala Arg
65                  70                  75                  80

Leu Arg Asp Leu Asp Met Leu Leu Ser Glu Leu Gly Trp Thr Pro Leu
                85                  90                  95

Pro Asp Lys Asn Val Ser Pro Val Asp Ala Trp Leu Ala Arg Lys Arg
            100                 105                 110

Leu Ala Glu Glu Tyr Val Val Asp Glu Thr Glu Arg Arg Arg Leu Leu
        115                 120                 125

Gly Tyr Ala Val Ser His Met Ala Arg His Arg Gly Trp Arg Asn Pro
    130                 135                 140

Trp Thr Thr Ile Lys Asp Leu Lys Asn Leu Pro Gln Pro Ser Asp Ser
145                 150                 155                 160

Trp Glu Arg Thr Arg Glu Ser Leu Glu Ala Arg Tyr Ser Val Ser Leu
                165                 170                 175

Glu Pro Gly Thr Val Gly Gln Trp Ala Gly Tyr Leu Leu Gln Arg Ala
            180                 185                 190

Pro Gly Ile Arg Leu Asn Pro Thr Gln Gln Ser Ala Gly Arg Arg Ala
        195                 200                 205

Glu Leu Ser Asn Ala Thr Ala Phe Glu Thr Arg Leu Arg Gln Glu Asp
    210                 215                 220

Val Leu Trp Glu Leu Arg Cys Ile Ala Asp Val Gln Gly Leu Pro Glu
225                 230                 235                 240

Asp Val Val Ser Asn Val Ile Asp Ala Val Phe Cys Gln Lys Arg Pro
                245                 250                 255

Ser Val Pro Ala Glu Arg Ile Gly Arg Asp Pro Leu Asp Pro Ser Gln
            260                 265                 270

Leu Arg Ala Ser Arg Ala Cys Leu Glu Phe Gln Glu Tyr Arg Ile Val
        275                 280                 285

Ala Ala Val Ala Asn Leu Arg Ile Arg Asp Gly Ser Gly Ser Arg Pro
    290                 295                 300

Leu Ser Leu Glu Glu Arg Asn Ala Val Ile Glu Ala Leu Leu Ala Gln
305                 310                 315                 320

Thr Glu Arg Ser Leu Thr Trp Ser Asp Ile Ala Leu Glu Ile Leu Lys
                325                 330                 335

Leu Pro Asn Glu Ser Asp Leu Thr Ser Val Pro Glu Glu Asp Gly Pro
            340                 345                 350

Ser Ser Leu Ala Tyr Ser Gln Phe Ala Pro Phe Asp Glu Thr Ser Ala
        355                 360                 365

Arg Ile Ala Glu Phe Ile Ala Lys Asn Arg Arg Lys Ile Pro Thr Phe
    370                 375                 380

Ala Gln Trp Trp Gln Glu Gln Asp Arg Thr Ser Arg Ser Asp Leu Val
```

```
            385                 390                 395                 400
        Ala Ala Leu Ala Asp Asn Ser Ile Ala Gly Glu Glu Gln Glu Leu
                        405                 410                 415
        Leu Val His Leu Pro Asp Ala Glu Leu Glu Ala Leu Glu Gly Leu Ala
                        420                 425                 430
        Leu Pro Ser Gly Arg Val Ala Tyr Ser Arg Leu Thr Leu Ser Gly Leu
                        435                 440                 445
        Thr Arg Val Met Arg Asp Asp Gly Val Asp Val His Asn Ala Arg Lys
                    450                 455                 460
        Thr Cys Phe Gly Val Asp Asp Asn Trp Arg Pro Leu Pro Ala Leu
        465                 470                 475                 480
        His Glu Ala Thr Gly His Pro Val Val Asp Arg Asn Leu Ala Ile Leu
                            485                 490                 495
        Arg Lys Phe Leu Ser Ser Ala Thr Met Arg Trp Gly Pro Pro Gln Ser
                        500                 505                 510
        Ile Val Val Glu Leu Ala Arg Gly Ala Ser Glu Ser Arg Glu Arg Gln
                        515                 520                 525
        Ala Glu Glu Glu Ala Ala Arg Arg Ala His Arg Lys Ala Asn Asp Arg
                    530                 535                 540
        Ile Arg Ala Glu Leu Arg Ala Ser Gly Leu Ser Asp Pro Ser Pro Ala
        545                 550                 555                 560
        Asp Leu Val Arg Ala Arg Leu Leu Glu Leu Tyr Asp Cys His Cys Met
                            565                 570                 575
        Tyr Cys Gly Ala Pro Ile Ser Trp Glu Asn Ser Glu Leu Asp His Ile
                        580                 585                 590
        Val Pro Arg Thr Asp Gly Gly Ser Asn Arg His Glu Asn Leu Ala Ile
                        595                 600                 605
        Thr Cys Gly Ala Cys Asn Lys Glu Lys Gly Arg Arg Pro Phe Ala Ser
                    610                 615                 620
        Trp Ala Glu Thr Ser Asn Arg Val Gln Leu Arg Asp Val Ile Asp Arg
        625                 630                 635                 640
        Val Gln Lys Leu Lys Tyr Ser Gly Asn Met Tyr Trp Thr Arg Asp Glu
                            645                 650                 655
        Phe Ser Arg Tyr Lys Lys Ser Val Val Ala Arg Leu Lys Arg Arg Thr
                        660                 665                 670
        Ser Asp Pro Glu Val Ile Gln Ser Ile Glu Ser Thr Gly Tyr Ala Ala
                        675                 680                 685
        Val Ala Leu Arg Asp Arg Leu Leu Ser Tyr Gly Glu Lys Asn Gly Val
                    690                 695                 700
        Ala Gln Val Ala Val Phe Arg Gly Gly Val Thr Ala Glu Ala Arg Arg
        705                 710                 715                 720
        Trp Leu Asp Ile Ser Ile Glu Arg Leu Phe Ser Arg Val Ala Ile Phe
                            725                 730                 735
        Ala Gln Ser Thr Ser Thr Lys Arg Leu Asp Arg Arg His His Ala Val
                        740                 745                 750
        Asp Ala Val Val Leu Thr Thr Leu Thr Pro Gly Val Ala Lys Thr Leu
                    755                 760                 765
        Ala Asp Ala Arg Ser Arg Arg Val Ser Ala Glu Phe Trp Arg Arg Pro
                    770                 775                 780
        Ser Asp Val Asn Arg His Ser Thr Glu Glu Pro Gln Ser Pro Ala Tyr
        785                 790                 795                 800
        Arg Gln Trp Lys Glu Ser Cys Ser Gly Leu Gly Asp Leu Leu Ile Ser
                            805                 810                 815
```

-continued

Thr Ala Ala Arg Asp Ser Ile Ala Val Ala Ala Pro Leu Arg Leu Arg
            820                 825                 830

Pro Thr Gly Ala Leu His Glu Glu Thr Leu Arg Ala Phe Ser Glu His
        835                 840                 845

Thr Val Gly Ala Ala Trp Lys Gly Ala Glu Leu Arg Arg Ile Val Glu
    850                 855                 860

Pro Glu Val Tyr Ala Ala Phe Leu Ala Leu Thr Asp Pro Gly Gly Arg
865                 870                 875                 880

Phe Leu Lys Val Ser Pro Ser Glu Asp Val Leu Pro Ala Asp Glu Asn
                885                 890                 895

Arg His Ile Val Leu Ser Asp Arg Val Leu Gly Pro Arg Asp Arg Val
            900                 905                 910

Lys Leu Phe Pro Asp Asp Arg Gly Ser Ile Arg Val Arg Gly Gly Ala
        915                 920                 925

Ala Tyr Ile Ala Ser Phe His His Ala Arg Val Phe Arg Trp Gly Ser
    930                 935                 940

Ser His Ser Pro Ser Phe Ala Leu Leu Arg Val Ser Leu Ala Asp Leu
945                 950                 955                 960

Ala Val Ala Gly Leu Leu Arg Asp Gly Val Asp Val Phe Thr Ala Glu
                965                 970                 975

Leu Pro Pro Trp Thr Pro Ala Trp Arg Tyr Ala Ser Ile Ala Leu Val
            980                 985                 990

Lys Ala Val Glu Ser Gly Asp Ala Lys Gln Val Gly Trp Leu Val Pro
        995                 1000                1005

Gly Asp Glu Leu Asp Phe Gly Pro Glu Gly Val Thr Thr Ala Ala
        1010                1015                1020

Gly Asp Leu Ser Met Phe Leu Lys Tyr Phe Pro Glu Arg His Trp
        1025                1030                1035

Val Val Thr Gly Phe Glu Asp Lys Arg Ile Asn Leu Lys Pro
        1040                1045                1050

Ala Phe Leu Ser Ala Glu Gln Ala Glu Val Leu Arg Thr Glu Arg
        1055                1060                1065

Ser Asp Arg Pro Asp Thr Leu Thr Glu Ala Gly Glu Ile Leu Ala
        1070                1075                1080

Gln Phe Phe Pro Arg Cys Trp Arg Ala Thr Val Ala Lys Val Leu
        1085                1090                1095

Cys His Pro Gly Leu Thr Val Ile Arg Arg Thr Ala Leu Gly Gln
        1100                1105                1110

Pro Arg Trp Arg Arg Gly His Leu Pro Tyr Ser Trp Arg Pro Trp
        1115                1120                1125

Ser Ala Asp Pro Trp Ser Gly Thr Pro Pro Lys Lys Lys Arg
        1130                1135                1140

Lys Val
1145

<210> SEQ ID NO 21
<211> LENGTH: 3459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atggcctata gactgggcct cgacatcggc atcacatctg ttggatgggc cgtcgtggcc        60

```
ctggaaaagg atgagtctgg actgaagccc gtgcgcatcc aggatctggg cgtcagaatc    120
ttcgacaagg ccgaggatag caagaccggc gcttctctgg ctctgcccag aagagaagcc    180
agaagcgcca gaagaagaac ccggcggaga aggcacagac tgtggcgcgt gaaaagactg    240
ctggaacagc acggcatcct gagcatggaa cagatcgagg ccctgtacgc ccagagaaca    300
agcagccctg atgtgtatgc cctgagagtg gccggcctgg acagatgtct gatcgccgaa    360
gagatcgccc gggtgctgat tcacattgcc cacagaagag gcttccagag caacagaaag    420
agcgagatca aggacagcga cgccggcaag ctgctgaagg ccgtgcaaga aacgagaac     480 ctgatgcaga gcaagggcta cagaaccgtg gccgagatgc tggtgtctga ggccacaaag    540
acagacgccg agggaaagct ggtgcacggc aagaagcacg gctacgtcag caacgtgcgg    600
aacaaggccg gcgagtacag acacacagtg tccagacagg ccatcgtgga cgaagtgcgg    660
aagattttcg ccgctcagag agccctgggc aacgacgtga tgagcgagga actggaagat    720
agctacctga agatcctgtg cagccagcgg aacttcgatg atgggccctgg cggcgattct   780 ccttatggac acggaagcgt tagccccgac ggcgtcagac agagcatcta cgagagaatg    840
gtcggaagct gcaccttcga caggcgag aagagagccc ctagaagcag ctacagcttc      900
gagcggtttc agctgctgac caaggtggtc aacctgcgga tctaccggca gcaagaggat    960
ggcggcagat acccttgtga actgaccag accgagcggg ccagagtgat cgattgtgcc    1020
tacgagcaga ccaagatcac ctacggaaag ctgagaaagc tgctggacat gaaggacacc    1080
gagagctttg ccggcctgac ctacggcctg aacagaagca gaaacaagac cgaggacacc    1140
gtgttcgtgg aaatgaagtt ctaccacgaa gtccgcaagg ccctgcagag agccggggtt    1200
ttcattcagg acctgagcat cgagacactg accagatcg gctggattct gagcgtgtgg    1260
aagtccgacg acaaccggcg gaagaagctg tctacactgg gcctgagcga caacgtgatc    1320
gaagaactgc tgcccctgaa cggctccaag tttggccacc tgagcctgaa ggccatcaga    1380
aagatcctgc ctttcctgga agatgggtac agctacgacg tggcctgtga actggccggc    1440
tatcagtttc agggcaagac agagtacgtg aagcagcggc tgctgcctcc acttggagaa    1500
ggcgaagtga caaaccccgt tgtgcgcaga gcactgagcc aggccatcaa ggttgtgaac    1560
gccgtgatca gaaagcacgg cagcccagag agcatccaca tcgaactggc cagagagctg    1620
agcaagaacc tggacgagcg gagaaagatc gagaaggccc agaaagaaaa tcagaagaac    1680
aacgagcaga ttaaggacga gatccgcgag atcctgggat ccgcccatgt gaccggaaga    1740
gacatcgtga agtacaagct gttcaaacag caacaagagt tctgcatgta cagcggcgag    1800
aagctggacg tgaccagact gtttgagcct ggctatgccg aggtggacca catcatccct    1860 tacgcatca gcttcgacga ctcctacgac aacaaggtgc tggttaagac cgagcagaac    1920
cggcagaagg gcaatagaac ccctctggaa tacctgcggg acaagcctga gcagaaggcc    1980
aagtttatcg ccctggtgga atctatccct ctgagccaga aaagaaaaa ccacctcctg     2040 atggacaagc gggccatcga cctggaacaa gagggcttca gagagcggaa cctgagcgat    2100
acccggtaca tcacacgggc cctgatgaac cacatccagg cttggctgct gttcgacgag    2160
acagccagca ccagatccaa gagggtcgtg tgtgtgaatg cgccgtgac cgcctacatg    2220 agagctagat ggggcctgac aaaggataga gatgccggcg ataagcacca cgccgctgat    2280
gctgtggtgg tggcctgtat cggagacagc ctgatccaga gagtgaccaa atacgacaag    2340
ttcaagcgga acgccctggc cgaccggaac agatatgtgc agcaggtttc caagagcgag    2400
```

-continued

```
ggcatcaccc agtacgtgga caaagaaacc ggcgaggtgt tcacctggga gtccttcgat   2460
gagcggaagt tcctgcctaa cgagcccctg gaaccttggc cattcttcag ggatgagctg   2520
ctggccagac tgagcgacga cccctccaag aacatcagag ccatcggcct gctgacctac   2580
agcgagactg agcagatcga tcccatcttc gtgtccagaa tgcccaccag aaaagtgacc   2640
ggcgcagccc acaaagagac aatcagatcc ccacggatcg tgaaggtgga cgataacaag   2700
ggcaccgaga tccaggtggt ggtgtctaag gtggccctga ccgagctgaa gctgaccaaa   2760
gacggcgaaa tcaaggatta cttcaggccc gaggacgacc ccagactgta caacaccctg   2820
agagaacggc tggtgcagtt cggcggagat gccaaggccg ccttcaaaga acccgtgtac   2880
aagatcagca aggacggctc tgtgcggacc cctgtgcgga aagtgaagat tcaagagaag   2940
ctgacactgg gcgtgccagt gcatggcgga agaggaattg ccgagaatgg cggcatggtc   3000
cgaatcgacg tgttcgccaa aggcggcaag tactacttcg tgcccatcta cgtggccgac   3060
gtgctgaaga gagagctgcc caacagactg gccaccgctc acaagcctta cagcgaatgg   3120
cgcgtggtgg acgacagcta ccagttcaag ttctctctgt accccaacga tgccgtgatg   3180
atcaagccca gcagagaggt ggacatcacc tacaaggacc ggaaagagcc cgtcggctgc   3240
cggatcatgt actttgtgtc cgccaatatc gccagcgcct ccatcagcct gagaacccac   3300
gataactccg gcgagctgga aggactgggc atccaaggac tggaagtgtt cgagaaatac   3360
gtcgtgggcc ctctgggcga cacacaccct gtgtacaaag aacggcggat gcccttcaga   3420
gtggaacgga agatgaaccc caagaagaag aggaaggtg                          3459
```

<210> SEQ ID NO 22
<211> LENGTH: 1153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Ala Tyr Arg Leu Gly Leu Asp Ile Gly Ile Thr Ser Val Gly Trp
1               5                   10                  15

Ala Val Val Ala Leu Glu Lys Asp Glu Ser Gly Leu Lys Pro Val Arg
            20                  25                  30

Ile Gln Asp Leu Gly Val Arg Ile Phe Asp Lys Ala Glu Asp Ser Lys
        35                  40                  45

Thr Gly Ala Ser Leu Ala Leu Pro Arg Arg Glu Ala Arg Ser Ala Arg
    50                  55                  60

Arg Arg Thr Arg Arg Arg Arg His Arg Leu Trp Arg Val Lys Arg Leu
65                  70                  75                  80

Leu Glu Gln His Gly Ile Leu Ser Met Glu Gln Ile Glu Ala Leu Tyr
                85                  90                  95

Ala Gln Arg Thr Ser Ser Pro Asp Val Tyr Ala Leu Arg Val Ala Gly
            100                 105                 110

Leu Asp Arg Cys Leu Ile Ala Glu Glu Ile Ala Arg Val Leu Ile His
        115                 120                 125

Ile Ala His Arg Arg Gly Phe Gln Ser Asn Arg Lys Ser Glu Ile Lys
    130                 135                 140

Asp Ser Asp Ala Gly Lys Leu Leu Lys Ala Val Gln Glu Asn Glu Asn
145                 150                 155                 160

Leu Met Gln Ser Lys Gly Tyr Arg Thr Val Ala Glu Met Leu Val Ser
                165                 170                 175
```

```
Glu Ala Thr Lys Thr Asp Ala Glu Gly Lys Leu Val His Gly Lys Lys
            180                 185                 190

His Gly Tyr Val Ser Asn Val Arg Asn Lys Ala Gly Glu Tyr Arg His
        195                 200                 205

Thr Val Ser Arg Gln Ala Ile Val Asp Glu Val Arg Lys Ile Phe Ala
    210                 215                 220

Ala Gln Arg Ala Leu Gly Asn Asp Val Met Ser Glu Glu Leu Glu Asp
225                 230                 235                 240

Ser Tyr Leu Lys Ile Leu Cys Ser Gln Arg Asn Phe Asp Asp Gly Pro
                245                 250                 255

Gly Gly Asp Ser Pro Tyr Gly His Gly Ser Val Ser Pro Asp Gly Val
            260                 265                 270

Arg Gln Ser Ile Tyr Glu Arg Met Val Gly Ser Cys Thr Phe Glu Thr
        275                 280                 285

Gly Glu Lys Arg Ala Pro Arg Ser Ser Tyr Ser Phe Glu Arg Phe Gln
    290                 295                 300

Leu Leu Thr Lys Val Val Asn Leu Arg Ile Tyr Arg Gln Gln Glu Asp
305                 310                 315                 320

Gly Gly Arg Tyr Pro Cys Glu Leu Thr Gln Thr Glu Arg Ala Arg Val
                325                 330                 335

Ile Asp Cys Ala Tyr Glu Gln Thr Lys Ile Thr Tyr Gly Lys Leu Arg
            340                 345                 350

Lys Leu Leu Asp Met Lys Asp Thr Glu Ser Phe Ala Gly Leu Thr Tyr
        355                 360                 365

Gly Leu Asn Arg Ser Arg Asn Lys Thr Glu Asp Thr Val Phe Val Glu
    370                 375                 380

Met Lys Phe Tyr His Glu Val Arg Lys Ala Leu Gln Arg Ala Gly Val
385                 390                 395                 400

Phe Ile Gln Asp Leu Ser Ile Glu Thr Leu Asp Gln Ile Gly Trp Ile
                405                 410                 415

Leu Ser Val Trp Lys Ser Asp Asn Arg Arg Lys Lys Leu Ser Thr
            420                 425                 430

Leu Gly Leu Ser Asp Asn Val Ile Glu Glu Leu Leu Pro Leu Asn Gly
        435                 440                 445

Ser Lys Phe Gly His Leu Ser Leu Lys Ala Ile Arg Lys Ile Leu Pro
    450                 455                 460

Phe Leu Glu Asp Gly Tyr Ser Tyr Asp Val Ala Cys Glu Leu Ala Gly
465                 470                 475                 480

Tyr Gln Phe Gln Gly Lys Thr Glu Tyr Val Lys Gln Arg Leu Leu Pro
                485                 490                 495

Pro Leu Gly Glu Gly Glu Val Thr Asn Pro Val Val Arg Arg Ala Leu
            500                 505                 510

Ser Gln Ala Ile Lys Val Val Asn Ala Val Ile Arg Lys His Gly Ser
        515                 520                 525

Pro Glu Ser Ile His Ile Glu Leu Ala Arg Glu Leu Ser Lys Asn Leu
    530                 535                 540

Asp Glu Arg Arg Lys Ile Glu Lys Ala Gln Lys Glu Asn Gln Lys Asn
545                 550                 555                 560

Asn Glu Gln Ile Lys Asp Glu Ile Arg Glu Ile Leu Gly Ser Ala His
                565                 570                 575

Val Thr Gly Arg Asp Ile Val Lys Tyr Lys Leu Phe Lys Gln Gln Gln
            580                 585                 590
```

-continued

```
Glu Phe Cys Met Tyr Ser Gly Glu Lys Leu Asp Val Thr Arg Leu Phe
            595                 600                 605

Glu Pro Gly Tyr Ala Glu Val Asp His Ile Ile Pro Tyr Gly Ile Ser
        610                 615                 620

Phe Asp Asp Ser Tyr Asp Asn Lys Val Leu Val Lys Thr Glu Gln Asn
625                 630                 635                 640

Arg Gln Lys Gly Asn Arg Thr Pro Leu Glu Tyr Leu Arg Asp Lys Pro
                645                 650                 655

Glu Gln Lys Ala Lys Phe Ile Ala Leu Val Glu Ser Ile Pro Leu Ser
            660                 665                 670

Gln Lys Lys Asn His Leu Leu Met Asp Lys Arg Ala Ile Asp Leu
        675                 680                 685

Glu Gln Glu Gly Phe Arg Glu Arg Asn Leu Ser Asp Thr Arg Tyr Ile
            690                 695                 700

Thr Arg Ala Leu Met Asn His Ile Gln Ala Trp Leu Leu Phe Asp Glu
705                 710                 715                 720

Thr Ala Ser Thr Arg Ser Lys Arg Val Val Cys Val Asn Gly Ala Val
                725                 730                 735

Thr Ala Tyr Met Arg Ala Arg Trp Gly Leu Thr Lys Asp Arg Asp Ala
            740                 745                 750

Gly Asp Lys His His Ala Ala Asp Ala Val Val Ala Cys Ile Gly
        755                 760                 765

Asp Ser Leu Ile Gln Arg Val Thr Lys Tyr Asp Lys Phe Lys Arg Asn
        770                 775                 780

Ala Leu Ala Asp Arg Asn Arg Tyr Val Gln Gln Val Ser Lys Ser Glu
785                 790                 795                 800

Gly Ile Thr Gln Tyr Val Asp Lys Glu Thr Gly Glu Val Phe Thr Trp
                805                 810                 815

Glu Ser Phe Asp Glu Arg Lys Phe Leu Pro Asn Glu Pro Leu Glu Pro
            820                 825                 830

Trp Pro Phe Phe Arg Asp Glu Leu Leu Ala Arg Leu Ser Asp Asp Pro
        835                 840                 845

Ser Lys Asn Ile Arg Ala Ile Gly Leu Leu Thr Tyr Ser Glu Thr Glu
850                 855                 860

Gln Ile Asp Pro Ile Phe Val Ser Arg Met Pro Thr Arg Lys Val Thr
865                 870                 875                 880

Gly Ala Ala His Lys Glu Thr Ile Arg Ser Pro Arg Ile Val Lys Val
                885                 890                 895

Asp Asp Asn Lys Gly Thr Glu Ile Gln Val Val Ser Lys Val Ala
                900                 905                 910

Leu Thr Glu Leu Lys Leu Thr Lys Asp Gly Glu Ile Lys Asp Tyr Phe
            915                 920                 925

Arg Pro Glu Asp Asp Pro Arg Leu Tyr Asn Thr Leu Arg Glu Arg Leu
930                 935                 940

Val Gln Phe Gly Gly Asp Ala Lys Ala Phe Lys Glu Pro Val Tyr
945                 950                 955                 960

Lys Ile Ser Lys Asp Gly Ser Val Arg Thr Pro Val Arg Lys Val Lys
                965                 970                 975

Ile Gln Glu Lys Leu Thr Leu Gly Pro Val His Gly Gly Arg Gly
            980                 985                 990

Ile Ala Glu Asn Gly Gly Met Val  Arg Ile Asp Val Phe  Ala Lys Gly
        995                 1000                1005

Gly Lys  Tyr Tyr Phe Val Pro  Ile Tyr Val Ala Asp  Val Leu Lys
```

```
          1010                1015                1020
Arg Glu Leu Pro Asn Arg Leu Ala Thr Ala His Lys Pro Tyr Ser
        1025                1030                1035

Glu Trp Arg Val Val Asp Asp Ser Tyr Gln Phe Lys Phe Ser Leu
        1040                1045                1050

Tyr Pro Asn Asp Ala Val Met Ile Lys Pro Ser Arg Glu Val Asp
        1055                1060                1065

Ile Thr Tyr Lys Asp Arg Lys Glu Pro Val Gly Cys Arg Ile Met
        1070                1075                1080

Tyr Phe Val Ser Ala Asn Ile Ala Ser Ala Ser Ile Ser Leu Arg
        1085                1090                1095

Thr His Asp Asn Ser Gly Glu Leu Glu Gly Leu Gly Ile Gln Gly
        1100                1105                1110

Leu Glu Val Phe Glu Lys Tyr Val Val Gly Pro Leu Gly Asp Thr
        1115                1120                1125

His Pro Val Tyr Lys Glu Arg Arg Met Pro Phe Arg Val Glu Arg
        1130                1135                1140

Lys Met Asn Pro Lys Lys Lys Arg Lys Val
        1145                1150

<210> SEQ ID NO 23
<211> LENGTH: 4248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgctggtgt ccctatctc tgtggatctc ggcggcaaga ataccggctt cttcagcttc      60
accgacagcc tggacaatag ccagagcggc accgtgatct acgacgagag cttcgtgctg     120
agccaagtgg gcagaagaag caagcggcac agcaagcgga caaacctgag aaacaagctg     180
gtcaagcggc tgttcctgct gatcctgcaa gagcaccacg gcctgagcat cgacgttctg     240
cccgatgaga tccggggcct gttcaacaag agaggctaca cctacgccgg cttcgagctg     300
gacgagaaga agaaggacgc cctggaaagc gataccctga agagttcct gagcgagaag     360 ctgcagtcca tcgacagaga cagcgacgtg aagatttcc tgaaccagat cgccagcaac     420
gccgagagct ttaaggacta caagaaaggc ttcgaggccg tgttcgccag cgccacacac     480
agccccaaca gaagctgga actgaaggac gagctgaagt ccgagtacgg cgagaacgcc     540
aaagaactgc tggccggcct gagagtgacc aaagagatcc tggacgagtt cgacaagcaa     600
gagaaccagg caaccctgcc tcgggccaag tactttgagg aactgggcga gtatatcgcc     660
accaacgaga aagtcaagag cttcttcgac agcaacagcc tgaagctgac cgacatgacc     720
aagctgatcg cgaacatcag caactaccag ctgaaagagc tgcggcggta cttcaacgac     780
aaagagatgg aaaagggcga catctggatt cccaacaagc tgcacaagat caccgagaga     840
tttgtgcgga gctggcaccc caagaacgac gccgatagac agaagggc cgagctgatg     900 aaggacctga gtccaaaga aatcatggaa ctgctgacca ccaccgagcc tgtgatgaca     960
atccctcctt acgacgacat gaacaacaga ggcgccgtga agtgtcagac cctgcggctg    1020
aatgaggaat acctggacaa acatctgccc aactggcggg atatcgccaa gagactgaac    1080
cacggcaagt tcaacgacga cctggccgac tctaccgtga agggctacag cgaggatagc    1140
accctgctgc acagactgct ggacacctct aaagagatcg acatctacga gctgcgggc    1200
```

```
aagaagccca acgagctgct ggttaagaca ctgggccaga gcgacgccaa cagactgtat   1260
ggcttcgccc agaactacta tgagctgatc cggcagaaag tgcgcgctgg catttgggtg   1320
cccgtgaaga acaaggatga ctccctgaac ctggaagata actccaacat gctgaagcgg   1380
tgcaaccaca atcctccaca caagaagaat cagatccaca acctggtggc cggcatcctg   1440
ggagtgaaac tggatgaggc caagttcgcc gagttcgaga agagctttg gagcgccaaa   1500 gtgggcaaca agaaactgag cgcctactgc aagaacatcg aggaactgag aaagacccac   1560
ggcaacacct tcaagatcga tatagaggaa ctgcgcaaga aggaccccgc cgagctgtcc   1620
aaagaggaaa aggccaagct gagactgacc gacgacgtga tcctgaatga gtggtcccag   1680
aagatcgcca acttctttga catcgacgac aagcaccggc agcggttcaa caacctgttc   1740
agcatggccc agctgcacac agtgatcgac acacccagaa gcggcttcag ctctacctgc   1800
aaaagatgca ccgccagaaa caggttcaga agcgagacag ccttctacaa cgacgagaca   1860
ggcgagttcc acaagaaggc cacagccacc tgtcagagac tgcccgctga tacccagagg   1920
cctttcagcg gaaagatcga gcggtacatc gacaagctgg gatacgagct ggccaagatc   1980
aaggctaaag aactggaagg catggaagct aaagaaatca aggtgcccat catcctggaa   2040
cagaacgcct tcgagtacga ggaaagcctg cggaagtcta agaccggatc caacgacaga   2100
gtgatcaact ccaagaaaga ccgcgacgga aagaaactgg ccaaggccaa agagaacgcc   2160
gaggacagga tgaaggacaa ggacaagcgg atcaaggcct tcagcagcgg catctgccct   2220
tactgcggag ataccatcgg agatgacggc gagatcgacc acatcctgcc tagaagccac   2280
acactgaaaa tctacgggac cgtgttcaac cccgagggca atctgatcta cgtgcaccag   2340
aagtgcaacc aggccaaagc cgacagcatc tacaagctga gcgatatcaa ggccggcgtg   2400
tcagcccagt ggattgaaga acaggtggcc aacattaagg ggtacaagac cttcagcgtg   2460
ctgtccgccg aacagcagaa ggcctttaga tacgccctgt tcctccagaa cgacaacgag   2520
gcctacaaaa aggtggtgga ctggctgcgg accgaccagt ctgctagagt gaacggcaca   2580
cagaagtacc tggccaaaaa gatccaagag aagctcacca agatgctgcc taacaagcac   2640
ctgagcttcg agttcatcct ggccgatgcc accgaggtgt cagagctgag aaggcagtac   2700
gccagacaga acctctgct ggctaaggcc gagaagcagg ccccttcttc tcacgccatt   2760
gatgccgtga tggccttcgt ggccagatac cagaaggtgt caaggacgg caccctcct   2820 aacgccgatg aggtggcaaa actggctatg ctggacagct ggaaccccgc ctctaatgag   2880
cctctgacaa agggcctgtc cacgaaccag aaaatcgaga gatgatcaa gagcggcgac   2940 tacggccaga aaaacatgag agaggtgttc ggcaagtcca tcttcggaga atgccatc   3000 ggcgagagat acaagcccat cgtggttcaa gaaggcggct actacatcgg ctaccccgcc   3060
acagtgaaaa agggctacga actgaagaac tgcaaggtgg tcaccagcaa gaacgatatt   3120
gccaagctgg aaaagatcat caagaaccag gacctgatcc tctgaaaga gaatcagtac   3180 atcaaaatct tctccatcaa caagcagacc atcagcgagc tgagcaaccg ctacttcaac   3240
atgaattaca agaacctggt cgagcgggac aaagaaattg tgggactgct tgagtttatc   3300
gtcgagaact gccggtacta caccaagaaa gtggacgtga agttcgcccc taagtacatc   3360
cacgagacaa agtacccctt ctacgatgac tggcggagat cgacgaggc ctggcggtat   3420 ctgcaagaaa accagaacaa gaccagctcc aaggaccgct tcgtgatcga taagagcagc   3480
ctgaacgagt actaccagcc agacaagaat gagtacaagc tggacgtgga cacccagcct   3540
```

```
atctgggacg acttctgccg gtggtacttc ctggacagat acaagaccgc caacgacaag    3600
aagtccatcc gcatcaaggc ccgcaagaca ttctccctgc tggctgagtc tggcgtgcag    3660
ggcaaagtgt tccgggccaa gagaaagatc cctaccggct acgcctatca ggccctgcct    3720
atggacaaca acgtgatcgc tggcgattac gccaacattc tgctggaagc caacagcaag    3780
accctgagcc tggtgcctaa gagcggcatc agcattgaga agcagctgga caaaaagctc    3840
gacgtcatca aaagaccga cgtgcgcggc ctggcaatcg acaacaactc cttcttcaac    3900
gccgacttcg acacacacgg catccggctg atcgtggaaa acaccagcgt gaaagtggga    3960
aacttcccca tcagcgccat cgataagtcc gccaagcgga tgatcttcag agccctgttt    4020
gagaaagaga aggggaagcg caagaaaaag accaccatca gcttcaaaga aagcggccct    4080
gtgcaggact acctcaaggt gttcctgaaa aagatcgtga agatccagct gagaaccgac    4140
ggctccatct ccaacatcgt cgtgcggaag aatgccgccg atttcaccct gagctttaga    4200
agcgagcaca tccagaaact gctgaagccc aagaagaaga ggaaggtg                 4248
```

<210> SEQ ID NO 24
<211> LENGTH: 1416
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

```
Met Leu Val Ser Pro Ile Ser Val Asp Leu Gly Gly Lys Asn Thr Gly
1               5                   10                  15

Phe Phe Ser Phe Thr Asp Ser Leu Asp Asn Ser Gln Ser Gly Thr Val
            20                  25                  30

Ile Tyr Asp Glu Ser Phe Val Leu Ser Gln Val Gly Arg Arg Ser Lys
        35                  40                  45

Arg His Ser Lys Arg Asn Asn Leu Arg Asn Lys Leu Val Lys Arg Leu
    50                  55                  60

Phe Leu Ile Leu Gln Glu His His Gly Leu Ser Ile Asp Val Leu
65                  70                  75                  80

Pro Asp Glu Ile Arg Gly Leu Phe Asn Lys Arg Gly Tyr Thr Tyr Ala
                85                  90                  95

Gly Phe Glu Leu Asp Glu Lys Lys Lys Asp Ala Leu Glu Ser Asp Thr
            100                 105                 110

Leu Lys Glu Phe Leu Ser Glu Lys Leu Gln Ser Ile Asp Arg Asp Ser
        115                 120                 125

Asp Val Glu Asp Phe Leu Asn Gln Ile Ala Ser Asn Ala Glu Ser Phe
    130                 135                 140

Lys Asp Tyr Lys Lys Gly Phe Glu Ala Val Phe Ala Ser Ala Thr His
145                 150                 155                 160

Ser Pro Asn Lys Lys Leu Glu Leu Lys Asp Glu Leu Lys Ser Glu Tyr
                165                 170                 175

Gly Glu Asn Ala Lys Glu Leu Leu Ala Gly Leu Arg Val Thr Lys Glu
            180                 185                 190

Ile Leu Asp Glu Phe Asp Lys Gln Glu Asn Gly Asn Leu Pro Arg
        195                 200                 205

Ala Lys Tyr Phe Glu Glu Leu Gly Glu Tyr Ile Ala Thr Asn Glu Lys
    210                 215                 220

Val Lys Ser Phe Phe Asp Ser Asn Ser Leu Lys Leu Thr Asp Met Thr
225                 230                 235                 240
```

-continued

```
Lys Leu Ile Gly Asn Ile Ser Asn Tyr Gln Leu Lys Glu Leu Arg Arg
                245                 250                 255

Tyr Phe Asn Asp Lys Glu Met Glu Lys Gly Asp Ile Trp Ile Pro Asn
                260                 265                 270

Lys Leu His Lys Ile Thr Glu Arg Phe Val Arg Ser Trp His Pro Lys
                275                 280                 285

Asn Asp Ala Asp Arg Gln Arg Arg Ala Glu Leu Met Lys Asp Leu Lys
                290                 295                 300

Ser Lys Glu Ile Met Glu Leu Leu Thr Thr Thr Glu Pro Val Met Thr
305                 310                 315                 320

Ile Pro Pro Tyr Asp Asp Met Asn Asn Arg Gly Ala Val Lys Cys Gln
                325                 330                 335

Thr Leu Arg Leu Asn Glu Glu Tyr Leu Asp Lys His Leu Pro Asn Trp
                340                 345                 350

Arg Asp Ile Ala Lys Arg Leu Asn His Gly Lys Phe Asn Asp Asp Leu
                355                 360                 365

Ala Asp Ser Thr Val Lys Gly Tyr Ser Glu Asp Ser Thr Leu Leu His
                370                 375                 380

Arg Leu Leu Asp Thr Ser Lys Glu Ile Asp Ile Tyr Glu Leu Arg Gly
385                 390                 395                 400

Lys Lys Pro Asn Glu Leu Leu Val Lys Thr Leu Gly Gln Ser Asp Ala
                405                 410                 415

Asn Arg Leu Tyr Gly Phe Ala Gln Asn Tyr Tyr Glu Leu Ile Arg Gln
                420                 425                 430

Lys Val Arg Ala Gly Ile Trp Val Pro Val Lys Asn Lys Asp Asp Ser
                435                 440                 445

Leu Asn Leu Glu Asp Asn Ser Asn Met Leu Lys Arg Cys Asn His Asn
                450                 455                 460

Pro Pro His Lys Lys Asn Gln Ile His Asn Leu Val Ala Gly Ile Leu
465                 470                 475                 480

Gly Val Lys Leu Asp Glu Ala Lys Phe Ala Glu Phe Glu Lys Glu Leu
                485                 490                 495

Trp Ser Ala Lys Val Gly Asn Lys Lys Leu Ser Ala Tyr Cys Lys Asn
                500                 505                 510

Ile Glu Glu Leu Arg Lys Thr His Gly Asn Thr Phe Lys Ile Asp Ile
                515                 520                 525

Glu Glu Leu Arg Lys Lys Asp Pro Ala Glu Leu Ser Lys Glu Glu Lys
                530                 535                 540

Ala Lys Leu Arg Leu Thr Asp Asp Val Ile Leu Asn Glu Trp Ser Gln
545                 550                 555                 560

Lys Ile Ala Asn Phe Phe Asp Ile Asp Lys His Arg Gln Arg Phe
                565                 570                 575

Asn Asn Leu Phe Ser Met Ala Gln Leu His Thr Val Ile Asp Thr Pro
                580                 585                 590

Arg Ser Gly Phe Ser Ser Thr Cys Lys Arg Cys Thr Ala Glu Asn Arg
                595                 600                 605

Phe Arg Ser Glu Thr Ala Phe Tyr Asn Asp Glu Thr Gly Glu Phe His
                610                 615                 620

Lys Lys Ala Thr Ala Thr Cys Gln Arg Leu Pro Ala Asp Thr Gln Arg
625                 630                 635                 640

Pro Phe Ser Gly Lys Ile Glu Arg Tyr Ile Asp Lys Leu Gly Tyr Glu
                645                 650                 655
```

```
Leu Ala Lys Ile Lys Ala Lys Glu Leu Glu Gly Met Glu Ala Lys Glu
            660                 665                 670

Ile Lys Val Pro Ile Ile Leu Glu Gln Asn Ala Phe Glu Tyr Glu Glu
            675                 680                 685

Ser Leu Arg Lys Ser Lys Thr Gly Ser Asn Asp Arg Val Ile Asn Ser
            690                 695                 700

Lys Lys Asp Arg Asp Gly Lys Lys Leu Ala Lys Ala Lys Glu Asn Ala
705                 710                 715                 720

Glu Asp Arg Leu Lys Asp Lys Asp Lys Arg Ile Lys Ala Phe Ser Ser
                    725                 730                 735

Gly Ile Cys Pro Tyr Cys Gly Asp Thr Ile Gly Asp Asp Gly Glu Ile
                740                 745                 750

Asp His Ile Leu Pro Arg Ser His Thr Leu Lys Ile Tyr Gly Thr Val
            755                 760                 765

Phe Asn Pro Glu Gly Asn Leu Ile Tyr Val His Gln Lys Cys Asn Gln
            770                 775                 780

Ala Lys Ala Asp Ser Ile Tyr Lys Leu Ser Asp Ile Lys Ala Gly Val
785                 790                 795                 800

Ser Ala Gln Trp Ile Glu Glu Gln Val Ala Asn Ile Lys Gly Tyr Lys
                    805                 810                 815

Thr Phe Ser Val Leu Ser Ala Glu Gln Lys Ala Phe Arg Tyr Ala
                820                 825                 830

Leu Phe Leu Gln Asn Asp Asn Glu Ala Tyr Lys Lys Val Val Asp Trp
                    835                 840                 845

Leu Arg Thr Asp Gln Ser Ala Arg Val Asn Gly Thr Gln Lys Tyr Leu
            850                 855                 860

Ala Lys Lys Ile Gln Glu Lys Leu Thr Lys Met Leu Pro Asn Lys His
865                 870                 875                 880

Leu Ser Phe Glu Phe Ile Leu Ala Asp Ala Thr Glu Val Ser Glu Leu
                    885                 890                 895

Arg Arg Gln Tyr Ala Arg Gln Asn Pro Leu Leu Ala Lys Ala Glu Lys
                900                 905                 910

Gln Ala Pro Ser Ser His Ala Ile Asp Ala Val Met Ala Phe Val Ala
            915                 920                 925

Arg Tyr Gln Lys Val Phe Lys Asp Gly Thr Pro Asn Ala Asp Glu
930                 935                 940

Val Ala Lys Leu Ala Met Leu Asp Ser Trp Asn Pro Ala Ser Asn Glu
945                 950                 955                 960

Pro Leu Thr Lys Gly Leu Ser Thr Asn Gln Lys Ile Glu Lys Met Ile
                    965                 970                 975

Lys Ser Gly Asp Tyr Gly Gln Lys Asn Met Arg Glu Val Phe Gly Lys
                980                 985                 990

Ser Ile Phe Gly Glu Asn Ala Ile Gly Glu Arg Tyr Lys Pro Ile Val
            995                 1000                1005

Val Gln Glu Gly Gly Tyr Tyr Ile Gly Tyr Pro Ala Thr Val Lys
        1010                1015                1020

Lys Gly Tyr Glu Leu Lys Asn Cys Lys Val Val Thr Ser Lys Asn
        1025                1030                1035

Asp Ile Ala Lys Leu Glu Lys Ile Ile Lys Asn Gln Asp Leu Ile
        1040                1045                1050

Ser Leu Lys Glu Asn Gln Tyr Ile Lys Ile Phe Ser Ile Asn Lys
        1055                1060                1065

Gln Thr Ile Ser Glu Leu Ser Asn Arg Tyr Phe Asn Met Asn Tyr
```

```
                   1070                1075                1080

Lys Asn Leu Val Glu Arg Asp Lys Glu Ile Val Gly Leu Leu Glu
    1085                1090                1095

Phe Ile Val Glu Asn Cys Arg Tyr Tyr Thr Lys Lys Val Asp Val
    1100                1105                1110

Lys Phe Ala Pro Lys Tyr Ile His Glu Thr Lys Tyr Pro Phe Tyr
    1115                1120                1125

Asp Asp Trp Arg Arg Phe Asp Glu Ala Trp Arg Tyr Leu Gln Glu
    1130                1135                1140

Asn Gln Asn Lys Thr Ser Ser Lys Asp Arg Phe Val Ile Asp Lys
    1145                1150                1155

Ser Ser Leu Asn Glu Tyr Tyr Gln Pro Asp Lys Asn Glu Tyr Lys
    1160                1165                1170

Leu Asp Val Asp Thr Gln Pro Ile Trp Asp Phe Cys Arg Trp
    1175                1180                1185

Tyr Phe Leu Asp Arg Tyr Lys Thr Ala Asn Asp Lys Lys Ser Ile
    1190                1195                1200

Arg Ile Lys Ala Arg Lys Thr Phe Ser Leu Leu Ala Glu Ser Gly
    1205                1210                1215

Val Gln Gly Lys Val Phe Arg Ala Lys Arg Lys Ile Pro Thr Gly
    1220                1225                1230

Tyr Ala Tyr Gln Ala Leu Pro Met Asp Asn Asn Val Ile Ala Gly
    1235                1240                1245

Asp Tyr Ala Asn Ile Leu Leu Glu Ala Asn Ser Lys Thr Leu Ser
    1250                1255                1260

Leu Val Pro Lys Ser Gly Ile Ser Ile Glu Lys Gln Leu Asp Lys
    1265                1270                1275

Lys Leu Asp Val Ile Lys Lys Thr Asp Val Arg Gly Leu Ala Ile
    1280                1285                1290

Asp Asn Asn Ser Phe Phe Asn Ala Asp Phe Asp Thr His Gly Ile
    1295                1300                1305

Arg Leu Ile Val Glu Asn Thr Ser Val Lys Val Gly Asn Phe Pro
    1310                1315                1320

Ile Ser Ala Ile Asp Lys Ser Ala Lys Arg Met Ile Phe Arg Ala
    1325                1330                1335

Leu Phe Glu Lys Glu Lys Gly Lys Arg Lys Lys Lys Thr Thr Ile
    1340                1345                1350

Ser Phe Lys Glu Ser Gly Pro Val Gln Asp Tyr Leu Lys Val Phe
    1355                1360                1365

Leu Lys Lys Ile Val Lys Ile Gln Leu Arg Thr Asp Gly Ser Ile
    1370                1375                1380

Ser Asn Ile Val Val Arg Lys Asn Ala Ala Asp Phe Thr Leu Ser
    1385                1390                1395

Phe Arg Ser Glu His Ile Gln Lys Leu Leu Lys Pro Lys Lys Lys
    1400                1405                1410

Arg Lys Val
    1415

<210> SEQ ID NO 25
<211> LENGTH: 3417
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 25

```
atgaagaaga tcctgggcgt cgacctgggc atcaccagct tggatacgc catcctgcaa      60
gagacaggca aggacctgta cagatgcctg gacaacagcg tggtcatgcg gaacaacccc    120
tacgacgaga agtctggcga gagcagccag agcatccgca gcacccagaa atccatgcgg    180
cggctgatcg agaagcggaa gaaacggatc agatgcgtgg cccagacaat ggaacgctac    240
ggcatcctgg actactccga gacaatgaag atcaacgacc caagaacaa cccgatcaag      300
aacagatggc agctgagagc cgtggacgcc tggaaaagac ctctgagccc tcaagagctg    360
ttcgccatct tgcccacat ggccaagcac cggggctaca gtctatcgc caccgaggac       420
ctgatctacg agctggaact ggaactcggc ctgaacgacc ctgagaaaga gtccgagaag    480
aaggccgacg agcggagaca ggtgtacaac gccctgagac acctggaaga actgcggaag    540
aagtacggcg gcgagacaat cgcccagacc atccacagag ctgtggaagc cggcgacctg    600
cggagctaca gaaaccacga cgactacgag aagatgatcc gcagagagga catcgaggaa    660
gagattgaga aggtcctgct gcggcaggct gaactgggag cacttggact gcctgaggaa    720
caggtgtccg agctgatcga tgagctgaag gcctgcatca ccgaccaaga gatgcccacc    780
atcgacgaga gcctgttcgg caagtgcacc ttctacaagg acgagctggc cgctcctgcc    840
tacagctacc tgtacgacct gtaccggctg tacaagaagc tggccgacct gaacatcgac    900
ggctacgaag tgacccaaga ggaccgcgag aaagtgatcg agtgggtcga gaaaagatc     960
gcccagggca agaacctgaa gaaaatcacc cacaaggacc tccggaagat cctcggactg    1020
gcccctgagc agaagattt cggcgtcgag gacgagagaa tcgtcaaggg aaagaaagaa     1080
ccccggacct tcgtgccctt cttcttcctg gccgatatcg ccaagttcaa gaactgttt     1140
gccagcatcc agaagcaccc cgacgctctg cagatttca gagaactggc cgagatcctg     1200
cagcggagca agacacctca agaggccctg gatagactga gagccctgat ggccggcaag    1260
ggcatcgaca ccgatgacag agagctgctg gaactcttca gaacaagcg gagcggcaca     1320
agagagctga gccaccgcta tatcctggaa gccctgcctc tgttcctgga aggctatgac    1380
gagaaagagg tgcagagaat cctgggcttt gacgaccgcg aggactacag cagataccc     1440
aagagcctgc ggcatctgca cctgagagag ggcaacctgt tcgagaaaga agagaatccc    1500
atcaacaacc acgccgtgaa gtccctggct cttgggccc tgggactgat cgctgacctg    1560
tcttggagat acggcccctt cgatgagatc atcctggaaa ccaccaggga cgccctgcct    1620
gagaagatcc ggaaagaaat cgacaaggcc atgcgcgaga gagagaaagc cctggacaag    1680
atcatcggca gtacaagaa agagttcccc agcatcgaca gcggctggc cagaaagatt     1740
cagctgtggg agagacagaa aggcctcgat ctgtactccg gcaaagtgat caacctgagc    1800
cagctgctcg atggatccgc cgacatcgag cacatcgtgc ctcagtctct cggcggcctg    1860
agcaccgact acaataccat cgtgaccctg aagtccgtga acgccgccaa gggcaataga    1920
ctgcctggcg attggctggc cggaaatccc gactacagag aacggatcgg catgctgtct    1980
gagaagggcc tgatcgactg gaagaagagg aagaacctgc tggcccagag cctggacgaa    2040
atctacaccg agaacaccca cagcaaaggc atccggggcc aagctacct ggaagctctg      2100
gttgcccagg tgctgaagcg gtactaccca tttcctgatc ctgagctgcg caagaatggc    2160
atcggcgtgc ggatgatccc cggaaaagtg accagcaaga ccagaagcct gctgggaatc    2220
aagagcaaga gccgcgagac aaacttccac cacgccgagg atgccctgat tctgagcaca    2280
```

```
ctgaccagag gctggcagaa ccggctgcac agaatgctga gagacaacta cggcaagagc      2340
gaggccgagc tgaaagaact ctggaaaaag tacatgcccc acatcgaggg cctgacactg      2400
gccgactata tcgatgaggc cttccggcgg ttcatgagca agggcgaaga gtccctgttc      2460
taccgggaca tgttcgacac catccggtcc atcagctact gggtcgacaa gaagcctctg      2520
agcgccagca gccacaaaga aaccgtgtac agcagcagac acgaggtgcc cacactgagg      2580
aaaaacattc tggaagcctt cgacagcctg aacgtgatca aggaccggca aagctgacc       2640 accgaagagt tcatgaagcg ctacgacaaa gagatccggc agaagctgtg gctgcaccgc      2700
atcggcaaca ccaacgacga gtcttaccgc gccgtggaag agagagccac acagattgcc      2760
cagatcctga ccagatacca gctcatggac gcccagaatg acaaagaaat tgatgagaag      2820
tttcagcagg ccctgaaaga gctgatcaca agccccatcg aagtgactgg caagctgctg      2880
cggaaaatga gattcgtgta cgacaagctg aacgccatgc agatcgacag aggcctggtg      2940
gaaaccgaca gaacatgct gggcatccac atcagcaagg cccccaatga aagctgatc        3000 ttcagacgga tggacgtgaa caacgcccac gagctgcaaa agaacgcag cggaatcctg       3060 tgctacctga cgagatgct gttcatcttc aacaagaagg ggctgattca ctacggctgc      3120
ctgcggtctt acctcgaaaa aggccagggc agcaagtata tcgccctgtt caaccctcgg     3180
ttccccgcca atcctaaggc tcagcctagc aagttcacca gcgacagcaa gatcaagcaa     3240
gtcggcatcg gcagcgccac cggaatcatt aaggcccacc tggatctgga tggccacgtg      3300
cgctcttatg aggtgttcgg aacactgccc gagggcagca tcgagtggtt caaagaggaa     3360
agcggctacg gcagagtgga agatgaccct caccacccca agaagaagag gaaggtg         3417
```

<210> SEQ ID NO 26
<211> LENGTH: 1139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Lys Lys Ile Leu Gly Val Asp Leu Gly Ile Thr Ser Phe Gly Tyr
1               5                   10                  15

Ala Ile Leu Gln Glu Thr Gly Lys Asp Leu Tyr Arg Cys Leu Asp Asn
                20                  25                  30

Ser Val Val Met Arg Asn Asn Pro Tyr Asp Glu Lys Ser Gly Glu Ser
            35                  40                  45

Ser Gln Ser Ile Arg Ser Thr Gln Lys Ser Met Arg Arg Leu Ile Glu
        50                  55                  60

Lys Arg Lys Lys Arg Ile Arg Cys Val Ala Gln Thr Met Glu Arg Tyr
65                  70                  75                  80

Gly Ile Leu Asp Tyr Ser Glu Thr Met Lys Ile Asn Asp Pro Lys Asn
                85                  90                  95

Asn Pro Ile Lys Asn Arg Trp Gln Leu Arg Ala Val Asp Ala Trp Lys
                100                 105                 110

Arg Pro Leu Ser Pro Gln Glu Leu Phe Ala Ile Phe Ala His Met Ala
            115                 120                 125

Lys His Arg Gly Tyr Lys Ser Ile Ala Thr Glu Asp Leu Ile Tyr Glu
        130                 135                 140

Leu Glu Leu Glu Leu Gly Leu Asn Asp Pro Glu Lys Glu Ser Glu Lys
145                 150                 155                 160

-continued

Lys Ala Asp Glu Arg Arg Gln Val Tyr Asn Ala Leu Arg His Leu Glu
                165                 170                 175
Glu Leu Arg Lys Lys Tyr Gly Gly Glu Thr Ile Ala Gln Thr Ile His
            180                 185                 190
Arg Ala Val Glu Ala Gly Asp Leu Arg Ser Tyr Arg Asn His Asp Asp
        195                 200                 205
Tyr Glu Lys Met Ile Arg Arg Glu Asp Ile Glu Glu Ile Glu Lys
    210                 215                 220
Val Leu Leu Arg Gln Ala Glu Leu Gly Ala Leu Gly Leu Pro Glu Glu
225                 230                 235                 240
Gln Val Ser Glu Leu Ile Asp Glu Leu Lys Ala Cys Ile Thr Asp Gln
                245                 250                 255
Glu Met Pro Thr Ile Asp Glu Ser Leu Phe Gly Lys Cys Thr Phe Tyr
            260                 265                 270
Lys Asp Glu Leu Ala Ala Pro Ala Tyr Ser Tyr Leu Tyr Asp Leu Tyr
        275                 280                 285
Arg Leu Tyr Lys Lys Leu Ala Asp Leu Asn Ile Asp Gly Tyr Glu Val
    290                 295                 300
Thr Gln Glu Asp Arg Glu Lys Val Ile Glu Trp Val Glu Lys Lys Ile
305                 310                 315                 320
Ala Gln Gly Lys Asn Leu Lys Lys Ile Thr His Lys Asp Leu Arg Lys
                325                 330                 335
Ile Leu Gly Leu Ala Pro Glu Gln Lys Ile Phe Gly Val Glu Asp Glu
            340                 345                 350
Arg Ile Val Lys Gly Lys Lys Glu Pro Arg Thr Phe Val Pro Phe Phe
        355                 360                 365
Phe Leu Ala Asp Ile Ala Lys Phe Lys Glu Leu Phe Ala Ser Ile Gln
    370                 375                 380
Lys His Pro Asp Ala Leu Gln Ile Phe Arg Glu Leu Ala Glu Ile Leu
385                 390                 395                 400
Gln Arg Ser Lys Thr Pro Gln Glu Ala Leu Asp Arg Leu Arg Ala Leu
                405                 410                 415
Met Ala Gly Lys Gly Ile Asp Thr Asp Asp Arg Glu Leu Leu Glu Leu
            420                 425                 430
Phe Lys Asn Lys Arg Ser Gly Thr Arg Glu Leu Ser His Arg Tyr Ile
        435                 440                 445
Leu Glu Ala Leu Pro Leu Phe Leu Glu Gly Tyr Asp Glu Lys Glu Val
    450                 455                 460
Gln Arg Ile Leu Gly Phe Asp Asp Arg Glu Asp Tyr Ser Arg Tyr Pro
465                 470                 475                 480
Lys Ser Leu Arg His Leu His Leu Arg Glu Gly Asn Leu Phe Glu Lys
                485                 490                 495
Glu Glu Asn Pro Ile Asn Asn His Ala Val Lys Ser Leu Ala Ser Trp
            500                 505                 510
Ala Leu Gly Leu Ile Ala Asp Leu Ser Trp Arg Tyr Gly Pro Phe Asp
        515                 520                 525
Glu Ile Ile Leu Glu Thr Thr Arg Asp Ala Leu Pro Glu Lys Ile Arg
    530                 535                 540
Lys Glu Ile Asp Lys Ala Met Arg Glu Arg Lys Ala Leu Asp Lys
545                 550                 555                 560
Ile Ile Gly Lys Tyr Lys Lys Glu Phe Pro Ser Ile Asp Lys Arg Leu
                565                 570                 575
Ala Arg Lys Ile Gln Leu Trp Glu Arg Gln Lys Gly Leu Asp Leu Tyr

```
                    580                585                590
    Ser Gly Lys Val Ile Asn Leu Ser Gln Leu Leu Asp Gly Ser Ala Asp
                595                600                605

Ile Glu His Ile Val Pro Gln Ser Leu Gly Gly Leu Ser Thr Asp Tyr
                610                615                620

Asn Thr Ile Val Thr Leu Lys Ser Val Asn Ala Ala Lys Gly Asn Arg
    625                630                635                640

Leu Pro Gly Asp Trp Leu Ala Gly Asn Pro Asp Tyr Arg Glu Arg Ile
                    645                650                655

Gly Met Leu Ser Glu Lys Gly Leu Ile Asp Trp Lys Arg Lys Asn
                660                665                670

Leu Leu Ala Gln Ser Leu Asp Glu Ile Tyr Thr Glu Asn Thr His Ser
                675                680                685

Lys Gly Ile Arg Ala Thr Ser Tyr Leu Glu Ala Leu Val Ala Gln Val
                690                695                700

Leu Lys Arg Tyr Tyr Pro Phe Pro Asp Pro Glu Leu Arg Lys Asn Gly
    705                710                715                720

Ile Gly Val Arg Met Ile Pro Gly Lys Val Thr Ser Lys Thr Arg Ser
                    725                730                735

Leu Leu Gly Ile Lys Ser Lys Ser Arg Glu Thr Asn Phe His His Ala
                740                745                750

Glu Asp Ala Leu Ile Leu Ser Thr Leu Thr Arg Gly Trp Gln Asn Arg
                755                760                765

Leu His Arg Met Leu Arg Asp Asn Tyr Gly Lys Ser Glu Ala Glu Leu
                770                775                780

Lys Glu Leu Trp Lys Lys Tyr Met Pro His Ile Glu Gly Leu Thr Leu
    785                790                795                800

Ala Asp Tyr Ile Asp Glu Ala Phe Arg Arg Phe Met Ser Lys Gly Glu
                    805                810                815

Glu Ser Leu Phe Tyr Arg Asp Met Phe Asp Thr Ile Arg Ser Ile Ser
                820                825                830

Tyr Trp Val Asp Lys Lys Pro Leu Ser Ala Ser Ser His Lys Glu Thr
                835                840                845

Val Tyr Ser Ser Arg His Glu Val Pro Thr Leu Arg Lys Asn Ile Leu
                850                855                860

Glu Ala Phe Asp Ser Leu Asn Val Ile Lys Asp Arg His Lys Leu Thr
    865                870                875                880

Thr Glu Glu Phe Met Lys Arg Tyr Asp Lys Glu Ile Arg Gln Lys Leu
                    885                890                895

Trp Leu His Arg Ile Gly Asn Thr Asn Asp Glu Ser Tyr Arg Ala Val
                900                905                910

Glu Glu Arg Ala Thr Gln Ile Ala Gln Ile Leu Thr Arg Tyr Gln Leu
                915                920                925

Met Asp Ala Gln Asn Asp Lys Glu Ile Asp Glu Lys Phe Gln Gln Ala
                930                935                940

Leu Lys Glu Leu Ile Thr Ser Pro Ile Glu Val Thr Gly Lys Leu Leu
    945                950                955                960

Arg Lys Met Arg Phe Val Tyr Asp Lys Leu Asn Ala Met Gln Ile Asp
                    965                970                975

Arg Gly Leu Val Glu Thr Asp Lys Asn Met Leu Gly Ile His Ile Ser
                980                985                990

Lys Gly Pro Asn Glu Lys Leu Ile  Phe Arg Arg Met Asp  Val Asn Asn
                995                1000                1005
```

| | | | | | | | | | | | |
|---|---|---|---|---|---|---|---|---|---|---|---|
| Ala | His | Glu | Leu | Gln | Lys | Glu | Arg | Ser | Gly | Ile | Leu | Cys | Tyr | Leu |
| | 1010 | | | | 1015 | | | | 1020 | | |

Asn Glu Met Leu Phe Ile Phe Asn Lys Lys Gly Leu Ile His Tyr
     1025                    1030                    1035

Gly Cys Leu Arg Ser Tyr Leu Glu Lys Gly Gln Gly Ser Lys Tyr
     1040                    1045                    1050

Ile Ala Leu Phe Asn Pro Arg Phe Pro Ala Asn Pro Lys Ala Gln
     1055                    1060                    1065

Pro Ser Lys Phe Thr Ser Asp Ser Lys Ile Lys Gln Val Gly Ile
     1070                    1075                    1080

Gly Ser Ala Thr Gly Ile Ile Lys Ala His Leu Asp Leu Asp Gly
     1085                    1090                    1095

His Val Arg Ser Tyr Glu Val Phe Gly Thr Leu Pro Glu Gly Ser
     1100                    1105                    1110

Ile Glu Trp Phe Lys Glu Glu Ser Gly Tyr Gly Arg Val Glu Asp
     1115                    1120                    1125

Asp Pro His His Pro Lys Lys Lys Arg Lys Val
     1130                    1135

```
<210> SEQ ID NO 27
<211> LENGTH: 3207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggccgaga agcagcacag atggggactc gacatcggca ccaattctat cggctgggcc      60
gtgatcgccc tgatcgaagg cagacctgct ggactggtgg ctaccggcag cagaatcttt     120
agcgacggca gaaaccccaa ggacggcagc tctctggccg tcgagaagag ggacctcgg     180 cagatgcggc ggagaagaga cagatatctc cggcggaggg acagattcat gcaggccctg     240
atcaacgtgg gcctgatgcc tgggatgcc gccgctagaa aagccctggt caccgagaat     300
ccctacgtgc tgagacagag aggcctggac caagctctga ccctgcctga atttggcaga     360
gccctgttcc acctgaacca gcggagaggc ttccagagca cagaaagac cgatcgggcc     420 accgccaaag aaagcggcaa agtgaagaac gccattgccg ccttcagagc cggcatgggc     480
aatgccagaa cagtgggaga agccctggcc agacgactgg aagatggcag accagtgcgg     540
gccagaatgg tcgacagggg caaagatgag cactacgagc tgtatatcgc cagagagtgg     600
atcgcccaag agttcgatgc cctgtgggcc agccagcaga gatttcatgc tgaggtgctg     660
gccgacgccg ccagagatag actgagagcc atcctgctgt ccagcggaa gctgctgcct     720 gtgcctgtgg gcaagtgctt cctggaacct aaccagccta gagtggccgc tgctctgcct     780
agcgctcaga gattcagact gatgcaagag ctgaaccacc tgagagtgat gaccctggcc     840
gacaagagag agaggcccct gagcttccaa gagagaaacg atctgctggc ccagctggtg     900
gccagaccta gtgcggcttc gacatgctg cggaagatcg tgttcggcgc caacaaagag     960
gcctacagat tcaccatcga gagcgagcgg cggaagaac tgaagggctg tgatacagcc    1020
gccaagctgg ccaaagtgaa tgccctggga actagatggc aggctctgtc cctggacgag    1080
caggatagac tcgtgtgcct gctgctggac ggcgagaatg atgctgtgct ggctgatgcc    1140
ctgcgggaac actatggact gacagacgcc cagatcgaca cactgctggg cctgtctttt    1200
```

```
gaggacggcc acatgagact ggggagaagc gctctgctga gagtcctgga tgccctggaa    1260
tccggaagag atgagcaggg actgcccctg tcctacgata aggctgttgt ggctgccggc    1320
tatccagctc acacagccga tctggaaaac ggcgagagag atgcactgcc ctactacggc    1380
gagctgctgt ggcggtatac acaggatgcc cctaccgcca agaacgacgc cgagagaaag    1440
ttcggcaaga tcgccaatcc taccgtgcac atcggcctga atcagctgag aaagcttgtc    1500
aatgccctga tccagagata cggcaagccc gctcagatcg tggtggaact ggccagaaat    1560
ctgaaggctg gcctggaaga gaaagagcgg atcaagaaac agcagaccgc caacctggaa    1620
cggaacgaga gaatccggca gaagctgcag gacgctggcg tgcccgacaa cagagaaaac    1680
cggctgcgga tgcggctgtt cgaggaactc ggacaaggca atggactggg cacccttgc    1740 atctactccg gcagacagat cagcctgcag agactgttca gcaacgacgt gcaggtcgac    1800
cacatcctgc ctttcagcaa gacctggat gacagcttcg ccaacaaggt gctcgcccag    1860
cacgacgcca acagatacaa gggcaacaga ggcccttcg aggccttcgg agccaacaga    1920
gatggctacg cctgggacga cattagagcc agagcagccg tgctgccccg gaacaagaga    1980
aacagatttg ccgagacagc catgcaggac tggctgcaca acgagactga ctttctggct    2040
cggcagctga ccgataccgc ctaccttagc agagtggcca ggcagtacct gaccgccatc    2100
tgcagcaagg acgacgtgta cgttagcccc ggcagactga ctgccatgct gagagctaag    2160
tggggcctga acagagtgct ggatggcgtg atggaagaac agggcagacc cgccgtgaag    2220
aaccgggatg atcacagaca ccacgccatc gacgccgtgg ttattggcgc cacagataga    2280
gccatgctgc aacaggtggc cacactggcc gctagagcta gagaacagga cgccgaaagg    2340
ctgatcggcg acatgcctac gccttggcct aatttccttg aggacgtgcg ggctgccgtg    2400
gccagatgtg tggttctca caagcccgac cacggaccag aaggcggcct gcataacgat    2460
acagcctacg gcattgtggc cggaccattc gaggatggca gatacagagt gcggcaccgg    2520
gtgtccctgt tcgatctgaa acctggcgac ctgagcaacg tccgctgtga tgctcctctg    2580
caagccgagc tggaacccat cttcgagcag gacgatgcca gggccagaga gtggctctt    2640 acagccctgc tgagcggta cagacagcgg aaagtgtggc tggaagaact gatgagcgtg    2700
ctgcctatca gacccagagg cgaggacgga agaccctgc cagatagcgc tccttacaag    2760
gcctacaagg gcgactccaa ctactgctat gagctgttca tcaatgagcg cggcagatgg    2820
gatggcgagc tgatctctac cttccgggcc aatcaggccg cttaccggcg gttcagaaat    2880
gacccagcca ggttcagaag atacaccgct ggcggtagac ccctgctgat gagactgtgt    2940
atcaacgact atatcgccgt gggcacagcc gccgagagga ccatctttag agtggtcaag    3000
atgagcgaga acaagatcac tctggccgag cacttcgaag gcggaaccct gaaacagagg    3060
gatgccgaca aggacgatcc cttcaagtat ctgacaaaga gccctggcgc tctgcgcgat    3120
ctgggagcta aagaatcttt cgtggacctg atcggccgcg tgctggaccc aggcattaag    3180
ggcgatccca agaagaagag gaaggtg                                        3207
```

<210> SEQ ID NO 28
<211> LENGTH: 1069
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

-continued

```
Met Ala Glu Lys Gln His Arg Trp Gly Leu Asp Ile Gly Thr Asn Ser
1               5                   10                  15

Ile Gly Trp Ala Val Ile Ala Leu Ile Glu Gly Arg Pro Ala Gly Leu
            20                  25                  30

Val Ala Thr Gly Ser Arg Ile Phe Ser Asp Gly Arg Asn Pro Lys Asp
            35                  40                  45

Gly Ser Ser Leu Ala Val Glu Arg Arg Gly Pro Arg Gln Met Arg Arg
        50                  55                  60

Arg Arg Asp Arg Tyr Leu Arg Arg Asp Arg Phe Met Gln Ala Leu
65                  70                  75                  80

Ile Asn Val Gly Leu Met Pro Gly Asp Ala Ala Arg Lys Ala Leu
                85                  90                  95

Val Thr Glu Asn Pro Tyr Val Leu Arg Gln Arg Gly Leu Asp Gln Ala
                100                 105                 110

Leu Thr Leu Pro Glu Phe Gly Arg Ala Leu Phe His Leu Asn Gln Arg
            115                 120                 125

Arg Gly Phe Gln Ser Asn Arg Lys Thr Asp Arg Ala Thr Ala Lys Glu
    130                 135                 140

Ser Gly Lys Val Lys Asn Ala Ile Ala Ala Phe Arg Ala Gly Met Gly
145                 150                 155                 160

Asn Ala Arg Thr Val Gly Glu Ala Leu Ala Arg Arg Leu Glu Asp Gly
                165                 170                 175

Arg Pro Val Arg Ala Arg Met Val Gly Gln Gly Lys Asp Glu His Tyr
            180                 185                 190

Glu Leu Tyr Ile Ala Arg Glu Trp Ile Ala Gln Glu Phe Asp Ala Leu
        195                 200                 205

Trp Ala Ser Gln Gln Arg Phe His Ala Glu Val Leu Ala Asp Ala Ala
    210                 215                 220

Arg Asp Arg Leu Arg Ala Ile Leu Leu Phe Gln Arg Lys Leu Leu Pro
225                 230                 235                 240

Val Pro Val Gly Lys Cys Phe Leu Glu Pro Asn Gln Pro Arg Val Ala
                245                 250                 255

Ala Ala Leu Pro Ser Ala Gln Arg Phe Arg Leu Met Gln Glu Leu Asn
            260                 265                 270

His Leu Arg Val Met Thr Leu Ala Asp Lys Arg Glu Arg Pro Leu Ser
        275                 280                 285

Phe Gln Glu Arg Asn Asp Leu Leu Ala Gln Leu Val Ala Arg Pro Lys
    290                 295                 300

Cys Gly Phe Asp Met Leu Arg Lys Ile Val Phe Gly Ala Asn Lys Glu
305                 310                 315                 320

Ala Tyr Arg Phe Thr Ile Glu Ser Glu Arg Arg Lys Glu Leu Lys Gly
                325                 330                 335

Cys Asp Thr Ala Ala Lys Leu Ala Lys Val Asn Ala Leu Gly Thr Arg
            340                 345                 350

Trp Gln Ala Leu Ser Leu Asp Glu Gln Asp Arg Leu Val Cys Leu Leu
        355                 360                 365

Leu Asp Gly Glu Asn Asp Ala Val Leu Ala Asp Ala Leu Arg Glu His
    370                 375                 380

Tyr Gly Leu Thr Asp Ala Gln Ile Asp Thr Leu Leu Gly Leu Ser Phe
385                 390                 395                 400

Glu Asp Gly His Met Arg Leu Gly Arg Ser Ala Leu Leu Arg Val Leu
                405                 410                 415

Asp Ala Leu Glu Ser Gly Arg Asp Glu Gln Gly Leu Pro Leu Ser Tyr
```

```
                420             425             430
Asp Lys Ala Val Val Ala Gly Tyr Pro Ala His Thr Ala Asp Leu
            435             440             445

Glu Asn Gly Glu Arg Asp Ala Leu Pro Tyr Tyr Gly Glu Leu Leu Trp
        450             455             460

Arg Tyr Thr Gln Asp Ala Pro Thr Ala Lys Asn Asp Ala Glu Arg Lys
465             470             475             480

Phe Gly Lys Ile Ala Asn Pro Thr Val His Ile Gly Leu Asn Gln Leu
            485             490             495

Arg Lys Leu Val Asn Ala Leu Ile Gln Arg Tyr Gly Lys Pro Ala Gln
        500             505             510

Ile Val Val Glu Leu Ala Arg Asn Leu Lys Ala Gly Leu Glu Glu Lys
            515             520             525

Glu Arg Ile Lys Lys Gln Gln Thr Ala Asn Leu Glu Arg Asn Glu Arg
        530             535             540

Ile Arg Gln Lys Leu Gln Asp Ala Gly Val Pro Asp Asn Arg Glu Asn
545             550             555             560

Arg Leu Arg Met Arg Leu Phe Glu Glu Leu Gly Gln Gly Asn Gly Leu
            565             570             575

Gly Thr Pro Cys Ile Tyr Ser Gly Arg Gln Ile Ser Leu Gln Arg Leu
        580             585             590

Phe Ser Asn Asp Val Gln Val Asp His Ile Leu Pro Phe Ser Lys Thr
            595             600             605

Leu Asp Asp Ser Phe Ala Asn Lys Val Leu Ala Gln His Asp Ala Asn
        610             615             620

Arg Tyr Lys Gly Asn Arg Gly Pro Phe Glu Ala Phe Gly Ala Asn Arg
625             630             635             640

Asp Gly Tyr Ala Trp Asp Asp Ile Arg Ala Arg Ala Val Leu Pro
            645             650             655

Arg Asn Lys Arg Asn Arg Phe Ala Glu Thr Ala Met Gln Asp Trp Leu
        660             665             670

His Asn Glu Thr Asp Phe Leu Ala Arg Gln Leu Thr Asp Thr Ala Tyr
            675             680             685

Leu Ser Arg Val Ala Arg Gln Tyr Leu Thr Ala Ile Cys Ser Lys Asp
        690             695             700

Asp Val Tyr Val Ser Pro Gly Arg Leu Thr Ala Met Leu Arg Ala Lys
705             710             715             720

Trp Gly Leu Asn Arg Val Leu Asp Gly Val Met Glu Glu Gln Gly Arg
            725             730             735

Pro Ala Val Lys Asn Arg Asp Asp His Arg His His Ala Ile Asp Ala
        740             745             750

Val Val Ile Gly Ala Thr Asp Arg Ala Met Leu Gln Val Ala Thr
            755             760             765

Leu Ala Ala Arg Ala Arg Glu Gln Asp Ala Glu Arg Leu Ile Gly Asp
        770             775             780

Met Pro Thr Pro Trp Pro Asn Phe Leu Glu Asp Val Arg Ala Ala Val
785             790             795             800

Ala Arg Cys Val Val Ser His Lys Pro Asp His Gly Pro Glu Gly Gly
            805             810             815

Leu His Asn Asp Thr Ala Tyr Gly Ile Val Ala Gly Pro Phe Glu Asp
            820             825             830

Gly Arg Tyr Arg Val Arg His Arg Val Ser Leu Phe Asp Leu Lys Pro
            835             840             845
```

Gly Asp Leu Ser Asn Val Arg Cys Asp Ala Pro Leu Gln Ala Glu Leu
        850                 855                 860

Glu Pro Ile Phe Glu Gln Asp Asp Ala Arg Ala Arg Glu Val Ala Leu
865                 870                 875                 880

Thr Ala Leu Ala Glu Arg Tyr Arg Gln Arg Lys Val Trp Leu Glu Glu
                885                 890                 895

Leu Met Ser Val Leu Pro Ile Arg Pro Arg Gly Glu Asp Gly Lys Thr
            900                 905                 910

Leu Pro Asp Ser Ala Pro Tyr Lys Ala Tyr Lys Gly Asp Ser Asn Tyr
        915                 920                 925

Cys Tyr Glu Leu Phe Ile Asn Glu Arg Gly Arg Trp Asp Gly Glu Leu
    930                 935                 940

Ile Ser Thr Phe Arg Ala Asn Gln Ala Ala Tyr Arg Arg Phe Arg Asn
945                 950                 955                 960

Asp Pro Ala Arg Phe Arg Arg Tyr Thr Ala Gly Gly Arg Pro Leu Leu
                965                 970                 975

Met Arg Leu Cys Ile Asn Asp Tyr Ile Ala Val Gly Thr Ala Ala Glu
            980                 985                 990

Arg Thr Ile Phe Arg Val Val Lys  Met Ser Glu Asn Lys  Ile Thr Leu
        995                 1000                1005

Ala Glu His Phe Glu Gly Gly  Thr Leu Lys Gln Arg  Asp Ala Asp
    1010                1015                1020

Lys Asp Asp Pro Phe Lys Tyr  Leu Thr Lys Ser Pro  Gly Ala Leu
    1025                1030                1035

Arg Asp Leu Gly Ala Arg Arg  Ile Phe Val Asp Leu  Ile Gly Arg
    1040                1045                1050

Val Leu Asp Pro Gly Ile Lys  Gly Asp Pro Lys Lys  Lys Arg Lys
    1055                1060                1065

Val

<210> SEQ ID NO 29
<211> LENGTH: 3273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atgaagtacc acgtgggcat cgacgtgggc acctttctg ttggactggc cgccatcgaa      60
gtggacgatg ccggaatgcc tatcaagacc ctgagcctgg tgtcccacat ccacgattct    120
ggactggacc ccgacgagat caagagcgcc gttacaagac tggccagcag cggaatcgcc    180
agaagaacca gacggctgta ccggcggaag agaagaaggc tgcagcagct ggacaagttc    240
atccagagac aaggctggcc cgtgatcgag ctggaagatt acagcgaccc tctgtacccc    300
tggaaagtgc gggctgaact ggctgccagc tatatcgccg atgagaaaga gcggggcgag    360
aagctgtctg tggccctgag acacattgcc agacacagag gatggcggaa ccctacgcc     420 aaggtgtcct ctctgtatct gcctgacggc cctagcgacg ccttcaaggc catcagagag    480
gaaatcaaga gagccagcgg ccagcctgtg cctgaaacag ctacagtggg ccagatggtc    540
accctgtgtg aactgggcac cctgaagttg agaggcgaag cggagtgct gtctgccaga    600 ctccagcaga gcgattacgc cagagagatc caagagattt gccggatgca agatcggc      660 caagagctgt acagaaagat catcgatgtg gtgttcgccg ccgagtctcc taagggatct    720

```
gcctctagca gagtgggcaa agaccctctg cagcccggca agaatagagc cctgaaagcc    780
tccgatgcct tccagagata ccggatcgcc gctctgatcg gcaacctgag agttagagtg    840
gacggcgaga agaggattct gagcgtggaa gagaaaaacc tggtgttcga ccacctggtc    900
aatctgaccc ctaagaaaga acccgagtgg gtcacaatcg ccgagatcct gggaatcgac    960
agaggccagc tgatcggaac cgccaccatg acagatgatg cgaaagagc cggcgctcgg   1020
cctcctacac atgacaccaa tcggagcatc gtgaacagca gaatcgcccc tctggtggac   1080
tggtggaaaa ccgcctctgc tctggaacag cacgctatgg tcaaggccct gtccaatgcc   1140
gaggtggacg acttcgattc tcctgagggc gccaaagtgc aggccttctt tgccgacctg   1200
gacgacgatg tgcacgccaa gctggatagc ctgcatctgc tgttggcag agccgcctac   1260
agcgaggata cacttgtgcg gctgaccaga cggatgctga gtgatggcgt ggacctgtac   1320
accgccagac tgcaagagtt tggcatcgag cctagctgga cccctccaac acctagaatc   1380
ggagagcccg tgggaaaccc cgctgtggac agagtgctga aaaccgtgtc cagatggctg   1440
gaaagcgcca ccaaaacatg gggcgctccc gagagagtga tcatcgaaca cgtgcgcgag   1500
ggcttcgtga ccgagaaaag ggccagagaa atggatggcg acatgcggag aagggccgcc   1560
agaaatgcca agctgttcca agaaatgcaa gaaaagctga acgtgcaggg caagccctcc   1620
agagccgacc tttggagata ccagagcgtg cagagacaga actgccagtg cgcctactgt   1680
ggcagcccta tcaccttcag caacagcgag atggaccaca tcgtgcctag agccggccag   1740
ggatccacca acaccagaga aaatctggtg gccgtgtgcc acagatgcaa ccagagcaag   1800
ggcaacaccc cattcgccat ctgggccaag aacacctcta tcgagggcgt gtccgtgaaa   1860
gaagccgtgg aaagaaccag gcactgggtc accgataccg gcatgagaag caccgacttc   1920
aagaaattca ccaaggccgt ggtggaacgg ttccagaggg ccacaatgga cgaggaaatt   1980
gacgcccgca gcatggaaag cgtggcctgg atggccaatg agctgagaag tagagtggcc   2040
cagcacttcg ccagccacgg cacaacagtc agagtgtaca gaggcagcct gaccgccgaa   2100
gctcgtagag cctctggaat cagcggcaag ctgaagttct tgacggcgt gggcaagagc   2160
agactggaca gaaggcacca cgccattgat gccgccgtga tcgccttcac cagcgactat   2220
gtggccgaaa cactgccgt gcggagcaac ctcaaacaga gccaggctca cagacaagag   2280
gctcctcagt ggcgcgagtt cacaggcaaa gatgccgaac acagagccgc ttggagagtg   2340
tggtgccaga agatggaaaa actgagcgcc ctgctgaccg aggacctgag agatgataga   2400
gtggtggtca tgagcaacgt gcgcctgaga ctcggaaatg gcagcgccca aaagagaca   2460
atcggaaagc tgagcaaagt gaagctgtcc agccagctga gcgtgtccga catcgataag   2520
gccagctctg aggccctttg gtgcgccctg acaagagaac ctggcttcga ccccaaagag   2580
ggactgcctg ccaatcctga gcggcacatc agagtgaatg gcacccatgt gtacgccggc   2640
gacaacatcg gcctgtttcc agtgtctgcc ggatctatcg ctctgagagg cggatatgcc   2700
gagctgggca gctctttcca tcacgccagg gtgtacaaga tcacaagcgg caagaaaccc   2760
gcctttgcca tgctgagagt gtataccatc gacctgctgc cttaccggaa ccaggacctg   2820
ttcagcgtgg aactgaagcc ccagaccatg agcatgacag aggccgagaa gaagctgagg   2880
gacgccctgg ctacaggcaa cgccgaatat cttggatggc tggtggtgga tgacgagctg   2940
gtggtcgata ccagcaagat cgccaccgac caagtgaagg ctgtgaaagc cgaactggga   3000
accatcagac gttggcgcgt ggacggcttt ttcagcccct ctaagctgag actgcggccc   3060
```

```
ctgcagatga gcaaagaggg catcaagaaa gagagcgccc ctgagctgtc caagatcatt    3120
gacagacctg gctggctgcc cgccgtgaac aagctgtttt ctgacggcaa cgtgaccgtc    3180
gtgcggagag attctctggg cagagtgcgc ctggaaagca cagcacatct gcccgtgaca    3240
tggaaggtgc agcccaagaa gaagaggaag gtg                                 3273
```

<210> SEQ ID NO 30
<211> LENGTH: 1091
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Met Lys Tyr His Val Gly Ile Asp Val Gly Thr Phe Ser Val Gly Leu
1               5                   10                  15

Ala Ala Ile Glu Val Asp Asp Ala Gly Met Pro Ile Lys Thr Leu Ser
            20                  25                  30

Leu Val Ser His Ile His Asp Ser Gly Leu Asp Pro Asp Lys Ile Lys
        35                  40                  45

Ser Ala Val Thr Arg Leu Ala Ser Ser Gly Ile Ala Arg Arg Thr Arg
    50                  55                  60

Arg Leu Tyr Arg Arg Lys Arg Arg Leu Gln Gln Leu Asp Lys Phe
65                  70                  75                  80

Ile Gln Arg Gln Gly Trp Pro Val Ile Glu Leu Glu Asp Tyr Ser Asp
                85                  90                  95

Pro Leu Tyr Pro Trp Lys Val Arg Ala Glu Leu Ala Ala Ser Tyr Ile
            100                 105                 110

Ala Asp Glu Lys Glu Arg Gly Glu Lys Leu Ser Val Ala Leu Arg His
        115                 120                 125

Ile Ala Arg His Arg Gly Trp Arg Asn Pro Tyr Ala Lys Val Ser Ser
    130                 135                 140

Leu Tyr Leu Pro Asp Glu Pro Ser Asp Ala Phe Lys Ala Ile Arg Glu
145                 150                 155                 160

Glu Ile Lys Arg Ala Ser Gly Gln Pro Val Pro Glu Thr Ala Thr Val
                165                 170                 175

Gly Gln Met Val Thr Leu Cys Glu Leu Gly Thr Leu Lys Leu Arg Gly
            180                 185                 190

Glu Gly Gly Val Leu Ser Ala Arg Leu Gln Gln Ser Asp His Ala Arg
        195                 200                 205

Glu Ile Gln Glu Ile Cys Arg Met Gln Glu Ile Gly Gln Glu Leu Tyr
    210                 215                 220

Arg Lys Ile Ile Asp Val Val Phe Ala Ala Glu Ser Pro Lys Gly Ser
225                 230                 235                 240

Ala Ser Ser Arg Val Gly Lys Asp Pro Leu Gln Pro Gly Lys Asn Arg
                245                 250                 255

Ala Leu Lys Ala Ser Asp Ala Phe Gln Arg Tyr Arg Ile Ala Ala Leu
            260                 265                 270

Ile Gly Asn Leu Arg Val Arg Val Asp Gly Glu Lys Arg Ile Leu Ser
        275                 280                 285

Val Glu Glu Lys Asn Leu Val Phe Asp His Leu Val Asn Leu Ala Pro
    290                 295                 300

Lys Lys Glu Pro Glu Trp Val Thr Ile Ala Glu Ile Leu Gly Ile Asp
305                 310                 315                 320
```

```
Arg Gly Gln Leu Ile Gly Thr Ala Thr Met Thr Asp Asp Gly Glu Arg
                325                 330                 335

Ala Gly Ala Arg Pro Pro Thr His Asp Thr Asn Arg Ser Ile Val Asn
            340                 345                 350

Ser Arg Ile Ala Pro Leu Val Asp Trp Trp Lys Thr Ala Ser Ala Leu
        355                 360                 365

Glu Gln His Ala Met Val Lys Ala Leu Ser Asn Ala Glu Val Asp Asp
    370                 375                 380

Phe Asp Ser Pro Glu Gly Ala Lys Val Gln Ala Phe Phe Ala Asp Leu
385                 390                 395                 400

Asp Asp Asp Val His Ala Lys Leu Asp Ser Leu His Leu Pro Val Gly
                405                 410                 415

Arg Ala Ala Tyr Ser Glu Asp Thr Leu Val Arg Leu Thr Arg Arg Met
            420                 425                 430

Leu Ala Asp Gly Val Asp Leu Tyr Thr Ala Arg Leu Gln Glu Phe Gly
        435                 440                 445

Ile Glu Pro Ser Trp Thr Pro Pro Ala Pro Arg Ile Gly Glu Pro Val
    450                 455                 460

Gly Asn Pro Ala Val Asp Arg Val Leu Lys Thr Val Ser Arg Trp Leu
465                 470                 475                 480

Glu Ser Ala Thr Lys Thr Trp Gly Ala Pro Glu Arg Val Ile Ile Glu
                485                 490                 495

His Val Arg Glu Gly Phe Val Thr Glu Lys Arg Ala Arg Glu Met Asp
            500                 505                 510

Gly Asp Met Arg Arg Arg Ala Ala Arg Asn Ala Lys Leu Phe Gln Glu
        515                 520                 525

Met Gln Glu Lys Leu Asn Val Gln Gly Lys Pro Ser Arg Ala Asp Leu
    530                 535                 540

Trp Arg Tyr Gln Ser Val Gln Arg Gln Asn Cys Gln Cys Ala Tyr Cys
545                 550                 555                 560

Gly Ser Pro Ile Thr Phe Ser Asn Ser Glu Met Asp His Ile Val Pro
                565                 570                 575

Arg Ala Gly Gln Gly Ser Thr Asn Thr Arg Glu Asn Leu Val Ala Val
            580                 585                 590

Cys His Arg Cys Asn Gln Ser Lys Gly Asn Thr Pro Phe Ala Ile Trp
        595                 600                 605

Ala Lys Asn Thr Ser Ile Glu Gly Val Ser Val Lys Glu Ala Val Glu
    610                 615                 620

Arg Thr Arg His Trp Val Thr Asp Thr Gly Met Arg Ser Thr Asp Phe
625                 630                 635                 640

Lys Lys Phe Thr Lys Ala Val Val Glu Arg Phe Gln Arg Ala Thr Met
                645                 650                 655

Asp Glu Glu Ile Asp Ala Arg Ser Met Glu Ser Val Ala Trp Met Ala
            660                 665                 670

Asn Glu Leu Arg Ser Arg Val Ala Gln His Phe Ala Ser His Gly Thr
        675                 680                 685

Thr Val Arg Val Tyr Arg Gly Ser Leu Thr Ala Glu Ala Arg Arg Ala
    690                 695                 700

Ser Gly Ile Ser Gly Lys Leu Glu Phe Leu Asp Gly Val Gly Lys Ser
705                 710                 715                 720

Arg Leu Asp Arg Arg His His Ala Ile Asp Ala Ala Val Ile Ala Phe
                725                 730                 735

Thr Ser Asp Tyr Val Ala Glu Thr Leu Ala Val Arg Ser Asn Leu Lys
```

```
                    740                 745                 750
Gln Ser Gln Ala His Arg Gln Glu Ala Pro Gln Trp Arg Glu Phe Thr
        755                 760                 765
Gly Lys Asp Ala Glu His Arg Ala Ala Trp Arg Val Trp Cys Gln Lys
    770                 775                 780
Met Glu Lys Leu Ser Ala Leu Leu Thr Glu Asp Leu Arg Asp Asp Arg
785                 790                 795                 800
Val Val Val Met Ser Asn Val Arg Leu Arg Leu Gly Asn Gly Ser Ala
                805                 810                 815
His Glu Glu Thr Ile Gly Lys Leu Ser Lys Val Lys Leu Gly Ser Gln
            820                 825                 830
Leu Ser Val Ser Asp Ile Asp Lys Ala Ser Ser Glu Ala Leu Trp Cys
        835                 840                 845
Ala Leu Thr Arg Glu Pro Asp Phe Asp Pro Lys Asp Gly Leu Pro Ala
    850                 855                 860
Asn Pro Glu Arg His Ile Arg Val Asn Gly Thr His Val Tyr Ala Gly
865                 870                 875                 880
Asp Asn Ile Gly Leu Phe Pro Val Ser Ala Gly Ser Ile Ala Leu Arg
                885                 890                 895
Gly Gly Tyr Ala Glu Leu Gly Ser Ser Phe His His Ala Arg Val Tyr
            900                 905                 910
Lys Ile Thr Ser Gly Lys Lys Pro Ala Phe Ala Met Leu Arg Val Tyr
        915                 920                 925
Thr Ile Asp Leu Leu Pro Tyr Arg Asn Gln Asp Leu Phe Ser Val Glu
    930                 935                 940
Leu Lys Pro Gln Thr Met Ser Met Arg Gln Ala Glu Lys Lys Leu Arg
945                 950                 955                 960
Asp Ala Leu Ala Thr Gly Asn Ala Glu Tyr Leu Gly Trp Leu Val Val
                965                 970                 975
Asp Asp Glu Leu Val Val Asp Thr Ser Lys Ile Ala Thr Asp Gln Val
            980                 985                 990
Lys Ala Val Glu Ala Glu Leu Gly Thr Ile Arg Arg Trp Arg Val Asp
        995                 1000                1005
Gly Phe Phe Gly Asp Thr Arg Leu Arg Leu Arg Pro Leu Gln Met
    1010                1015                1020
Ser Lys Glu Gly Ile Lys Lys Glu Ser Ala Pro Glu Leu Ser Lys
    1025                1030                1035
Ile Ile Asp Arg Pro Gly Trp Leu Pro Ala Val Asn Lys Leu Phe
    1040                1045                1050
Ser Glu Gly Asn Val Thr Val Val Arg Arg Asp Ser Leu Gly Arg
    1055                1060                1065
Val Arg Leu Glu Ser Thr Ala His Leu Pro Val Thr Trp Lys Val
    1070                1075                1080
Gln Pro Lys Lys Lys Arg Lys Val
    1085                1090

<210> SEQ ID NO 31
<211> LENGTH: 160
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
```

<223> OTHER INFORMATION: a, c, u, g, unknown or other

<400> SEQUENCE: 31

| nnnnnnnnnn nnnnnnnnnn gucauaguuc cccuaagauu auugaaacaa ugaucuuagg | 60 |
| guuacuauga uaagggcuuu cuacuuuagg gguagagaug ucccgcggcg uuggggaucg | 120 |
| ccuauugccc uuaaagggca cucccccauuu uaauuuuuuu | 160 |

<210> SEQ ID NO 32
<211> LENGTH: 166
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 32

| nnnnnnnnnn nnnnnnnnnn gucucaggua gaugucagau caaucagaaa ugauugaucu | 60 |
| gacaucuacg aguugagauc aaacaaagcu ucagcuagu uucaauuucu gagcccaugu | 120 |
| ugggccauac auaugccacc cgagugcaaa ucggguggcu uuuuu | 166 |

<210> SEQ ID NO 33
<211> LENGTH: 170
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 33

| nnnnnnnnnn nnnnnnnnnn guuucaguag uuguuagaag aaugaaaauu cuuuuaacaa | 60 |
| cgaagucgcc uucgggcgag cugaaaucaa uuugauuaaa uauuagaucc ggcuacuag | 120 |
| gucuuugacc uuauccggau uaacgaagag ccuccgagga ggcuuuuuuu | 170 |

<210> SEQ ID NO 34
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 34

| nnnnnnnnnn nnnnnnnnnn guuuagugu uguacaauau uugggugaaa acccaaauau | 60 |
| uguacauccu aaaucaaggc gcuuaauugc ugccguaauu gcugaaagcg uagcuuucag | 120 |
| uuuuuuu | 127 |

<210> SEQ ID NO 35
<211> LENGTH: 152
<212> TYPE: RNA
<213> ORGANISM: Artificial Sequence
<220> FEATURE:

<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 35
nnnnnnnnnn nnnnnnnnnn guuuuagcac uguacaauac uuguguaagc aauaacgaaa      60
auuauugcuu acacaauuau ugucgugcua aaauaaggcg cguuaaugc agcugccgca      120 uccgccagag cauuuaugcu cuggcuuuuu uu                                    152

<210> SEQ ID NO 36
<211> LENGTH: 147
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 36
nnnnnnnnnn nnnnnnnnnn guuuugccuu gaauccaaag uaaggcaugg uagaaauauu      60
auuccugugg auucaagaca aaauuugaaa ugcaaaccga uccccggcu gcaagccagc      120 cacaccgguc uuucaaagca uuuuuuu                                          147

<210> SEQ ID NO 37
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 37
nnnnnnnnnn nnnnnnnnnn guuuugccuu gaauccaaaa cggauucaag acaaaauuug      60
aaaugcaaac cgauuuuccu gacugccagc cagucacacc gguaacaaaa gcauuuuuu      120

<210> SEQ ID NO 38
<211> LENGTH: 186
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 38
nnnnnnnnnn nnnnnnnnnn gcuucagaug ugucagau caaugagaaa ucauugaucu      60
gacacacagc auugaaguaa agcaagauua auucaagcu uaauuucuu cacauuuau      120 gugcagaagg gcuuaugccc acaauacaua aaagccgc auucacuugc ggacuuuuau      180
uuuuuu                                                                  186

```
<210> SEQ ID NO 39
<211> LENGTH: 138
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 39
nnnnnnnnnn nnnnnnnnnn guuucaaauu caaucuaaag cgaaagcuau acuuauuauu      60
gaauuugaaa uaaggcuguu ccuucguuag uucagucgau ugcuccuccg guauugcuua     120
ugcaugccgg aguuuuuu                                                  138

<210> SEQ ID NO 40
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 40
nnnnnnnnnn nnnnnnnnnn gcuggggagc cugucugaaa agacaggcua ccuagcaaga      60
ccccuucgug gggucgcauu cuucacccccc ucgcagcagc gagggguuc guuuuuu       118

<210> SEQ ID NO 41
<211> LENGTH: 144
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 41
nnnnnnnnnn nnnnnnnnnn gucauaguuc ccucacaagc cucgaugugg aaacacauca      60
aggcuugcga gguugcuaug auaaggcaac aggccgcaaa gcacugaccc gcauccaau     120 gaaugcgggu caucuacuuu uuuu                                           144

<210> SEQ ID NO 42
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 42
nnnnnnnnnn nnnnnnnnnn guuucacagg cuaagcggau uugcgaaagc aaauccguuc      60
gaugccuuga aaucaucaaa aagauauaau agacccgccc acuguauugu acauggcggg    120
``` acuuuuuuu                                                                 129

<210> SEQ ID NO 43
<211> LENGTH: 156
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 43
nnnnnnnnnn nnnnnnnnnn guuauaagac cccucaaaac cccacccugu acaauguug          60 uaacagggua ggguuauuug aggggucuua uaaucaagaa cuguuacaac aguccauuc         120 uagggcccau cuucggacgg gccucagccu uuuuuu                                 156

<210> SEQ ID NO 44
<211> LENGTH: 155
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 44
nnnnnnnnnn nnnnnnnnnn guuguagcca gagcgcaauu cccgaucugc ugaaaagcag        60
aucgggaauu gcgcuuugcu acuaacaagc ugaauccguu aggaguaaau gcaccaaaug       120
agagggccgg cuuaugccgg cccuuugcuu uuuuu                                  155

<210> SEQ ID NO 45
<211> LENGTH: 171
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 45
nnnnnnnnnn nnnnnnnnnn acuggggguuc aguucucaaa aacccugaua gacuucgaaa        60
agucacuaac uuaauuaaau agaacugaac cucaguaagc auuggcucgu uccaauguu        120 gauugcuccg ccggugcucc uuauuauuaa gggcgccggc uuucuuuuuu u               171

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(28)
<223> OTHER INFORMATION: a, c, t, g, unknown or other

<400> SEQUENCE: 46

```
gtacaaacgg cagaagctgg nnnnnnnn                                           28

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctgtttcctg ggttccaata acaagac                                            27

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acaagggctc aagtggagtg                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atgggagcag ctggtcagag                                                    20

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cagcccattg cttgtccct                                                     19

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctcgccattc cagccactca aac                                                23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
```
ggttaagtcg ggtttccttg cag                                              23

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttcgggtcac ctctcactcc                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggctccatcg taagcaaacc                                                  20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctcccctgct tcttgtcgta t                                                21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acaggtcgtg gacactcaca                                                  20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggatcaagtc aagggcatgt                                                  20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
atgtagctgg acaggcttgg                                                  20

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctcatacatg gctataatag aa                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gaaggtgtgg ttccagaacc gg                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tggttccaga accggaggac aa                                              22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cccaggtgaa ggtgtggttc ca                                              22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agaaccggag gacaaagtac aa                                              22

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctctggcac atcctccaaa                                                 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ctagggacag gattggtgac                                              20

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gctcgtactg gcgaatgct                                               19

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gctgaagagc tacgagaacc                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
catgggggag atgggccggc                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agagactctc tagaagggac                                              20

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtgagagtct cctccccaat g                                            21

-continued

```
<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gggaggagac tctcacctga                                                    20

<210> SEQ ID NO 72
<211> LENGTH: 100
<212> TYPE: PRT
<213> ORGANISM: Homo sapiens

<400> SEQUENCE: 72

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Pro Ala Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp
            100

<210> SEQ ID NO 73
<211> LENGTH: 84
<212> TYPE: PRT
<213> ORGANISM: Homo sapiens

<400> SEQUENCE: 73

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu

<210> SEQ ID NO 74
<211> LENGTH: 80
<212> TYPE: PRT
<213> ORGANISM: Homo sapiens

<400> SEQUENCE: 74

Ser Thr Asp His Pro Lys Tyr Ser Asp Met Ile Val Ala Ala Ile Gln
1               5                   10                  15

Ala Glu Lys Asn Arg Ala Gly Ser Ser Arg Gln Ser Ile Gln Lys Tyr
                20                  25                  30
```

Ile Lys Ser His Tyr Lys Val Gly Glu Asn Ala Asp Ser Gln Ile Lys
            35                  40                  45

Leu Ser Ile Lys Arg Leu Val Thr Thr Gly Val Leu Lys Gln Thr Lys
     50                  55                  60

Gly Val Gly Ala Ser Gly Ser Phe Arg Leu Ala Lys Ser Asp Glu Pro
 65                  70                  75                  80

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tgtacatggg ggagatgggc                                              20

<210> SEQ ID NO 76
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 76
guucuagugu uguacaauau uugggugaaa acccaaauau uguacauccu agaucaaggc   60
gcuuaauugc ugccguaauu gcugaaagcg uagcuuucag uuuuuuu                107

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atagatgcgg ccaaggtgta ca                                           22

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro Lys Lys Lys Arg Lys Val
 1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Lys Lys Lys Arg Arg Val
 1               5

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Arg Pro Ala Ala Thr Lys Lys Ala Gly Gln Ala Lys Lys Lys Lys
1               5                   10                  15

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Gly Arg Lys Lys Arg Arg Gln Arg Arg Arg
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Lys Lys Arg Arg Gln Arg Arg Arg
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Ala Ala Lys Arg Val Lys Leu Asp
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Gln Arg Arg Asn Glu Leu Lys Arg Ser Pro
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 85

Val Ser Arg Lys Arg Pro Arg Pro
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Pro Pro Lys Lys Ala Arg Glu Asp
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Gln Pro Lys Lys Lys Pro Leu
1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ala Leu Ile Lys Lys Lys Lys Lys Met Ala Pro
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Pro Lys Gln Lys Lys Arg Lys
1               5

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Lys Leu Lys Lys Lys Ile Lys Lys Leu
1               5                   10

<210> SEQ ID NO 91
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 91

Arg Glu Lys Lys Lys Phe Leu Lys Arg Arg
1               5                   10

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Arg Lys Gly Asp Glu Val Asp Gly Val Asp Glu Val Ala Lys Lys
1               5                   10                  15

Lys Ser Lys Lys
            20

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Lys Cys Leu Gln Ala Gly Met Asn Leu Glu Ala Arg Lys Thr Lys
1               5                   10                  15

Lys

<210> SEQ ID NO 94
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 95
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30
```

Asp Glu Gln Ile Leu Lys Arg Arg Asn Val
        35                  40

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Arg Lys Lys Arg Arg Gln Arg Arg Pro Pro Gln Pro Lys Lys
1               5                   10                  15

Lys Arg Lys Val
            20

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Pro Leu Ser Ser Ile Phe Ser Arg Ile Gly Asp Pro Pro Lys Lys Lys
1               5                   10                  15

Arg Lys Val

<210> SEQ ID NO 98
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 100

Lys Glu Thr Trp Trp Glu Thr Trp Thr Glu Trp Ser Gln Pro Lys
1               5                   10                  15

Lys Lys Arg Lys Val
            20

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Ala Arg Ala Ala Ala Arg Gln Ala Arg Ala
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr His Arg Leu Pro Arg Arg Arg Arg Arg Arg
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Arg Arg Ala Arg Arg Arg Arg Arg Arg
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Arg Gln Arg Arg Thr Ser Lys Leu Met Lys Arg
1               5                   10

<210> SEQ ID NO 105
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Trp Thr Leu Asn Ser Ala Gly Tyr Leu Leu Gly Lys Ile Asn Leu
1               5                   10                  15
```

```
Lys Ala Leu Ala Ala Leu Ala Lys Lys Ile Leu
            20                  25
```

<210> SEQ ID NO 106
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Arg Gln Ile Lys Ile Trp Phe Gln Asn Arg Arg Met Lys Trp Lys Lys
1               5                   10                  15
```

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Leu Glu Gly Gly Gly Ser
1               5
```

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Thr Gly Ser Gly
1
```

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Gly Gly Ser Gly Gly Gly Ser Gly
1               5
```

```
<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 111

Gly Gly Gly Gly Ser Gly Gly Gly Gly Ser Gly Gly Gly Gly Ser Gly
1               5                   10                  15

Gly Gly Gly Ser
            20

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6-8 residues

<400> SEQUENCE: 112

Gly Gly Gly Gly Gly Gly Gly Gly
1               5

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Glu Ala Ala
      Ala Lys" repeating units

<400> SEQUENCE: 113

Glu Ala Ala Ala Lys Glu Ala Ala Ala Lys Glu Ala Ala Ala Lys Glu
1               5                   10                  15

Ala Ala Ala Lys
            20

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(26)
<223> OTHER INFORMATION: This region may encompass 2-5 "Glu Ala Ala Ala
      Lys" repeating units

<400> SEQUENCE: 114

Ala Glu Ala Ala Ala Lys Glu Ala Ala Ala Lys Glu Ala Ala Ala Lys
1               5                   10                  15
```

```
Glu Ala Ala Ala Lys Glu Ala Ala Ala Lys Ala
            20                  25
```

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Pro Ala Pro Ala Pro
1               5
```

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 6-8 "Ala Pro"
      repeating units

<400> SEQUENCE: 116

```
Ala Pro Ala Pro Ala Pro Ala Pro Ala Pro Ala Pro Ala Pro Ala Pro
1               5                  10                  15
```

<210> SEQ ID NO 117
<211> LENGTH: 1629
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Met Pro Lys Arg Lys Val Ser Ser Ala Glu Gly Ala Ala Lys Glu Glu
1               5                  10                  15

Pro Lys Arg Arg Ser Ala Arg Leu Ser Ala Lys Pro Pro Ala Lys Val
                20                  25                  30

Glu Ala Lys Pro Lys Lys Ala Ala Ala Lys Asp Lys Ser Ser Asp Lys
                35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Gly Lys Thr His Ile Ile Gly
                100                 105                 110

Val Gly Leu Asp Leu Gly Gly Thr Tyr Thr Gly Thr Phe Ile Thr Ser
            115                 120                 125

His Pro Ser Asp Glu Ala Glu His Arg Asp His Ser Ser Ala Phe Thr
        130                 135                 140

Val Val Asn Ser Glu Lys Leu Ser Phe Ser Lys Ser Arg Thr Ala
145                 150                 155                 160

Val Arg His Arg Val Arg Ser Tyr Lys Gly Phe Asp Leu Arg Arg Arg
```

-continued

```
            165                 170                 175
Leu Leu Leu Leu Val Ala Glu Tyr Gln Leu Leu Gln Lys Lys Gln Thr
        180                 185                 190

Leu Ala Pro Glu Glu Arg Glu Asn Leu Arg Ile Ala Leu Ser Gly Tyr
        195                 200                 205

Leu Lys Arg Arg Gly Tyr Ala Arg Thr Glu Ala Glu Thr Asp Thr Ser
        210                 215                 220

Val Leu Glu Ser Leu Asp Pro Ser Val Phe Ser Ala Pro Ser Phe
225                 230                 235                 240

Thr Asn Phe Phe Asn Asp Ser Glu Pro Leu Asn Ile Gln Trp Glu Ala
                245                 250                 255

Ile Ala Asn Ser Pro Glu Thr Thr Lys Ala Leu Asn Lys Glu Leu Ser
                260                 265                 270

Gly Gln Lys Glu Ala Asp Phe Lys Lys Tyr Ile Lys Thr Ser Phe Pro
                275                 280                 285

Glu Tyr Ser Ala Lys Glu Ile Leu Ala Asn Tyr Val Glu Gly Arg Arg
                290                 295                 300

Ala Ile Leu Asp Ala Ser Lys Tyr Ile Ala Asn Leu Gln Ser Leu Gly
305                 310                 315                 320

His Lys His Arg Ser Lys Tyr Leu Ser Asp Ile Leu Gln Asp Met Lys
                325                 330                 335

Arg Asp Ser Arg Ile Thr Arg Leu Ser Glu Ala Phe Gly Ser Thr Asp
                340                 345                 350

Asn Leu Trp Arg Ile Ile Gly Asn Ile Ser Asn Leu Gln Glu Arg Ala
                355                 360                 365

Val Arg Trp Tyr Phe Asn Asp Ala Lys Phe Glu Gln Gly Gln Glu Gln
                370                 375                 380

Leu Asp Ala Val Lys Leu Lys Asn Val Leu Val Arg Ala Leu Lys Tyr
385                 390                 395                 400

Leu Arg Ser Asp Asp Lys Glu Trp Ser Ala Ser Gln Lys Gln Ile Ile
                405                 410                 415

Gln Ser Leu Glu Gln Ser Gly Asp Val Leu Asp Val Leu Ala Gly Leu
                420                 425                 430

Asp Pro Asp Arg Thr Ile Pro Pro Tyr Glu Asp Gln Asn Asn Arg Arg
                435                 440                 445

Pro Pro Glu Asp Gln Thr Leu Tyr Leu Asn Pro Lys Ala Leu Ser Ser
        450                 455                 460

Glu Tyr Gly Glu Lys Trp Lys Ser Trp Ala Asn Lys Phe Ala Gly Ala
465                 470                 475                 480

Tyr Pro Leu Leu Thr Glu Asp Leu Thr Glu Ile Leu Lys Asn Thr Asp
                485                 490                 495

Arg Lys Ser Arg Ile Lys Ile Arg Ser Asp Val Leu Pro Asp Ser Asp
                500                 505                 510

Tyr Arg Leu Ala Tyr Ile Leu Gln Arg Ala Phe Asp Arg Ser Ile Ala
                515                 520                 525

Leu Asp Glu Cys Ser Ile Arg Arg Thr Ala Glu Asp Phe Glu Asn Gly
                530                 535                 540

Val Val Ile Lys Asn Glu Lys Leu Glu Asp Val Leu Ser Gly His Gln
545                 550                 555                 560

Leu Glu Glu Phe Leu Glu Phe Ala Asn Arg Tyr Tyr Gln Glu Thr Ala
                565                 570                 575

Lys Ala Lys Asn Gly Leu Trp Phe Pro Glu Asn Ala Leu Leu Glu Arg
                580                 585                 590
```

```
Ala Asp Leu His Pro Pro Met Lys Asn Lys Ile Leu Asn Val Ile Val
        595                 600                 605

Gly Gln Ala Leu Gly Val Ser Pro Ala Glu Gly Thr Asp Phe Ile Glu
610                 615                 620

Glu Ile Trp Asn Ser Lys Val Lys Gly Arg Ser Thr Val Arg Ser Ile
625                 630                 635                 640

Cys Asn Ala Ile Glu Asn Glu Arg Lys Thr Tyr Gly Pro Tyr Phe Ser
                645                 650                 655

Glu Asp Tyr Lys Phe Val Lys Thr Ala Leu Lys Glu Gly Lys Thr Glu
                660                 665                 670

Lys Glu Leu Ser Lys Lys Phe Ala Ala Val Ile Lys Val Leu Lys Met
            675                 680                 685

Val Ser Glu Val Val Pro Phe Ile Gly Lys Glu Leu Arg Leu Ser Asp
            690                 695                 700

Glu Ala Gln Ser Lys Phe Asp Asn Leu Tyr Ser Leu Ala Gln Leu Tyr
705                 710                 715                 720

Asn Leu Ile Glu Thr Glu Arg Asn Gly Phe Ser Lys Val Ser Leu Ala
                725                 730                 735

Ala His Leu Glu Asn Ala Trp Arg Met Thr Met Thr Asp Gly Ser Ala
                740                 745                 750

Gln Cys Cys Arg Leu Pro Ala Asp Cys Val Arg Pro Phe Asp Gly Phe
            755                 760                 765

Ile Arg Lys Ala Ile Asp Arg Asn Ser Trp Glu Val Ala Lys Arg Ile
            770                 775                 780

Ala Glu Glu Val Lys Lys Ser Val Asp Phe Thr Asn Gly Thr Val Lys
785                 790                 795                 800

Ile Pro Val Ala Ile Glu Ala Asn Ser Phe Asn Phe Thr Ala Ser Leu
                805                 810                 815

Thr Asp Leu Lys Tyr Ile Gln Leu Lys Glu Gln Lys Leu Lys Lys Lys
                820                 825                 830

Leu Glu Asp Ile Gln Arg Asn Glu Glu Asn Gln Glu Lys Arg Trp Leu
            835                 840                 845

Ser Lys Glu Glu Arg Ile Arg Ala Asp Ser His Gly Ile Cys Ala Tyr
            850                 855                 860

Thr Gly Arg Pro Leu Asp Asp Val Gly Glu Ile Asp His Ile Ile Pro
865                 870                 875                 880

Arg Ser Leu Thr Leu Lys Lys Ser Glu Ser Ile Tyr Asn Ser Glu Val
                885                 890                 895

Asn Leu Ile Phe Val Ser Ala Gln Gly Asn Gln Glu Lys Lys Asn Asn
                900                 905                 910

Ile Tyr Leu Leu Ser Asn Leu Ala Lys Asn Tyr Leu Ala Ala Val Phe
            915                 920                 925

Gly Thr Ser Asp Leu Ser Gln Ile Thr Asn Glu Ile Glu Ser Thr Val
            930                 935                 940

Leu Gln Leu Lys Ala Ala Gly Arg Leu Gly Tyr Phe Asp Leu Leu Ser
945                 950                 955                 960

Glu Lys Glu Arg Ala Cys Ala Arg His Ala Leu Phe Leu Asn Ser Asp
                965                 970                 975

Ser Glu Ala Arg Arg Ala Val Ile Asp Val Leu Gly Ser Arg Arg Lys
                980                 985                 990

Ala Ser Val Asn Gly Thr Gln Ala  Trp Phe Val Arg Ser  Ile Phe Ser
            995                 1000                1005
```

```
Lys Val Arg Gln Ala Leu Ala Ala Trp Thr Gln Glu Thr Gly Asn
1010                1015                1020

Glu Leu Ile Phe Asp Ala Ile Ser Val Pro Ala Ala Asp Ser Ser
1025                1030                1035

Glu Met Arg Lys Arg Phe Ala Glu Tyr Arg Pro Glu Phe Arg Lys
1040                1045                1050

Pro Lys Val Gln Pro Val Ala Ser His Ser Ile Asp Ala Met Cys
1055                1060                1065

Ile Tyr Leu Ala Ala Cys Ser Asp Pro Phe Lys Thr Lys Arg Met
1070                1075                1080

Gly Ser Gln Leu Ala Ile Tyr Glu Pro Ile Asn Phe Asp Asn Leu
1085                1090                1095

Phe Thr Gly Ser Cys Gln Val Ile Gln Asn Thr Pro Arg Asn Phe
1100                1105                1110

Ser Asp Lys Thr Asn Ile Ala Asn Ser Pro Ile Phe Lys Glu Thr
1115                1120                1125

Ile Tyr Ala Glu Arg Phe Leu Asp Ile Ile Val Ser Arg Gly Glu
1130                1135                1140

Ile Phe Ile Gly Tyr Pro Ser Asn Met Pro Phe Glu Glu Lys Pro
1145                1150                1155

Asn Arg Ile Ser Ile Gly Gly Lys Asp Pro Phe Ser Ile Leu Ser
1160                1165                1170

Val Leu Gly Ala Tyr Leu Asp Lys Ala Pro Ser Ser Glu Lys Glu
1175                1180                1185

Lys Leu Thr Ile Tyr Arg Val Val Lys Asn Lys Ala Phe Glu Leu
1190                1195                1200

Phe Ser Lys Val Ala Gly Ser Lys Phe Thr Ala Glu Glu Asp Lys
1205                1210                1215

Ala Ala Lys Ile Leu Glu Ala Leu His Phe Val Thr Val Lys Gln
1220                1225                1230

Asp Val Ala Ala Thr Val Ser Asp Leu Ile Lys Ser Lys Lys Glu
1235                1240                1245

Leu Ser Lys Asp Ser Ile Glu Asn Leu Ala Lys Gln Lys Gly Cys
1250                1255                1260

Leu Lys Lys Val Glu Tyr Ser Ser Lys Glu Phe Lys Phe Lys Gly
1265                1270                1275

Ser Leu Ile Ile Pro Ala Ala Val Glu Trp Gly Lys Val Leu Trp
1280                1285                1290

Asn Val Phe Lys Glu Asn Thr Ala Glu Glu Leu Lys Asp Glu Asn
1295                1300                1305

Ala Leu Arg Lys Ala Leu Glu Ala Ala Trp Pro Ser Ser Phe Gly
1310                1315                1320

Thr Arg Asn Leu His Ser Lys Ala Lys Arg Val Phe Ser Leu Pro
1325                1330                1335

Val Val Ala Thr Gln Ser Gly Ala Val Arg Ile Arg Arg Lys Thr
1340                1345                1350

Ala Phe Gly Asp Phe Val Tyr Gln Ser Gln Asp Thr Asn Asn Leu
1355                1360                1365

Tyr Ser Ser Phe Pro Val Lys Asn Gly Lys Leu Asp Trp Ser Ser
1370                1375                1380

Pro Ile Ile His Pro Ala Leu Gln Asn Arg Asn Leu Thr Ala Tyr
1385                1390                1395

Gly Tyr Arg Phe Val Asp His Asp Arg Ser Ile Ser Met Ser Glu
```

Phe Arg Glu Val Tyr Asn Lys Asp Asp Leu Met Arg Ile Glu Leu
            1415                1420                1425

Ala Gln Gly Thr Ser Ser Arg Arg Tyr Leu Arg Val Glu Met Pro
    1430                1435                1440

Gly Glu Lys Phe Leu Ala Trp Phe Gly Glu Asn Ser Ile Ser Leu
    1445                1450                1455

Gly Ser Ser Phe Lys Phe Ser Val Ser Glu Val Phe Asp Asn Lys
    1460                1465                1470

Ile Tyr Thr Glu Asn Ala Glu Phe Thr Lys Phe Leu Pro Lys Pro
    1475                1480                1485

Arg Glu Asp Asn Lys His Asn Gly Thr Ile Phe Phe Glu Leu Val
    1490                1495                1500

Gly Pro Arg Val Ile Phe Asn Tyr Ile Val Gly Ala Ala Ser
    1505                1510                1515

Ser Leu Lys Glu Ile Phe Ser Glu Ala Gly Lys Glu Arg Ser Pro
    1520                1525                1530

Lys Lys Lys Arg Lys Val Leu Glu Gly Gly Gly Ser Gly Lys
    1535                1540                1545

Gly Asp Pro Lys Lys Pro Arg Gly Lys Met Ser Ser Tyr Ala Phe
    1550                1555                1560

Phe Val Gln Thr Cys Arg Glu Glu His Lys Lys Lys His Pro Asp
    1565                1570                1575

Ala Ser Val Asn Phe Ser Glu Phe Ser Lys Lys Cys Ser Glu Arg
    1580                1585                1590

Trp Lys Thr Met Ser Ala Lys Glu Lys Gly Lys Phe Glu Asp Met
    1595                1600                1605

Ala Lys Ala Asp Lys Ala Arg Tyr Glu Arg Glu Met Lys Thr Tyr
    1610                1615                1620

Ile Pro Pro Lys Gly Glu
    1625

<210> SEQ ID NO 118
<211> LENGTH: 1626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
        50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Gly Lys Thr His Ile Ile Gly
            100                 105                 110

Val Gly Leu Asp Leu Gly Gly Thr Tyr Thr Gly Thr Phe Ile Thr Ser
            115                 120                 125

His Pro Ser Asp Glu Ala Glu His Arg Asp His Ser Ser Ala Phe Thr
            130                 135                 140

Val Val Asn Ser Glu Lys Leu Ser Phe Ser Ser Lys Ser Arg Thr Ala
145                 150                 155                 160

Val Arg His Arg Val Arg Ser Tyr Lys Gly Phe Asp Leu Arg Arg Arg
                165                 170                 175

Leu Leu Leu Leu Val Ala Glu Tyr Gln Leu Leu Gln Lys Lys Gln Thr
            180                 185                 190

Leu Ala Pro Glu Glu Arg Glu Asn Leu Arg Ile Ala Leu Ser Gly Tyr
            195                 200                 205

Leu Lys Arg Arg Gly Tyr Ala Arg Thr Glu Ala Glu Thr Asp Thr Ser
210                 215                 220

Val Leu Glu Ser Leu Asp Pro Ser Val Phe Ser Ser Ala Pro Ser Phe
225                 230                 235                 240

Thr Asn Phe Phe Asn Asp Ser Glu Pro Leu Asn Ile Gln Trp Glu Ala
                245                 250                 255

Ile Ala Asn Ser Pro Glu Thr Thr Lys Ala Leu Asn Lys Glu Leu Ser
            260                 265                 270

Gly Gln Lys Glu Ala Asp Phe Lys Lys Tyr Ile Lys Thr Ser Phe Pro
            275                 280                 285

Glu Tyr Ser Ala Lys Glu Ile Leu Ala Asn Tyr Val Glu Gly Arg Arg
            290                 295                 300

Ala Ile Leu Asp Ala Ser Lys Tyr Ile Ala Asn Leu Gln Ser Leu Gly
305                 310                 315                 320

His Lys His Arg Ser Lys Tyr Leu Ser Asp Ile Leu Gln Asp Met Lys
                325                 330                 335

Arg Asp Ser Arg Ile Thr Arg Leu Ser Glu Ala Phe Gly Ser Thr Asp
            340                 345                 350

Asn Leu Trp Arg Ile Ile Gly Asn Ile Ser Asn Leu Gln Glu Arg Ala
            355                 360                 365

Val Arg Trp Tyr Phe Asn Asp Ala Lys Phe Glu Gln Gly Gln Glu Gln
370                 375                 380

Leu Asp Ala Val Lys Leu Lys Asn Val Leu Val Arg Ala Leu Lys Tyr
385                 390                 395                 400

Leu Arg Ser Asp Asp Lys Glu Trp Ser Ala Ser Gln Lys Gln Ile Ile
                405                 410                 415

Gln Ser Leu Glu Gln Ser Gly Asp Val Leu Asp Val Leu Ala Gly Leu
            420                 425                 430

Asp Pro Asp Arg Thr Ile Pro Pro Tyr Glu Asp Gln Asn Asn Arg Arg
            435                 440                 445

Pro Pro Glu Asp Gln Thr Leu Tyr Leu Asn Pro Lys Ala Leu Ser Ser
450                 455                 460

Glu Tyr Gly Glu Lys Trp Lys Ser Trp Ala Asn Lys Phe Ala Gly Ala
465                 470                 475                 480

Tyr Pro Leu Leu Thr Glu Asp Leu Thr Glu Ile Leu Lys Asn Thr Asp
                485                 490                 495

Arg Lys Ser Arg Ile Lys Ile Arg Ser Asp Val Leu Pro Asp Ser Asp
            500                 505                 510

Tyr Arg Leu Ala Tyr Ile Leu Gln Arg Ala Phe Asp Arg Ser Ile Ala
            515                 520                 525

Leu Asp Glu Cys Ser Ile Arg Arg Thr Ala Glu Asp Phe Glu Asn Gly

-continued

```
            530                 535                 540
Val Val Ile Lys Asn Glu Lys Leu Glu Asp Val Leu Ser Gly His Gln
545                 550                 555                 560

Leu Glu Glu Phe Leu Glu Phe Ala Asn Arg Tyr Tyr Gln Glu Thr Ala
                565                 570                 575

Lys Ala Lys Asn Gly Leu Trp Phe Pro Glu Asn Ala Leu Leu Glu Arg
                580                 585                 590

Ala Asp Leu His Pro Pro Met Lys Asn Lys Ile Leu Asn Val Ile Val
                595                 600                 605

Gly Gln Ala Leu Gly Val Ser Pro Ala Glu Gly Thr Asp Phe Ile Glu
                610                 615                 620

Glu Ile Trp Asn Ser Lys Val Lys Gly Arg Ser Thr Val Arg Ser Ile
625                 630                 635                 640

Cys Asn Ala Ile Glu Asn Glu Arg Lys Thr Tyr Gly Pro Tyr Phe Ser
                645                 650                 655

Glu Asp Tyr Lys Phe Val Lys Thr Ala Leu Lys Glu Gly Lys Thr Glu
                660                 665                 670

Lys Glu Leu Ser Lys Lys Phe Ala Ala Val Ile Lys Val Leu Lys Met
                675                 680                 685

Val Ser Glu Val Val Pro Phe Ile Gly Lys Glu Leu Arg Leu Ser Asp
690                 695                 700

Glu Ala Gln Ser Lys Phe Asp Asn Leu Tyr Ser Leu Ala Gln Leu Tyr
705                 710                 715                 720

Asn Leu Ile Glu Thr Glu Arg Asn Gly Phe Ser Lys Val Ser Leu Ala
                725                 730                 735

Ala His Leu Glu Asn Ala Trp Arg Met Thr Met Thr Asp Gly Ser Ala
                740                 745                 750

Gln Cys Cys Arg Leu Pro Ala Asp Cys Val Arg Pro Phe Asp Gly Phe
                755                 760                 765

Ile Arg Lys Ala Ile Asp Arg Asn Ser Trp Glu Val Ala Lys Arg Ile
                770                 775                 780

Ala Glu Glu Val Lys Lys Ser Val Asp Phe Thr Asn Gly Thr Val Lys
785                 790                 795                 800

Ile Pro Val Ala Ile Glu Ala Asn Ser Phe Asn Phe Thr Ala Ser Leu
                805                 810                 815

Thr Asp Leu Lys Tyr Ile Gln Leu Lys Glu Gln Lys Leu Lys Lys Lys
                820                 825                 830

Leu Glu Asp Ile Gln Arg Asn Glu Glu Asn Gln Glu Lys Arg Trp Leu
                835                 840                 845

Ser Lys Glu Glu Arg Ile Arg Ala Asp Ser His Gly Ile Cys Ala Tyr
850                 855                 860

Thr Gly Arg Pro Leu Asp Asp Val Gly Glu Ile Asp His Ile Ile Pro
865                 870                 875                 880

Arg Ser Leu Thr Leu Lys Lys Ser Glu Ser Ile Tyr Asn Ser Glu Val
                885                 890                 895

Asn Leu Ile Phe Val Ser Ala Gln Gly Asn Gln Glu Lys Lys Asn Asn
                900                 905                 910

Ile Tyr Leu Leu Ser Asn Leu Ala Lys Asn Tyr Leu Ala Ala Val Phe
                915                 920                 925

Gly Thr Ser Asp Leu Ser Gln Ile Thr Asn Glu Ile Glu Ser Thr Val
                930                 935                 940

Leu Gln Leu Lys Ala Ala Gly Arg Leu Gly Tyr Phe Asp Leu Leu Ser
945                 950                 955                 960
```

```
Glu Lys Glu Arg Ala Cys Ala Arg His Ala Leu Phe Leu Asn Ser Asp
            965                 970                 975

Ser Glu Ala Arg Arg Ala Val Ile Asp Val Leu Gly Ser Arg Arg Lys
            980                 985                 990

Ala Ser Val Asn Gly Thr Gln Ala Trp Phe Val Arg Ser Ile Phe Ser
        995                 1000                1005

Lys Val Arg Gln Ala Leu Ala Ala Trp Thr Gln Glu Thr Gly Asn
    1010                1015                1020

Glu Leu Ile Phe Asp Ala Ile Ser Val Pro Ala Asp Ser Ser
    1025                1030                1035

Glu Met Arg Lys Arg Phe Ala Glu Tyr Arg Pro Glu Phe Arg Lys
    1040                1045                1050

Pro Lys Val Gln Pro Val Ala Ser His Ser Ile Asp Ala Met Cys
    1055                1060                1065

Ile Tyr Leu Ala Ala Cys Ser Asp Pro Phe Lys Thr Lys Arg Met
    1070                1075                1080

Gly Ser Gln Leu Ala Ile Tyr Glu Pro Ile Asn Phe Asp Asn Leu
    1085                1090                1095

Phe Thr Gly Ser Cys Gln Val Ile Gln Asn Thr Pro Arg Asn Phe
    1100                1105                1110

Ser Asp Lys Thr Asn Ile Ala Asn Ser Pro Ile Phe Lys Glu Thr
    1115                1120                1125

Ile Tyr Ala Glu Arg Phe Leu Asp Ile Ile Val Ser Arg Gly Glu
    1130                1135                1140

Ile Phe Ile Gly Tyr Pro Ser Asn Met Pro Phe Glu Glu Lys Pro
    1145                1150                1155

Asn Arg Ile Ser Ile Gly Gly Lys Asp Pro Phe Ser Ile Leu Ser
    1160                1165                1170

Val Leu Gly Ala Tyr Leu Asp Lys Ala Pro Ser Ser Glu Lys Glu
    1175                1180                1185

Lys Leu Thr Ile Tyr Arg Val Val Lys Asn Lys Ala Phe Glu Leu
    1190                1195                1200

Phe Ser Lys Val Ala Gly Ser Lys Phe Thr Ala Glu Glu Asp Lys
    1205                1210                1215

Ala Ala Lys Ile Leu Glu Ala Leu His Phe Val Thr Val Lys Gln
    1220                1225                1230

Asp Val Ala Ala Thr Val Ser Asp Leu Ile Lys Ser Lys Lys Glu
    1235                1240                1245

Leu Ser Lys Asp Ser Ile Glu Asn Leu Ala Lys Gln Lys Gly Cys
    1250                1255                1260

Leu Lys Lys Val Glu Tyr Ser Ser Lys Glu Phe Lys Phe Lys Gly
    1265                1270                1275

Ser Leu Ile Ile Pro Ala Ala Val Glu Trp Gly Lys Val Leu Trp
    1280                1285                1290

Asn Val Phe Lys Glu Asn Thr Ala Glu Glu Leu Lys Asp Glu Asn
    1295                1300                1305

Ala Leu Arg Lys Ala Leu Glu Ala Ala Trp Pro Ser Ser Phe Gly
    1310                1315                1320

Thr Arg Asn Leu His Ser Lys Ala Lys Arg Val Phe Ser Leu Pro
    1325                1330                1335

Val Val Ala Thr Gln Ser Gly Ala Val Arg Ile Arg Arg Lys Thr
    1340                1345                1350
```

```
Ala Phe Gly Asp Phe Val Tyr Gln Ser Gln Asp Thr Asn Asn Leu
    1355                1360                1365

Tyr Ser Ser Phe Pro Val Lys Asn Gly Lys Leu Asp Trp Ser Ser
1370                1375                1380

Pro Ile Ile His Pro Ala Leu Gln Asn Arg Asn Leu Thr Ala Tyr
    1385                1390                1395

Gly Tyr Arg Phe Val Asp His Asp Arg Ser Ile Ser Met Ser Glu
    1400                1405                1410

Phe Arg Glu Val Tyr Asn Lys Asp Asp Leu Met Arg Ile Glu Leu
    1415                1420                1425

Ala Gln Gly Thr Ser Ser Arg Arg Tyr Leu Arg Val Glu Met Pro
    1430                1435                1440

Gly Glu Lys Phe Leu Ala Trp Phe Gly Glu Asn Ser Ile Ser Leu
    1445                1450                1455

Gly Ser Ser Phe Lys Phe Ser Val Ser Glu Val Phe Asp Asn Lys
    1460                1465                1470

Ile Tyr Thr Glu Asn Ala Glu Phe Thr Lys Phe Leu Pro Lys Pro
    1475                1480                1485

Arg Glu Asp Asn Lys His Asn Gly Thr Ile Phe Phe Glu Leu Val
    1490                1495                1500

Gly Pro Arg Val Ile Phe Asn Tyr Ile Val Gly Gly Ala Ala Ser
    1505                1510                1515

Ser Leu Lys Glu Ile Phe Ser Glu Ala Gly Lys Glu Arg Ser Pro
    1520                1525                1530

Lys Lys Lys Arg Lys Val Leu Glu Gly Gly Gly Ser Ser Thr
    1535                1540                1545

Asp His Pro Lys Tyr Ser Asp Met Ile Val Ala Ala Ile Gln Ala
    1550                1555                1560

Glu Lys Asn Arg Ala Gly Ser Ser Arg Gln Ser Ile Gln Lys Tyr
    1565                1570                1575

Ile Lys Ser His Tyr Lys Val Gly Glu Asn Ala Asp Ser Gln Ile
    1580                1585                1590

Lys Leu Ser Ile Lys Arg Leu Val Thr Thr Gly Val Leu Lys Gln
    1595                1600                1605

Thr Lys Gly Val Gly Ala Ser Gly Ser Phe Arg Leu Ala Lys Ser
    1610                1615                1620

Asp Glu Pro
    1625

<210> SEQ ID NO 119
<211> LENGTH: 1289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
            20                  25                  30

Glu Ala Lys Pro Lys Lys Ala Ala Ala Lys Asp Lys Ser Ser Asp Lys
        35                  40                  45

Lys Val Gln Thr Lys Gly Lys Arg Gly Ala Lys Gly Lys Gln Ala Glu
    50                  55                  60
```

-continued

```
Val Ala Asn Gln Glu Thr Lys Glu Asp Leu Pro Ala Glu Asn Gly Glu
 65                  70                  75                  80

Thr Lys Thr Glu Glu Ser Pro Ala Ser Asp Glu Ala Gly Glu Lys Glu
                 85                  90                  95

Ala Lys Ser Asp Thr Gly Ser Gly Met Asn Tyr Lys Met Gly Leu Asp
            100                 105                 110

Ile Gly Ile Ala Ser Val Gly Trp Ala Val Ile Asn Leu Asp Leu Lys
        115                 120                 125

Arg Ile Glu Asp Leu Gly Val Arg Ile Phe Asp Lys Ala Glu His Pro
    130                 135                 140

Gln Asn Gly Glu Ser Leu Ala Leu Pro Arg Arg Ile Ala Arg Ser Ala
145                 150                 155                 160

Arg Arg Arg Leu Arg Arg Lys His Arg Leu Glu Arg Ile Arg Arg
                165                 170                 175

Leu Leu Val Ser Glu Asn Val Leu Thr Lys Glu Glu Met Asn Leu Leu
                180                 185                 190

Phe Lys Gln Lys Lys Gln Ile Asp Val Trp Gln Leu Arg Val Asp Ala
            195                 200                 205

Leu Glu Arg Lys Leu Asn Asn Asp Glu Leu Ala Arg Val Leu Leu His
        210                 215                 220

Leu Ala Lys Arg Arg Gly Phe Lys Ser Asn Arg Lys Ser Glu Arg Asn
225                 230                 235                 240

Ser Lys Glu Ser Ser Glu Phe Leu Lys Asn Ile Glu Glu Asn Gln Ser
                245                 250                 255

Ile Leu Ala Gln Tyr Arg Ser Val Gly Glu Met Ile Val Lys Asp Ser
            260                 265                 270

Lys Phe Ala Tyr His Lys Arg Asn Lys Leu Asp Ser Tyr Ser Asn Met
        275                 280                 285

Ile Ala Arg Asp Asp Leu Glu Arg Glu Ile Lys Leu Ile Phe Glu Lys
    290                 295                 300

Gln Arg Glu Phe Asn Asn Pro Val Cys Thr Glu Arg Leu Glu Glu Lys
305                 310                 315                 320

Tyr Leu Asn Ile Trp Ser Ser Gln Arg Pro Phe Ala Ser Lys Glu Asp
                325                 330                 335

Ile Glu Lys Lys Val Gly Phe Cys Thr Phe Glu Pro Lys Glu Lys Arg
            340                 345                 350

Ala Pro Lys Ala Thr Tyr Thr Phe Gln Ser Phe Ile Val Trp Glu His
        355                 360                 365

Ile Asn Lys Leu Arg Leu Val Ser Pro Asp Glu Thr Arg Ala Leu Thr
    370                 375                 380

Glu Ile Glu Arg Asn Leu Leu Tyr Lys Gln Ala Phe Ser Lys Asn Lys
385                 390                 395                 400

Met Thr Tyr Tyr Asp Ile Arg Lys Leu Leu Asn Leu Ser Asp Ile
                405                 410                 415

His Phe Lys Gly Leu Leu Tyr Asp Pro Lys Ser Ser Leu Lys Gln Ile
            420                 425                 430

Glu Asn Ile Arg Phe Leu Glu Leu Asp Ser Tyr His Lys Ile Arg Lys
        435                 440                 445

Cys Ile Glu Asn Val Tyr Gly Lys Asp Gly Ile Arg Met Phe Asn Glu
    450                 455                 460

Thr Asp Ile Asp Thr Phe Gly Tyr Ala Leu Thr Ile Phe Lys Asp Asp
465                 470                 475                 480
```

```
Glu Asp Ile Val Ala Tyr Leu Gln Asn Glu Tyr Ile Thr Lys Asn Gly
                485                 490                 495

Lys Arg Val Ser Asn Leu Ala Asn Lys Val Tyr Asp Lys Ser Leu Ile
            500                 505                 510

Asp Glu Leu Leu Asn Leu Ser Phe Ser Lys Phe Ala His Leu Ser Met
        515                 520                 525

Lys Ala Ile Arg Asn Ile Leu Pro Tyr Met Glu Gln Gly Glu Ile Tyr
    530                 535                 540

Ser Lys Ala Cys Glu Leu Ala Gly Tyr Asn Phe Thr Gly Pro Lys Lys
545                 550                 555                 560

Lys Glu Lys Ala Leu Leu Pro Val Ile Pro Asn Ile Ala Asn Pro
                565                 570                 575

Val Val Met Arg Ala Leu Thr Gln Ser Arg Lys Val Val Asn Ala Ile
            580                 585                 590

Ile Lys Lys Tyr Gly Ser Pro Val Ser Ile His Ile Glu Leu Ala Arg
        595                 600                 605

Asp Leu Ser His Ser Phe Asp Glu Arg Lys Lys Ile Gln Lys Asp Gln
    610                 615                 620

Thr Glu Asn Arg Lys Lys Asn Glu Thr Ala Ile Lys Gln Leu Ile Glu
625                 630                 635                 640

Tyr Glu Leu Thr Lys Asn Pro Thr Gly Leu Asp Ile Val Lys Phe Lys
                645                 650                 655

Leu Trp Ser Glu Gln Gln Gly Arg Cys Met Tyr Ser Leu Lys Pro Ile
            660                 665                 670

Glu Leu Glu Arg Leu Leu Glu Pro Gly Tyr Val Glu Val Asp His Ile
        675                 680                 685

Leu Pro Tyr Ser Arg Ser Leu Asp Asp Ser Tyr Ala Asn Lys Val Leu
    690                 695                 700

Val Leu Thr Lys Glu Asn Arg Glu Lys Gly Asn His Thr Pro Val Glu
705                 710                 715                 720

Tyr Leu Gly Leu Gly Ser Glu Arg Trp Lys Lys Phe Glu Lys Phe Val
                725                 730                 735

Leu Ala Asn Lys Gln Phe Ser Lys Lys Lys Gln Asn Leu Leu Arg
            740                 745                 750

Leu Arg Tyr Glu Glu Thr Glu Glu Lys Glu Phe Lys Glu Arg Asn Leu
        755                 760                 765

Asn Asp Thr Arg Tyr Ile Ser Lys Phe Phe Ala Asn Phe Ile Lys Glu
    770                 775                 780

His Leu Lys Phe Ala Asp Gly Asp Gly Gly Gln Lys Val Tyr Thr Ile
785                 790                 795                 800

Asn Gly Lys Ile Thr Ala His Leu Arg Ser Arg Trp Asp Phe Asn Lys
                805                 810                 815

Asn Arg Glu Glu Ser Asp Leu His His Ala Val Asp Ala Val Ile Val
            820                 825                 830

Ala Cys Ala Thr Gln Gly Met Ile Lys Lys Ile Thr Glu Phe Tyr Lys
        835                 840                 845

Ala Arg Glu Gln Asn Lys Glu Ser Ala Lys Lys Glu Pro Ile Phe
    850                 855                 860

Pro Gln Pro Trp Pro His Phe Ala Asp Glu Leu Lys Ala Arg Leu Ser
865                 870                 875                 880

Lys Phe Pro Gln Glu Ser Ile Glu Ala Phe Ala Leu Gly Asn Tyr Asp
                885                 890                 895

Arg Lys Lys Leu Glu Ser Leu Arg Pro Val Phe Val Ser Arg Met Pro
```

```
                    900             905             910
Lys Arg Ser Val Thr Gly Ala Ala His Gln Glu Thr Leu Arg Arg Cys
        915             920             925
Val Gly Ile Asp Glu Gln Ser Gly Lys Ile Gln Thr Ala Val Lys Thr
    930             935             940
Lys Leu Ser Asp Ile Lys Leu Asp Lys Asp Gly His Phe Pro Met Tyr
945             950             955             960
Gln Lys Glu Ser Asp Pro Arg Thr Tyr Glu Ala Ile Arg Gln Arg Leu
        965             970             975
Leu Glu His Asn Asn Asp Pro Lys Lys Ala Phe Gln Glu Pro Leu Tyr
            980             985             990
Lys Pro Lys Lys Asn Gly Glu Pro Gly Pro Val Ile Arg Thr Val Lys
        995             1000            1005
Ile Ile Asp Thr Lys Asn Lys Val Val His Leu Asp Gly Ser Lys
    1010            1015            1020
Thr Val Ala Tyr Asn Ser Asn Ile Val Arg Thr Asp Val Phe Glu
    1025            1030            1035
Lys Asp Gly Lys Tyr Tyr Cys Val Pro Val Tyr Thr Met Asp Ile
    1040            1045            1050
Met Lys Gly Thr Leu Pro Asn Lys Ala Ile Glu Ala Asn Lys Pro
    1055            1060            1065
Tyr Ser Glu Trp Lys Glu Met Thr Glu Glu Tyr Thr Phe Gln Phe
    1070            1075            1080
Ser Leu Phe Pro Asn Asp Leu Val Arg Ile Val Leu Pro Arg Glu
    1085            1090            1095
Lys Thr Ile Lys Thr Ser Thr Asn Glu Glu Ile Ile Ile Lys Asp
    1100            1105            1110
Ile Phe Ala Tyr Tyr Lys Thr Ile Asp Ser Ala Thr Gly Gly Leu
    1115            1120            1125
Glu Leu Ile Ser His Asp Arg Asn Phe Ser Leu Arg Gly Val Gly
    1130            1135            1140
Ser Lys Thr Leu Lys Arg Phe Glu Lys Tyr Gln Val Asp Val Leu
    1145            1150            1155
Gly Asn Ile His Lys Val Lys Gly Glu Lys Arg Val Gly Leu Ala
    1160            1165            1170
Ala Pro Thr Asn Gln Lys Lys Gly Lys Thr Val Asp Ser Leu Gln
    1175            1180            1185
Ser Val Ser Asp Pro Lys Lys Arg Lys Val Leu Glu Gly Gly
    1190            1195            1200
Gly Gly Ser Gly Lys Gly Asp Pro Lys Lys Pro Arg Gly Lys Met
    1205            1210            1215
Ser Ser Tyr Ala Phe Phe Val Gln Thr Cys Arg Glu Glu His Lys
    1220            1225            1230
Lys Lys His Pro Asp Ala Ser Val Asn Phe Ser Glu Phe Ser Lys
    1235            1240            1245
Lys Cys Ser Glu Arg Trp Lys Thr Met Ser Ala Lys Glu Lys Gly
    1250            1255            1260
Lys Phe Glu Asp Met Ala Lys Ala Asp Lys Ala Arg Tyr Glu Arg
    1265            1270            1275
Glu Met Lys Thr Tyr Ile Pro Pro Lys Gly Glu
    1280            1285

<210> SEQ ID NO 120
```

<211> LENGTH: 1286
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Pro Ala Lys Val
            20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
        50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Asn Tyr Lys Met Gly Leu Asp
            100                 105                 110

Ile Gly Ile Ala Ser Val Gly Trp Ala Val Ile Asn Leu Asp Leu Lys
        115                 120                 125

Arg Ile Glu Asp Leu Gly Val Arg Ile Phe Asp Lys Ala Glu His Pro
    130                 135                 140

Gln Asn Gly Glu Ser Leu Ala Leu Pro Arg Arg Ile Ala Arg Ser Ala
145                 150                 155                 160

Arg Arg Arg Leu Arg Arg Arg Lys His Arg Leu Glu Arg Ile Arg Arg
                165                 170                 175

Leu Leu Val Ser Glu Asn Val Leu Thr Lys Glu Glu Met Asn Leu Leu
            180                 185                 190

Phe Lys Gln Lys Lys Gln Ile Asp Val Trp Gln Leu Arg Val Asp Ala
        195                 200                 205

Leu Glu Arg Lys Leu Asn Asn Asp Glu Leu Ala Arg Val Leu Leu His
    210                 215                 220

Leu Ala Lys Arg Arg Gly Phe Lys Ser Asn Arg Lys Ser Glu Arg Asn
225                 230                 235                 240

Ser Lys Glu Ser Ser Glu Phe Leu Lys Asn Ile Glu Glu Asn Gln Ser
                245                 250                 255

Ile Leu Ala Gln Tyr Arg Ser Val Gly Glu Met Ile Val Lys Asp Ser
            260                 265                 270

Lys Phe Ala Tyr His Lys Arg Asn Lys Leu Asp Ser Tyr Ser Asn Met
        275                 280                 285

Ile Ala Arg Asp Asp Leu Glu Arg Glu Ile Lys Leu Ile Phe Glu Lys
    290                 295                 300

Gln Arg Glu Phe Asn Asn Pro Val Cys Thr Glu Arg Leu Glu Glu Lys
305                 310                 315                 320

Tyr Leu Asn Ile Trp Ser Ser Gln Arg Pro Phe Ala Ser Lys Glu Asp
                325                 330                 335

Ile Glu Lys Lys Val Gly Phe Cys Thr Phe Glu Pro Lys Glu Lys Arg
            340                 345                 350

Ala Pro Lys Ala Thr Tyr Thr Phe Gln Ser Phe Ile Val Trp Glu His
        355                 360                 365

Ile Asn Lys Leu Arg Leu Val Ser Pro Asp Glu Thr Arg Ala Leu Thr

```
                 370                 375                 380
Glu Ile Glu Arg Asn Leu Leu Tyr Lys Gln Ala Phe Ser Lys Asn Lys
385                 390                 395                 400

Met Thr Tyr Tyr Asp Ile Arg Lys Leu Leu Asn Leu Ser Asp Asp Ile
                405                 410                 415

His Phe Lys Gly Leu Leu Tyr Asp Pro Lys Ser Ser Leu Lys Gln Ile
                420                 425                 430

Glu Asn Ile Arg Phe Leu Glu Leu Asp Ser Tyr His Lys Ile Arg Lys
                435                 440                 445

Cys Ile Glu Asn Val Tyr Gly Lys Asp Gly Ile Arg Met Phe Asn Glu
                450                 455                 460

Thr Asp Ile Asp Thr Phe Gly Tyr Ala Leu Thr Ile Phe Lys Asp Asp
465                 470                 475                 480

Glu Asp Ile Val Ala Tyr Leu Gln Asn Glu Tyr Ile Thr Lys Asn Gly
                485                 490                 495

Lys Arg Val Ser Asn Leu Ala Asn Lys Val Tyr Asp Lys Ser Leu Ile
                500                 505                 510

Asp Glu Leu Leu Asn Leu Ser Phe Ser Lys Phe Ala His Leu Ser Met
                515                 520                 525

Lys Ala Ile Arg Asn Ile Leu Pro Tyr Met Glu Gln Gly Glu Ile Tyr
                530                 535                 540

Ser Lys Ala Cys Glu Leu Ala Gly Tyr Asn Phe Thr Gly Pro Lys Lys
545                 550                 555                 560

Lys Glu Lys Ala Leu Leu Leu Pro Val Ile Pro Asn Ile Ala Asn Pro
                565                 570                 575

Val Val Met Arg Ala Leu Thr Gln Ser Arg Lys Val Val Asn Ala Ile
                580                 585                 590

Ile Lys Lys Tyr Gly Ser Pro Val Ser Ile His Ile Glu Leu Ala Arg
                595                 600                 605

Asp Leu Ser His Ser Phe Asp Glu Arg Lys Lys Ile Gln Lys Asp Gln
                610                 615                 620

Thr Glu Asn Arg Lys Lys Asn Glu Thr Ala Ile Lys Gln Leu Ile Glu
625                 630                 635                 640

Tyr Glu Leu Thr Lys Asn Pro Thr Gly Leu Asp Ile Val Lys Phe Lys
                645                 650                 655

Leu Trp Ser Glu Gln Gln Gly Arg Cys Met Tyr Ser Leu Lys Pro Ile
                660                 665                 670

Glu Leu Glu Arg Leu Leu Glu Pro Gly Tyr Val Glu Val Asp His Ile
                675                 680                 685

Leu Pro Tyr Ser Arg Ser Leu Asp Asp Ser Tyr Ala Asn Lys Val Leu
                690                 695                 700

Val Leu Thr Lys Glu Asn Arg Glu Lys Gly Asn His Thr Pro Val Glu
705                 710                 715                 720

Tyr Leu Gly Leu Gly Ser Glu Arg Trp Lys Lys Phe Glu Lys Phe Val
                725                 730                 735

Leu Ala Asn Lys Gln Phe Ser Lys Lys Lys Gln Asn Leu Leu Arg
                740                 745                 750

Leu Arg Tyr Glu Glu Thr Glu Glu Lys Glu Phe Lys Glu Arg Asn Leu
                755                 760                 765

Asn Asp Thr Arg Tyr Ile Ser Lys Phe Phe Ala Asn Phe Ile Lys Glu
                770                 775                 780

His Leu Lys Phe Ala Asp Gly Asp Gly Gly Gln Lys Val Tyr Thr Ile
785                 790                 795                 800
```

-continued

```
Asn Gly Lys Ile Thr Ala His Leu Arg Ser Arg Trp Asp Phe Asn Lys
            805                 810                 815

Asn Arg Glu Glu Ser Asp Leu His His Ala Val Asp Ala Val Ile Val
            820                 825                 830

Ala Cys Ala Thr Gln Gly Met Ile Lys Lys Ile Thr Glu Phe Tyr Lys
            835                 840                 845

Ala Arg Glu Gln Asn Lys Glu Ser Ala Lys Lys Glu Pro Ile Phe
    850                 855                 860

Pro Gln Pro Trp Pro His Phe Ala Asp Glu Leu Lys Ala Arg Leu Ser
865                 870                 875                 880

Lys Phe Pro Gln Glu Ser Ile Glu Ala Phe Ala Leu Gly Asn Tyr Asp
            885                 890                 895

Arg Lys Lys Leu Glu Ser Leu Arg Pro Val Phe Val Ser Arg Met Pro
            900                 905                 910

Lys Arg Ser Val Thr Gly Ala Ala His Gln Glu Thr Leu Arg Arg Cys
            915                 920                 925

Val Gly Ile Asp Glu Gln Ser Gly Lys Ile Gln Thr Ala Val Lys Thr
    930                 935                 940

Lys Leu Ser Asp Ile Lys Leu Asp Lys Asp Gly His Phe Pro Met Tyr
945                 950                 955                 960

Gln Lys Glu Ser Asp Pro Arg Thr Tyr Glu Ala Ile Arg Gln Arg Leu
            965                 970                 975

Leu Glu His Asn Asn Asp Pro Lys Lys Ala Phe Gln Glu Pro Leu Tyr
            980                 985                 990

Lys Pro Lys Lys Asn Gly Glu Pro Gly Pro Val Ile Arg Thr Val Lys
            995                 1000                1005

Ile Ile Asp Thr Lys Asn Lys Val Val His Leu Asp Gly Ser Lys
    1010                1015                1020

Thr Val Ala Tyr Asn Ser Asn Ile Val Arg Thr Asp Val Phe Glu
    1025                1030                1035

Lys Asp Gly Lys Tyr Tyr Cys Val Pro Val Tyr Thr Met Asp Ile
    1040                1045                1050

Met Lys Gly Thr Leu Pro Asn Lys Ala Ile Glu Ala Asn Lys Pro
    1055                1060                1065

Tyr Ser Glu Trp Lys Glu Met Thr Glu Glu Tyr Thr Phe Gln Phe
    1070                1075                1080

Ser Leu Phe Pro Asn Asp Leu Val Arg Ile Val Leu Pro Arg Glu
    1085                1090                1095

Lys Thr Ile Lys Thr Ser Thr Asn Glu Glu Ile Ile Ile Lys Asp
    1100                1105                1110

Ile Phe Ala Tyr Tyr Lys Thr Ile Asp Ser Ala Thr Gly Gly Leu
    1115                1120                1125

Glu Leu Ile Ser His Asp Arg Asn Phe Ser Leu Arg Gly Val Gly
    1130                1135                1140

Ser Lys Thr Leu Lys Arg Phe Glu Lys Tyr Gln Val Asp Val Leu
    1145                1150                1155

Gly Asn Ile His Lys Val Lys Gly Glu Lys Arg Val Gly Leu Ala
    1160                1165                1170

Ala Pro Thr Asn Gln Lys Lys Gly Lys Thr Val Asp Ser Leu Gln
    1175                1180                1185

Ser Val Ser Asp Pro Lys Lys Lys Arg Lys Val Leu Glu Gly Gly
    1190                1195                1200
```

```
Gly Gly Ser Ser Thr Asp His Pro Lys Tyr Ser Asp Met Ile Val
    1205                1210                1215

Ala Ala Ile Gln Ala Glu Lys Asn Arg Ala Gly Ser Ser Arg Gln
    1220                1225                1230

Ser Ile Gln Lys Tyr Ile Lys Ser His Tyr Lys Val Gly Glu Asn
    1235                1240                1245

Ala Asp Ser Gln Ile Lys Leu Ser Ile Lys Arg Leu Val Thr Thr
    1250                1255                1260

Gly Val Leu Lys Gln Thr Lys Gly Val Gly Ala Ser Gly Ser Phe
    1265                1270                1275

Arg Leu Ala Lys Ser Asp Glu Pro
    1280                1285

<210> SEQ ID NO 121
<211> LENGTH: 1564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Thr Lys Leu Asn Gln Pro Tyr
            100                 105                 110

Gly Ile Gly Leu Asp Ile Gly Ser Asn Ser Ile Gly Phe Ala Val Val
        115                 120                 125

Asp Ala Asn Ser His Leu Leu Arg Leu Lys Gly Glu Thr Ala Ile Gly
    130                 135                 140

Ala Arg Leu Phe Arg Glu Gly Gln Ser Ala Ala Asp Arg Arg Gly Ser
145                 150                 155                 160

Arg Thr Thr Arg Arg Arg Leu Ser Arg Thr Arg Trp Arg Leu Ser Phe
                165                 170                 175

Leu Arg Asp Phe Phe Ala Pro His Ile Thr Lys Ile Asp Pro Asp Phe
            180                 185                 190

Phe Leu Arg Gln Lys Tyr Ser Glu Ile Ser Pro Lys Asp Lys Asp Arg
        195                 200                 205

Phe Lys Tyr Glu Lys Arg Leu Phe Asn Asp Arg Thr Asp Ala Glu Phe
    210                 215                 220

Tyr Glu Asp Tyr Pro Ser Met Tyr His Leu Arg Leu His Leu Met Thr
225                 230                 235                 240

His Thr His Lys Ala Asp Pro Arg Glu Ile Phe Leu Ala Ile His His
                245                 250                 255

Ile Leu Lys Ser Arg Gly His Phe Leu Thr Pro Gly Ala Ala Lys Asp
            260                 265                 270
```

```
Phe Asn Thr Asp Lys Val Asp Leu Glu Asp Ile Phe Pro Ala Leu Thr
        275                 280                 285

Glu Ala Tyr Ala Gln Val Tyr Pro Asp Leu Glu Leu Thr Phe Asp Leu
290                 295                 300

Ala Lys Ala Asp Asp Phe Lys Ala Lys Leu Leu Asp Glu Gln Ala Thr
305                 310                 315                 320

Pro Ser Asp Thr Gln Lys Ala Leu Val Asn Leu Leu Leu Ser Ser Asp
                325                 330                 335

Gly Glu Lys Glu Ile Val Lys Lys Arg Lys Gln Val Leu Thr Glu Phe
                340                 345                 350

Ala Lys Ala Ile Thr Gly Leu Lys Thr Lys Phe Asn Leu Ala Leu Gly
                355                 360                 365

Thr Glu Val Asp Glu Ala Asp Ala Ser Asn Trp Gln Phe Ser Met Gly
370                 375                 380

Gln Leu Asp Asp Lys Trp Ser Asn Ile Glu Thr Ser Met Thr Asp Gln
385                 390                 395                 400

Gly Thr Glu Ile Phe Glu Gln Ile Gln Glu Leu Tyr Arg Ala Arg Leu
                405                 410                 415

Leu Asn Gly Ile Val Pro Ala Gly Met Ser Leu Ser Gln Ala Lys Val
                420                 425                 430

Ala Asp Tyr Gly Gln His Lys Glu Asp Leu Glu Leu Phe Lys Thr Tyr
            435                 440                 445

Leu Lys Lys Leu Asn Asp His Glu Leu Ala Lys Thr Ile Arg Gly Leu
450                 455                 460

Tyr Asp Arg Tyr Ile Asn Gly Asp Asp Ala Lys Pro Phe Leu Arg Glu
465                 470                 475                 480

Asp Phe Val Lys Ala Leu Thr Lys Glu Val Thr Ala His Pro Asn Glu
                485                 490                 495

Val Ser Glu Gln Leu Leu Asn Arg Met Gly Gln Ala Asn Phe Met Leu
            500                 505                 510

Lys Gln Arg Thr Lys Ala Asn Gly Ala Ile Pro Ile Gln Leu Gln Gln
        515                 520                 525

Arg Glu Leu Asp Gln Ile Ile Ala Asn Gln Ser Lys Tyr Tyr Asp Trp
    530                 535                 540

Leu Ala Ala Pro Asn Pro Val Glu Ala His Arg Trp Lys Met Pro Tyr
545                 550                 555                 560

Gln Leu Asp Glu Leu Leu Asn Phe His Ile Pro Tyr Tyr Val Gly Pro
                565                 570                 575

Leu Ile Thr Pro Lys Gln Gln Ala Glu Ser Gly Glu Asn Val Phe Ala
                580                 585                 590

Trp Met Val Arg Lys Asp Pro Ser Gly Asn Ile Thr Pro Tyr Asn Phe
        595                 600                 605

Asp Glu Lys Val Asp Arg Glu Ala Ser Ala Asn Thr Phe Ile Gln Arg
610                 615                 620

Met Lys Thr Thr Asp Thr Tyr Leu Ile Gly Glu Asp Val Leu Pro Lys
625                 630                 635                 640

Gln Ser Leu Leu Tyr Gln Lys Tyr Glu Val Leu Asn Glu Leu Asn Asn
                645                 650                 655

Val Arg Ile Asn Asn Glu Cys Leu Gly Thr Asp Gln Lys Gln Arg Leu
                660                 665                 670

Ile Arg Glu Val Phe Glu Arg His Ser Ser Val Thr Ile Lys Gln Val
            675                 680                 685
```

```
Ala Asp Asn Leu Val Ala His Gly Asp Phe Ala Arg Arg Pro Glu Ile
690                 695                 700

Arg Gly Leu Ala Asp Glu Lys Arg Phe Leu Ser Ser Leu Ser Thr Tyr
705                 710                 715                 720

His Gln Leu Lys Glu Ile Leu His Glu Ala Ile Asp Asp Pro Thr Lys
        725                 730                 735

Leu Leu Asp Ile Glu Asn Ile Ile Thr Trp Ser Thr Val Phe Glu Asp
            740                 745                 750

His Thr Ile Phe Glu Thr Lys Leu Ala Glu Ile Glu Trp Leu Asp Pro
        755                 760                 765

Lys Lys Ile Asn Glu Leu Ser Gly Ile Arg Tyr Arg Gly Trp Gly Gln
770                 775                 780

Phe Ser Arg Lys Leu Leu Asp Gly Leu Lys Leu Gly Asn Gly His Thr
785                 790                 795                 800

Val Ile Gln Glu Leu Met Leu Ser Asn His Asn Leu Met Gln Ile Leu
                805                 810                 815

Ala Asp Glu Thr Leu Lys Glu Thr Met Thr Glu Leu Asn Gln Asp Lys
                820                 825                 830

Leu Lys Thr Asp Asp Ile Glu Asp Val Ile Asn Asp Ala Tyr Thr Ser
            835                 840                 845

Pro Ser Asn Lys Lys Ala Leu Arg Gln Val Leu Arg Val Val Glu Asp
850                 855                 860

Ile Lys His Ala Ala Asn Gly Gln Asp Pro Ser Trp Leu Phe Ile Glu
865                 870                 875                 880

Thr Ala Asp Gly Thr Gly Thr Ala Gly Lys Arg Thr Gln Ser Arg Gln
                885                 890                 895

Lys Gln Ile Gln Thr Val Tyr Ala Asn Ala Ala Gln Glu Leu Ile Asp
            900                 905                 910

Ser Ala Val Arg Gly Glu Leu Glu Asp Lys Ile Ala Asp Lys Ala Ser
        915                 920                 925

Phe Thr Asp Arg Leu Val Leu Tyr Phe Met Gln Gly Gly Arg Asp Ile
930                 935                 940

Tyr Thr Gly Ala Pro Leu Asn Ile Asp Gln Leu Ser His Tyr Asp Ile
945                 950                 955                 960

Asp His Ile Leu Pro Gln Ser Leu Ile Lys Asp Asp Ser Leu Asp Asn
            965                 970                 975

Arg Val Leu Val Asn Ala Thr Ile Asn Arg Glu Lys Asn Asn Val Phe
                980                 985                 990

Ala Ser Thr Leu Phe Ala Gly Lys Met Lys Ala Thr Trp Arg Lys Trp
        995                 1000                1005

His Glu Ala Gly Leu Ile Ser Gly Arg Lys Leu Arg Asn Leu Met
   1010                 1015                1020

Leu Arg Pro Asp Glu Ile Asp Lys Phe Ala Lys Gly Phe Val Ala
   1025                 1030                1035

Arg Gln Leu Val Glu Thr Arg Gln Ile Ile Lys Leu Thr Glu Gln
   1040                 1045                1050

Ile Ala Ala Ala Gln Tyr Pro Asn Thr Lys Ile Ile Ala Val Lys
   1055                 1060                1065

Ala Gly Leu Ser His Gln Leu Arg Glu Glu Leu Asp Phe Pro Lys
   1070                 1075                1080

Asn Arg Asp Val Asn His Tyr His His Ala Phe Asp Ala Phe Leu
   1085                 1090                1095

Ala Ala Arg Ile Gly Thr Tyr Leu Leu Lys Arg Tyr Pro Lys Leu
```

-continued

```
                1100                1105                1110
Ala  Pro  Phe  Phe  Thr  Tyr  Gly  Glu  Phe  Ala  Lys  Val  Asp  Val  Lys
     1115                1120                1125
Lys  Phe  Arg  Glu  Phe  Asn  Phe  Ile  Gly  Ala  Leu  Thr  His  Ala  Lys
     1130                1135                1140
Lys  Asn  Ile  Ile  Ala  Lys  Asp  Thr  Gly  Glu  Ile  Val  Trp  Asp  Lys
     1145                1150                1155
Glu  Arg  Asp  Ile  Arg  Glu  Leu  Asp  Arg  Ile  Tyr  Asn  Phe  Lys  Arg
     1160                1165                1170
Met  Leu  Ile  Thr  His  Glu  Val  Tyr  Phe  Glu  Thr  Ala  Asp  Leu  Phe
     1175                1180                1185
Lys  Gln  Thr  Ile  Tyr  Ala  Ala  Lys  Asp  Ser  Lys  Glu  Arg  Gly  Gly
     1190                1195                1200
Ser  Lys  Gln  Leu  Ile  Pro  Lys  Gln  Gly  Tyr  Pro  Thr  Gln  Val
     1205                1210                1215
Tyr  Gly  Gly  Tyr  Thr  Gln  Glu  Ser  Gly  Ser  Tyr  Asn  Ala  Leu  Val
     1220                1225                1230
Arg  Val  Ala  Glu  Ala  Asp  Thr  Thr  Ala  Tyr  Gln  Val  Ile  Lys  Ile
     1235                1240                1245
Ser  Ala  Gln  Asn  Ala  Ser  Lys  Ile  Ala  Ser  Ala  Asn  Leu  Lys  Ser
     1250                1255                1260
Arg  Glu  Lys  Gly  Lys  Gln  Leu  Leu  Asn  Glu  Ile  Val  Val  Lys  Gln
     1265                1270                1275
Leu  Ala  Lys  Arg  Arg  Lys  Asn  Trp  Lys  Pro  Ser  Ala  Asn  Ser  Phe
     1280                1285                1290
Lys  Ile  Val  Ile  Pro  Arg  Phe  Gly  Met  Gly  Thr  Leu  Phe  Gln  Asn
     1295                1300                1305
Ala  Lys  Tyr  Gly  Leu  Phe  Met  Val  Asn  Ser  Asp  Thr  Tyr  Tyr  Arg
     1310                1315                1320
Asn  Tyr  Gln  Glu  Leu  Trp  Leu  Ser  Arg  Glu  Asn  Gln  Lys  Leu  Leu
     1325                1330                1335
Lys  Lys  Leu  Phe  Ser  Ile  Lys  Tyr  Glu  Lys  Thr  Gln  Met  Asn  His
     1340                1345                1350
Asp  Ala  Leu  Gln  Val  Tyr  Lys  Ala  Ile  Ile  Asp  Gln  Val  Glu  Lys
     1355                1360                1365
Phe  Phe  Lys  Leu  Tyr  Asp  Ile  Asn  Gln  Phe  Arg  Ala  Lys  Leu  Ser
     1370                1375                1380
Asp  Ala  Ile  Glu  Arg  Phe  Glu  Lys  Leu  Pro  Ile  Asn  Thr  Asp  Gly
     1385                1390                1395
Asn  Lys  Ile  Gly  Lys  Thr  Glu  Thr  Leu  Arg  Gln  Ile  Leu  Ile  Gly
     1400                1405                1410
Leu  Gln  Ala  Asn  Gly  Thr  Arg  Ser  Asn  Val  Lys  Asn  Leu  Gly  Ile
     1415                1420                1425
Lys  Thr  Asp  Leu  Gly  Leu  Leu  Gln  Val  Gly  Ser  Gly  Ile  Lys  Leu
     1430                1435                1440
Asp  Lys  Asp  Thr  Gln  Ile  Val  Tyr  Gln  Ser  Pro  Ser  Gly  Leu  Phe
     1445                1450                1455
Lys  Arg  Arg  Ile  Pro  Leu  Ala  Asp  Leu  Pro  Lys  Lys  Lys  Arg  Lys
     1460                1465                1470
Val  Leu  Glu  Gly  Gly  Gly  Gly  Ser  Gly  Lys  Gly  Asp  Pro  Lys  Lys
     1475                1480                1485
Pro  Arg  Gly  Lys  Met  Ser  Ser  Tyr  Ala  Phe  Phe  Val  Gln  Thr  Cys
     1490                1495                1500
```

```
Arg Glu Glu His Lys Lys Lys His Pro Asp Ala Ser Val Asn Phe
    1505            1510                1515

Ser Glu Phe Ser Lys Lys Cys Ser Glu Arg Trp Lys Thr Met Ser
    1520            1525                1530

Ala Lys Glu Lys Gly Lys Phe Glu Asp Met Ala Lys Ala Asp Lys
    1535            1540                1545

Ala Arg Tyr Glu Arg Glu Met Lys Thr Tyr Ile Pro Pro Lys Gly
    1550            1555                1560

Glu

<210> SEQ ID NO 122
<211> LENGTH: 1561
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
            20                  25                  30

Glu Ala Lys Pro Lys Lys Ala Ala Lys Asp Lys Ser Ser Asp Lys
        35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Thr Lys Leu Asn Gln Pro Tyr
            100                 105                 110

Gly Ile Gly Leu Asp Ile Gly Ser Asn Ser Ile Gly Phe Ala Val Val
        115                 120                 125

Asp Ala Asn Ser His Leu Leu Arg Leu Lys Gly Glu Thr Ala Ile Gly
    130                 135                 140

Ala Arg Leu Phe Arg Glu Gly Gln Ser Ala Ala Asp Arg Arg Gly Ser
145                 150                 155                 160

Arg Thr Thr Arg Arg Arg Leu Ser Arg Thr Arg Trp Arg Leu Ser Phe
                165                 170                 175

Leu Arg Asp Phe Phe Ala Pro His Ile Thr Lys Ile Asp Pro Asp Phe
            180                 185                 190

Phe Leu Arg Gln Lys Tyr Ser Glu Ile Ser Pro Lys Asp Lys Asp Arg
        195                 200                 205

Phe Lys Tyr Glu Lys Arg Leu Phe Asn Asp Arg Thr Asp Ala Glu Phe
    210                 215                 220

Tyr Glu Asp Tyr Pro Ser Met Tyr His Leu Arg Leu His Leu Met Thr
225                 230                 235                 240

His Thr His Lys Ala Asp Pro Arg Glu Ile Phe Leu Ala Ile His His
                245                 250                 255

Ile Leu Lys Ser Arg Gly His Phe Leu Thr Pro Gly Ala Ala Lys Asp
            260                 265                 270

Phe Asn Thr Asp Lys Val Asp Leu Glu Asp Ile Phe Pro Ala Leu Thr
        275                 280                 285
```

Glu Ala Tyr Ala Gln Val Tyr Pro Asp Leu Glu Leu Thr Phe Asp Leu
    290                 295                 300

Ala Lys Ala Asp Asp Phe Lys Ala Lys Leu Leu Asp Glu Gln Ala Thr
305                 310                 315                 320

Pro Ser Asp Thr Gln Lys Ala Leu Val Asn Leu Leu Leu Ser Ser Asp
                325                 330                 335

Gly Glu Lys Glu Ile Val Lys Arg Lys Gln Val Leu Thr Glu Phe
                340                 345                 350

Ala Lys Ala Ile Thr Gly Leu Lys Thr Lys Phe Asn Leu Ala Leu Gly
            355                 360                 365

Thr Glu Val Asp Glu Ala Asp Ala Ser Asn Trp Gln Phe Ser Met Gly
    370                 375                 380

Gln Leu Asp Asp Lys Trp Ser Asn Ile Glu Thr Ser Met Thr Asp Gln
385                 390                 395                 400

Gly Thr Glu Ile Phe Glu Gln Ile Gln Glu Leu Tyr Arg Ala Arg Leu
                405                 410                 415

Leu Asn Gly Ile Val Pro Ala Gly Met Ser Leu Ser Gln Ala Lys Val
            420                 425                 430

Ala Asp Tyr Gly Gln His Lys Glu Asp Leu Glu Leu Phe Lys Thr Tyr
            435                 440                 445

Leu Lys Lys Leu Asn Asp His Glu Leu Ala Lys Thr Ile Arg Gly Leu
450                 455                 460

Tyr Asp Arg Tyr Ile Asn Gly Asp Asp Ala Lys Pro Phe Leu Arg Glu
465                 470                 475                 480

Asp Phe Val Lys Ala Leu Thr Lys Glu Val Thr Ala His Pro Asn Glu
                485                 490                 495

Val Ser Glu Gln Leu Leu Asn Arg Met Gly Gln Ala Asn Phe Met Leu
                500                 505                 510

Lys Gln Arg Thr Lys Ala Asn Gly Ala Ile Pro Ile Gln Leu Gln Gln
            515                 520                 525

Arg Glu Leu Asp Gln Ile Ile Ala Asn Gln Ser Lys Tyr Tyr Asp Trp
    530                 535                 540

Leu Ala Ala Pro Asn Pro Val Glu Ala His Arg Trp Lys Met Pro Tyr
545                 550                 555                 560

Gln Leu Asp Glu Leu Leu Asn Phe His Ile Pro Tyr Tyr Val Gly Pro
                565                 570                 575

Leu Ile Thr Pro Lys Gln Gln Ala Glu Ser Gly Glu Asn Val Phe Ala
            580                 585                 590

Trp Met Val Arg Lys Asp Pro Ser Gly Asn Ile Thr Pro Tyr Asn Phe
            595                 600                 605

Asp Glu Lys Val Asp Arg Glu Ala Ser Ala Asn Thr Phe Ile Gln Arg
    610                 615                 620

Met Lys Thr Thr Asp Thr Tyr Leu Ile Gly Glu Asp Val Leu Pro Lys
625                 630                 635                 640

Gln Ser Leu Leu Tyr Gln Lys Tyr Glu Val Leu Asn Glu Leu Asn Asn
                645                 650                 655

Val Arg Ile Asn Asn Glu Cys Leu Gly Thr Asp Gln Lys Gln Arg Leu
            660                 665                 670

Ile Arg Glu Val Phe Glu Arg His Ser Ser Val Thr Ile Lys Gln Val
        675                 680                 685

Ala Asp Asn Leu Val Ala His Gly Asp Phe Ala Arg Arg Pro Glu Ile
    690                 695                 700

-continued

Arg Gly Leu Ala Asp Glu Lys Arg Phe Leu Ser Ser Leu Ser Thr Tyr
705                 710                 715                 720

His Gln Leu Lys Glu Ile Leu His Glu Ala Ile Asp Asp Pro Thr Lys
            725                 730                 735

Leu Leu Asp Ile Glu Asn Ile Ile Thr Trp Ser Thr Val Phe Glu Asp
            740                 745                 750

His Thr Ile Phe Glu Thr Lys Leu Ala Glu Ile Glu Trp Leu Asp Pro
            755                 760                 765

Lys Lys Ile Asn Glu Leu Ser Gly Ile Arg Tyr Arg Gly Trp Gly Gln
        770                 775                 780

Phe Ser Arg Lys Leu Leu Asp Gly Leu Lys Leu Gly Asn Gly His Thr
785                 790                 795                 800

Val Ile Gln Glu Leu Met Leu Ser Asn His Asn Leu Met Gln Ile Leu
            805                 810                 815

Ala Asp Glu Thr Leu Lys Glu Thr Met Thr Glu Leu Asn Gln Asp Lys
            820                 825                 830

Leu Lys Thr Asp Asp Ile Glu Asp Val Ile Asn Asp Ala Tyr Thr Ser
        835                 840                 845

Pro Ser Asn Lys Lys Ala Leu Arg Gln Val Leu Arg Val Val Glu Asp
850                 855                 860

Ile Lys His Ala Ala Asn Gly Gln Asp Pro Ser Trp Leu Phe Ile Glu
865                 870                 875                 880

Thr Ala Asp Gly Thr Gly Thr Ala Gly Lys Arg Thr Gln Ser Arg Gln
            885                 890                 895

Lys Gln Ile Gln Thr Val Tyr Ala Asn Ala Ala Gln Glu Leu Ile Asp
        900                 905                 910

Ser Ala Val Arg Gly Glu Leu Glu Asp Lys Ile Ala Asp Lys Ala Ser
        915                 920                 925

Phe Thr Asp Arg Leu Val Leu Tyr Phe Met Gln Gly Gly Arg Asp Ile
930                 935                 940

Tyr Thr Gly Ala Pro Leu Asn Ile Asp Gln Leu Ser His Tyr Asp Ile
945                 950                 955                 960

Asp His Ile Leu Pro Gln Ser Leu Ile Lys Asp Asp Ser Leu Asp Asn
            965                 970                 975

Arg Val Leu Val Asn Ala Thr Ile Asn Arg Glu Lys Asn Asn Val Phe
            980                 985                 990

Ala Ser Thr Leu Phe Ala Gly Lys Met Lys Ala Thr Trp Arg Lys Trp
            995                 1000                1005

His Glu Ala Gly Leu Ile Ser Gly Arg Lys Leu Arg Asn Leu Met
    1010                1015                1020

Leu Arg Pro Asp Glu Ile Asp Lys Phe Ala Lys Gly Phe Val Ala
    1025                1030                1035

Arg Gln Leu Val Glu Thr Arg Gln Ile Ile Lys Leu Thr Glu Gln
    1040                1045                1050

Ile Ala Ala Gln Tyr Pro Asn Thr Lys Ile Ile Ala Val Lys
    1055                1060                1065

Ala Gly Leu Ser His Gln Leu Arg Glu Glu Leu Asp Phe Pro Lys
    1070                1075                1080

Asn Arg Asp Val Asn His Tyr His His Ala Phe Asp Ala Phe Leu
    1085                1090                1095

Ala Ala Arg Ile Gly Thr Tyr Leu Leu Lys Arg Tyr Pro Lys Leu
    1100                1105                1110

Ala Pro Phe Phe Thr Tyr Gly Glu Phe Ala Lys Val Asp Val Lys

```
           1115                1120                1125
Lys Phe Arg Glu Phe Asn Phe Ile Gly Ala Leu Thr His Ala Lys
       1130                1135                1140
Lys Asn Ile Ile Ala Lys Asp Thr Gly Glu Ile Val Trp Asp Lys
       1145                1150                1155
Glu Arg Asp Ile Arg Glu Leu Asp Arg Ile Tyr Asn Phe Lys Arg
       1160                1165                1170
Met Leu Ile Thr His Glu Val Tyr Phe Glu Thr Ala Asp Leu Phe
       1175                1180                1185
Lys Gln Thr Ile Tyr Ala Ala Lys Asp Ser Lys Glu Arg Gly Gly
       1190                1195                1200
Ser Lys Gln Leu Ile Pro Lys Lys Gln Gly Tyr Pro Thr Gln Val
       1205                1210                1215
Tyr Gly Gly Tyr Thr Gln Glu Ser Gly Ser Tyr Asn Ala Leu Val
       1220                1225                1230
Arg Val Ala Glu Ala Asp Thr Thr Ala Tyr Gln Val Ile Lys Ile
       1235                1240                1245
Ser Ala Gln Asn Ala Ser Lys Ile Ala Ser Ala Asn Leu Lys Ser
       1250                1255                1260
Arg Glu Lys Gly Lys Gln Leu Leu Asn Glu Ile Val Val Lys Gln
       1265                1270                1275
Leu Ala Lys Arg Arg Lys Asn Trp Lys Pro Ser Ala Asn Ser Phe
       1280                1285                1290
Lys Ile Val Ile Pro Arg Phe Gly Met Gly Thr Leu Phe Gln Asn
       1295                1300                1305
Ala Lys Tyr Gly Leu Phe Met Val Asn Ser Asp Thr Tyr Tyr Arg
       1310                1315                1320
Asn Tyr Gln Glu Leu Trp Leu Ser Arg Glu Asn Gln Lys Leu Leu
       1325                1330                1335
Lys Lys Leu Phe Ser Ile Lys Tyr Glu Lys Thr Gln Met Asn His
       1340                1345                1350
Asp Ala Leu Gln Val Tyr Lys Ala Ile Ile Asp Gln Val Glu Lys
       1355                1360                1365
Phe Phe Lys Leu Tyr Asp Ile Asn Gln Phe Arg Ala Lys Leu Ser
       1370                1375                1380
Asp Ala Ile Glu Arg Phe Glu Lys Leu Pro Ile Asn Thr Asp Gly
       1385                1390                1395
Asn Lys Ile Gly Lys Thr Glu Thr Leu Arg Gln Ile Leu Ile Gly
       1400                1405                1410
Leu Gln Ala Asn Gly Thr Arg Ser Asn Val Lys Asn Leu Gly Ile
       1415                1420                1425
Lys Thr Asp Leu Gly Leu Leu Gln Val Gly Ser Gly Ile Lys Leu
       1430                1435                1440
Asp Lys Asp Thr Gln Ile Val Tyr Gln Ser Pro Ser Gly Leu Phe
       1445                1450                1455
Lys Arg Arg Ile Pro Leu Ala Asp Leu Pro Lys Lys Arg Lys
       1460                1465                1470
Val Leu Glu Gly Gly Gly Gly Ser Ser Thr Asp His Pro Lys Tyr
       1475                1480                1485
Ser Asp Met Ile Val Ala Ala Ile Gln Ala Glu Lys Asn Arg Ala
       1490                1495                1500
Gly Ser Ser Arg Gln Ser Ile Gln Lys Tyr Ile Lys Ser His Tyr
       1505                1510                1515
```

```
Lys Val Gly Glu Asn Ala Asp Ser Gln Ile Lys Leu Ser Ile Lys
    1520                1525                1530

Arg Leu Val Thr Thr Gly Val Leu Lys Gln Thr Lys Gly Val Gly
    1535                1540                1545

Ala Ser Gly Ser Phe Arg Leu Ala Lys Ser Asp Glu Pro
    1550                1555                1560

<210> SEQ ID NO 123
<211> LENGTH: 1434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
            20                  25                  30

Glu Ala Lys Pro Lys Lys Ala Ala Ala Lys Asp Lys Ser Ser Asp Lys
        35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Glu Lys Lys Arg Lys Val Thr
            100                 105                 110

Leu Gly Phe Asp Leu Gly Ile Ala Ser Val Gly Trp Ala Ile Val Asp
        115                 120                 125

Ser Glu Thr Asn Gln Val Tyr Lys Leu Gly Ser Arg Leu Phe Asp Ala
    130                 135                 140

Pro Asp Thr Asn Leu Glu Arg Arg Thr Gln Arg Gly Thr Arg Arg Leu
145                 150                 155                 160

Leu Arg Arg Arg Lys Tyr Arg Asn Gln Lys Phe Tyr Asn Leu Val Lys
                165                 170                 175

Arg Thr Glu Val Phe Gly Leu Ser Ser Arg Glu Ala Ile Glu Asn Arg
            180                 185                 190

Phe Arg Glu Leu Ser Ile Lys Tyr Pro Asn Ile Glu Leu Lys Thr
        195                 200                 205

Lys Ala Leu Ser Gln Glu Val Cys Pro Asp Glu Ile Ala Trp Ile Leu
    210                 215                 220

His Asp Tyr Leu Lys Asn Arg Gly Tyr Phe Tyr Asp Glu Lys Glu Thr
225                 230                 235                 240

Lys Glu Asp Phe Asp Gln Gln Thr Val Glu Ser Met Pro Ser Tyr Lys
                245                 250                 255

Leu Asn Glu Phe Tyr Lys Lys Tyr Gly Tyr Phe Lys Gly Ala Leu Ser
            260                 265                 270

Gln Pro Thr Glu Ser Glu Met Lys Asp Asn Lys Asp Leu Lys Glu Ala
        275                 280                 285

Phe Phe Phe Asp Phe Ser Asn Lys Glu Trp Leu Lys Glu Ile Asn Tyr
    290                 295                 300

Phe Phe Asn Val Gln Lys Asn Ile Leu Ser Glu Thr Phe Ile Glu Glu
```

-continued

```
            305                 310                 315                 320
        Phe Lys Lys Ile Phe Ser Phe Thr Arg Asp Ile Ser Lys Gly Pro Gly
                        325                 330                 335
        Ser Asp Asn Met Pro Ser Pro Tyr Gly Ile Phe Gly Glu Phe Gly Asp
                        340                 345                 350
        Asn Gly Gln Gly Gly Arg Tyr Glu His Ile Trp Asp Lys Asn Ile Gly
                        355                 360                 365
        Lys Cys Ser Ile Phe Thr Asn Glu Gln Arg Ala Pro Lys Tyr Leu Pro
                        370                 375                 380
        Ser Ala Leu Ile Phe Asn Phe Leu Asn Glu Leu Ala Asn Ile Arg Leu
        385                 390                 395                 400
        Tyr Ser Thr Asp Lys Lys Asn Ile Gln Pro Leu Trp Lys Leu Ser Ser
                        405                 410                 415
        Ile Asp Lys Leu Asn Ile Leu Leu Asn Leu Phe Asn Leu Pro Ile Ser
                        420                 425                 430
        Glu Lys Lys Lys Lys Leu Thr Ser Thr Asn Ile Asn Asp Ile Val Lys
                        435                 440                 445
        Lys Glu Ser Ile Lys Ser Ile Met Leu Ser Val Glu Asp Ile Asp Met
                        450                 455                 460
        Ile Lys Asp Glu Trp Ala Gly Lys Glu Pro Asn Val Tyr Gly Val Gly
        465                 470                 475                 480
        Leu Ser Gly Leu Asn Ile Glu Glu Ser Ala Lys Glu Asn Lys Phe Lys
                        485                 490                 495
        Phe Gln Asp Leu Lys Ile Leu Asn Val Leu Ile Asn Leu Leu Asp Asn
                        500                 505                 510
        Val Gly Ile Lys Phe Glu Phe Lys Asp Arg Ser Asp Ile Ile Lys Asn
                        515                 520                 525
        Leu Glu Leu Leu Asp Asn Leu Tyr Leu Phe Leu Ile Tyr Gln Lys Glu
                        530                 535                 540
        Ser Asn Asn Lys Asp Ser Ser Ile Asp Leu Phe Ile Ala Lys Asn Lys
        545                 550                 555                 560
        Ser Leu Asn Ile Glu Asn Leu Lys Leu Lys Leu Lys Glu Phe Leu Leu
                        565                 570                 575
        Gly Ala Gly Asn Glu Phe Glu Asn His Asn Ser Lys Thr His Ser Leu
                        580                 585                 590
        Ser Lys Lys Ala Ile Asp Ala Ile Leu Pro Lys Leu Leu Asp Asn Asn
                        595                 600                 605
        Glu Gly Trp Asn Leu Glu Ala Ile Lys Asn Tyr Asp Glu Glu Ile Lys
                        610                 615                 620
        Ser Gln Ile Glu Asp Asn Ser Ser Leu Met Ala Lys Gln Asp Lys Lys
        625                 630                 635                 640
        Tyr Leu Asn Asp Asn Phe Leu Lys Asp Ala Ile Leu Pro Pro Asn Val
                        645                 650                 655
        Lys Val Thr Phe Gln Gln Ala Ile Leu Ile Phe Asn Lys Ile Ile Gln
                        660                 665                 670
        Lys Phe Ser Lys Asp Phe Glu Ile Asp Lys Val Val Ile Glu Leu Ala
                        675                 680                 685
        Arg Glu Met Thr Gln Asp Gln Asn Asp Ala Leu Lys Gly Ile Ala
                        690                 695                 700
        Lys Ala Gln Lys Ser Lys Lys Ser Leu Val Glu Glu Arg Leu Glu Ala
        705                 710                 715                 720
        Asn Asn Ile Asp Lys Ser Val Phe Asn Asp Lys Tyr Glu Lys Leu Ile
                        725                 730                 735
```

```
Tyr Lys Ile Phe Leu Trp Ile Ser Gln Asp Phe Lys Asp Pro Tyr Thr
                740                 745                 750

Gly Ala Lys Ile Ser Ala Asn Glu Ile Val Asp Asn Lys Val Glu Ile
                755                 760                 765

Asp His Ile Ile Pro Tyr Ser Leu Cys Phe Asp Ser Ser Ala Asn
770                 775                 780

Lys Val Leu Val His Lys Gln Ser Asn Gln Glu Lys Ser Asn Ser Leu
785                 790                 795                 800

Pro Tyr Glu Tyr Ile Lys Gln Gly His Ser Gly Trp Asn Trp Asp Glu
                805                 810                 815

Phe Thr Lys Tyr Val Lys Arg Val Phe Val Asn Asn Val Asp Ser Ile
                820                 825                 830

Leu Ser Lys Lys Glu Arg Leu Lys Lys Ser Glu Asn Leu Leu Thr Thr
                835                 840                 845

Ser Tyr Asp Gly Tyr Glu Lys Leu Gly Phe Leu Ala Arg Asn Leu Asn
850                 855                 860

Asp Thr Arg Tyr Ala Thr Ile Leu Phe Arg Asp Gln Leu Asn Asn Tyr
865                 870                 875                 880

Ala Glu His His Leu Ile Asp Asn Lys Lys Met Phe Lys Val Ile Ala
                885                 890                 895

Met Asn Gly Ala Val Thr Ser Phe Ile Arg Lys Asn Met Ser Tyr Asp
                900                 905                 910

Asn Lys Leu Arg Leu Lys Asp Arg Ser Asp Phe Ser His His Ala Tyr
                915                 920                 925

Asp Ala Ala Ile Ile Ala Leu Phe Ser Asn Lys Thr Lys Thr Leu Tyr
                930                 935                 940

Asn Leu Ile Asp Pro Ser Leu Asn Gly Ile Ile Ser Lys Arg Ser Glu
945                 950                 955                 960

Gly Tyr Trp Val Ile Glu Asp Arg Tyr Thr Gly Glu Ile Lys Glu Leu
                965                 970                 975

Lys Lys Glu Asp Trp Thr Ser Ile Lys Asn Asn Val Gln Ala Arg Lys
                980                 985                 990

Ile Ala Lys Glu Ile Glu Glu Tyr Leu Ile Asp Leu Asp Asp Glu Val
                995                 1000                1005

Phe Phe Ser Arg Lys Thr Lys Arg Lys Thr Asn Arg Gln Leu Tyr
     1010                1015                1020

Asn Glu Thr Ile Tyr Gly Ile Ala Ala Lys Thr Asp Glu Asp Gly
     1025                1030                1035

Ile Thr Asn Tyr Tyr Lys Lys Glu Lys Phe Ser Ile Leu Asp Asp
     1040                1045                1050

Lys Asp Ile Tyr Leu Arg Leu Leu Arg Glu Arg Glu Lys Phe Val
     1055                1060                1065

Ile Asn Gln Ser Asn Pro Glu Val Ile Asp Gln Ile Ile Glu Ile
     1070                1075                1080

Ile Glu Ser Tyr Gly Lys Glu Asn Asn Ile Pro Ser Arg Asp Glu
     1085                1090                1095

Ala Ile Asn Ile Lys Tyr Thr Lys Asn Lys Ile Asn Tyr Asn Leu
     1100                1105                1110

Tyr Leu Lys Gln Tyr Met Arg Ser Leu Thr Lys Ser Leu Asp Gln
     1115                1120                1125

Phe Ser Glu Gly Phe Ile Asn Gln Met Ile Ala Asn Lys Thr Phe
     1130                1135                1140
```

```
Val Leu Tyr Asn Pro Thr Lys Asn Thr Thr Arg Lys Ile Lys Phe
    1145                1150                1155

Leu Arg Leu Val Asn Asp Val Lys Ile Asn Asp Ile Arg Lys Asn
    1160                1165                1170

Gln Val Ile Asn Lys Phe Asn Gly Lys Asn Asn Glu Pro Lys Ala
    1175                1180                1185

Phe Tyr Glu Asn Ile Asn Ser Leu Gly Ala Ile Val Phe Lys Ser
    1190                1195                1200

Ser Ala Asn Asn Phe Lys Thr Leu Ser Ile Asn Thr Gln Ile Ala
    1205                1210                1215

Ile Phe Gly Asp Lys Asn Trp Asp Ile Glu Asp Phe Lys Thr Tyr
    1220                1225                1230

Asn Met Glu Lys Ile Glu Lys Tyr Lys Glu Ile Tyr Gly Ile Asp
    1235                1240                1245

Lys Thr Tyr Asn Phe His Ser Phe Ile Phe Pro Gly Thr Ile Leu
    1250                1255                1260

Leu Asp Lys Gln Asn Lys Glu Phe Tyr Tyr Ile Ser Ser Ile Gln
    1265                1270                1275

Thr Val Asn Asp Gln Ile Glu Leu Lys Phe Leu Asn Lys Ile Glu
    1280                1285                1290

Phe Lys Asn Asp Asp Asn Thr Ser Gly Ala Asn Lys Pro Pro Arg
    1295                1300                1305

Arg Leu Arg Phe Gly Ile Lys Ser Ile Met Asn Asn Tyr Glu Gln
    1310                1315                1320

Val Asp Ile Ser Pro Phe Gly Ile Asn Lys Lys Ile Phe Glu Pro
    1325                1330                1335

Lys Lys Lys Arg Lys Val Leu Glu Gly Gly Gly Ser Gly Lys
    1340                1345                1350

Gly Asp Pro Lys Lys Pro Arg Gly Lys Met Ser Ser Tyr Ala Phe
    1355                1360                1365

Phe Val Gln Thr Cys Arg Glu Glu His Lys Lys Lys His Pro Asp
    1370                1375                1380

Ala Ser Val Asn Phe Ser Glu Phe Ser Lys Lys Cys Ser Glu Arg
    1385                1390                1395

Trp Lys Thr Met Ser Ala Lys Glu Lys Gly Lys Phe Glu Asp Met
    1400                1405                1410

Ala Lys Ala Asp Lys Ala Arg Tyr Glu Arg Glu Met Lys Thr Tyr
    1415                1420                1425

Ile Pro Pro Lys Gly Glu
    1430

<210> SEQ ID NO 124
<211> LENGTH: 1431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
                20                  25                  30

Glu Ala Lys Pro Lys Lys Ala Ala Ala Lys Asp Lys Ser Ser Asp Lys
                35                  40                  45
```

-continued

```
Lys Val Gln Thr Lys Gly Lys Arg Gly Ala Lys Gly Lys Gln Ala Glu
            50                  55                  60

Val Ala Asn Gln Glu Thr Lys Glu Asp Leu Pro Ala Glu Asn Gly Glu
65                      70                  75                  80

Thr Lys Thr Glu Glu Ser Pro Ala Ser Asp Glu Ala Gly Glu Lys Glu
                    85                  90                  95

Ala Lys Ser Asp Thr Gly Ser Gly Met Glu Lys Lys Arg Lys Val Thr
                100                 105                 110

Leu Gly Phe Asp Leu Gly Ile Ala Ser Val Gly Trp Ala Ile Val Asp
                115                 120                 125

Ser Glu Thr Asn Gln Val Tyr Lys Leu Gly Ser Arg Leu Phe Asp Ala
            130                 135                 140

Pro Asp Thr Asn Leu Glu Arg Arg Thr Gln Arg Gly Thr Arg Arg Leu
145                 150                 155                 160

Leu Arg Arg Arg Lys Tyr Arg Asn Gln Lys Phe Tyr Asn Leu Val Lys
                165                 170                 175

Arg Thr Glu Val Phe Gly Leu Ser Ser Arg Glu Ala Ile Glu Asn Arg
                180                 185                 190

Phe Arg Glu Leu Ser Ile Lys Tyr Pro Asn Ile Ile Glu Leu Lys Thr
                195                 200                 205

Lys Ala Leu Ser Gln Glu Val Cys Pro Asp Glu Ile Ala Trp Ile Leu
            210                 215                 220

His Asp Tyr Leu Lys Asn Arg Gly Tyr Phe Tyr Asp Glu Lys Glu Thr
225                 230                 235                 240

Lys Glu Asp Phe Asp Gln Thr Val Glu Ser Met Pro Ser Tyr Lys
                245                 250                 255

Leu Asn Glu Phe Tyr Lys Lys Tyr Gly Tyr Phe Lys Gly Ala Leu Ser
                260                 265                 270

Gln Pro Thr Glu Ser Glu Met Lys Asp Asn Lys Asp Leu Lys Glu Ala
            275                 280                 285

Phe Phe Phe Asp Phe Ser Asn Lys Glu Trp Leu Lys Glu Ile Asn Tyr
            290                 295                 300

Phe Phe Asn Val Gln Lys Asn Ile Leu Ser Glu Thr Phe Ile Glu Glu
305                 310                 315                 320

Phe Lys Lys Ile Phe Ser Phe Thr Arg Asp Ile Ser Lys Gly Pro Gly
                325                 330                 335

Ser Asp Asn Met Pro Ser Pro Tyr Gly Ile Phe Gly Glu Phe Gly Asp
                340                 345                 350

Asn Gly Gln Gly Gly Arg Tyr Glu His Ile Trp Asp Lys Asn Ile Gly
            355                 360                 365

Lys Cys Ser Ile Phe Thr Asn Glu Gln Arg Ala Pro Lys Tyr Leu Pro
370                 375                 380

Ser Ala Leu Ile Phe Asn Phe Leu Asn Glu Leu Ala Asn Ile Arg Leu
385                 390                 395                 400

Tyr Ser Thr Asp Lys Lys Asn Ile Gln Pro Leu Trp Lys Leu Ser Ser
                405                 410                 415

Ile Asp Lys Leu Asn Ile Leu Leu Asn Leu Phe Asn Leu Pro Ile Ser
                420                 425                 430

Glu Lys Lys Lys Lys Leu Thr Ser Thr Asn Ile Asn Asp Ile Val Lys
                435                 440                 445

Lys Glu Ser Ile Lys Ser Ile Met Leu Ser Val Glu Asp Ile Asp Met
450                 455                 460
```

-continued

Ile Lys Asp Glu Trp Ala Gly Lys Glu Pro Asn Val Tyr Gly Val Gly
465                 470                 475                 480

Leu Ser Gly Leu Asn Ile Glu Ser Ala Lys Glu Asn Lys Phe Lys
            485                 490                 495

Phe Gln Asp Leu Lys Ile Leu Asn Val Leu Ile Asn Leu Leu Asp Asn
            500                 505                 510

Val Gly Ile Lys Phe Glu Phe Lys Asp Arg Ser Asp Ile Ile Lys Asn
            515                 520                 525

Leu Glu Leu Leu Asp Asn Leu Tyr Leu Phe Leu Ile Tyr Gln Lys Glu
            530                 535                 540

Ser Asn Asn Lys Asp Ser Ser Ile Asp Leu Phe Ile Ala Lys Asn Lys
545                 550                 555                 560

Ser Leu Asn Ile Glu Asn Leu Lys Leu Lys Leu Lys Glu Phe Leu Leu
                565                 570                 575

Gly Ala Gly Asn Glu Phe Glu Asn His Asn Ser Lys Thr His Ser Leu
                580                 585                 590

Ser Lys Lys Ala Ile Asp Ala Ile Leu Pro Lys Leu Leu Asp Asn Asn
                595                 600                 605

Glu Gly Trp Asn Leu Glu Ala Ile Lys Asn Tyr Asp Glu Glu Ile Lys
                610                 615                 620

Ser Gln Ile Glu Asp Asn Ser Ser Leu Met Ala Lys Gln Asp Lys Lys
625                 630                 635                 640

Tyr Leu Asn Asp Asn Phe Leu Lys Asp Ala Ile Leu Pro Pro Asn Val
                    645                 650                 655

Lys Val Thr Phe Gln Gln Ala Ile Leu Ile Phe Asn Lys Ile Ile Gln
                660                 665                 670

Lys Phe Ser Lys Asp Phe Glu Ile Asp Lys Val Val Ile Glu Leu Ala
                675                 680                 685

Arg Glu Met Thr Gln Asp Gln Glu Asn Asp Ala Leu Lys Gly Ile Ala
                690                 695                 700

Lys Ala Gln Lys Ser Lys Lys Ser Leu Val Glu Glu Arg Leu Glu Ala
705                 710                 715                 720

Asn Asn Ile Asp Lys Ser Val Phe Asn Asp Lys Tyr Glu Lys Leu Ile
                725                 730                 735

Tyr Lys Ile Phe Leu Trp Ile Ser Gln Asp Phe Lys Asp Pro Tyr Thr
                740                 745                 750

Gly Ala Lys Ile Ser Ala Asn Glu Ile Val Asp Asn Lys Val Glu Ile
                755                 760                 765

Asp His Ile Ile Pro Tyr Ser Leu Cys Phe Asp Asp Ser Ser Ala Asn
770                 775                 780

Lys Val Leu Val His Lys Gln Ser Asn Gln Glu Lys Ser Asn Ser Leu
785                 790                 795                 800

Pro Tyr Glu Tyr Ile Lys Gln Gly His Ser Gly Trp Asn Trp Asp Glu
                805                 810                 815

Phe Thr Lys Tyr Val Lys Arg Val Phe Val Asn Asn Val Asp Ser Ile
                820                 825                 830

Leu Ser Lys Lys Glu Arg Leu Lys Lys Ser Glu Asn Leu Leu Thr Thr
                835                 840                 845

Ser Tyr Asp Gly Tyr Glu Lys Leu Gly Phe Leu Ala Arg Asn Leu Asn
                850                 855                 860

Asp Thr Arg Tyr Ala Thr Ile Leu Phe Arg Asp Gln Leu Asn Asn Tyr
865                 870                 875                 880

Ala Glu His His Leu Ile Asp Asn Lys Lys Met Phe Lys Val Ile Ala

-continued

```
            885                 890                 895
Met Asn Gly Ala Val Thr Ser Phe Ile Arg Lys Asn Met Ser Tyr Asp
                900                 905                 910
Asn Lys Leu Arg Leu Lys Asp Arg Ser Asp Phe Ser His His Ala Tyr
                915                 920                 925
Asp Ala Ala Ile Ile Ala Leu Phe Ser Asn Lys Thr Lys Thr Leu Tyr
930                 935                 940
Asn Leu Ile Asp Pro Ser Leu Asn Gly Ile Ile Ser Lys Arg Ser Glu
945                 950                 955                 960
Gly Tyr Trp Val Ile Glu Asp Arg Tyr Thr Gly Glu Ile Lys Glu Leu
                965                 970                 975
Lys Lys Glu Asp Trp Thr Ser Ile Lys Asn Asn Val Gln Ala Arg Lys
                980                 985                 990
Ile Ala Lys Glu Ile Glu Glu Tyr Leu Ile Asp Leu Asp Asp Glu Val
                995                 1000                1005
Phe Phe Ser Arg Lys Thr Lys Arg Lys Thr Asn Arg Gln Leu Tyr
    1010                1015                1020
Asn Glu Thr Ile Tyr Gly Ile Ala Ala Lys Thr Asp Glu Asp Gly
    1025                1030                1035
Ile Thr Asn Tyr Tyr Lys Lys Glu Lys Phe Ser Ile Leu Asp Asp
    1040                1045                1050
Lys Asp Ile Tyr Leu Arg Leu Arg Glu Arg Glu Lys Phe Val
    1055                1060                1065
Ile Asn Gln Ser Asn Pro Glu Val Ile Asp Gln Ile Ile Glu Ile
    1070                1075                1080
Ile Glu Ser Tyr Gly Lys Glu Asn Asn Ile Pro Ser Arg Asp Glu
    1085                1090                1095
Ala Ile Asn Ile Lys Tyr Thr Lys Asn Lys Ile Asn Tyr Asn Leu
    1100                1105                1110
Tyr Leu Lys Gln Tyr Met Arg Ser Leu Thr Lys Ser Leu Asp Gln
    1115                1120                1125
Phe Ser Glu Gly Phe Ile Asn Gln Met Ile Ala Asn Lys Thr Phe
    1130                1135                1140
Val Leu Tyr Asn Pro Thr Lys Asn Thr Thr Arg Lys Ile Lys Phe
    1145                1150                1155
Leu Arg Leu Val Asn Asp Val Lys Ile Asn Asp Ile Arg Lys Asn
    1160                1165                1170
Gln Val Ile Asn Lys Phe Asn Gly Lys Asn Asn Glu Pro Lys Ala
    1175                1180                1185
Phe Tyr Glu Asn Ile Asn Ser Leu Gly Ala Ile Val Phe Lys Ser
    1190                1195                1200
Ser Ala Asn Asn Phe Lys Thr Leu Ser Ile Asn Thr Gln Ile Ala
    1205                1210                1215
Ile Phe Gly Asp Lys Asn Trp Asp Ile Glu Asp Phe Lys Thr Tyr
    1220                1225                1230
Asn Met Glu Lys Ile Glu Lys Tyr Lys Glu Ile Tyr Gly Ile Asp
    1235                1240                1245
Lys Thr Tyr Asn Phe His Ser Phe Ile Phe Pro Gly Thr Ile Leu
    1250                1255                1260
Leu Asp Lys Gln Asn Lys Glu Phe Tyr Tyr Ile Ser Ser Ile Gln
    1265                1270                1275
Thr Val Asn Asp Gln Ile Glu Leu Lys Phe Leu Asn Lys Ile Glu
    1280                1285                1290
```

```
Phe Lys Asn Asp Asp Asn Thr Ser Gly Ala Asn Lys Pro Pro Arg
    1295                1300                1305

Arg Leu Arg Phe Gly Ile Lys Ser Ile Met Asn Asn Tyr Glu Gln
    1310                1315                1320

Val Asp Ile Ser Pro Phe Gly Ile Asn Lys Lys Ile Phe Glu Pro
    1325                1330                1335

Lys Lys Lys Arg Lys Val Leu Glu Gly Gly Gly Ser Ser Thr
    1340                1345                1350

Asp His Pro Lys Tyr Ser Asp Met Ile Val Ala Ala Ile Gln Ala
    1355                1360                1365

Glu Lys Asn Arg Ala Gly Ser Ser Arg Gln Ser Ile Gln Lys Tyr
    1370                1375                1380

Ile Lys Ser His Tyr Lys Val Gly Glu Asn Ala Asp Ser Gln Ile
    1385                1390                1395

Lys Leu Ser Ile Lys Arg Leu Val Thr Thr Gly Val Leu Lys Gln
    1400                1405                1410

Thr Lys Gly Val Gly Ala Ser Gly Ser Phe Arg Leu Ala Lys Ser
    1415                1420                1425

Asp Glu Pro
    1430

<210> SEQ ID NO 125
<211> LENGTH: 26
<212> TYPE: DNA
<213> ORGANISM: Unknown
<220> FEATURE:
<223> OTHER INFORMATION: Description of Unknown:
      Cas9 target site

<400> SEQUENCE: 125
atagatgcgg ccaaggtgta catggg                                        26

<210> SEQ ID NO 126
<211> LENGTH: 26
<212> TYPE: DNA
<213> ORGANISM: Unknown
<220> FEATURE:
<223> OTHER INFORMATION: Description of Unknown:
      Cas9 target site

<400> SEQUENCE: 126
ctacgagaac cagaagccgt gagtgg                                        26

<210> SEQ ID NO 127
<211> LENGTH: 30
<212> TYPE: DNA
<213> ORGANISM: Unknown
<220> FEATURE:
<223> OTHER INFORMATION: Description of Unknown:
      Cas9 target site

<400> SEQUENCE: 127
ctcatacatg gctataatag aaggagcaaa                                    30

<210> SEQ ID NO 128
<211> LENGTH: 30
<212> TYPE: DNA
<213> ORGANISM: Unknown
<220> FEATURE:
<223> OTHER INFORMATION: Description of Unknown:
      Cas9 target site
```

<400> SEQUENCE: 128
gaaggtgtgg ttccagaacc ggaggacaaa                                              30

<210> SEQ ID NO 129
<211> LENGTH: 30
<212> TYPE: DNA
<213> ORGANISM: Unknown
<220> FEATURE:
<223> OTHER INFORMATION: Description of Unknown:
      Cas9 target site

<400> SEQUENCE: 129
tggttccaga accggaggac aaagtacaaa                                              30

<210> SEQ ID NO 130
<211> LENGTH: 23
<212> TYPE: DNA
<213> ORGANISM: Unknown
<220> FEATURE:
<223> OTHER INFORMATION: Description of Unknown:
      Cas9 target site

<400> SEQUENCE: 130
tgtacatggg ggagatgggc cgg                                                     23

<210> SEQ ID NO 131
<211> LENGTH: 23
<212> TYPE: DNA
<213> ORGANISM: Unknown
<220> FEATURE:
<223> OTHER INFORMATION: Description of Unknown:
      Cas9 target site

<400> SEQUENCE: 131
ggggccacta gggacaggat tgg                                                     23

<210> SEQ ID NO 132
<211> LENGTH: 25
<212> TYPE: DNA
<213> ORGANISM: Unknown
<220> FEATURE:
<223> OTHER INFORMATION: Description of Unknown:
      Cas9 target site

<400> SEQUENCE: 132
agctcgtact ggcgaatgct ggaaa                                                   25

<210> SEQ ID NO 133
<211> LENGTH: 25
<212> TYPE: DNA
<213> ORGANISM: Unknown
<220> FEATURE:
<223> OTHER INFORMATION: Description of Unknown:
      Cas9 target site

<400> SEQUENCE: 133
cctctggcac atcctccaaa tgaaa                                                   25

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

```
<400> SEQUENCE: 134

His His His His His His
1               5
```